US011686014B2

United States Patent
Baek et al.

(10) Patent No.: US 11,686,014 B2
(45) Date of Patent: Jun. 27, 2023

(54) VECTOR LIBRARY FOR YEAST TWO HYBRID SCREENING AND METHOD FOR IDENTIFYING DEUBIQUITINATING ENZYME BINDING TO TARGET PROTEIN USING SAME

(71) Applicant: CHA UNIVERSITY INDUSTRY-ACADEMIC COOPERATION FOUNDATION, Pocheon-si (KR)

(72) Inventors: Kwang-Hyun Baek, Seoul (KR); So-Ra Kim, Gimcheon-si (KR); Seul-Ki Kwon, Seongnam-si (KR); Soo-Yeon Kim, Chuncheon-si (KR); Da-Hye Lee, Seoul (KR)

(73) Assignee: CHA UNIVERSITY INDUSTRY-ACADEMIC COOPERATION FOUNDATION, Pocheon-si (KR)

(*) Notice: Subject to any disclaimer, the term of this patent is extended or adjusted under 35 U.S.C. 154(b) by 522 days.

(21) Appl. No.: 16/636,523

(22) PCT Filed: Aug. 6, 2018

(86) PCT No.: PCT/KR2018/008876
§ 371 (c)(1),
(2) Date: Feb. 4, 2020

(87) PCT Pub. No.: WO2019/031781
PCT Pub. Date: Feb. 14, 2019

(65) Prior Publication Data
US 2021/0032619 A1    Feb. 4, 2021

(30) Foreign Application Priority Data
Aug. 8, 2017    (KR) .................. 10-2017-0100255

(51) Int. Cl.
*C40B 30/06* (2006.01)
*C12N 9/48* (2006.01)
(Continued)

(52) U.S. Cl.
CPC ................ *C40B 30/06* (2013.01); *C12N 9/48* (2013.01); *C12N 15/1055* (2013.01);
(Continued)

(58) Field of Classification Search
None
See application file for complete search history.

(56) References Cited

FOREIGN PATENT DOCUMENTS

KR    10-2003-0002460 A    1/2003

OTHER PUBLICATIONS

Wertz et al. (2010) Cell Death and Differentiation vol. 17 pp. 14 to 24.*

(Continued)

*Primary Examiner* — Christian C Boesen
(74) *Attorney, Agent, or Firm* — Vorys, Sater, Seymour and Pease LLP; Mih Suhn Koh

(57) ABSTRACT

The present invention provides a vector library for yeast two-hybrid screening of a deubiquitinating enzyme that binds to a target protein and a method for identifying a deubiquitinating enzyme binding to a target protein using the same. Also, the present invention provides a method for screening an agent having anti-cancer activity targeting the deubiquitinating enzyme USP1, USP7, USP12, or USP49 identified by said identifying method.

2 Claims, 13 Drawing Sheets

Specification includes a Sequence Listing.

(51) Int. Cl.
  *C12N 15/10* (2006.01)
  *C12N 15/81* (2006.01)
  *C12Q 1/37* (2006.01)
  *C40B 40/02* (2006.01)
  *C40B 40/08* (2006.01)

(52) U.S. Cl.
  CPC .............. *C12N 15/81* (2013.01); *C12Q 1/37* (2013.01); *C40B 40/02* (2013.01); *C40B 40/08* (2013.01)

(56) References Cited

OTHER PUBLICATIONS

Zhang et al. (2013) Genes and Development vol. 27 pp. 1581 to 1595.*

Davis et al., "Ubiquitin-Specific Proteases as Druggable Targets", Drug Target Rev., 2015, vol. 2, No. 3, pp. 30-64.

Kwon et al., "Ubiquitin-specific protease 21 regulating the K48-linked polyubiquitination of NANOG", Biochemical and Biophysical Research Communications, 2017, vol. 482, pp. 1443-1448.

Liu et al., "USP21 deubiquitylates Nanog to regulate protein stability and stem cell pluripotency", Signal Transduction and Targeted Therapy, 2016, vol. 1, e16024, 10 pages.

Quesada et al., "Cloning and enzymatic analysis of 22 novel human ubiquitin-specific proteases", Biochemical and Biophysical Research Communications, 2004, vol. 314, pp. 54-62.

Sowa et al., "Defining the Human Deubiquitinating Enzyme Interaction Landscape", Cell, 2009, vol. 138, pp. 389-403.

Tseng et al., "New Classes of Mind Bomb-Interacting Proteins Identified from Yeast Two-Hybrid Screens", PLoS ONE, 2014, vol. 9, Issue 4, e93394, 12 pages.

Zhang et al., "The deubiquitinating protein USP24 interacts with DDB2 and regulates DDB2 stability", Cell Cycle, 2012, vol. 11, No. 23, pp. 4378-4384.

\* cited by examiner

| | DNA binding hybrid | | Activation hybrid | | Colony color |
|---|---|---|---|---|---|
| 1. | Gal4-DBD | USP49 | Gal4-AD | Bax | Blue |
| 2. | Gal4-DBD | | Gal4-AD | Bax | No colony |
| 3. | Gal4-DBD | Lamin C | Gal4-AD | Bax | No colony |
| 4. | Gal4-DBD | USP49 | Gal4-AD | | No colony |
| 5. | Gal4-DBD | | Gal4-AD | | No colony |
| 6. | Gal4-DBD | p53 | Gal4-AD | SV40T | Blue |

US 11,686,014 B2

VECTOR LIBRARY FOR YEAST TWO HYBRID SCREENING AND METHOD FOR IDENTIFYING DEUBIQUITINATING ENZYME BINDING TO TARGET PROTEIN USING SAME

SEQUENCE LISTING

The Sequence Listing submitted in text format (.txt) filed on Jun. 24, 2020, named "SequenceListing.txt", created on Jun. 23, 2020 (341 KB), is incorporated herein by reference.

TECHNICAL FIELD

The present invention relates to a vector library for yeast two-hybrid screening of a deubiquitinating enzyme that binds to a target protein and a method for identifying a deubiquitinating enzyme binding to a target protein using the same. Also, the present invention relates to a method for screening an agent having anti-cancer activity targeting the deubiquitinating enzyme USP1, USP7, USP12, or USP49 identified by said identifying method.

BACKGROUND ART

Proteins perform a variety of functions in cells and thus the expressions, degradations, and activity maintenances thereof greatly affect cell homeostasis. Ubiquitination is a process in which ubiquitin binds to a target protein, thereby proteasomes recognize the ubiquitin and degrade the target protein. In addition, ubiquitination is also involved in the function and activity of proteins, and thus regulates various signal pathways to determine cell fate. The process reversing this regulation is called as deubiquitination. A deubiquitinating enzyme cleaves ubiquitins bound to a target protein, thereby inhibiting the degradation by proteasomes or reversely-regulating function and activity of protein regulated by ubiquitination. Ubiquitination and deubiquitination play an important role in protein homeostasis and cell fate, and when this system works abnormally, it causes a variety of diseases, including cancer.

Abnormal protein expressions cause the onset of diseases. For example, improper expression or function of proteins may cause inhibition of apoptosis of cells, thereby resulting in excessive proliferation or may cause over-apoptosis of cells, thereby leading to diseases. In this regard, deubiquitinating enzymes are key molecules that can regulate the stability and function of proteins, attracting attention as a therapeutic agent for diseases. Therefore, it is important to identify the interaction of a target protein with deubiquitinating enzymes and their roles in intracellular signal pathway systems. For this purpose, the identification of a deubiquitinating enzyme that binds to a target protein will be a basis for the research thereon. However, since the identification of said interacting proteins requires high costs, there is a need for an efficient and relatively inexpensive screening system thereof.

DISCLOSURE

Technical Problem

The present invention provides a vector library for yeast two-hybrid screening of a deubiquitinating enzyme that binds to a target protein. And also, the present invention provides a method for identifying a deubiquitinating enzyme binding to a target protein, using the vector library.

In addition, it has been found by said identifying method that the deubiquitinating enzyme USP1, USP7, USP12, or USP49 specifically binds to Bax which is known to be involved in apoptosis of cells. Therefore, the present invention provides a method for screening an agent having anti-cancer activity targeting the deubiquitinating enzyme USP1, USP7, USP12, or USP49.

Technical Solution

In accordance with an aspect of the present invention, there is provided a vector library for yeast two-hybrid screening of a deubiquitinating enzyme that binds to a target protein, comprising: a vector obtained by inserting a gene encoding a deubiquitinating enzyme USP1 in an empty vector having a DNA-binding domain; a vector obtained by inserting a gene encoding a deubiquitinating enzyme USP2 in an empty vector having a DNA-binding domain; a vector obtained by inserting a gene encoding a deubiquitinating enzyme USP3 in an empty vector having a DNA-binding domain; a vector obtained by inserting a gene encoding a deubiquitinating enzyme USP4 in an empty vector having a DNA-binding domain; a vector obtained by inserting a gene encoding a deubiquitinating enzyme USP5 in an empty vector having a DNA-binding domain; a vector obtained by inserting a gene encoding a deubiquitinating enzyme USP6 in an empty vector having a DNA-binding domain; a vector obtained by inserting a gene encoding a deubiquitinating enzyme USP7 in an empty vector having a DNA-binding domain; a vector obtained by inserting a gene encoding a deubiquitinating enzyme USP8 in an empty vector having a DNA-binding domain; a vector obtained by inserting a gene encoding a deubiquitinating enzyme USP10 in an empty vector having a DNA-binding domain; a vector obtained by inserting a gene encoding a deubiquitinating enzyme USP11 in an empty vector having a DNA-binding domain; a vector obtained by inserting a gene encoding a deubiquitinating enzyme USP12 in an empty vector having a DNA-binding domain; a vector obtained by inserting a gene encoding a deubiquitinating enzyme USP14 in an empty vector having a DNA-binding domain; a vector obtained by inserting a gene encoding a deubiquitinating enzyme USP15 in an empty vector having a DNA-binding domain; a vector obtained by inserting a gene encoding a deubiquitinating enzyme USP16 in an empty vector having a DNA-binding domain; a vector obtained by inserting a gene encoding a deubiquitinating enzyme USP17 in an empty vector having a DNA-binding domain; a vector obtained by inserting a gene encoding a deubiquitinating enzyme USP18 in an empty vector having a DNA-binding domain; a vector obtained by inserting a gene encoding a deubiquitinating enzyme USP19 in an empty vector having a DNA-binding domain; a vector obtained by inserting a gene encoding a deubiquitinating enzyme USP20 in an empty vector having a DNA-binding domain; a vector obtained by inserting a gene encoding a deubiquitinating enzyme USP21 in an empty vector having a DNA-binding domain; a vector obtained by inserting a gene encoding a deubiquitinating enzyme USP25 in an empty vector having a DNA-binding domain; a vector obtained by inserting a gene encoding a deubiquitinating enzyme USP28 in an empty vector having a DNA-binding domain; a vector obtained by inserting a gene encoding a deubiquitinating enzyme USP30 in an empty vector having a DNA-binding domain; a vector obtained by inserting a gene encoding a deubiquitinating enzyme USP33 in an empty vector having a DNA-binding domain; a vector obtained by inserting a gene encoding a deubiquitinating enzyme USP34 in an empty vector having a DNA-binding domain; a vector obtained by inserting a gene encoding a deubiquitinating enzyme USP35 in an empty vector having a DNA-binding domain; a vector obtained by inserting a gene encoding a deubiquitinating enzyme USP36 in an empty vector having a DNA-binding domain; a vector obtained by inserting a gene encoding a deubiquitinating enzyme USP37 in an empty vector having a DNA-binding domain; a vector obtained by inserting a gene encoding a deubiquitinating enzyme USP38 in an empty vector having a DNA-binding domain; a vector obtained by inserting a gene encoding a deubiquitinating enzyme USP39 in an empty vector having a DNA-binding domain; a vector obtained by inserting a gene encoding a deubiquitinating enzyme USP44 in an empty vector having a DNA-binding domain; a vector obtained by inserting a gene encoding a deubiquitinating enzyme USP46 in an empty vector having a DNA-binding domain; and a vector obtained by inserting a gene encoding a deubiquitinating enzyme USP49 in an empty vector having a DNA-binding domain. In an embodiment, the empty vector having a DNA-binding domain may a pGBT9 vector.

In accordance with another aspect of the present invention, there is provided a method for identifying a deubiquitinating enzyme binding to a target protein, the method comprising: (a) inserting a gene encoding a target protein into an empty vector having a transcription activation domain to prepare a vector; (b) transforming yeasts with each vector of the vector library and the vector prepared in Step (a); and (c) culturing the yeasts obtained in Step (b) in a medium containing X-gal and free of tryptophan and leucine. In an embodiment, the empty vector having a transcription activation domain may a pGAD424 vector.

In accordance with still another aspect of the present invention, there is provided a method for screening an agent having anti-cancer activity, the method comprising: (i) treating with candidate materials a cell overexpressing a deubiquitinating enzyme USP1, USP7, USP12, or USP49 and Bax protein, followed by culturing the cell; and (ii) measuring apoptosis of the cell cultured in Step (i) and selecting a material inducing apoptosis of the cell. In an embodiment, the deubiquitinating enzyme of Step (i) may USP49.

Advantageous Effects

The vector library of the present invention can be used to identify the deubiquitinating enzymes binding to a target protein efficiently and at low cost, and thus can be usefully applied for elucidating various mechanisms thereof in cells. In addition, by applying the vector library of the present invention, it has been found that the deubiquitinating enzymes USP1, USP7, USP12, and USP49 specifically bind to Bax, an apoptosis-associated protein. Therefore, the screening method of the present invention can be usefully applied for screening an agent having anti-cancer activity targeting the deubiquitinating enzymes USP1, USP7, USP12, and USP49.

BEST MODE

Figure 1:
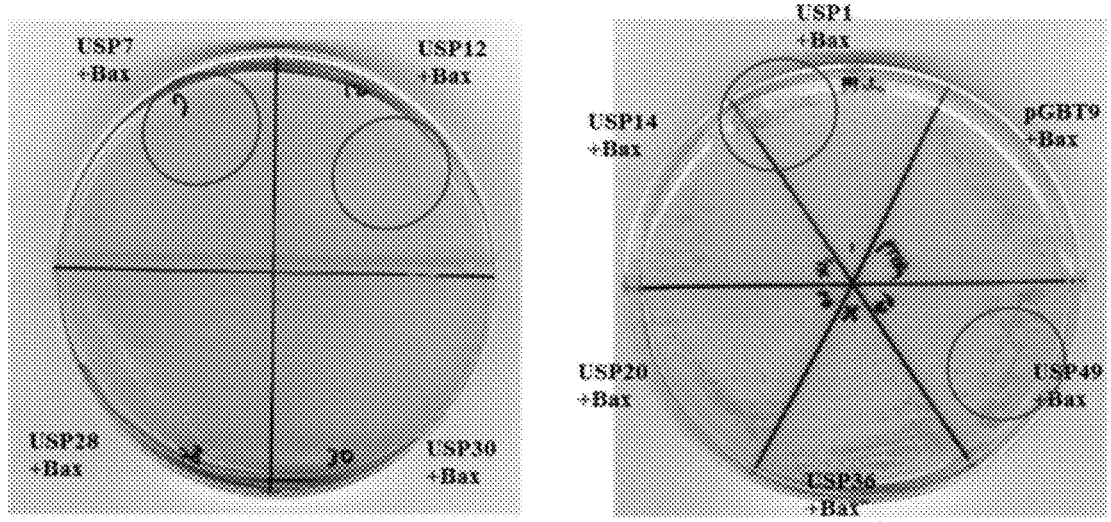
FIG. 1 shows the results obtained by screening deubiquitinating enzymes that bind to Bax protein with the vector library of the present invention.

The present invention provides a vector library for yeast two-hybrid screening of a deubiquitinating enzyme that binds to a target protein. Specifically, the present invention provides a vector library for yeast two-hybrid screening of a deubiquitinating enzyme that binds to a target protein, comprising: a vector obtained by inserting a gene encoding a deubiquitinating enzyme USP1 in an empty vector having a DNA-binding domain; a vector obtained by inserting a gene encoding a deubiquitinating enzyme USP2 in an empty vector having a DNA-binding domain; a vector obtained by inserting a gene encoding a deubiquitinating enzyme USP3 in an empty vector having a DNA-binding domain; a vector obtained by inserting a gene encoding a deubiquitinating enzyme USP4 in an empty vector having a DNA-binding domain; a vector obtained by inserting a gene encoding a deubiquitinating enzyme USP5 in an empty vector having a DNA-binding domain; a vector obtained by inserting a gene encoding a deubiquitinating enzyme USP6 in an empty vector having a DNA-binding domain; a vector obtained by inserting a gene encoding a deubiquitinating enzyme USP7 in an empty vector having a DNA-binding domain; a vector obtained by inserting a gene encoding a deubiquitinating enzyme USP8 in an empty vector having a DNA-binding domain; a vector obtained by inserting a gene encoding a deubiquitinating enzyme USP10 in an empty vector having a DNA-binding domain; a vector obtained by inserting a gene encoding a deubiquitinating enzyme USP11 in an empty vector having a DNA-binding domain; a vector obtained by inserting a gene encoding a deubiquitinating enzyme USP12 in an empty vector having a DNA-binding domain; a vector obtained by inserting a gene encoding a deubiquitinating enzyme USP14 in an empty vector having a DNA-binding domain; a vector obtained by inserting a gene encoding a deubiquitinating enzyme USP15 in an empty vector having a DNA-binding domain; a vector obtained by inserting a gene encoding a deubiquitinating enzyme USP16 in an empty vector having a DNA-binding domain; a vector obtained by inserting a gene encoding a deubiquitinating enzyme USP17 in an empty vector having a DNA-binding domain; a vector obtained by inserting a gene encoding a deubiquitinating enzyme USP18 in an empty vector having a DNA-binding domain; a vector obtained by inserting a gene encoding a deubiquitinating enzyme USP19 in an empty vector having a DNA-binding domain; a vector obtained by inserting a gene encoding a deubiquitinating enzyme USP20 in an empty vector having a DNA-binding domain; a vector obtained by inserting a gene encoding a deubiquitinating enzyme USP21 in an empty vector having a DNA-binding domain; a vector obtained by inserting a gene encoding a deubiquitinating enzyme USP25 in an empty vector having a DNA-binding domain; a vector obtained by inserting a gene encoding a deubiquitinating enzyme USP28 in an empty vector having a DNA-binding domain; a vector obtained by inserting a gene encoding a deubiquitinating enzyme USP30 in an empty vector having a DNA-binding domain; a vector obtained by inserting a gene encoding a deubiquitinating enzyme USP33 in an empty vector having a DNA-binding domain; a vector obtained by inserting a gene encoding a deubiquitinating enzyme USP34 in an empty vector having a DNA-binding domain; a vector obtained by inserting a gene encoding a deubiquitinating enzyme USP35 in an empty vector having a DNA-binding domain; a vector obtained by inserting a gene encoding a deubiquitinating enzyme USP36 in an empty vector having a DNA-binding domain; a vector obtained by inserting a gene encoding a deubiquitinating enzyme USP37 in an empty vector having a DNA-binding domain; a vector obtained by inserting a gene encoding a deubiquitinating enzyme USP38 in an empty vector having a DNA-binding domain; a vector obtained by inserting a gene encoding a deubiquitinating enzyme USP39 in an empty vector having a DNA-binding domain; a vector obtained by inserting a gene encoding a deubiquitinating enzyme USP44 in an empty vector having a DNA-binding domain; a vector obtained by inserting a gene encoding a deubiquitinating enzyme USP46 in an empty vector having a DNA-binding domain; and a vector obtained by inserting a gene encoding a deubiquitinating enzyme USP49 in an empty vector having a DNA-binding domain.

Figure 12:
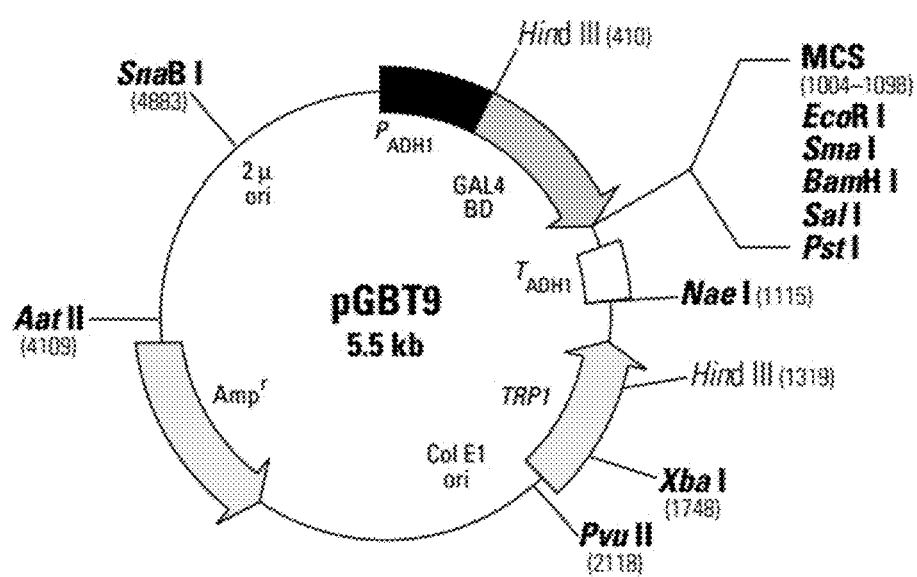
FIG. 12 shows a cleavage map of the pGBT9 vector.

In the vector library of the present invention, as the empty vector having a DNA-binding domain (DNA-BD), any vector capable of providing a DNA-binding domain to yeast may be used without limitation. For example, the empty vector having a DNA-binding domain (DNA-BD) may be the pGBT9 vector having a cleavage map of FIG. 12, but is not limited thereto. Insertion of the gene encoding a deubiquitinating enzyme into an empty vector having a DNA-binding domain may be performed by a conventional method used in the field of biotechnology. For example, said insertion may be carried to out by incubating an empty vector having a DNA-binding domain along with the gene encoding a deubiquitinating enzyme, using appropriate restriction enzymes. All of the genes encoding deubiquitinating enzymes are known in GenBank. In addition, the restriction enzymes include e.g., EcoR I, Sma I, BamH I, Sal I, Pst I, but are not limited thereto.

The present invention also provides a method for identifying a deubiquitinating enzyme binding to a target protein, using the vector library. That is, the present invention provides a method for identifying a deubiquitinating enzyme binding to a target protein, the method comprising: (a) inserting a gene encoding a target protein into an empty vector having a transcription activation domain to prepare a vector; (b) transforming yeasts with each vector of the vector library and the vector prepared in Step (a); and (c) culturing the yeasts obtained in Step (b) in a medium containing X-gal and free of tryptophan and leucine.

Figure 13:
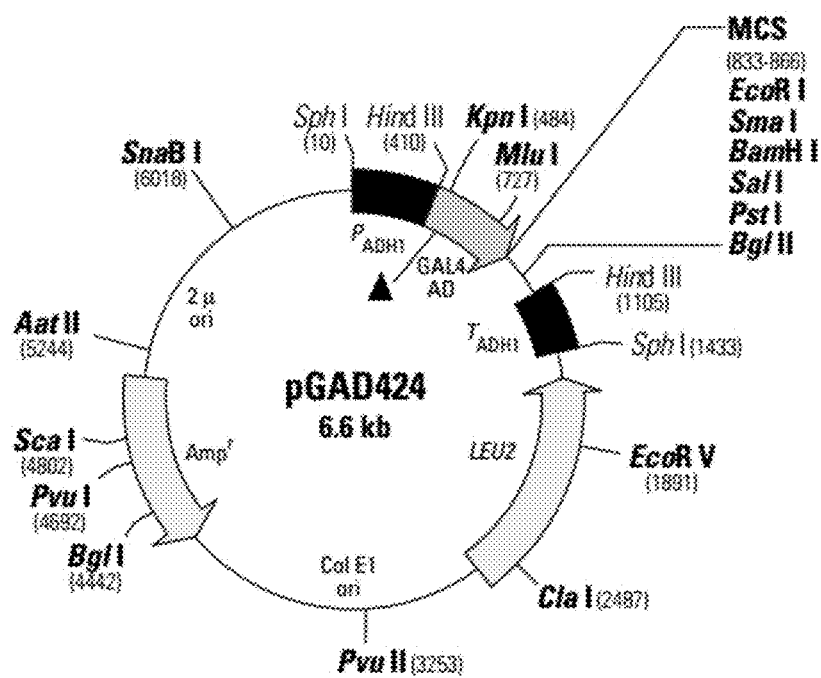
FIG. 13 shows a cleavage map of the pGAD424 vector.

In the method for identifying a deubiquitinating enzyme of the present invention, as the empty vector having a transcription activation domain, any vector capable of providing a transcription activation domain to yeast may be used without limitation. For example, the empty vector having a transcription activation domain may be the pGAD424 vector having a cleavage map of FIG. 13, but is not limited thereto. Insertion of the gene encoding a gene encoding a target protein into an empty vector having a transcription activation domain may be performed by a conventional method used in the field of biotechnology. For example, said insertion may be carried out by incubating an empty vector having a transcription activation domain along with the gene encoding a target protein, using appropriate restriction enzymes. In addition, the restriction enzymes include e.g., EcoR I, Sma I, BamH I, Sal I, Pst I, Bgl II, but are not limited thereto.

It has been found by the identifying method of the present invention that the deubiquitinating enzyme USP1, USP7, USP12, or USP49 specifically binds to Bax which is known to be involved in apoptosis of cells.

Bax belongs to the proapoptotic group of Bcl-2 proteins and is a key molecule in the induction of apoptosis. Bax is present in the cytosol as a monomer in unstressed cells. When the cells undergo stress, Bax is activated by the proapoptotic BH3-proteins. The activated Bax is translocated to the surface of the mitochondria and inserted into the mitochondrial outer membrane (MOM). Bax then undergoes homo-oligomerization, leading to pore formation in the MOM. Then, the proapoptotic molecule cytochrome c is released and apoptosis is induced. If the gene that encodes Bax is mutated, cells may be less susceptible to cell death. The expression level of Bax is related to malignant transformation, tumor progression, and metastasis, thereby low expression of Bax is considered as a negative factor in cancer diseases. Decreased level of Bax degradation is appeared in aggressive human prostate cancer.

Figure 11:
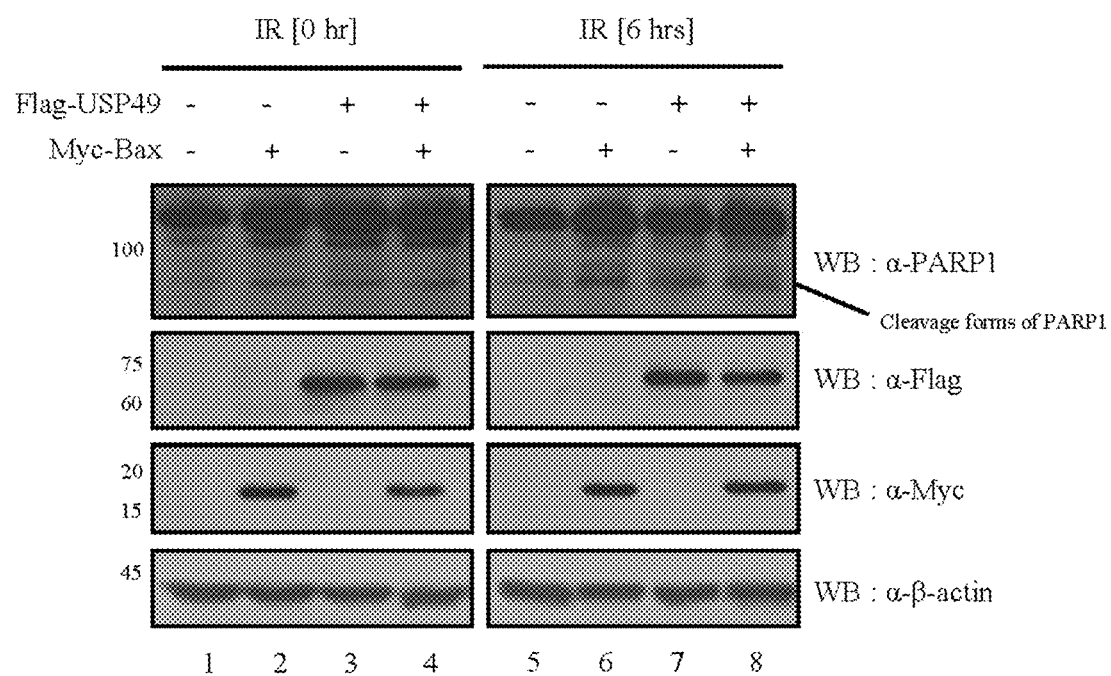
FIG. 11 shows the results obtained by evaluating whether USP49 regulates Bax, through treating the HCT116 cells overexpressed with Flag-USP49 or Myc-Bax with IR irradiation (10 Gy) and then harvesting the cells after 6 hours.

Therefore, the deubiquitinating enzyme USP1, USP7, USP12, or USP49 may function as a novel target for screening an agent having anti-cancer activity. Especially, it has been found by the present invention that, even if Bax-overexpressed cells are allowed to overexpress USP49, Bax can be regulated in a proteasome-independent pathway without apoptosis of the cells, thereby being suitably applicable to a screening method (FIG. 11). Therefore, an agent having anti-cancer activity may be screened by treating with candidate materials cells overexpressing the deubiquitinating enzyme USP1, USP7, USP12, or USP49 and Bax protein; and then measuring apoptosis of the cultured cells. That is, the present invention provides a method for screening an agent having anti-cancer activity, the method comprising: (i) treating with candidate materials a cell overexpressing a deubiquitinating enzyme USP1, USP7, USP12, or USP49 and Bax protein, followed by culturing the cell; and (ii) measuring apoptosis of the cell cultured in Step (i) and selecting a material inducing apoptosis of the cell. In an embodiment, the deubiquitinating enzyme of Step (i) may USP49.

Hereinafter, the present invention will be described more specifically by the following examples. However, the following examples are provided only for illustrations and thus the present invention is not limited to or by them.

EXAMPLES

1. Materials and Methods (1) Cell Culture and Transfection 293T cells were grown with Dulbecco's modified Eagle's medium (DMEM, Gibco, Grand Island, N.Y., USA) containing 10% fetal bovine serum (FBS, Gibco, Grand Island, N.Y., USA), 1% penicillin-streptomycin (Gibco, Grand Island, N.Y., USA). HCT116 cells were grown in RPMI 1640 medium (Gibco, Grand Island, N.Y., USA) supplemented with 10% FBS and 1% penicillin-streptomycin. The cells were grown in a 5% $CO_2$ incubator at 37° C. Transfections were performed with 150 mM NaCl and 10 mM polyethylenimine (PEI, Polysciences, Inc., Warrington, Pa., USA).

(2) Antibodies

Monoclonal anti-Bax (2D2) (1:1000, Santa Cruz Biotechnology, Santa Cruz, Calif., USA), anti-6-actin (1:1000, Santa Cruz, Calif., USA), anti-HA (1:1000, 12CA5, Roche, Basel, Switzerland), anti-Flag (1:1000, Sigma-Aldrich, St. Louis, Mo., USA) and anti-PARP1 (1:1000, Santa Cruz, Calif., USA) antibodies were used for Western blotting, immunoprecipitation, and immunocytochemical staining. Anti-K48 (1:500, Cell signaling, Danvers, Mass., USA) and anti-K63 (1:100, Cell signaling, Danvers, Mass., USA) antibodies were used for DUB assay. Easy Blot antibody (1:1000, GeneTex, TX, USA) was used for decreasing the signal of chains of IgG.

(3) Construction of Expression Vectors and Primers

To generate deletion mutants of Bax (1-219), Bax (220-334) and Bax (335-579), we used the forward primers, (5'-GAA TTC GCA TGG ACG GGT-3'), (5'-GAA TTC CGA TGG AGC TGC A-3') and (5'-GAA TTC GCA AAC TGG TGC TC-3'). And also, the reverse primers, (5'-CTC GAG CGG TTA CTG TCC AG-3'), (5'-CTC GAG CCG CTG GCA AAG-3') and (5'-CTC GAG CGT CAG CCC ATC-3') were used.

Point mutation of USP49 (C262S) was generated through the site-directed mutagenesis. The forward primer (5'-CTG GGC AAC ACC AGC TAC ATG-3') and the reverse primer (5'-TGG AGT TCA TGT AGC TGG TGT-3') were used for generating a mutant. After purification of PCR product, Dpn I (Enzynomics, Daejeon, Korea) enzyme was added. The construct was confirmed by sequencing.

To generate deletion mutants of USP49 (1-762), USP49 (763-1131), and USP49 (1132-2067), we used the forward primers (5'-GAA TTC GAT GGA TAG ATG C-3'), (5'-GAA TTC TCT GCG CAA CCT G-3'), and (5'-TCT AGA ACC CTT CGC CAT GC-3'), and the reverse primers (5'-CTC GAG GCC CGT GAC GCC-3'), (5'-CTC GAG CGA CAC TAG GGC-3'), and (5'-TAC GTA TCA ACC CCT TTC C-3').

For the generation of shUSP49, three kinds of shRNAs for USP49 were constructed and inserted into the pSilencer 3.1 H1 neo vector (Ambion, Austin, Tex., USA). The target sequences of shUSP49s are: #1 (5'-GTC TTC ACT GTA GCT CAA G-3'), #2 (5'-GGA CTA CGT GCT CAA TGA T-3') and #3 (5'-GGA CTA CGT GCT CAA TGA T-3') (UbiProtein Corp, Seongnam, Republic of Korea).

To perform RT-PCR, we used the forward primer (5'-AGG ACT ACG TGC TCA ATG ATA ACC-3') and the reverse primer (5'-GCA GGA GCA GCC GTG CAC TCT-3') for targeting USP49. The forward primer (5'-ATC CCA TCA CCA TCT TCC-3') and the revers primer (5'-CCA TCA CGC CAC AGT TTC-3') were also used for targeting GAPDH.

(4) Preparation of the Vector Library for Yeast Two-Hybrid Screening

Each full-length cDNAs encoding the deubiquitinating enzymes shown in Table 1 were obtained from GenBank. The pGBT9-deubiquitinating enzyme library for yeast two-hybrid screening was prepared by performing the respective cloning, through incubating the pGBT9 vectors (Clontech, Palo Alto, Calif., USA) along with said cDNAs, using appropriate restriction enzymes.

TABLE 1

| Deubiquitinating enzyme | Molecular weight (kDa) |
| --- | --- |
| USP1 | 90.5 |
| USP2 | 68 |
| USP3 | 59 |
| USP4 | 108 |
| USP5 | 95.8 |
| USP6 | 90 |
| USP7 | 130 |
| USP8 | 123 |
| USP10 | 87 |
| USP11 | 110 |
| USP12 | 60 |
| USP14 | 56 |
| USP15 | 112 |
| USP16 | 47 |
| USP17 | 22 |
| USP18 | 43 |
| USP19 | 145 |
| USP20 | 102 |
| USP21 | 62 |
| USP25 | 126 |
| USP28 | 122 |
| USP30 | 59 |
| USP33 | 107 |
| USP34 | 387 |
| USP35 | 113.4 |
| USP36 | 123 |
| USP37 | 110 |
| USP38 | 117 |
| USP39 | 65 |
| USP44 | 81 |
| USP46 | 42 |
| USP49 | 73 |

(5) Yeast Two-Hybrid Screening (5-1) Transformation of pGBT9-Deubiquitinating Enzyme to Yeast Cells (First Transformation)

Yeast strain (*Saccharomyces cerevisiae* AH109) was streaked on YPD (Clontech, Palo Alto, Calif., USA) agar plates and incubated at 30° C. for 3-4 days. The colony was cultured in YPD liquid media (Clontech, Palo Alto, Calif., USA) and the cultured yeast cells were centrifuged at 2500 rpm for 2 minutes 30 seconds when $OD_{600}$ value thereof reached 0.8-1.0. After removing the supernatant, the cells were treated with distilled water (3 ml), centrifuged at 2500 rpm for 2 minutes 30 seconds, resuspended with the lithium acetate (LiAc) solution, and then incubated at room temperature for 5 minutes. After centrifuging the cells at 2500 rpm for 5 minutes, the LiAc solution (600 µl) was added for resuspension of the cells. The pGBT9 containing a deubiquitinating enzyme gene (1 µg) and the yeast (100 µl) were then mixed in the LiAc solution, followed by incubating for 15 minutes at 30° C. in a shaking incubator. The polyethylene glycol (PEG) in LiAc solution (600 µl) was added thereto and the mixture was incubated at 30° C. for 30 minutes in a shaking incubator. DMSO (50 µl) was then added, and the cells were heat-shocked at 42° C. for 15 minutes, followed by centrifuging to remove the supernatant. Fresh YPD media (600 μl) was added for resuspension of the cells, which were incubated for 1-2 hours, and centrifuged to precipitate the cells. After removing the supernatant (500 μl), the cells were streaked on −Trp minimal agar plate and then incubated at 30° C. for 3-4 days.

(5-2) Transformation of Bax and Nanog to the First-Transformed Yeast Cells (Second Transformation)

The yeast cells transformed with each deubiquitinating enzyme were cultured in in a −Trp liquid media and the cultured yeast cells were centrifuged at 2500 rpm for 2 minutes 30 seconds when $OD_{600}$ value thereof reached 0.8-1.0. After removing the supernatant, the cells were treated with distilled water (3 ml), centrifuged at 2500 rpm for 2 minutes 30 seconds, resuspended with the LiAc solution, and then incubated at room temperature for 5 minutes. After centrifuging the cells at 2500 rpm for 5 minutes, the LiAc solution (600 μl) was added for resuspension of the cells. The cDNAs encoding target proteins (Bax and Nanog) were inserted into a pGAD424 vector having a transcription activation domain, to prepare pGAD424-Bax and pGAD424-Nanog, respectively. pGAD424-Bax (1 μg) or pGAD424-Nanog (1 μg) and the yeast (100 μl) were then mixed in the LiAc solution, followed by incubating for 15 minutes in a shaking incubator. The PEG in LiAc solution (600 μl) was added thereto and the mixture was incubated for 30 minutes in a shaking incubator. DMSO (50 μl) was then added, and the cells were heat-shocked at 42° C. for 15 minutes, followed by centrifuging to remove the supernatant. −Trp liquid media (600 μl) was added for resuspension of the cells, which were incubated for 1-2 hours, and centrifuged to precipitate the cells. After removing the supernatant (500 μl), the cells were streaked on −Trp/−Leu minimal agar plate containing X-gal (Clontech, Palo Alto, Calif., USA) and then incubated at 30° C. for 3-4 days. In this process, the yeast transformed with a deubiquitinating enzyme is transformed with the target protein cDNA; and when the two proteins bind each other, blue colonies appear.

(6) Preparation of Cell Lysates, Western Blotting, and Immunoprecipitation

Cells were washed with phosphate buffered saline (PBS) and lysed in a lysis buffer (Tris-HCl [pH 7.5] 50 mM, NaCl 300 mM, EDTA 1 mM, Glycerol 10%, Triton X-100 1%), CHAPS buffer (150 mM NaCl, 10 mM HEPES at pH 7.4 and 1.0% CHAPS) and NP40 buffer (145.2 mM potassium chloride, 5 mM $MgCl_2$, 1 mM EGTA 10 mM HEPES at pH 7.4 and 0.2% NP40). The samples were incubated for 20 minutes on ice and then insoluble material was pelleted by a 20-minute centrifugation at 13,000 rpm at 4° C. The resulting supernatant was collected.

Western blotting was conducted by loading 20 μg of protein per lane on an 8-12% SDS-PAGE and the proteins were transferred onto polyvinylidene fluoride (PVDF) microporous membranes (Millipore, Billerica, Mass., USA). Membranes were blocked in TTBS (20 mM Tris-HCl [pH 7.5], 150 mM NaCl, 0.05% Tween 20) containing 5% skim milk for 20 minutes and incubated with primary antibodies at 4° C. overnight. The blots were then washed in TTBS and incubated in TTBS containing 3% skim milk and secondary antibodies for 1 hour. The membranes were washed again in TTBS and visualized with ECL reagent solution (Young In Frontier, Seoul, Korea).

For immunoprecipitation of proteins, cell lysates were incubated with antibodies at 4° C. overnight and protein A/G PLUS agarose beads (Santa Cruz Biotechnology, Santa Cruz, Calif., USA) were added and rotated for 2 hours. The washed samples were boiled in SDS sample buffer and detected by Western blotting.

(7) GST Pull-Down Assay

E. coli BL21 cells transformed with pGEX-4T-3 vector or pGEX-4T-3-Bax were grown at 37° C. When cell density ($OD_{600}$ value) reached 0.6, expressions of recombinant proteins were induced by 5 mM IPTG (Promega, Madison, Wis., USA) at 31° C. for 4 hours. The cells were lysed and the lysates containing proteins were rotated with Gluta-thione-Sepharose beads (GST beads) (Pharmacia Biotech, Uppsala, Sweden), so as to induce the binding between the GST beads and GST or GST-Bax. 293T cells overexpressed with Myc-USP12 or Flag-USP49 were lysed and the cell extracts were mixed with GST and GST-Bax tagging GST beads. The mixtures were washed to collect GST and GST-Bax from the lysate. The protein bound to GST and GST-Bax was analyzed by Western blotting and probed with an anti-Myc antibody (1:1000 Sigma-Aldrich, St. Louis, Mo., USA) and an anti-Flag antibody (1:1000 Sigma-Aldrich, St. Louis, Mo., USA). GST proteins were visualized by Coomassie Brilliant Blue (CBB) staining (Sigma-Aldrich, St. Louis, Mo., USA).

(8) Immunocytochemical Staining and Confocal Microscopy

HCT116 cells were seeded on glass coverslips placed on a 12-well plate. The cells were fixed with 4% formaldehyde for 15 minutes and were blocked with PBS containing 2% normal goat serum and 1% triton X-100 for 1 hour at room temperature. The cells were incubated with primary antibodies overnight at 4° C. and then incubated with Alexa-Fluor-488-cojugated goat anti-mouse (1:100, Invitrogen, Carlsbad, Calif., USA) and goat anti-rabbit 1:100, Invitrogen, Carlsbad, Calif., USA) for 1 hour at room temperature. The samples were visualized with a confocal microscope (TCSSPS II, Leica, Mannheim, Germany).

(9) Ubiquitination and Deubiquitination Assays

For the ubiquitination assay, HA-ubiquitin, HA-ubiquitin (K48R), and HA-ubiquitin (K63R) were transfected into 293T cells. Cells were harvested and cell lysates were used for immunoprecipitation with an anti-Bax antibody (1:1000, Santa Cruz Biotechnology, Santa Cruz, Calif., USA). Deubiquitination assay was performed with HA-Ubiquitin and Flag-Usp49. MG132 was treated for 4 hours before harvest. An anti-Bax antibody (1:1000, Santa Cruz Biotechnology, Santa Cruz, Calif., USA) was used to precipitate proteins and the samples were analyzed by Western blotting. Ubiquitination level was detected by an anti-HA antibody (1:1000, 12CA5, Roche, Basel, Switzerland).

2. Results

FIG. 1 shows the results obtained by screening the deubiquitinating enzymes that regulate Bax, an apoptosis-associated protein, with the vector library prepared the present invention. As the results of the screening, the colonies transformed with USP1, USP7, USP12, and USP49 showed blue color.

Figure 2:
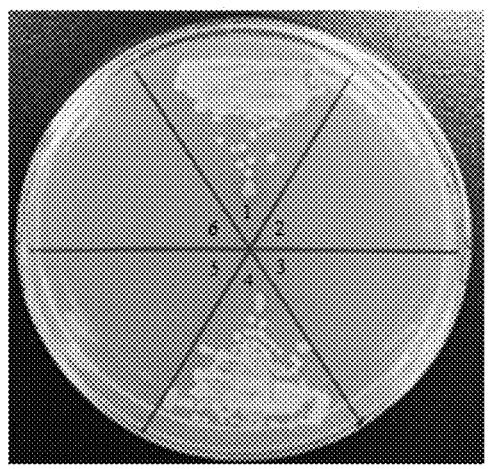
FIG. 2 shows the results obtained by confirming using a negative control and a positive control, after screening deubiquitinating enzymes that bind to Bax protein with the vector library of the present invention.
Figure 2:
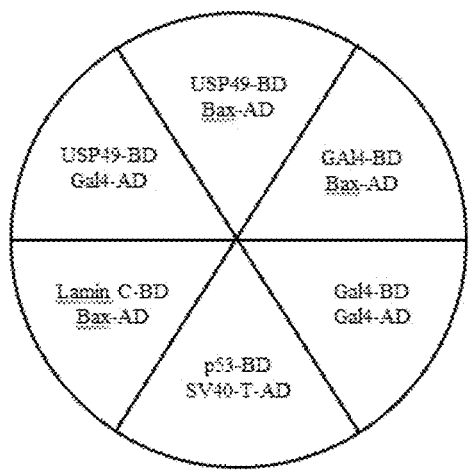

FIG. 2 shows the results obtained by confirming the results of FIG. 1 using controls. pGBT9 and pGAD424 vectors, i.e., empty vectors without cDNA insertion, were used as negative controls; and p53 and SV40 large T antigens, which were known to interact each other, were used as positive controls. Blue colonies were formed in the yeasts transformed with p53 and SV40 large T antigen and in the yeasts transformed with USP49 and Bax, while the colonies did not grow in the yeast transformed with the negative controls. These results indicate that the two proteins specifically interact.

Figure 3:
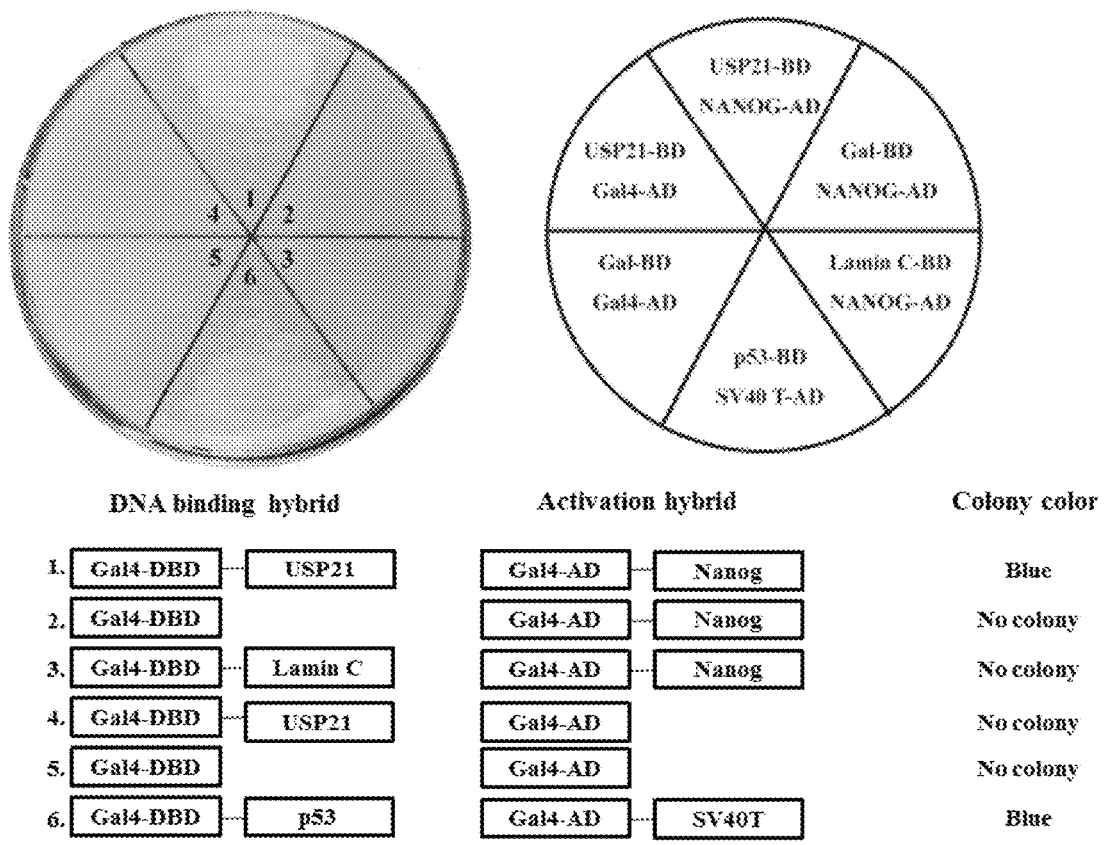
FIG. 3 shows the results obtained by confirming using a negative control and a positive control, after screening deubiquitinating enzymes that bind to NANOG protein with the vector library of the present invention.

FIG. 3 shows the results obtained by screening with the vector library prepared by the present invention. From the results thereof, it can be seen that USP21 and NANOG specifically interact. These results are consistent with the report (Liu et al., USP21 deubiquitylates Nanog to regulate protein stability and stem cell pluripotency, *Signal Transduction and Targeted Therapy* (2016), 1 e16024).

Figure 4:
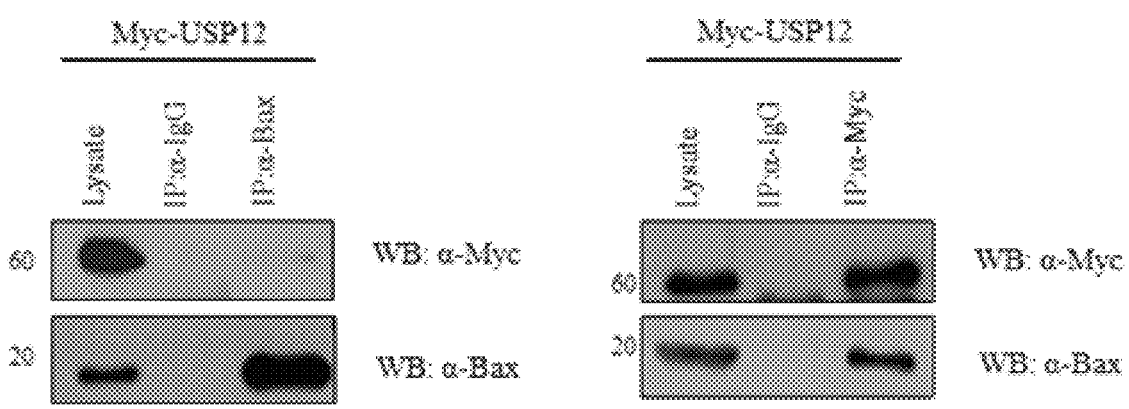
FIG. 4 shows the results obtained by confirming through immunoprecipitation that Bax and USP12 are bound in the cells.
Figure 5:
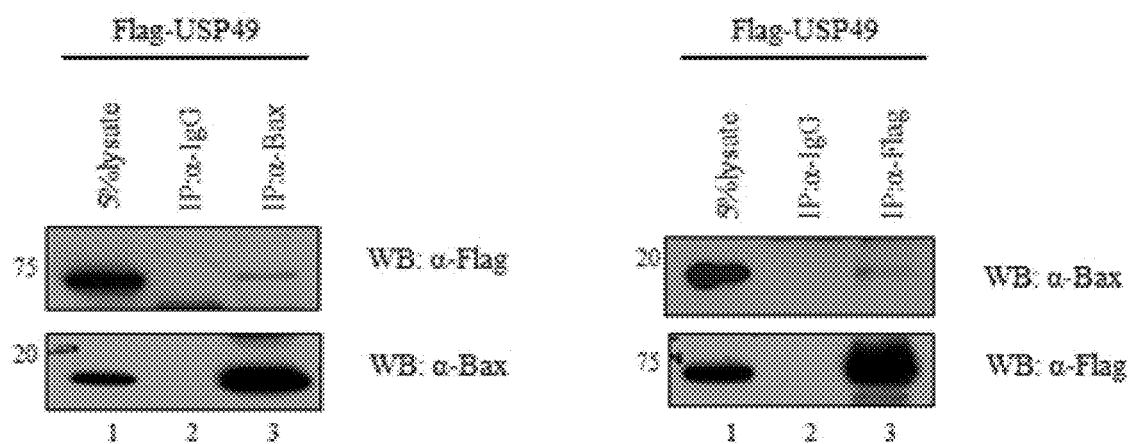
FIG. 5 shows the results obtained by confirming through immunoprecipitation that Bax and USP49 are bound in the cells.

FIG. 4 shows the results obtained by confirming through immunoprecipitation that, among the deubiquitinating enzymes binding to Bax, USP12 binds to Bax in the cells. Myc-USP12 was overexpressed in 293T cells, followed by immunoprecipitation with Myc or Bax antibody. The Bax or Myc-USP12 bound to the immunoprecipitated protein was confirmed by Western blotting. FIG. 5 shows the results obtained by confirming through immunoprecipitation that USP49 and Bax are bound in the cells. Flag-USP49 was overexpressed in 293T cells, followed by immunoprecipitation with Flag or Bax antibody. The Bax or Flag-USP49 bound to the immunoprecipitated protein was confirmed by Western blotting. The results of FIGS. 4 and 5 show that the Bax-binding deubiquitinating enzymes USP12 and USP49 obtained by performing the screening according to the present invention bind to Bax in vivo in cells.

Figure 6:
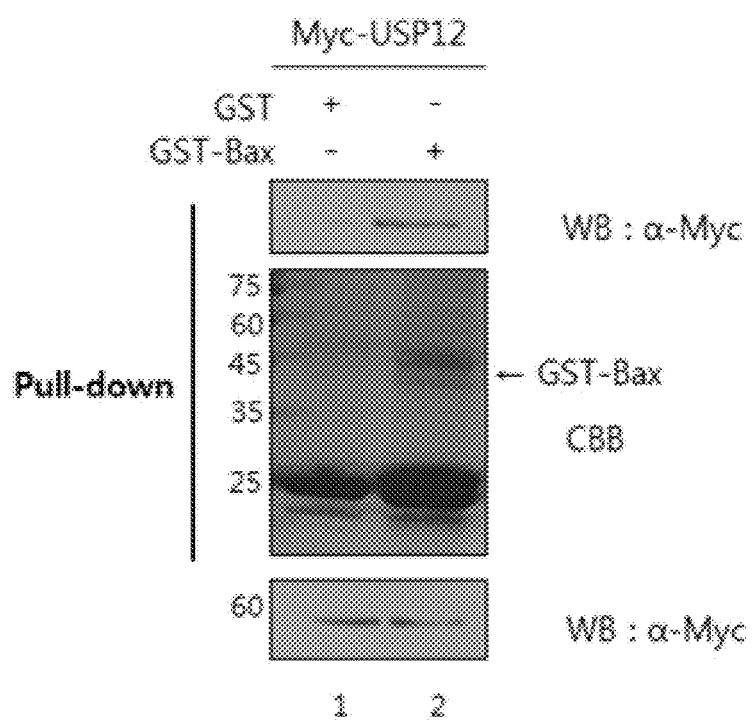
FIG. 6 shows the results obtained by confirming through GST pull-down assay that Bax and USP12 are directly bound.
Figure 7:
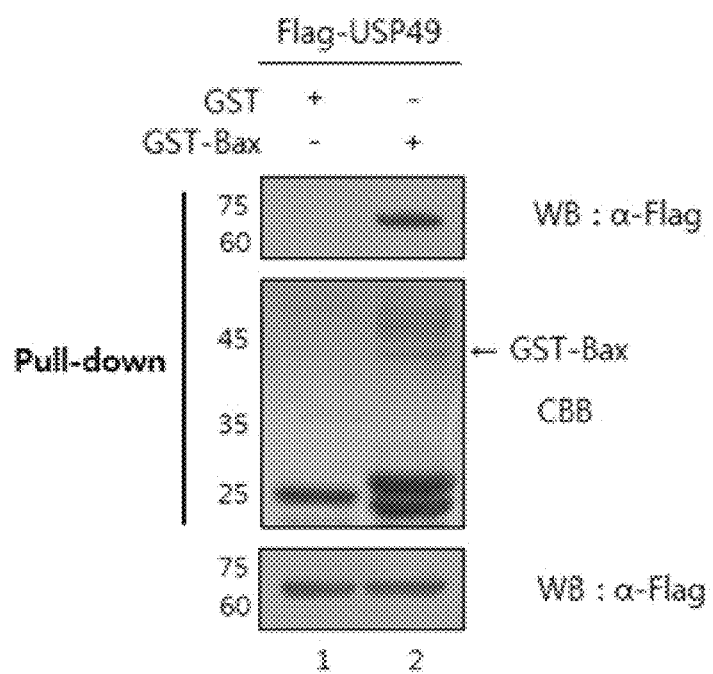
FIG. 7 shows the results obtained by confirming through GST pull-down assay that Bax and USP49 are directly bound.
Figure 8:
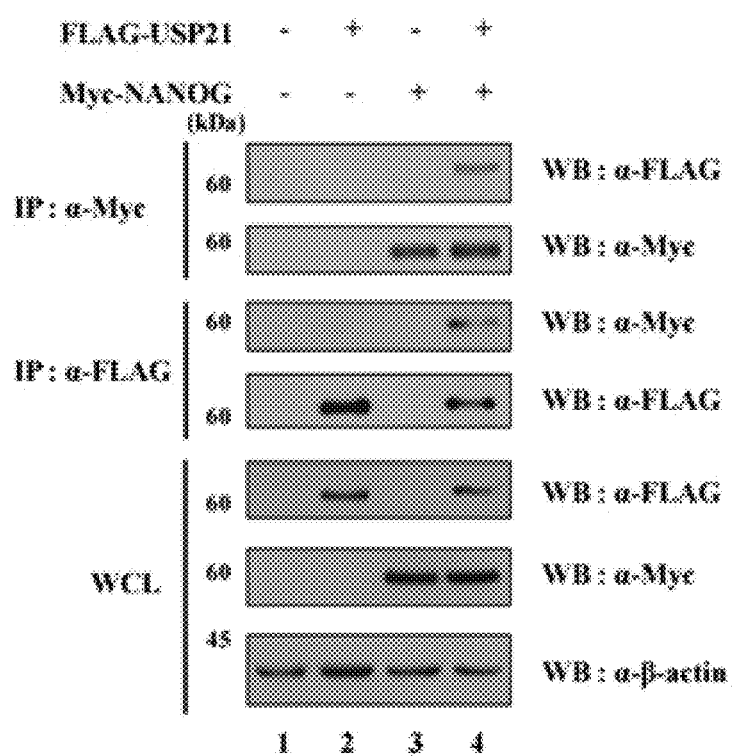
FIG. 8 shows the results obtained by confirming through immunoprecipitation that NANOG and USP21 are bound in the cells.
Figure 9:
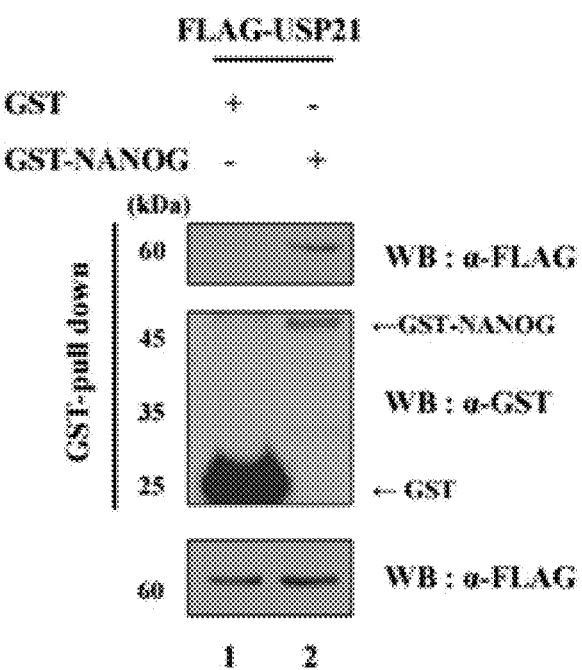
FIG. 9 shows the results obtained by confirming through GST pull-down assay that NANOG and USP21 are directly bound.

FIG. 6 shows the results obtained by confirming through GST pull-down assay that USP12 and Bax are directly bound. The recombinant protein GST-Bax was mixed with the lysate derived from the 293T cells overexpressing Myc-USP12, so as to confirm Myc-USP12 bound to GST-Bax. FIG. 7 shows the result obtained by confirming through GST pull-down assay, as in FIG. 6, that USP49 is directly bound to Bax. FIG. 8 is the results obtained by carrying out immunoprecipitation of the NANOG-binding deubiquitinating enzyme USP21 identified in FIG. 3, which show the interaction of the two proteins. After lysing the 293T cells transfected with Flag-USP21 and NANOG, immunoprecipitation analysis was performed. The analysis revealed that they bind each other. FIG. 9 shows through GST pull-down assay that USP21 and NANOG are directly bound.

Figure 10:
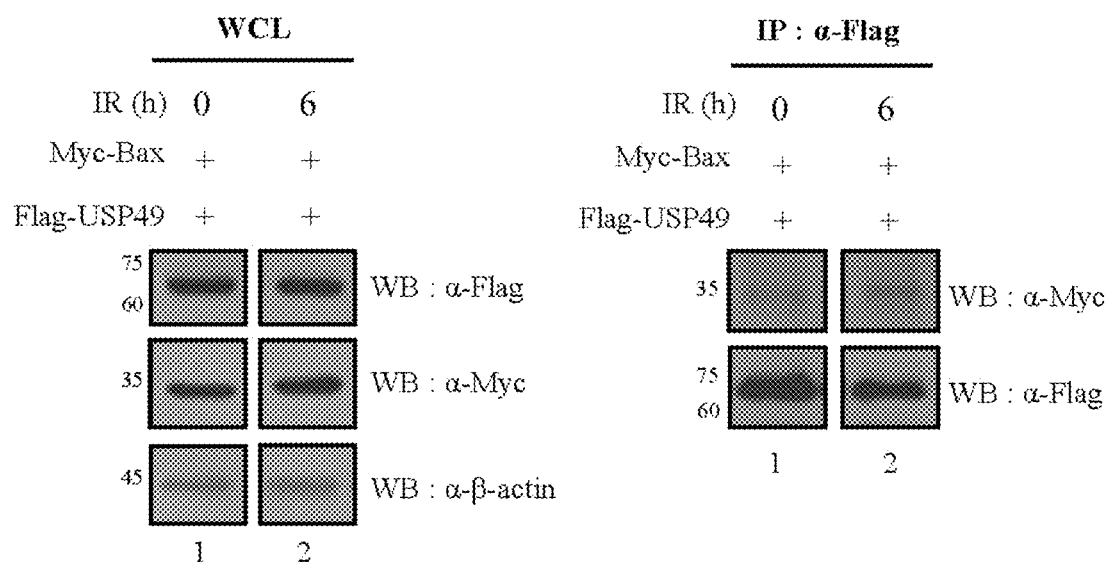
FIG. 10 shows the results obtained by evaluating whether USP49 regulates Bax during IR-induced apoptosis when IR was irradiated after transforming Flag-USP49 and Myc-Bax into HCT116 cells.

FIG. 10 shows the results obtained by evaluating whether USP49 regulates Bax during IR-induced apoptosis when IR was irradiated after transforming Flag-USP49 and Myc-Bax into HCT116 cells. FIG. 11 shows the results obtained by evaluating whether USP49 regulates Bax to promote the apoptosis of cells, through treating the HCT116 cells overexpressed with Flag-USP49 or Myc-Bax with IR irradiation (10 Gy) and then harvesting the cells after 6 hours. When HCT116 cells received IR irradiation, cleavage of PARP1 was increased (lanes 1 and 5 in FIG. 11). Binding affinity of USP49 to Bax in apoptotic cells was increased, indicating that USP49 is involved in IR-induced apoptosis through its interaction with Bax (FIG. 10). Therefore, the present inventors investigated whether USP49 promotes IR-induced apoptosis through deubiquitination of Bax. Overexpression of USP49 in HCT116 cells increased cleavage of PARP1 after IR irradiation (FIG. 11). However, overexpression of USP49 in cells overexpressed with Bax did not further increase the cleavage of PARP1 (FIG. 11). These results suggest that, although USP49 cannot promote IR-induced apoptosis with Bax, USP49 can regulate Bax in a proteasome-independent pathway during IR-induced apoptosis.

3. Discussion

In order to elucidate the causes and solutions of various diseases, various studies are being conducted to establish intracellular signal pathways. The present inventors have focused on deubiquitinating enzymes that regulate the degradation and function of proteins, so as to contribute to the development of effective therapeutics against diseases. It is required to identify deubiquitinating enzymes that interact to regulate cellular mechanisms by regulating certain proteins present in various signal pathways. Therefore, the vector library according to the present invention is expected to be able to provide an efficient help. The present inventors construct a deubiquitinating enzyme screening system by preparing a library capable of expressing each deubiquitinating enzyme in yeast through inserting the genes encoding said deubiquitinating enzyme into the pGBT9 vector having a DNA binding domain. To test this system, cDNA of Bax protein, an apoptosis-associated protein, was used and thus USP1, USP7, USP12, and USP49 are confirmed to be deubiquitinating enzymes binding thereto. Therefore, said system can contribute to the development of therapeutic agents that can effectively induce apoptosis of cancer cells. Among them, it is demonstrated that USP12 and USP49 interact with and bind to the cells in vivo. In addition, the present inventors screened a deubiquitinating enzyme that binds to NANOG protein, and as a result thereof, USP21 was found to be a deubiquitinating enzyme that regulates NANOG. The present inventors also demonstrated that it binds thereto in vivo and in vitro through immunoprecipitation and GST pull-down analysis. In addition, since the results obtained through the screening were consistent with the results of immunoprecipitation and GST-pull down analysis, the screening platform exhibit efficacy. Therefore, the library prepared by the present inventors can efficiently identify the deubiquitinating enzyme binding to the target protein, and can be applied to the development of effective cell therapeutics and anticancer agents through applying the present identifying method.

The invention claimed is:

1. A method for screening an agent having anti-cancer activity, the method comprising:
   (i) treating with candidate materials a cell overexpressing a deubiquitinating enzyme USP1, USP7, USP12, or USP49 and Bax protein, followed by culturing the cell; and
   (ii) measuring apoptosis of the cell cultured in Step (i) and selecting a material inducing apoptosis of the cell.

2. The method of claim 1, wherein the deubiquitinating enzyme is USP49.

* * * * *

SEQUENCE LISTING

```
<160> NUMBER OF SEQ ID NOS: 89

<210> SEQ ID NO 1
<211> LENGTH: 2358
<212> TYPE: DNA
<213> ORGANISM: Homo sapiens

<400> SEQUENCE: 1
atgcctggtg tcatacctag tgaaagtaat ggactttcaa gaggtagccc ttcaaagaaa      60
aacagacttt ccttaaagtt ttttcagaaa aaggaaacta agagagcttt ggatttcaca     120
gattctcaag aaaatgaaga aaaagcttct gaatatagag catctgaaat tgatcaagtt     180
gttcctgcag cacagtcttc acctataaac tgtgagaaga gagaaaactt gttaccattt     240
```
gtgggactga ataatctcgg caatacttgc tatcttaata gtatacttca ggtattatat      300
ttttgtcccg gttttaaatc tggagtaaag cacttattta atattatttc aaggaagaaa      360
gaagctctaa aggatgaagc caatcaaaaa gacaagggaa attgcaaaga agattctttg      420
gcaagttatg aattgatatg cagtttacag tccttaatca tttcggttga acagctccag      480
gctagttttc tcttaaatcc agagaaatat actgatgaac ttgccactca gccaaggcga      540
ctgcttaaca cactgaggga actcaaccct atgtatgaag atatctaca gcatgatgca       600 caggaagtat tacaatgtat tttgggaaac attcaagaaa catgccaact cctaaaaaaa      660
gaagaagtaa aaaatgtggc agaattacct actaaggtag aagaaatacc tcatccgaaa      720
gaggaaatga atggtattaa cagcatagag atggacagta tgaggcattc tgaagacttt      780
aaagagaaac tcccaaaagg aaatgggaaa agaaaaagtg acactgaatt tggtaacatg      840
aagaaaaaag ttaaattatc caaggaacac cagtcattgg aagagaacca gagacaaact      900
agatcaaaaa gaaaagctac aagtgataca ttagagagtc ctcctaaaat aattcccaag      960
tatatttctg aaaatgagag tccaagaccc tcacaaaaga aatcaagagt taaaataaat     1020
tggttaaagt ctgcaactaa gcaacccagc attctttcta aattttgtag tctgggaaaa     1080
ataacaacaa accaaggagt caaggacaa tctaaagaaa atgaatgtga tcctgaagag      1140
gacttgggga agtgtgaaag tgataacaca actaatggtt gtggacttga atctccagga     1200
aatactgtta cacctgtaaa tgttaatgaa gttaaaccca taaacaaagg tgaagaacaa     1260
attggttttg agctagtgga gaaattattt caaggtcagc tggtattaag gacgcgttgc     1320
ttggaatgtg aaagtttaac agaaagaaga gaagattttc aagacatcag tgtgccagta     1380
caagaagatg agctttccaa agtagaggag agttctgaaa tttctccaga gccaaaaaca     1440
gaaatgaaga ccctgagatg ggcaatttca caatttgctt cagtagaaag gattgtagga     1500
gaagataaat atttctgtga aaactgccat cattatactg aagctgaacg aagtcttttg     1560
tttgacaaaa tgcctgaagt tataactatt catttgaagt gctttgctgc tagtggtttg     1620
gagtttgatt gttatggtgg tggactttcc aagatcaaca ctccttatt gacacctctt      1680 aaattgtcac tagaagaatg gagcacaaag ccaactaacg acagctatgg attatttgcg     1740
gttgtgatgc atagtggcat tacaattagt agtgggcatt acactgcttc tgttaaagtc     1800
actgacctta acagtttaga actagataaa ggaaattttg tggttgacca aatgtgtgaa     1860
ataggtaagc cagaaccatt gaatgaggag gaagcaaggg gtgtggttga gaattataat     1920
gatgaagaag tgtcaattag agttggtgga aatacacagc caagtaaagt tttgaacaaa     1980
aaaaatgtag aagctattgg acttcttgga ggacaaaaga gcaaagcaga ttatgagcta     2040
tacaacaaag cctctaatcc tgataaggtt gctagtacag cgtttgctga aaatagaaat     2100
tctgagacta gtgatactac tgggacccat gaatctgata gaaacaagga atccagtgac     2160
caaacaggca ttaatattag tggatttgag aacaaaattt catacgtagt gcaaagctta     2220
aaggagtatg aggggaagtg gttgcttttt gatgattctg aagtcaaagt tactgaagag     2280
aaggactttc tgaattctct ttccccttct acatctccta cttctactcc ttacttgcta     2340 tttttataaga aattatag                                                  2358

<210> SEQ ID NO 2
<211> LENGTH: 785
<212> TYPE: PRT
<213> ORGANISM: Homo sapiens

```
<400> SEQUENCE: 2

Met Pro Gly Val Ile Pro Ser Glu Ser Asn Gly Leu Ser Arg Gly Ser
1               5                   10                  15

Pro Ser Lys Lys Asn Arg Leu Ser Leu Lys Phe Phe Gln Lys Lys Glu
            20                  25                  30

Thr Lys Arg Ala Leu Asp Phe Thr Asp Ser Gln Glu Asn Glu Glu Lys
        35                  40                  45

Ala Ser Glu Tyr Arg Ala Ser Glu Ile Asp Gln Val Val Pro Ala Ala
    50                  55                  60

Gln Ser Ser Pro Ile Asn Cys Glu Lys Arg Glu Asn Leu Leu Pro Phe
65                  70                  75                  80

Val Gly Leu Asn Asn Leu Gly Asn Thr Cys Tyr Leu Asn Ser Ile Leu
                85                  90                  95

Gln Val Leu Tyr Phe Cys Pro Gly Phe Lys Ser Gly Val Lys His Leu
            100                 105                 110

Phe Asn Ile Ile Ser Arg Lys Lys Glu Ala Leu Lys Asp Glu Ala Asn
        115                 120                 125

Gln Lys Asp Lys Gly Asn Cys Lys Glu Asp Ser Leu Ala Ser Tyr Glu
    130                 135                 140

Leu Ile Cys Ser Leu Gln Ser Leu Ile Ile Ser Val Glu Gln Leu Gln
145                 150                 155                 160

Ala Ser Phe Leu Leu Asn Pro Glu Lys Tyr Thr Asp Glu Leu Ala Thr
                165                 170                 175

Gln Pro Arg Arg Leu Leu Asn Thr Leu Arg Glu Leu Asn Pro Met Tyr
            180                 185                 190

Glu Gly Tyr Leu Gln His Asp Ala Gln Glu Val Leu Gln Cys Ile Leu
        195                 200                 205

Gly Asn Ile Gln Glu Thr Cys Gln Leu Leu Lys Lys Glu Glu Val Lys
    210                 215                 220

Asn Val Ala Glu Leu Pro Thr Lys Val Glu Glu Ile Pro His Pro Lys
225                 230                 235                 240

Glu Glu Met Asn Gly Ile Asn Ser Ile Glu Met Asp Ser Met Arg His
                245                 250                 255

Ser Glu Asp Phe Lys Glu Lys Leu Pro Lys Gly Asn Gly Lys Arg Lys
            260                 265                 270

Ser Asp Thr Glu Phe Gly Asn Met Lys Lys Val Lys Leu Ser Lys
        275                 280                 285

Glu His Gln Ser Leu Glu Glu Asn Gln Arg Gln Thr Arg Ser Lys Arg
    290                 295                 300

Lys Ala Thr Ser Asp Thr Leu Glu Ser Pro Pro Lys Ile Ile Pro Lys
305                 310                 315                 320

Tyr Ile Ser Glu Asn Glu Ser Pro Arg Pro Ser Gln Lys Lys Ser Arg
                325                 330                 335

Val Lys Ile Asn Trp Leu Lys Ser Ala Thr Lys Gln Pro Ser Ile Leu
            340                 345                 350

Ser Lys Phe Cys Ser Leu Gly Lys Ile Thr Thr Asn Gln Gly Val Lys
        355                 360                 365

Gly Gln Ser Lys Glu Asn Glu Cys Asp Pro Glu Asp Leu Gly Lys
    370                 375                 380

Cys Glu Ser Asp Asn Thr Thr Asn Gly Cys Gly Leu Glu Ser Pro Gly
385                 390                 395                 400

Asn Thr Val Thr Pro Val Asn Val Asn Glu Val Lys Pro Ile Asn Lys
                405                 410                 415
```

Gly Glu Glu Gln Ile Gly Phe Glu Leu Val Glu Lys Leu Phe Gln Gly
            420                 425                 430

Gln Leu Val Leu Arg Thr Arg Cys Leu Glu Cys Glu Ser Leu Thr Glu
            435                 440                 445

Arg Arg Glu Asp Phe Gln Asp Ile Ser Val Pro Val Gln Glu Asp Glu
450                 455                 460

Leu Ser Lys Val Glu Glu Ser Ser Glu Ile Ser Pro Glu Pro Lys Thr
465                 470                 475                 480

Glu Met Lys Thr Leu Arg Trp Ala Ile Ser Gln Phe Ala Ser Val Glu
                485                 490                 495

Arg Ile Val Gly Glu Asp Lys Tyr Phe Cys Glu Asn Cys His His Tyr
            500                 505                 510

Thr Glu Ala Glu Arg Ser Leu Leu Phe Asp Lys Met Pro Glu Val Ile
            515                 520                 525

Thr Ile His Leu Lys Cys Phe Ala Ala Ser Gly Leu Glu Phe Asp Cys
            530                 535                 540

Tyr Gly Gly Gly Leu Ser Lys Ile Asn Thr Pro Leu Leu Thr Pro Leu
545                 550                 555                 560

Lys Leu Ser Leu Glu Glu Trp Ser Thr Lys Pro Thr Asn Asp Ser Tyr
                565                 570                 575

Gly Leu Phe Ala Val Val Met His Ser Gly Ile Thr Ile Ser Ser Gly
            580                 585                 590

His Tyr Thr Ala Ser Val Lys Val Thr Asp Leu Asn Ser Leu Glu Leu
            595                 600                 605

Asp Lys Gly Asn Phe Val Val Asp Gln Met Cys Glu Ile Gly Lys Pro
            610                 615                 620

Glu Pro Leu Asn Glu Glu Ala Arg Gly Val Val Glu Asn Tyr Asn
625                 630                 635                 640

Asp Glu Glu Val Ser Ile Arg Val Gly Gly Asn Thr Gln Pro Ser Lys
                645                 650                 655

Val Leu Asn Lys Lys Asn Val Glu Ala Ile Gly Leu Leu Gly Gly Gln
            660                 665                 670

Lys Ser Lys Ala Asp Tyr Glu Leu Tyr Asn Lys Ala Ser Asn Pro Asp
            675                 680                 685

Lys Val Ala Ser Thr Ala Phe Ala Glu Asn Arg Asn Ser Glu Thr Ser
            690                 695                 700

Asp Thr Thr Gly Thr His Glu Ser Asp Arg Asn Lys Glu Ser Ser Asp
705                 710                 715                 720

Gln Thr Gly Ile Asn Ile Ser Gly Phe Glu Asn Lys Ile Ser Tyr Val
                725                 730                 735

Val Gln Ser Leu Lys Glu Tyr Glu Gly Lys Trp Leu Leu Phe Asp Asp
            740                 745                 750

Ser Glu Val Lys Val Thr Glu Glu Lys Asp Phe Leu Asn Ser Leu Ser
            755                 760                 765

Pro Ser Thr Ser Pro Thr Ser Thr Pro Tyr Leu Leu Phe Tyr Lys Lys
            770                 775                 780

Leu
785

<210> SEQ ID NO 3
<211> LENGTH: 1818
<212> TYPE: DNA
<213> ORGANISM: Homo sapiens

```
<400> SEQUENCE: 3
atgtcccagc tctcctccac cctgaagcgc tacacagaat cggcccgcta cacagatgcc      60
cactatgcca agtcgggcta tggtgcctac accccatcct cctatggggc aatctggct     120 gcctccttac tggagaagga gaaacttggt ttcaagccgg tccccaccag cagcttcctc     180
acccgtcccc gtacctatgg cccctcctcc ctcctggact atgaccgggg ccgcccctg     240 ctgagacccg acatcactgg gggtggtaag cgggcagaga gccagacccg ggtactgag     300 cggcctttag gcagtggcct cagcggggc agcggattcc cttatggagt gaccaacaac     360
tgcctcagct acctgccat caatgccat gaccagggg tgaccctaac ccagaagctg      420
gacagccaat cagacctggc ccgggatttc tccagcctcc ggacctcaga tagctaccgg     480
atagacccca ggaacctggg ccgcagcccc atgctggccc ggacgcgcaa ggagctctgc     540
accctgcagg ggctctacca gacagccagc tgccctgaat acctggtcga ctacctggag     600
aactatggtc gcaagggcag tgcatctcag gtgccctccc aggcccctcc ctcacgagtc     660
cctgaaatca tcagcccaac ctaccgaccc attggccgct acgcgtgtg ggagacggga     720 aagggtcagg cccctgggcc cagccgctcc agctccccgg aagagacgg catgaattct     780 aagagtgccc agggtctggc tggtcttcga aaccttggga cacgtgctt catgaactca     840 attctgcagt gcctgagcaa cactcgggag ttgagagatt actgcctcca gaggctctac     900
atgcgggacc tgcaccacgg cagcaatgca cacacagccc tcgtggaaga gtttgcaaaa     960
ctaattcaga ccatatggac ttcatccccc aatgatgtgg tgagcccatc tgagttcaag    1020
acccagatcc agagatatgc accgcgcttt gttggctata atcagcagga tgctcaggag    1080
ttccttcgct ttcttctgga tgggctccat aacgaggtga accgagtgac actgagacct    1140
aagtccaacc ctgagaacct cgatcatctt cctgatgacg agaaaggccg acagatgtgg    1200
agaaaatatc tagaacggga agacagtagg atcgggatc tctttgttgg gcagctaaag    1260
agctcgctga cgtgtacaga ttgtggttac tgttctacgg tcttcgaccc cttctgggac    1320
ctctcactgc ccattgctaa gcgaggttat cctgaggtga cattaatgga ctgcatgagg    1380
ctcttcacca agaggatgt gcttgatgga gatgaaaagc caacatgctg tcgctgccga    1440
ggcagaaaac ggtgtataaa gaagttctcc atccagaggt tcccaaagat cttggtgctc    1500
catctgaagc ggttctcaga atccaggatc cgaaccagca agctcacaac atttgtgaac    1560 ttcccccctaa gagacctgga cttaagagaa tttgcctcag aaaacaccaa ccatgctgtt    1620
tacaacctgt acgctgtgtc caatcactcc ggaaccacca tgggtggcca ctatacagcc    1680
tactgtcgca gtccagggac aggagaatgg cacactttca acgactccag cgtcactccc    1740
atgtcctcca gccaagtgcg caccagcgac gcctacctgc tcttctacga actggccagc    1800
ccgccctccc gaatgtag                                                 1818

<210> SEQ ID NO 4
<211> LENGTH: 605
<212> TYPE: PRT
<213> ORGANISM: Homo sapiens

<400> SEQUENCE: 4

Met Ser Gln Leu Ser Ser Thr Leu Lys Arg Tyr Thr Glu Ser Ala Arg
1               5                   10                  15

Tyr Thr Asp Ala His Tyr Ala Lys Ser Gly Tyr Gly Ala Tyr Thr Pro
            20                  25                  30

Ser Ser Tyr Gly Ala Asn Leu Ala Ala Ser Leu Leu Glu Lys Glu Lys
```

-continued

```
              35                  40                  45
Leu Gly Phe Lys Pro Val Pro Thr Ser Ser Phe Leu Thr Arg Pro Arg
 50                  55                  60

Thr Tyr Gly Pro Ser Ser Leu Leu Asp Tyr Asp Arg Gly Arg Pro Leu
 65                  70                  75                  80

Leu Arg Pro Asp Ile Thr Gly Gly Lys Arg Ala Glu Ser Gln Thr
                     85                  90                  95

Arg Gly Thr Glu Arg Pro Leu Gly Ser Gly Leu Ser Gly Gly Ser Gly
                100                 105                 110

Phe Pro Tyr Gly Val Thr Asn Asn Cys Leu Ser Tyr Leu Pro Ile Asn
                115                 120                 125

Ala Tyr Asp Gln Gly Val Thr Leu Thr Gln Lys Leu Asp Ser Gln Ser
 130                 135                 140

Asp Leu Ala Arg Asp Phe Ser Ser Leu Arg Thr Ser Asp Ser Tyr Arg
 145                 150                 155                 160

Ile Asp Pro Arg Asn Leu Gly Arg Ser Pro Met Leu Ala Arg Thr Arg
                165                 170                 175

Lys Glu Leu Cys Thr Leu Gln Gly Leu Tyr Gln Thr Ala Ser Cys Pro
                180                 185                 190

Glu Tyr Leu Val Asp Tyr Leu Glu Asn Tyr Gly Arg Lys Gly Ser Ala
                195                 200                 205

Ser Gln Val Pro Ser Gln Ala Pro Pro Ser Arg Val Pro Glu Ile Ile
 210                 215                 220

Ser Pro Thr Tyr Arg Pro Ile Gly Arg Tyr Thr Leu Trp Glu Thr Gly
 225                 230                 235                 240

Lys Gly Gln Ala Pro Gly Pro Ser Arg Ser Ser Pro Gly Arg Asp
                245                 250                 255

Gly Met Asn Ser Lys Ser Ala Gln Gly Leu Ala Gly Leu Arg Asn Leu
                260                 265                 270

Gly Asn Thr Cys Phe Met Asn Ser Ile Leu Gln Cys Leu Ser Asn Thr
                275                 280                 285

Arg Glu Leu Arg Asp Tyr Cys Leu Gln Arg Leu Tyr Met Arg Asp Leu
                290                 295                 300

His His Gly Ser Asn Ala His Thr Ala Leu Val Glu Glu Phe Ala Lys
 305                 310                 315                 320

Leu Ile Gln Thr Ile Trp Thr Ser Ser Pro Asn Asp Val Val Ser Pro
                325                 330                 335

Ser Glu Phe Lys Thr Gln Ile Gln Arg Tyr Ala Pro Arg Phe Val Gly
                340                 345                 350

Tyr Asn Gln Gln Asp Ala Gln Glu Phe Leu Arg Phe Leu Leu Asp Gly
                355                 360                 365

Leu His Asn Glu Val Asn Arg Val Thr Leu Arg Pro Lys Ser Asn Pro
                370                 375                 380

Glu Asn Leu Asp His Leu Pro Asp Glu Lys Gly Arg Gln Met Trp
 385                 390                 395                 400

Arg Lys Tyr Leu Glu Arg Glu Asp Ser Arg Ile Gly Asp Leu Phe Val
                405                 410                 415

Gly Gln Leu Lys Ser Ser Leu Thr Cys Thr Asp Cys Gly Tyr Cys Ser
                420                 425                 430

Thr Val Phe Asp Pro Phe Trp Asp Leu Ser Leu Pro Ile Ala Lys Arg
                435                 440                 445

Gly Tyr Pro Glu Val Thr Leu Met Asp Cys Met Arg Leu Phe Thr Lys
 450                 455                 460
```

```
Glu Asp Val Leu Asp Gly Asp Glu Lys Pro Thr Cys Cys Arg Cys Arg
465                 470                 475                 480

Gly Arg Lys Arg Cys Ile Lys Lys Phe Ser Ile Gln Arg Phe Pro Lys
                485                 490                 495

Ile Leu Val Leu His Leu Lys Arg Phe Ser Glu Ser Arg Ile Arg Thr
            500                 505                 510

Ser Lys Leu Thr Thr Phe Val Asn Phe Pro Leu Arg Asp Leu Asp Leu
            515                 520                 525

Arg Glu Phe Ala Ser Glu Asn Thr Asn His Ala Val Tyr Asn Leu Tyr
            530                 535                 540

Ala Val Ser Asn His Ser Gly Thr Thr Met Gly Gly His Tyr Thr Ala
545                 550                 555                 560

Tyr Cys Arg Ser Pro Gly Thr Gly Glu Trp His Thr Phe Asn Asp Ser
                565                 570                 575

Ser Val Thr Pro Met Ser Ser Ser Gln Val Arg Thr Ser Asp Ala Tyr
            580                 585                 590

Leu Leu Phe Tyr Glu Leu Ala Ser Pro Pro Ser Arg Met
            595                 600                 605
```

<210> SEQ ID NO 5
<211> LENGTH: 1566
<212> TYPE: DNA
<213> ORGANISM: Homo sapiens

<400> SEQUENCE: 5

```
atggagtgtc cacacctgag ctccagcgtc tgcattgctc cggactcagc caagttcccc      60
aacggctccc cgtcgtcctg gtgctgcagc gtgtgccggt ccaacaaaag cccttgggtc     120
tgtttgactt gttcaagtgt ccactgtgga aggtatgtga atggccatgc aaaaaaacat     180
tatgaagatg cacaagtacc tttaaccaac cataagaaat cagaaaagca agataaagtt     240
cagcacacag tatgtatgga ttgcagtagc tacagtacat actgttatcg ctgtgatgat     300
tttgtggtta atgacaccaa gctgggactg gtacagaaag tcagagaaca cttacagaac     360
ttggaaaact cagcttttca cagctgacag cataagaaaa gaaaactttt ggaaaactca     420
acactaaaca gcaagttatt aaaagtaaat ggaagcacca ctgccatttg tgccacaggc     480
cttcggaatt tggggaacac atgtttcatg aatgccatcc ttcagtcact cagtaacatt     540
gagcagtttt gctgttattt caaagaactg cccgccgtgg agttaaggaa tgggaaaaca     600
gcaggaaggc ggacatacca caccaggagc caagggggata caatgtgtc tttggtagaa     660
gagtttagaa agacactctg tgctttatgg caaggcagcc agactgcatt tagcccagag     720
tccttatttt atgttgtttg gaagattatg ccaaacttta ggggctatca acagcaggac     780
gcccatgaat tcaatgcgct accttttgga ccacctacac ttgggaactt cagggcggtt     840
tcaacggtgt ttcccgctca gcaattctgc aggagaattc tactctgtct gcaagtaaac     900
aagtgttgca taaatggagc atctactgtt gtcacggcta tattcggagg cattctccaa     960
aatgaggtta actgcctcat atgtgggaca gaatctagaa agtttgatcc attcctagac    1020
ctttcattag atattccaag tcagttcaga agtaagcgct ctaagaatca gaaaatggaa    1080
ccagtttgtt cgttacgaga ttgtcttcgc agttttaccg acttagaaga acttgatgag    1140
acagagttat atatgtgcca taatgcaaa aagaaacaaa gtccacaaa aaagttttgg     1200
attcaaaaac tacccaaggt gctatgctta catttgaaaa gatttcattg acagcatat     1260
ttaagaaata agttgatac atacgtagaa tttccactga gaggcctaga catgaaatgg    1320
```

-continued

```
tacttactag agcctgagaa cagtggcccg gagagctgcc tgtatgacct cgccgctgtg    1380
gtggtgcacc atggttccgg ggttggttct ggacattaca cagcatacgc aactcacgaa    1440
ggccgctggt tccacttcaa tgacagtact gtaacactga ctgacgagga gactgtggtg    1500
aaggcgaagg cctacatcct tttctacgtg gaacaccagg ccaaagctgg atcggataaa    1560
ctttaa                                                              1566
```

<210> SEQ ID NO 6
<211> LENGTH: 521
<212> TYPE: PRT
<213> ORGANISM: Homo sapiens

<400> SEQUENCE: 6

| Met | Glu | Cys | Pro | His | Leu | Ser | Ser | Val | Cys | Ile | Ala | Pro | Asp | Ser |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ala Lys Phe Pro Asn Gly Ser Pro Ser Ser Trp Cys Cys Ser Val Cys
            20                  25                  30

Arg Ser Asn Lys Ser Pro Trp Val Cys Leu Thr Cys Ser Ser Val His
        35                  40                  45

Cys Gly Arg Tyr Val Asn Gly His Ala Lys Lys His Tyr Glu Asp Ala
    50                  55                  60

Gln Val Pro Leu Thr Asn His Lys Lys Ser Glu Lys Gln Asp Lys Val
65                  70                  75                  80

Gln His Thr Val Cys Met Asp Cys Ser Ser Tyr Ser Thr Tyr Cys Tyr
                85                  90                  95

Arg Cys Asp Asp Phe Val Val Asn Asp Thr Lys Leu Gly Leu Val Gln
            100                 105                 110

Lys Val Arg Glu His Leu Gln Asn Leu Glu Asn Ser Ala Phe Thr Ala
        115                 120                 125

Asp Arg His Lys Lys Arg Lys Leu Leu Glu Asn Ser Thr Leu Asn Ser
    130                 135                 140

Lys Leu Leu Lys Val Asn Gly Ser Thr Thr Ala Ile Cys Ala Thr Gly
145                 150                 155                 160

Leu Arg Asn Leu Gly Asn Thr Cys Phe Met Asn Ala Ile Leu Gln Ser
                165                 170                 175

Leu Ser Asn Ile Glu Gln Phe Cys Cys Tyr Phe Lys Glu Leu Pro Ala
            180                 185                 190

Val Glu Leu Arg Asn Gly Lys Thr Ala Gly Arg Arg Thr Tyr His Thr
        195                 200                 205

Arg Ser Gln Gly Asp Asn Asn Val Ser Leu Val Glu Glu Phe Arg Lys
    210                 215                 220

Thr Leu Cys Ala Leu Trp Gln Gly Ser Gln Thr Ala Phe Ser Pro Glu
225                 230                 235                 240

Ser Leu Phe Tyr Val Val Trp Lys Ile Met Pro Asn Phe Arg Gly Tyr
                245                 250                 255

Gln Gln Gln Asp Ala His Glu Phe Asn Ala Leu Pro Phe Gly Pro Pro
            260                 265                 270

Thr Leu Gly Asn Phe Arg Ala Val Ser Thr Val Phe Pro Ala Gln Gln
        275                 280                 285

Phe Cys Arg Arg Ile Leu Leu Cys Leu Gln Val Asn Lys Cys Cys Ile
    290                 295                 300

Asn Gly Ala Ser Thr Val Val Thr Ala Ile Phe Gly Gly Ile Leu Gln
305                 310                 315                 320

Asn Glu Val Asn Cys Leu Ile Cys Gly Thr Glu Ser Arg Lys Phe Asp
            325                 330                 335

Pro Phe Leu Asp Leu Ser Leu Asp Ile Pro Ser Gln Phe Arg Ser Lys
        340                 345                 350

Arg Ser Lys Asn Gln Glu Asn Gly Pro Val Cys Ser Leu Arg Asp Cys
    355                 360                 365

Leu Arg Ser Phe Thr Asp Leu Glu Glu Leu Asp Glu Thr Glu Leu Tyr
370                 375                 380

Met Cys His Lys Cys Lys Lys Gln Lys Ser Thr Lys Lys Phe Trp
385                 390                 395                 400

Ile Gln Lys Leu Pro Lys Val Leu Cys Leu His Leu Lys Arg Phe His
            405                 410                 415

Trp Thr Ala Tyr Leu Arg Asn Lys Val Asp Thr Tyr Val Glu Phe Pro
        420                 425                 430

Leu Arg Gly Leu Asp Met Lys Trp Tyr Leu Leu Glu Pro Glu Asn Ser
    435                 440                 445

Gly Pro Glu Ser Cys Leu Tyr Asp Leu Ala Ala Val Val Val His His
450                 455                 460

Gly Ser Gly Val Gly Ser Gly His Tyr Thr Ala Tyr Ala Thr His Glu
465                 470                 475                 480

Gly Arg Trp Phe His Phe Asn Asp Ser Thr Val Thr Leu Thr Asp Glu
            485                 490                 495

Glu Thr Val Val Lys Ala Lys Ala Tyr Ile Leu Phe Tyr Val Glu His
        500                 505                 510

Gln Ala Lys Ala Gly Ser Asp Lys Leu
    515                 520

<210> SEQ ID NO 7
<211> LENGTH: 2892
<212> TYPE: DNA
<213> ORGANISM: Homo sapiens

<400> SEQUENCE: 7

```
atggcggaag gtggaggctg ccgtgagcga ccgatgcgg agactcagaa gtccgagctt      60
ggacccttaa tgaggaccac actccaacgc ggggcgcagt ggtatcttat tgacagccgg     120
tggttcaagc agtggaagaa gtatgtgggc tttgacagct gggacatgta caatgtgggt     180
gaacataacc tatttcctgg cccaatagac aactctgggc tattttcaga tcctgagagt     240
cagaccttga agaacacttt aattgatgaa ttggactatg tattggtccc taccgaggcg     300
tggaataaac tactaaactg gtacggctgt gtagaaggcc agcaacccat cgtcagaaaa     360
gttgtggagc atggcctgtt tgtcaagcac tgcaaagtcg aggtgtattt gctggaactg     420
aagctctgtg agaacagtga ccccaccaat gtgctgagtt gccatttcag caaggcagac     480
accattgcaa ccatcgagaa agagatgcgg aagctattca acatccctgc ggagcgtgaa     540
acacggctct ggaacaaata catgagcaac acctacgagc agttgagcaa gctagcaaac     600
actgtccagg atgctgggct ataccagggt caggtgctag taattgagcc tcaaaatgaa     660
gatggcacat ggcccaggca gaccttgcag tcaaaatcaa gcactgcgcc tagcagaaat     720
tttactacct ctccaaaatc atcagcaagt ccctattcct cagtgtctgc ctctctcatt     780
gcaaatggtg atagcactag cacctgtggg atgcacagtt ccggtgtcag caggggtgga     840
tctggctttt ctgcttcgta taattgtcag gagccaccat cctctcatat acaacctggg     900
ctctgtggac ttggaaacct gggaaacacc tgcttcatga actccgcttt gcagtgtttg     960
```

```
agcaacactg caccactgac tgactacttt ctcaaagatg agtatgaagc cgaaatcaac   1020
agagacaacc ctctggggat gaaaggggaa attgcagaag cctatgctga actcattaag   1080
cagatgtggt ctggaaggga cgcccatgtg gcacctcgca tgttcaaaac tcaagtagga   1140
cgttttgctc ctcaatttc tggctaccag caacaagatt ctcaggagct gctggccttt   1200
cttctagatg gattgcatga agatctgaac cgggtaaaga aaaagcccta cttggagctg   1260
aaggatgcca atgggcggcc agatgcggtg gtggcaaagg aagcctggga gaatcacagg   1320
ttgaggaatg attctgtgat tgtggatact ttccatggcc tcttcaaatc tactttgggt   1380
tgcccagaat gtgctaaggt ttctgtgacc tttgacccat tttgctatct aacgctgcca   1440
ctgcccttga agaaagatcg agttatggag gttttcctgg ttcctgctga ccctcactgc   1500
agacctactc agtaccgtgt gactgtgccg ctgatggggg ctgtgtccga cctgtgcgag   1560
gctctctcca ggctgtctgg cattgctgca gaaaatatgg tggtcgcaga tgtgtataat   1620
caccgattcc acaaaatttt ccaaatggat gaaggtttaa accacatcat gcctcgggat   1680
gacattttcg tgtacgaggt ctgcagcact tccgtggatg gctcggaatg tgtcacgctt   1740
ccagtctact tcaggagag gaagtccagg ccatcaagca cttcctccgc atcagcgcta   1800
tatgggcagc cactattgct ttctgtcccc aagcacaagt taacccttga gtctttgtac   1860
caggctgttt gtgatcgtat cagccgctat gtgaaacagc ctttacctga gtgtttggc    1920 agctcaccct tggagccagg ggcctgcaat ggctccagga cagctgtga aggagaagat   1980 gaggaagaaa tggagcatca ggaagaaggc aaagagcagc tttcagaaac agaaggcagt   2040
ggggaagatg agccaggaaa tgaccccagt gagaccaccc aaaagaagat caaaggccag   2100
ccctgcccaa aaaggctttt taccttcagt cttgtgaact cctatggaac agctgacata   2160
aattcacttg cagctgatgg aaaactactt aaactcaact ctcgatctac actggccatg   2220
gattgggaca gtgaaactcg gagactttac tatgatgagc aagaatctga ggcctacgag   2280
aagcatgtga gcatgttgca gcctcagaag aagaagaaga ccacagtggc cctgagagac   2340
tgcatcgagc tcttcaccac catggagacc cttggggagc atgacccctg gtactgtccc   2400
aactgtaaga agcatcaaca ggccacaaaa aagtttgacc tatggtcctt gcccaagatc   2460
ctggtggtcc acctcaaacg tttctcctac aacagatact ggaggggataa gctcgacaca   2520 gtcgtagaat tcccaatcag agggctgaac atgtccgagt ttgtctgtaa cctgtcagca   2580
aggccttatg tgtacgacct cattgccgtg tccaatcatt atggagccat ggggggttggc   2640 cactacactg catatgcgaa gaacaaactg aatggtaaat ggtattactt tgatgatagc   2700
aacgtgtccc tggcctctga ggatcagata gtgactaaag cagcttatgt gctattttac   2760
caacgtcgag atgatgaatt ttataagaca ccttcactta gcagttctgg ttcctctgat   2820
ggagggacac gaccaagcag ctctcagcag ggctttgggg atgatgaggc ttgcagcatg   2880
gacaccaact aa                                                      2892
```

<210> SEQ ID NO 8
<211> LENGTH: 963
<212> TYPE: PRT
<213> ORGANISM: Homo sapiens

<400> SEQUENCE: 8

Met Ala Glu Gly Gly Gly Cys Arg Glu Arg Pro Asp Ala Glu Thr Gln
1               5                   10                  15

Lys Ser Glu Leu Gly Pro Leu Met Arg Thr Thr Leu Gln Arg Gly Ala
            20                  25                  30

```
Gln Trp Tyr Leu Ile Asp Ser Arg Trp Phe Lys Gln Trp Lys Lys Tyr
            35                  40                  45

Val Gly Phe Asp Ser Trp Asp Met Tyr Asn Val Gly Glu His Asn Leu
    50                  55                  60

Phe Pro Gly Pro Ile Asp Asn Ser Gly Leu Phe Ser Asp Pro Glu Ser
65                  70                  75                  80

Gln Thr Leu Lys Glu His Leu Ile Asp Glu Leu Asp Tyr Val Leu Val
                85                  90                  95

Pro Thr Glu Ala Trp Asn Lys Leu Leu Asn Trp Tyr Gly Cys Val Glu
                100                 105                 110

Gly Gln Gln Pro Ile Val Arg Lys Val Val Glu His Gly Leu Phe Val
                115                 120                 125

Lys His Cys Lys Val Glu Val Tyr Leu Leu Glu Leu Lys Leu Cys Glu
                130                 135                 140

Asn Ser Asp Pro Thr Asn Val Leu Ser Cys His Phe Ser Lys Ala Asp
145                 150                 155                 160

Thr Ile Ala Thr Ile Glu Lys Glu Met Arg Lys Leu Phe Asn Ile Pro
                165                 170                 175

Ala Glu Arg Glu Thr Arg Leu Trp Asn Lys Tyr Met Ser Asn Thr Tyr
                180                 185                 190

Glu Gln Leu Ser Lys Leu Asp Asn Thr Val Gln Asp Ala Gly Leu Tyr
                195                 200                 205

Gln Gly Gln Val Leu Val Ile Glu Pro Gln Asn Glu Asp Gly Thr Trp
                210                 215                 220

Pro Arg Gln Thr Leu Gln Ser Lys Ser Ser Thr Ala Pro Ser Arg Asn
225                 230                 235                 240

Phe Thr Thr Ser Pro Lys Ser Ser Ala Ser Pro Tyr Ser Ser Val Ser
                245                 250                 255

Ala Ser Leu Ile Ala Asn Gly Asp Ser Thr Ser Thr Cys Gly Met His
                260                 265                 270

Ser Ser Gly Val Ser Arg Gly Gly Ser Gly Phe Ser Ala Ser Tyr Asn
                275                 280                 285

Cys Gln Glu Pro Pro Ser Ser His Ile Gln Pro Gly Leu Cys Gly Leu
290                 295                 300

Gly Asn Leu Gly Asn Thr Cys Phe Met Asn Ser Ala Leu Gln Cys Leu
305                 310                 315                 320

Ser Asn Thr Ala Pro Leu Thr Asp Tyr Phe Leu Lys Asp Glu Tyr Glu
                325                 330                 335

Ala Glu Ile Asn Arg Asp Asn Pro Leu Gly Met Lys Gly Glu Ile Ala
                340                 345                 350

Glu Ala Tyr Ala Glu Leu Ile Lys Gln Met Trp Ser Gly Arg Asp Ala
                355                 360                 365

His Val Ala Pro Arg Met Phe Lys Thr Gln Val Gly Arg Phe Ala Pro
                370                 375                 380

Gln Phe Ser Gly Tyr Gln Gln Asp Ser Gln Glu Leu Leu Ala Phe
385                 390                 395                 400

Leu Leu Asp Gly Leu His Glu Asp Leu Asn Arg Val Lys Lys Lys Pro
                405                 410                 415

Tyr Leu Glu Leu Lys Asp Ala Asn Gly Arg Pro Asp Ala Val Val Ala
                420                 425                 430

Lys Glu Ala Trp Glu Asn His Arg Leu Arg Asn Asp Ser Val Ile Val
                435                 440                 445
```

```
Asp Thr Phe His Gly Leu Phe Lys Ser Thr Leu Gly Cys Pro Glu Cys
    450                 455                 460

Ala Lys Val Ser Val Thr Phe Asp Pro Phe Cys Tyr Leu Thr Leu Pro
465                 470                 475                 480

Leu Pro Leu Lys Lys Asp Arg Val Met Glu Val Phe Leu Val Pro Ala
                485                 490                 495

Asp Pro His Cys Arg Pro Thr Gln Tyr Arg Val Thr Val Pro Leu Met
                500                 505                 510

Gly Ala Val Ser Asp Leu Cys Glu Ala Leu Ser Arg Leu Ser Gly Ile
                515                 520                 525

Ala Ala Glu Asn Met Val Val Ala Asp Val Tyr Asn His Arg Phe His
530                 535                 540

Lys Ile Phe Gln Met Asp Glu Gly Leu Asn His Ile Met Pro Arg Asp
545                 550                 555                 560

Asp Ile Phe Val Tyr Glu Val Cys Ser Thr Ser Val Asp Gly Ser Glu
                565                 570                 575

Cys Val Thr Leu Pro Val Tyr Phe Arg Glu Arg Lys Ser Arg Pro Ser
            580                 585                 590

Ser Thr Ser Ser Ala Ser Ala Leu Tyr Gly Gln Pro Leu Leu Leu Ser
        595                 600                 605

Val Pro Lys His Lys Leu Thr Leu Glu Ser Leu Tyr Gln Ala Val Cys
    610                 615                 620

Asp Arg Ile Ser Arg Tyr Val Lys Gln Pro Leu Pro Asp Glu Phe Gly
625                 630                 635                 640

Ser Ser Pro Leu Glu Pro Gly Ala Cys Asn Gly Ser Arg Asn Ser Cys
                645                 650                 655

Glu Gly Glu Asp Glu Glu Glu Met Glu His Gln Glu Glu Gly Lys Glu
                660                 665                 670

Gln Leu Ser Glu Thr Glu Gly Ser Gly Glu Asp Glu Pro Gly Asn Asp
            675                 680                 685

Pro Ser Glu Thr Thr Gln Lys Lys Ile Lys Gly Gln Pro Cys Pro Lys
    690                 695                 700

Arg Leu Phe Thr Phe Ser Leu Val Asn Ser Tyr Gly Thr Ala Asp Ile
705                 710                 715                 720

Asn Ser Leu Ala Ala Asp Gly Lys Leu Leu Lys Leu Asn Ser Arg Ser
                725                 730                 735

Thr Leu Ala Met Asp Trp Asp Ser Glu Thr Arg Arg Leu Tyr Tyr Asp
                740                 745                 750

Glu Gln Glu Ser Glu Ala Tyr Glu Lys His Val Ser Met Leu Gln Pro
            755                 760                 765

Gln Lys Lys Lys Lys Thr Thr Val Ala Leu Arg Asp Cys Ile Glu Leu
    770                 775                 780

Phe Thr Thr Met Glu Thr Leu Gly Glu His Asp Pro Trp Tyr Cys Pro
785                 790                 795                 800

Asn Cys Lys Lys His Gln Gln Ala Thr Lys Lys Phe Asp Leu Trp Ser
                805                 810                 815

Leu Pro Lys Ile Leu Val Val His Leu Lys Arg Phe Ser Tyr Asn Arg
                820                 825                 830

Tyr Trp Arg Asp Lys Leu Asp Thr Val Val Glu Phe Pro Ile Arg Gly
            835                 840                 845

Leu Asn Met Ser Glu Phe Val Cys Asn Leu Ser Ala Arg Pro Tyr Val
    850                 855                 860

Tyr Asp Leu Ile Ala Val Ser Asn His Tyr Gly Ala Met Gly Val Gly
```

```
                865                 870                 875                 880
His Tyr Thr Ala Tyr Ala Lys Asn Lys Leu Asn Gly Lys Trp Tyr Tyr
                    885                 890                 895

Phe Asp Asp Ser Asn Val Ser Leu Ala Ser Glu Asp Gln Ile Val Thr
                900                 905                 910

Lys Ala Ala Tyr Val Leu Phe Tyr Gln Arg Arg Asp Glu Phe Tyr
                915                 920                 925

Lys Thr Pro Ser Leu Ser Ser Ser Gly Ser Ser Asp Gly Gly Thr Arg
            930                 935                 940

Pro Ser Ser Ser Gln Gln Gly Phe Gly Asp Asp Glu Ala Cys Ser Met
945                 950                 955                 960

Asp Thr Asn

<210> SEQ ID NO 9
<211> LENGTH: 2508
<212> TYPE: DNA
<213> ORGANISM: Homo sapiens

<400> SEQUENCE: 9
atggcggagc tgagtgagga ggcgctgctg tcagtattac cgacgatccg ggtccctaag      60
gctggagacc gggtccacaa agacgagtgc gccttctcct tcgacacgcc ggagtctgag     120
gggggcctct acatctgtat gaacacgttt ctgggctttg gaaacagta tgtggagaga     180 catttcaata agaccggcca gcgagtctac ttgcacctcc ggcggacccg cgcccgaaa     240 gaggaggacc ctgctacagg cactggagac ccaccccgga agaagcccac gcggctggct     300
attggtgttg aaggcggatt tgaccttagc gaggagaagt ttgaattaga cgaggatgtg     360
aagattgtca ttttgccaga ttacctggag attgcccggg atggactggg gggactgcct     420
gacattgtca gagatcgggt gaccagtgca gtggaggccc tactgtcggc cgactcagcc     480
tcccgcaagc aggaggtgca ggcatgggat ggggaagtac ggcaggtgtc taagcatgcc     540
ttcagcctca agcagttgga caaccctgct cgaatccctc cctgtggctg aagtgctcc     600 aagtgtgaca tgagagagaa cctgtggctc aacctgactg atggctccat cctctgtggg     660
cgacgctact tcgatggcag tgggggcaac aaccacgctg tggagcacta ccagagaca     720 ggctacccgt tagctgtcaa gctgggcacc atcacccctg atggagctga cgtgtactca     780
tatgatgagg atgacatggt cctggacccc agcctggctg agcacctgtc ccacttcggc     840
atcgacatgc tgaagatgca gaagacagac aagacgatga ctgagttgga gatagacatg     900
aaccagcgga ttggtgaatg ggagctgatc caggagtcag gtgtgccact caagcccctg     960
tttgggcctg gctacacagg catccggaac ctgggtaaca gctgctacct caactctgtg    1020
gtccaggtgc tcttcagcat ccctgacttc cagaggaagt atgtggataa gctggagaag    1080
atcttccaga tgcccgac ggaccctacc aggatttca gcacccaggt ggccaagctg    1140
ggccatggcc ttctctccgg ggagtattcc aagccagtac ggagtcggg cgatggggag    1200 cgggtgccag aacagaagga agttcaagat ggcattgccc ctcggatgtt caaggccctc    1260
atcggcaagg ccaccctga attctccacc aacggcagc aggatgccca ggagttcttc    1320 cttcaccta tcaacatggt ggagaggaat tgccggagct ctgaaaatcc taatgaagtg    1380
ttccgcttct tggtggagga aaagatcaag tgcctggcca cagagaaggt gaagtacacc    1440
cagcgagttg actacatcat gcagctgcct gtgcccatgg atgcagccct taacaaagag    1500
gagcttctgg agtacgagga aagaagcgg caagccgaag aggagaagat ggcactgcca    1560
```

```
gaactggttc gggcccaggt gcccttcagc tcttgcctgg aggcctacgg ggcccctgag    1620
caggtcgatg acttctggag cacggccctg caggccaagt cagtagctgt caagaccaca    1680
cgatttgcct cattccctga ctacctggtc atccagatca agaagttcac cttcggctta    1740
gactgggtgc ccaagaaact ggatgtgtcc atcgagatgc cagaggagct cgacatctcc    1800
cagttgaggg gcacagggct gcagcccgga gaggaggagc tgccagacat tgccccaccc    1860
ctggtcactc cggatgagcc caaagcgccc atgctggatg aatcagtcat catccagctg    1920
gtggagatgg gattccctat ggacgcctgc cgcaaagctg tctactacac gggcaacagc    1980
ggggctgagg ccgccatgaa ctgggtcatg tcacacatgg atgatccaga ttttgcaaac    2040
cccctcatcc tgcctggctc tagtgggccg ggctccacaa gcgcagcagc cgaccccccct   2100 cctgaggact gtgtgaccac cattgtctcc atgggcttct cccgggacca ggccttgaaa    2160
gcgctgcggg ccacgaacaa tagtttagaa cgggctgtgg actggatctt cagtcacatt    2220
gacgacctgg atgctgaagc tgccatggac atctcagagg ccgctcagc tgccgactcc     2280 atctctgagt ctgtgccagt gggacctaaa gtccgggatg gtcctggaaa gtatcagctc    2340
tttgccttca ttagtcacat gggcacctct accatgtgtg gtcactacgt ctgccacatc    2400
aagaaagaag gcagatgggt gatctacaat gaccagaaag tgtgtgcctc cgagaagccg    2460
cccaaggacc tgggctacat ctacttctac cagagagtgg ccagctaa              2508

<210> SEQ ID NO 10
<211> LENGTH: 835
<212> TYPE: PRT
<213> ORGANISM: Homo sapiens

<400> SEQUENCE: 10

Met Ala Glu Leu Ser Glu Glu Ala Leu Leu Ser Val Leu Pro Thr Ile
1               5                   10                  15

Arg Val Pro Lys Ala Gly Asp Arg Val His Lys Asp Glu Cys Ala Phe
            20                  25                  30

Ser Phe Asp Thr Pro Glu Ser Glu Gly Gly Leu Tyr Ile Cys Met Asn
        35                  40                  45

Thr Phe Leu Gly Phe Gly Lys Gln Tyr Val Glu Arg His Phe Asn Lys
    50                  55                  60

Thr Gly Gln Arg Val Tyr Leu His Leu Arg Arg Thr Arg Arg Pro Lys
65                  70                  75                  80

Glu Glu Asp Pro Ala Thr Gly Thr Gly Asp Pro Pro Arg Lys Lys Pro
                85                  90                  95

Thr Arg Leu Ala Ile Gly Val Glu Gly Gly Phe Asp Leu Ser Glu Glu
            100                 105                 110

Lys Phe Glu Leu Asp Glu Asp Val Lys Ile Val Ile Leu Pro Asp Tyr
        115                 120                 125

Leu Glu Ile Ala Arg Asp Gly Leu Gly Gly Leu Pro Asp Ile Val Arg
    130                 135                 140

Asp Arg Val Thr Ser Ala Val Glu Ala Leu Leu Ser Ala Asp Ser Ala
145                 150                 155                 160

Ser Arg Lys Gln Glu Val Gln Ala Trp Asp Gly Glu Val Arg Gln Val
                165                 170                 175

Ser Lys His Ala Phe Ser Leu Lys Gln Leu Asp Asn Pro Ala Arg Ile
            180                 185                 190

Pro Pro Cys Gly Trp Lys Cys Ser Cys Asp Met Arg Glu Asn Leu
        195                 200                 205
```

-continued

```
Trp Leu Asn Leu Thr Asp Gly Ser Ile Leu Cys Gly Arg Arg Tyr Phe
    210                 215                 220

Asp Gly Ser Gly Gly Asn Asn His Ala Val Glu His Tyr Arg Glu Thr
225                 230                 235                 240

Gly Tyr Pro Leu Ala Val Lys Leu Gly Thr Ile Thr Pro Asp Gly Ala
                245                 250                 255

Asp Val Tyr Ser Tyr Asp Glu Asp Met Val Leu Asp Pro Ser Leu
                260                 265                 270

Ala Glu His Leu Ser His Phe Gly Ile Asp Met Leu Lys Met Gln Lys
                275                 280                 285

Thr Asp Lys Thr Met Thr Glu Leu Glu Ile Asp Met Asn Gln Arg Ile
290                 295                 300

Gly Glu Trp Glu Leu Ile Gln Glu Ser Gly Val Pro Leu Lys Pro Leu
305                 310                 315                 320

Phe Gly Pro Gly Tyr Thr Gly Ile Arg Asn Leu Gly Asn Ser Cys Tyr
                325                 330                 335

Leu Asn Ser Val Val Gln Val Leu Phe Ser Ile Pro Asp Phe Gln Arg
                340                 345                 350

Lys Tyr Val Asp Lys Leu Glu Lys Ile Phe Gln Asn Ala Pro Thr Asp
                355                 360                 365

Pro Thr Gln Asp Phe Ser Thr Gln Val Ala Lys Leu Gly His Gly Leu
370                 375                 380

Leu Ser Gly Glu Tyr Ser Lys Pro Val Pro Glu Ser Gly Asp Gly Glu
385                 390                 395                 400

Arg Val Pro Glu Gln Lys Glu Val Gln Asp Gly Ile Ala Pro Arg Met
                405                 410                 415

Phe Lys Ala Leu Ile Gly Lys Gly His Pro Glu Phe Ser Thr Asn Arg
                420                 425                 430

Gln Gln Asp Ala Gln Glu Phe Phe Leu His Leu Ile Asn Met Val Glu
                435                 440                 445

Arg Asn Cys Arg Ser Ser Glu Asn Pro Asn Glu Val Phe Arg Phe Leu
                450                 455                 460

Val Glu Glu Lys Ile Lys Cys Leu Ala Thr Glu Lys Val Lys Tyr Thr
465                 470                 475                 480

Gln Arg Val Asp Tyr Ile Met Gln Leu Pro Val Pro Met Asp Ala Ala
                485                 490                 495

Leu Asn Lys Glu Glu Leu Leu Glu Tyr Glu Lys Lys Arg Gln Ala
                500                 505                 510

Glu Glu Glu Lys Met Ala Leu Pro Glu Leu Val Arg Ala Gln Val Pro
                515                 520                 525

Phe Ser Ser Cys Leu Glu Ala Tyr Gly Ala Pro Glu Gln Val Asp Asp
530                 535                 540

Phe Trp Ser Thr Ala Leu Gln Ala Lys Ser Val Ala Val Lys Thr Thr
545                 550                 555                 560

Arg Phe Ala Ser Phe Pro Asp Tyr Leu Val Ile Gln Ile Lys Lys Phe
                565                 570                 575

Thr Phe Gly Leu Asp Trp Val Pro Lys Lys Leu Asp Val Ser Ile Glu
                580                 585                 590

Met Pro Glu Glu Leu Asp Ile Ser Gln Leu Arg Gly Thr Gly Leu Gln
                595                 600                 605

Pro Gly Glu Glu Leu Pro Asp Ile Ala Pro Pro Leu Val Thr Pro
610                 615                 620

Asp Glu Pro Lys Ala Pro Met Leu Asp Glu Ser Val Ile Ile Gln Leu
```

```
                625            630            635            640
        Val Glu Met Gly Phe Pro Met Asp Ala Cys Arg Lys Ala Val Tyr Tyr
                           645            650            655

Thr Gly Asn Ser Gly Ala Glu Ala Ala Met Asn Trp Val Met Ser His
                           660            665            670

Met Asp Asp Pro Asp Phe Ala Asn Pro Leu Ile Leu Pro Gly Ser Ser
                           675            680            685

Gly Pro Gly Ser Thr Ser Ala Ala Ala Asp Pro Pro Glu Asp Cys
                           690            695            700

Val Thr Thr Ile Val Ser Met Gly Phe Ser Arg Asp Gln Ala Leu Lys
        705            710            715            720

Ala Leu Arg Ala Thr Asn Asn Ser Leu Glu Arg Ala Val Asp Trp Ile
                           725            730            735

Phe Ser His Ile Asp Asp Leu Asp Ala Glu Ala Ala Met Asp Ile Ser
                           740            745            750

Glu Gly Arg Ser Ala Ala Asp Ser Ile Ser Glu Ser Val Pro Val Gly
                           755            760            765

Pro Lys Val Arg Asp Gly Pro Gly Lys Tyr Gln Leu Phe Ala Phe Ile
                           770            775            780

Ser His Met Gly Thr Ser Thr Met Cys Gly His Tyr Val Cys His Ile
        785            790            795            800

Lys Lys Glu Gly Arg Trp Val Ile Tyr Asn Asp Gln Lys Val Cys Ala
                           805            810            815

Ser Glu Lys Pro Pro Lys Asp Leu Gly Tyr Ile Tyr Phe Tyr Gln Arg
                           820            825            830

Val Ala Ser
                835

<210> SEQ ID NO 11
<211> LENGTH: 4221
<212> TYPE: DNA
<213> ORGANISM: Homo sapiens

<400> SEQUENCE: 11
atggacatgg tagagaatgc agatagtttg caggcacagg agcggaagga catacttatg      60
aagtatgaca agggacaccg agctgggctg ccagaggaca aggggcctga gcccgttgga     120
atcaacagca gcattgatcg ttttggcatt ttgcatgaga cggagctgcc tcctgtgact     180
gcacgggagg cgaagaaaat tcggcgggag atgacacgaa cgagcaagtg gatggaaatg     240
ctgggagaat gggagacata taagcacagt agcaaactca tagatcgagt gtacaaggga     300
attcccatga acatccgggg cccggtgtgg tcagtcctcc tgaacattca ggaaatcaag     360
ttgaaaaacc ccggaagata ccagatcatg aaggagaggg gcaagaggtc atctgaacac     420
atccaccaca tcgacctgga cgtgaggacg actctccgga accatgtctt ctttagggat     480
cgatatggag ccaagcagag ggaactattc tacatcctcc tggcctattc ggagtataac     540
ccggaggtgg gctactgcag ggacctgagc cacatcaccg ccttgttcct cctttatctg     600
cctgaggagg acgcattctg ggcactggtg cagctgctgg ccagtgagag cactccctg     660 ccaggattcc acagcccaaa tggtgggaca gtccaggggc tccaagacca acaggagcat     720
gtggtaccca gtcacaacc aagaccatg tggcatcagg acaaggaagg tctatgcggg     780
cagtgtgcct cgttaggctg ccttctccgg aacctgattg acgggatctc tctcgggctc     840
accctgcgcc tgtgggacgt gtatttggtg gaaggagaac aggtgttgat gccaataacc     900
```

-continued

```
agcattgctc ttaaggttca gcagaagcgc ctcatgaaga catccaggtg tggcctgtgg    960
gcacgtctgc ggaaccaatt cttcgatacc tgggccatga acgatgacac cgtgctcaag   1020
catcttaggg cctctacgaa gaaactaaca aggaagcaag gggacctgcc acccccagcc   1080
aaacgcgagc aagggtcctt ggcacccagg cctgtgccgg cttcacgtgg tgggaagacc   1140
ctctgcaagg ggtataggca ggcccctcca ggcccaccag cccagttcca gcggcccatt   1200
tgctcagctt ccccgccatg gcatctcgt ttttccacgc cctgtcctgg tggggctgtc    1260
cgggaagaca cgtaccctgt gggcactcag ggtgtgccca gcctggccct ggctcaggga   1320
ggacctcagg gttcctggag attcctggag tggaagtcaa tgccccggct cccaacggac   1380
ctggatatag ggggcccttg gttcccccat tatgattttg aatggagctg ctgggtccgt   1440
gccatatccc aggaggacca gctggccacc tgctggcagg ctgaacactg cggagaggtt   1500
cacaacaaag atatgagttg gcctgaggag atgtctttta cagcaaatag tagtaaaata   1560
gatagacaaa aggttcccac agaaaaggga gccacaggtc taagcaacct gggaaacaca   1620
tgcttcatga actcaagcat ccagtgcgtt agtaacacac agccactgac acagtatttt   1680
atctcaggga gacatcttta tgaactcaac aggacaaatc ccattggtat gaaggggcat   1740
atggctaaat gctatggtga tttagtgcag gaactctgga gtggaactca gaaagagtgtt   1800
gccccattaa agcttcggcg gaccatagca aaatatgctc ccaagtttga tgggtttcag   1860
caacaagact cccaagaact tctggctttt ctcttggatg tcttcatga agatctcaac    1920
cgagtccatg aaaagccata tgtggaactg aaggacagtg atggccgacc agactgggaa   1980
gtagctgcag aggcctggga caaccatcta agaagaaata gatcaattat tgtggatttg   2040
ttccatgggc agctaagatc tcaagtcaaa tgcaagacat gtgggcatat aagtgtccga   2100
tttgaccctt tcaattttt gtctttgcca ctaccaatgg acagttacat ggacttagaa    2160
ataacagtga ttaagttaga tggtactacc cctgtacggt atggactaag actgaatatg   2220
gatgaaaagt acacaggttt aaaaaaacag ctgagggatc tctgtggact taattcagaa   2280
caaatcctac tagcagaagt acatgattcc aacataaaga actttcctca ggataaccaa   2340
aaagtacaac tctcagtgag cggattttg tgtgcatttg aaattcctgt cccttcatct    2400
ccaatttcag cttctagtcc aacacaaata gatttctcct cttcaccatc tacaaatgga   2460
atgttcaccc taactaccaa tggggaccta cccaaaccaa tattcatccc caatggaatg   2520
ccaaacactg ttgtgccatg tggaactgag aagaacttca caaatggaat ggttaatggt   2580
cacatgccat ctcttcctga cagcccctt acaggttaca tcattgcagt ccaccgaaaa    2640
atgatgagga cagaactgta tttcctgtca cctcaggaga atcgccccag cctcttggga   2700
atgccattga ttgttccatg cactgtgcat acccggaaga aagacctata tgatgcggtt   2760
tggattcaag tatcctggtt agcaagacca ctcccacctc aggaagctag tattcatgcc   2820
caggatcgtg ataactgtat gggctatcaa tatccattca ctctacgagt gtgcagaaa    2880
gatgggaact cctgtgcttg gtgcccacag tatagatttt gcagaggctg taaaattgat   2940
tgtggggaag acagagcttt cattggaaat gcctatattg ctgtggattg cacccccaca   3000
gccccttcacc ttcgctatca acatcccag gaaaggggttg tagataagca tgagagtgtg   3060
gagcagagtc ggcgagcgca agccgagccc atcaacctgg acagctgtct ccgtgctttc   3120
accagtgagg aagagctagg ggaaagtgag atgtactact gttccaagtg taagacccac   3180
tgcttagcaa caaagaagct ggatctctgg aggcttccac ccttcctgat tattcacctt   3240
aagcgatttc aatttgtaaa tgatcagtgg ataaaatcac agaaaattgt cagatttctt   3300
```

```
cgggaaagtt ttgatccgag tgcttttttg gtaccacgag acccggccct ctgccagcat    3360
aaaccactca caccccaggg ggatgagctc tccaagccca ggattctggc aagagaggtg    3420
aagaaagtgg atgcgcagag ttcggctgga aaagaggaca tgctcctaag caaaagccca    3480
tcctcactca gcgctaacat cagcagcagc ccaaaaggtt ctccttcttc atcaagaaaa    3540
agtggaacca gctgtccctc agcaaaaaac agcagcccta atagcagccc acggactttg    3600
gggaggagca aagggaggct ccggctgccc cagattggca gcaaaaataa gccgtcaagt    3660
agtaagaaga acttggatgc cagcaaagag aatggggctg ggcagatctg tgagctggct    3720
gacgccttga gccgagggca tatgcggggg ggcagccaac cagagctggt cactcctcag    3780
gaccatgagg tagctttggc caatggattc ctttatgagc atgaagcatg tggcaatggc    3840
tgtggcgatg gctacagcaa tggtcagctt ggaaaccaca gtgaagaaga cagcactgat    3900
gaccaaagag aagacactca tattaagcct atttataatc tatatgcaat tcatgccat    3960 tcaggaattc tgagtggggg ccattacatc acttatgcca aaaacccaaa ctgcaagtgg    4020
tactgttata atgacagcag ctgtgaggaa cttcaccctg atgaaattga caccgactct    4080
gcctacattc ttttctatga gcagcagggg atagactacg cacaatttct gccaaagatt    4140
gatggcaaaa agatggcaga cacaagcagt acggatgaag actctgagtc tgattacgaa    4200
aagtactcta tgttacagta a                                             4221

<210> SEQ ID NO 12
<211> LENGTH: 1406
<212> TYPE: PRT
<213> ORGANISM: Homo sapiens

<400> SEQUENCE: 12

Met Asp Met Val Glu Asn Ala Asp Ser Leu Gln Ala Gln Glu Arg Lys
1               5                   10                  15

Asp Ile Leu Met Lys Tyr Asp Lys Gly His Arg Ala Gly Leu Pro Glu
            20                  25                  30

Asp Lys Gly Pro Glu Pro Val Gly Ile Asn Ser Ser Ile Asp Arg Phe
        35                  40                  45

Gly Ile Leu His Glu Thr Glu Leu Pro Pro Val Thr Ala Arg Glu Ala
    50                  55                  60

Lys Lys Ile Arg Arg Glu Met Thr Arg Thr Ser Lys Trp Met Glu Met
65                  70                  75                  80

Leu Gly Glu Trp Glu Thr Tyr Lys His Ser Ser Lys Leu Ile Asp Arg
                85                  90                  95

Val Tyr Lys Gly Ile Pro Met Asn Ile Arg Gly Pro Val Trp Ser Val
            100                 105                 110

Leu Leu Asn Ile Gln Glu Ile Lys Leu Lys Asn Pro Gly Arg Tyr Gln
        115                 120                 125

Ile Met Lys Glu Arg Gly Lys Arg Ser Ser Glu His Ile His His Ile
    130                 135                 140

Asp Leu Asp Val Arg Thr Thr Leu Arg Asn His Val Phe Phe Arg Asp
145                 150                 155                 160

Arg Tyr Gly Ala Lys Gln Arg Glu Leu Phe Tyr Ile Leu Leu Ala Tyr
                165                 170                 175

Ser Glu Tyr Asn Pro Glu Val Gly Tyr Cys Arg Asp Leu Ser His Ile
            180                 185                 190

Thr Ala Leu Phe Leu Leu Tyr Leu Pro Glu Glu Asp Ala Phe Trp Ala
        195                 200                 205
```

-continued

Leu Val Gln Leu Leu Ala Ser Glu Arg His Ser Leu Pro Gly Phe His
    210                 215                 220

Ser Pro Asn Gly Gly Thr Val Gln Gly Leu Gln Asp Gln Gln Glu His
225                 230                 235                 240

Val Val Pro Lys Ser Gln Pro Lys Thr Met Trp His Gln Asp Lys Glu
                245                 250                 255

Gly Leu Cys Gly Gln Cys Ala Ser Leu Gly Cys Leu Leu Arg Asn Leu
            260                 265                 270

Ile Asp Gly Ile Ser Leu Gly Leu Thr Leu Arg Leu Trp Asp Val Tyr
        275                 280                 285

Leu Val Glu Gly Glu Gln Val Leu Met Pro Ile Thr Ser Ile Ala Leu
    290                 295                 300

Lys Val Gln Gln Lys Arg Leu Met Lys Thr Ser Arg Cys Gly Leu Trp
305                 310                 315                 320

Ala Arg Leu Arg Asn Gln Phe Phe Asp Thr Trp Ala Met Asn Asp Asp
                325                 330                 335

Thr Val Leu Lys His Leu Arg Ala Ser Thr Lys Lys Leu Thr Arg Lys
            340                 345                 350

Gln Gly Asp Leu Pro Pro Ala Lys Arg Glu Gln Gly Ser Leu Ala
        355                 360                 365

Pro Arg Pro Val Pro Ala Ser Arg Gly Gly Lys Thr Leu Cys Lys Gly
    370                 375                 380

Tyr Arg Gln Ala Pro Pro Gly Pro Pro Ala Gln Phe Gln Arg Pro Ile
385                 390                 395                 400

Cys Ser Ala Ser Pro Pro Trp Ala Ser Arg Phe Ser Thr Pro Cys Pro
                405                 410                 415

Gly Gly Ala Val Arg Glu Asp Thr Tyr Pro Val Gly Thr Gln Gly Val
            420                 425                 430

Pro Ser Leu Ala Leu Ala Gln Gly Gly Pro Gln Gly Ser Trp Arg Phe
        435                 440                 445

Leu Glu Trp Lys Ser Met Pro Arg Leu Pro Thr Asp Leu Asp Ile Gly
    450                 455                 460

Gly Pro Trp Phe Pro His Tyr Asp Phe Glu Trp Ser Cys Trp Val Arg
465                 470                 475                 480

Ala Ile Ser Gln Glu Asp Gln Leu Ala Thr Cys Trp Gln Ala Glu His
                485                 490                 495

Cys Gly Glu Val His Asn Lys Asp Met Ser Trp Pro Glu Glu Met Ser
            500                 505                 510

Phe Thr Ala Asn Ser Ser Lys Ile Asp Arg Gln Lys Val Pro Thr Glu
        515                 520                 525

Lys Gly Ala Thr Gly Leu Ser Asn Leu Gly Asn Thr Cys Phe Met Asn
    530                 535                 540

Ser Ser Ile Gln Cys Val Ser Asn Thr Gln Pro Leu Thr Gln Tyr Phe
545                 550                 555                 560

Ile Ser Gly Arg His Leu Tyr Glu Leu Asn Arg Thr Asn Pro Ile Gly
                565                 570                 575

Met Lys Gly His Met Ala Lys Cys Tyr Gly Asp Leu Val Gln Glu Leu
            580                 585                 590

Trp Ser Gly Thr Gln Lys Ser Val Ala Pro Leu Lys Leu Arg Arg Thr
        595                 600                 605

Ile Ala Lys Tyr Ala Pro Lys Phe Asp Gly Phe Gln Gln Gln Asp Ser
    610                 615                 620

```
Gln Glu Leu Leu Ala Phe Leu Leu Asp Gly Leu His Glu Asp Leu Asn
625                 630                 635                 640

Arg Val His Glu Lys Pro Tyr Val Glu Leu Lys Asp Ser Asp Gly Arg
            645                 650                 655

Pro Asp Trp Glu Val Ala Ala Glu Ala Trp Asp Asn His Leu Arg Arg
            660                 665                 670

Asn Arg Ser Ile Ile Val Asp Leu Phe His Gly Gln Leu Arg Ser Gln
            675                 680                 685

Val Lys Cys Lys Thr Cys Gly His Ile Ser Val Arg Phe Asp Pro Phe
690                 695                 700

Asn Phe Leu Ser Leu Pro Leu Pro Met Asp Ser Tyr Met Asp Leu Glu
705                 710                 715                 720

Ile Thr Val Ile Lys Leu Asp Gly Thr Thr Pro Val Arg Tyr Gly Leu
            725                 730                 735

Arg Leu Asn Met Asp Glu Lys Tyr Thr Gly Leu Lys Lys Gln Leu Arg
            740                 745                 750

Asp Leu Cys Gly Leu Asn Ser Glu Gln Ile Leu Leu Ala Glu Val His
            755                 760                 765

Asp Ser Asn Ile Lys Asn Phe Pro Gln Asp Asn Gln Lys Val Gln Leu
770                 775                 780

Ser Val Ser Gly Phe Leu Cys Ala Phe Glu Ile Pro Val Pro Ser Ser
785                 790                 795                 800

Pro Ile Ser Ala Ser Ser Pro Thr Gln Ile Asp Phe Ser Ser Ser Pro
            805                 810                 815

Ser Thr Asn Gly Met Phe Thr Leu Thr Thr Asn Gly Asp Leu Pro Lys
            820                 825                 830

Pro Ile Phe Ile Pro Asn Gly Met Pro Asn Thr Val Val Pro Cys Gly
            835                 840                 845

Thr Glu Lys Asn Phe Thr Asn Gly Met Val Asn Gly His Met Pro Ser
850                 855                 860

Leu Pro Asp Ser Pro Phe Thr Gly Tyr Ile Ile Ala Val His Arg Lys
865                 870                 875                 880

Met Met Arg Thr Glu Leu Tyr Phe Leu Ser Pro Gln Glu Asn Arg Pro
            885                 890                 895

Ser Leu Phe Gly Met Pro Leu Ile Val Pro Cys Thr Val His Thr Arg
            900                 905                 910

Lys Lys Asp Leu Tyr Asp Ala Val Trp Ile Gln Val Ser Trp Leu Ala
            915                 920                 925

Arg Pro Leu Pro Pro Gln Glu Ala Ser Ile His Ala Gln Asp Arg Asp
            930                 935                 940

Asn Cys Met Gly Tyr Gln Tyr Pro Phe Thr Leu Arg Val Val Gln Lys
945                 950                 955                 960

Asp Gly Asn Ser Cys Ala Trp Cys Pro Gln Tyr Arg Phe Cys Arg Gly
            965                 970                 975

Cys Lys Ile Asp Cys Gly Glu Asp Arg Ala Phe Ile Gly Asn Ala Tyr
            980                 985                 990

Ile Ala Val Asp Trp His Pro Thr Ala Leu His Leu Arg Tyr Gln Thr
            995                 1000                1005

Ser Gln Glu Arg Val Val Asp Lys His Glu Ser Val Glu Gln Ser Arg
            1010                1015                1020

Arg Ala Gln Ala Glu Pro Ile Asn Leu Asp Ser Cys Leu Arg Ala Phe
1025                1030                1035                1040

Thr Ser Glu Glu Glu Leu Gly Glu Ser Glu Met Tyr Tyr Cys Ser Lys
```

```
                        1045                1050                1055
Cys Lys Thr His Cys Leu Ala Thr Lys Lys Leu Asp Leu Trp Arg Leu
            1060                1065                1070

Pro Pro Phe Leu Ile Ile His Leu Lys Arg Phe Gln Phe Val Asn Asp
        1075                1080                1085

Gln Trp Ile Lys Ser Gln Lys Ile Val Arg Phe Leu Arg Glu Ser Phe
    1090                1095                1100

Asp Pro Ser Ala Phe Leu Val Pro Arg Asp Pro Ala Leu Cys Gln His
1105                1110                1115                1120

Lys Pro Leu Thr Pro Gln Gly Asp Glu Leu Ser Lys Pro Arg Ile Leu
            1125                1130                1135

Ala Arg Glu Val Lys Lys Val Asp Ala Gln Ser Ser Ala Gly Lys Glu
        1140                1145                1150

Asp Met Leu Leu Ser Lys Ser Pro Ser Ser Leu Ser Ala Asn Ile Ser
    1155                1160                1165

Ser Ser Pro Lys Gly Ser Pro Ser Ser Arg Lys Ser Gly Thr Ser
1170                1175                1180

Cys Pro Ser Ser Lys Asn Ser Ser Pro Asn Ser Ser Pro Arg Thr Leu
1185                1190                1195                1200

Gly Arg Ser Lys Gly Arg Leu Arg Leu Pro Gln Ile Gly Ser Lys Asn
            1205                1210                1215

Lys Pro Ser Ser Lys Lys Asn Leu Asp Ala Ser Lys Glu Asn Gly
        1220                1225                1230

Ala Gly Gln Ile Cys Glu Leu Ala Asp Ala Leu Ser Arg Gly His Met
    1235                1240                1245

Arg Gly Gly Ser Gln Pro Glu Leu Val Thr Pro Gln Asp His Glu Val
1250                1255                1260

Ala Leu Ala Asn Gly Phe Leu Tyr Glu His Glu Ala Cys Gly Asn Gly
1265                1270                1275                1280

Cys Gly Asp Gly Tyr Ser Asn Gly Gln Leu Gly Asn His Ser Glu Glu
            1285                1290                1295

Asp Ser Thr Asp Asp Gln Arg Glu Asp Thr His Ile Lys Pro Ile Tyr
        1300                1305                1310

Asn Leu Tyr Ala Ile Ser Cys His Ser Gly Ile Leu Ser Gly Gly His
    1315                1320                1325

Tyr Ile Thr Tyr Ala Lys Asn Pro Asn Cys Lys Trp Tyr Cys Tyr Asn
1330                1335                1340

Asp Ser Ser Cys Glu Glu Leu His Pro Asp Glu Ile Asp Thr Asp Ser
1345                1350                1355                1360

Ala Tyr Ile Leu Phe Tyr Glu Gln Gln Gly Ile Asp Tyr Ala Gln Phe
            1365                1370                1375

Leu Pro Lys Ile Asp Gly Lys Lys Met Ala Asp Thr Ser Thr Asp
        1380                1385                1390

Glu Asp Ser Glu Ser Asp Tyr Glu Lys Tyr Ser Met Leu Gln
    1395                1400                1405

<210> SEQ ID NO 13
<211> LENGTH: 3309
<212> TYPE: DNA
<213> ORGANISM: Homo sapiens

<400> SEQUENCE: 13
atgaaccacc agcagcagca gcagcagcag aaagcgggcg agcagcagtt gagcgagccc      60
gaggacatgg agatggaagc gggagataca gatgacccac caagaattac tcagaaccct    120
```

```
gtgatcaatg ggaatgtggc cctgagtgat ggacacaaca ccgcggagga ggacatggag      180
gatgacacca gttggcgctc cgaggcaacc tttcagttca ctgtggagcg cttcagcaga      240
ctgagtgagt cggtccttag ccctccgtgt tttgtgcgaa atctgccatg aagattatg      300 gtgatgccac gcttttatcc agacagacca caccaaaaaa gcgtaggatt ctttctccag      360
tgcaatgctg aatctgattc cacgtcatgg tcttgccatg cacaagcagt gctgaagata      420
ataaattaca gagatgatga aaagtcgttc agtcgtcgta ttagtcattt gttcttccat      480
aaagaaaatg attggggatt ttccaatttt atggcctgga gtgaagtgac cgatcctgag      540
aaaggattta tagatgatga caaagttacc tttgaagtct tgtacaggc ggatgctccc       600 catggagttg cgtgggattc aaagaagcac acaggctacg tcggcttaaa gaatcaggga      660
gcgacttgtt acatgaacag cctgctacag acgttatttt tcacgaatca gctacgaaag      720
gctgtgtaca tgatgccaac cgagggggat gattcgtcta aaagcgtccc tttagcatta      780
caaagagtgt tctatgaatt acagcatagt gataaacctg taggaacaaa aaagttaaca      840
aagtcatttg ggtgggaaac tttagatagc ttcatgcaac atgatgttca ggagctttgt      900
cgagtgttgc tcgataatgt ggaaaataag atgaaaggca cctgtgtaga gggcaccata      960
cccaaattat tccgcggcaa aatggtgtcc tatatccagt gtaaagaagt agactatcgg     1020
tctgatagaa gagaagatta ttatgatatc cagctaagta tcaaaggaaa gaaaatata      1080 tttgaatcat ttgtggatta tgtggcagta gaacagctcg atggggacaa taaatacgac     1140
gctggggaac atggcttaca ggaagcagag aaaggtgtga aattcctaac attgccacca     1200
gtgttacatc tacaactgat gagatttatg tatgaccctc agacggacca aaatatcaag     1260
atcaatgata ggtttgaatt cccagagcag ttaccacttg atgaattttt gcaaaaaaca     1320
gatcctaagg accctgcaaa ttatattctt catgcagtcc tggttcatag tggagataat     1380
catggtggac attatgtggt ttatctaaac cccaaagggg atggcaaatg tgtaaatttt     1440
gatgacgacg tggtgtcaag gtgtactaaa gaggaagcaa ttgagcacaa ttatgggggt     1500
cacgatgacg acctgtctgt tcgacactgc actaatgctt acatgttagt ctacatcagg     1560
gaatcaaaac tgagtgaagt tttacaggcg gtcaccgacc atgatattcc tcagcagttg     1620
gtggagcgat acaagaaga gaaaaggatc gaggctcaga agcggaagga gcggcaggaa     1680
gcccatctct atatgcaagt gcagatagtc gcagaggacc agttttgtgg ccaccaaggg     1740
aatgacatgt acgatgaaga aaaagtgaaa tacactgtgt tcaaagtatt gaagaactcc     1800
tcgcttgctg agtttgttca gagcctctct cagaccatgg gatttccaca agatcaaatt     1860
cgattgtggc ccatgcaagc aaggagtaat ggaacaaaac gaccagcaat gttagataat     1920
gaagccgacg gcaataaaac aatgattgag ctcagtgata atgaaaaccc cttggacaata     1980 ttcctggaaa cagttgatcc cgagctggct gctagtggag cgaccttacc caagtttgat     2040
aaagatcatg atgtaatgtt attttttgaag atgtatgatc ccaaaacgcg gagcttgaat     2100
tactgtgggc atatctacac accaatatcc tgtaaaatac gtgacttgct cccagttatg     2160
tgtgacagag caggatttat tcaagatact agccttatcc tctatgagga agttaaaccg     2220
aatttaacag agagaattca ggactatgac gtgtctcttg ataaagccct tgatgaacta     2280
atggatggtg acatcatagt atttcagaag gatgaccctg aaaatgataa cagtgaatta     2340
cccaccgcaa aggagtattt ccgagatctc taccaccgcg ttgatgtcat tttctgtgat     2400
aaaacaatcc ctaatgatcc tggatttgtg gttacgttat caaatagaat gaattatttt     2460
```

-continued

```
caggttgcaa agacagttgc acagaggctc aacacagatc caatgttgct gcagttttc   2520 aagtctcaag gttataggga tggcccaggt aatcctctta gacataatta tgaaggtact   2580
ttaagagatc ttctacagtt cttcaagcct agacaaccta agaaacttta ctatcagcag   2640
cttaagatga aaatcacaga ctttgagaac aggcgaagtt ttaaatgtat atggttaaac   2700
agccaattta gggaagagga ataacacta tatccagaca agcatgggtg tgtccgggac   2760
ctgttagaag aatgtaaaaa ggccgtggag cttggggaga aagcatcagg gaaacttagg   2820
ctgctagaaa ttgtaagcta caaatcatt ggtgttcatc aagaagatga actattagaa    2880
tgtttatctc ctgcaacgag ccggacgttt cgaatagagg aaatccctt ggaccaggtg    2940 gacatagaca aagagaatga gatgcttgtc acagtggcgc atttccacaa agaggtcttc   3000
ggaacgttcg gaatcccgtt tttgctgagg atacaccagg gcgagcattt tcgagaagtg   3060
atgaagcgaa tccagagcct gctggacatc aggagaagg agtttgagaa gtttaaattt    3120
gcaattgtaa tgatgggccg acaccagtac ataaatgaag acgagtatga agtaaatttg   3180
aaagactttg agccacagcc cggtaatatg tctcatcctc ggccttggct agggctcgac   3240
cacttcaaca aagccccaaa gaggagtcgc tacacttacc ttgaaaaggc cattaaaatc   3300
cataactga                                                          3309
```

<210> SEQ ID NO 14
<211> LENGTH: 1102
<212> TYPE: PRT
<213> ORGANISM: Homo sapiens

<400> SEQUENCE: 14

```
Met Asn His Gln Gln Gln Gln Gln Gln Lys Ala Gly Glu Gln Gln
1               5                   10                  15

Leu Ser Glu Pro Glu Asp Met Glu Met Glu Ala Gly Asp Thr Asp Asp
            20                  25                  30

Pro Pro Arg Ile Thr Gln Asn Pro Val Ile Asn Gly Asn Val Ala Leu
        35                  40                  45

Ser Asp Gly His Asn Thr Ala Glu Glu Asp Met Glu Asp Asp Thr Ser
    50                  55                  60

Trp Arg Ser Glu Ala Thr Phe Gln Phe Thr Val Glu Arg Phe Ser Arg
65                  70                  75                  80

Leu Ser Glu Ser Val Leu Ser Pro Pro Cys Phe Val Arg Asn Leu Pro
                85                  90                  95

Trp Lys Ile Met Val Met Pro Arg Phe Tyr Pro Asp Arg Pro His Gln
            100                 105                 110

Lys Ser Val Gly Phe Phe Leu Gln Cys Asn Ala Glu Ser Asp Ser Thr
        115                 120                 125

Ser Trp Ser Cys His Ala Gln Ala Val Leu Lys Ile Ile Asn Tyr Arg
    130                 135                 140

Asp Asp Glu Lys Ser Phe Ser Arg Arg Ile Ser His Leu Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Lys Val Thr Phe Glu
            180                 185                 190

Val Phe Val Gln Ala Asp Ala Pro His Gly Val Ala Trp Asp Ser Lys
        195                 200                 205

Lys His Thr Gly Tyr Val Gly Leu Lys Asn Gln Gly Ala Thr Cys Tyr
    210                 215                 220
```

```
Met Asn Ser Leu Leu Gln Thr Leu Phe Phe Thr Asn Gln Leu Arg Lys
225                 230                 235                 240

Ala Val Tyr Met Met Pro Thr Glu Gly Asp Asp Ser Ser Lys Ser Val
            245                 250                 255

Pro Leu Ala Leu Gln Arg Val Phe Tyr Glu Leu Gln His Ser Asp Lys
        260                 265                 270

Pro Val Gly Thr Lys Lys Leu Thr Lys Ser Phe Gly Trp Glu Thr Leu
    275                 280                 285

Asp Ser Phe Met Gln His Asp Val Gln Glu Leu Cys Arg Val Leu Leu
290                 295                 300

Asp Asn Val Glu Asn Lys Met Lys Gly Thr Cys Val Glu Gly Thr Ile
305                 310                 315                 320

Pro Lys Leu Phe Arg Gly Lys Met Val Ser Tyr Ile Gln Cys Lys Glu
                325                 330                 335

Val Asp Tyr Arg Ser Asp Arg Arg Glu Asp Tyr Tyr Asp Ile Gln Leu
            340                 345                 350

Ser Ile Lys Gly Lys Lys Asn Ile Phe Glu Ser Phe Val Asp Tyr Val
        355                 360                 365

Ala Val Glu Gln Leu Asp Gly Asp Asn Lys Tyr Asp Ala Gly Glu His
    370                 375                 380

Gly Leu Gln Glu Ala Glu Lys Gly Val Lys Phe Leu Thr Leu Pro Pro
385                 390                 395                 400

Val Leu His Leu Gln Leu Met Arg Phe Met Tyr Asp Pro Gln Thr Asp
                405                 410                 415

Gln Asn Ile Lys Ile Asn Asp Arg Phe Glu Phe Pro Glu Gln Leu Pro
            420                 425                 430

Leu Asp Glu Phe Leu Gln Lys Thr Asp Pro Lys Asp Pro Ala Asn Tyr
        435                 440                 445

Ile Leu His Ala Val Leu Val His Ser Gly Asp Asn His Gly Gly His
    450                 455                 460

Tyr Val Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                485                 490                 495

Asn Tyr Gly Gly His Asp Asp Leu Ser Val Arg His Cys Thr Asn
            500                 505                 510

Ala Tyr Met Leu Val Tyr Ile Arg Glu Ser Lys Leu Ser Glu Val Leu
    515                 520                 525

Gln Ala Val Thr Asp His Asp Ile Pro Gln Gln Leu Val Glu Arg Leu
530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
                565                 570                 575

Gly His Gln Gly Asn Asp Met Tyr Asp Glu Glu Lys Val Lys Tyr Thr
            580                 585                 590

Val Phe Lys Val Leu Lys Asn Ser Ser Leu Ala Glu Phe Val Gln Ser
        595                 600                 605

Leu Ser Gln Thr Met Gly Phe Pro Gln Asp Gln Ile Arg Leu Trp Pro
    610                 615                 620

Met Gln Ala Arg Ser Asn Gly Thr Lys Arg Pro Ala Met Leu Asp Asn
625                 630                 635                 640
```

-continued

Glu Ala Asp Gly Asn Lys Thr Met Ile Glu Leu Ser Asp Asn Glu Asn
            645                 650                 655

Pro Trp Thr Ile Phe Leu Glu Thr Val Asp Pro Glu Leu Ala Ala Ser
        660                 665                 670

Gly Ala Thr Leu Pro Lys Phe Asp Lys Asp His Asp Val Met Leu Phe
        675                 680                 685

Leu Lys Met Tyr Asp Pro Lys Thr Arg Ser Leu Asn Tyr Cys Gly His
        690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
                725                 730                 735

Glu Val Lys Pro Asn Leu Thr Glu Arg Ile Gln Asp Tyr Asp Val Ser
            740                 745                 750

Leu Asp Lys Ala Leu Asp Glu Leu Met Asp Gly Asp Ile Ile Val Phe
        755                 760                 765

Gln Lys Asp Asp Pro Glu Asn Asp Asn Ser Glu Leu Pro Thr Ala Lys
        770                 775                 780

Glu Tyr Phe Arg Asp Leu Tyr His Arg Val Asp Val Ile Phe Cys Asp
785                 790                 795                 800

Lys Thr Ile Pro Asn Asp Pro Gly Phe Val Val Thr Leu Ser Asn Arg
                805                 810                 815

Met Asn Tyr Phe Gln Val Ala Lys Thr Val Ala Gln Arg Leu Asn Thr
            820                 825                 830

Asp Pro Met Leu Leu Gln Phe Phe Lys Ser Gln Gly Tyr Arg Asp Gly
        835                 840                 845

Pro Gly Asn Pro Leu Arg His Asn Tyr Glu Gly Thr Leu Arg Asp Leu
        850                 855                 860

Leu Gln Phe Phe Lys Pro Arg Gln Pro Lys Lys Leu Tyr Tyr Gln Gln
865                 870                 875                 880

Leu Lys Met Lys Ile Thr Asp Phe Glu Asn Arg Arg Ser Phe Lys Cys
                885                 890                 895

Ile Trp Leu Asn Ser Gln Phe Arg Glu Glu Ile Thr Leu Tyr Pro
            900                 905                 910

Asp Lys His Gly Cys Val Arg Asp Leu Leu Glu Glu Cys Lys Lys Ala
        915                 920                 925

Val Glu Leu Gly Glu Lys Ala Ser Gly Lys Leu Arg Leu Leu Glu Ile
        930                 935                 940

Val Ser Tyr Lys Ile Ile Gly Val His Gln Glu Asp Glu Leu Leu Glu
945                 950                 955                 960

Cys Leu Ser Pro Ala Thr Ser Arg Thr Phe Arg Ile Glu Glu Ile Pro
                965                 970                 975

Leu Asp Gln Val Asp Ile Asp Lys Glu Asn Glu Met Leu Val Thr Val
            980                 985                 990

Ala His Phe His Lys Glu Val Phe Gly Thr Phe Gly Ile Pro Phe Leu
        995                 1000                1005

Leu Arg Ile His Gln Gly Glu His Phe Arg Glu Val Met Lys Arg Ile
        1010                1015                1020

Gln Ser Leu Leu Asp Ile Gln Glu Lys Glu Phe Glu Lys Phe Lys Phe
1025                1030                1035                1040

Ala Ile Val Met Met Gly Arg His Gln Tyr Ile Asn Glu Asp Glu Tyr
                1045                1050                1055

Glu Val Asn Leu Lys Asp Phe Glu Pro Gln Pro Gly Asn Met Ser His

```
                   1060               1065               1070
Pro Arg Pro Trp Leu Gly Leu Asp His Phe Asn Lys Ala Pro Lys Arg
        1075               1080               1085

Ser Arg Tyr Thr Tyr Leu Glu Lys Ala Ile Lys Ile His Asn
        1090               1095               1100

<210> SEQ ID NO 15
<211> LENGTH: 3357
<212> TYPE: DNA
<213> ORGANISM: Homo sapiens

<400> SEQUENCE: 15
atgcctgctg tggcttcagt tcctaaagaa ctctacctca gttcttcact aaaagacctt      60
aataagaaga cagaagttaa accagagaaa ataagcacta gagttatgt gcacagtgcc     120 ctgaagatct ttaagacagc agaagaatgc agattagatc gtgatgagga aagggcctat     180
gtactatata tgaaatacgt gactgtttat aatcttatca aaaaaagacc tgatttcaag     240
caacagcagg attatttcca ttcaatactt ggacctggaa catcaaaaaa agctgtcgaa     300
gaagctgaaa gactctctga aagccttaaa ttaagatatg aagaagctga agtccggaaa     360
aaacttgagg aaaaagacag gcaggaggaa gcacagcggc tacaacaaaa aaggcaggaa     420
acaggaagag aggatggtgg cacattggct aaaggctctt tggagaatgt tttggattcc     480
aaagacaaaa cccaaaagag caatggtgaa agaatgaaa atgtgagac aaagagaaa     540 ggagcaatca cagcaaagga actatacaca atgatgacgg ataaaaacat cagcttgatt     600
ataatggatg ctcgaagaat gcaggattat caggattcct gtattttaca ttctctcagt     660
gttcctgaag aagccatcag tccaggagtc actgctagtt ggattgaagc acacctgcca     720
gatgattcta agacacatg gaagaagagg gggaatgtgg agtatgtggt acttcttgac     780
tggtttagtt ctgccaaaga tttacagatt ggaacaactc tccggagtct gaaagatgca     840
cttttcaagt gggaaagtaa aactgtcctg cgcaatgagc ctttggtttt agagggaggc     900
tatgaaaact ggctcctttg ttatccccag tatacaacaa atgctaaggt cactccaccc     960
ccacgacgcc agaatgaaga ggtgtctatc tcattggatt ttacttatcc ctcattggaa    1020
gaatcaattc cttctaaacc tgctgcccag acgccacctg catctataga agtagatgaa    1080
aatatagaat tgataagtgg tcaaaatgag agaatgggac cactgaatat atcaactcca    1140
gttgaaccag ttgctgcttc taaatctgat gtttcaccca taattcagcc agtgcctagt    1200
ataaagaatg ttccacagat tgatcgtact aaaaaaaccag cagtcaaatt gcctgaagag    1260
catagaataa aatctgaaag tacaaaccat gagcaacaat ctccctcagag tggaaaagtt    1320 attcctgatc gttccaccaa gccagtagtt ttttctccaa ctctcatgtt aacagatgaa    1380
gaaaaggctc gtattcatgc agaaactgct cttctaatgg aaaaaaacaa acaagaaaaa    1440
gaacttcggg aaaggcagca agaggaacag aaagagaaac tgaggaagga agaacaagaa    1500
caaaaagcca aaagaaaca agaagctgaa gaaaatgaaa ttacagagaa gcaacaaaaa    1560 gcaaagaag aaatggagaa gaaagaaagt gaacaggcca agaagaaga taagaaaacc    1620 tcagcaaaga ggggcaaaga aataacagga gtaaaaagac aaagtaaaag tgaacatgaa    1680
acttctgatg ccaagaaatc tgtagaagat aggggggaaaa ggtgtccaac cccagaaata    1740
cagaaaaagt caacaggaga tgtgcccat acatctgtga caggggattc aggttcaggc    1800
aagccattta gattaaaagg acaaccgaaa agtggaattc taaggacagg aacttttaga    1860
gaggatacag acgataccga aagaaatgaaa gctcaacgag aacctttgac aagagcacga    1920
```

-continued

```
agtgaagaaa tggggaggat cgtaccagga ctgccttcag gctgggccaa gtttcttgac    1980
ccaatcactg gaacctttcg ttattatcat tcacccacca acactgttca tatgtaccca    2040
ccggaaatgg ctccttcatc tgcacctcct tccaccccctc caactcataa agccaagcca   2100
cagattcctg ctgagcggga tagggaacct tccaaactga agcgctccta ctcctcccca    2160
gatataaccc aggctattca agaggaagag aagaggaagc caacagtaac tccaacagtt    2220
aatcgggaaa acaagccaac atgttatcct aaagctgaga tctcaaggct ttctgcttct    2280
cagattcgga acctcaatcc tgttttgga ggttctggac cagctcttac tggacttcgt     2340
aacttaggaa atacttgtta tatgaactca atattgcagt gcctatgtaa cgctccacat    2400
ttggctgatt atttcaaccg aaactgttat caggatgata ttaacaggtc aaatttgttg    2460
gggcataaag gtgaagtggc agaagaattt ggtataatca tgaaagccct gtggacagga    2520
cagtatagat atatcagtcc aaaggacttt aaaatcacca ttgggaagat caatgaccag    2580
tttgcaggat acagtcagca agattcacaa gaattgcttc tgttcctaat ggatggtctc    2640
catgaagatc taaataaagc tgataatcgg aagagatata agaagaaaa taatgatcat      2700
ctcgatgact ttaaagctgc agaacatgcc tggcagaaac acaagcagct caatgagtct    2760
attattgttg cacttttca gggtcaattc aaatctacag tacagtgcct cacatgtcac     2820
aaaaagtcta ggacatttga ggccttcatg tatttgtctc taccactagc atccacaagt    2880
aaatgtacat tacaggattg ccttagatta ttttccaaag aagaaaaact cacagataac    2940
aacagatttt actgcagtca ttgcagagct cgacgggatt ctctaaaaaa gatagaaatc    3000
tggaagttac cacctgtgct tttagtgcat ctgaaacgtt tttcctacga tggcaggtgg    3060
aaacaaaaat tacagacatc tgtggacttc ccgttagaaa atcttgactt gtcacagtat    3120
gttattggtc caaagaacaa tttgaagaaa tataatttgt tttctgtttc aaatcactac    3180
ggtgggctgg atggaggcca ctacacagcc tattgtaaaa atgcagcaag acaacggtgg    3240
tttaagtttg atgatcatga agtttctgat atctccgttt cttctgtgaa atcttcagca    3300
gcttatatcc tcttttatac ttcattggga ccacgagtaa ctgatgtagc cacataa       3357
```

<210> SEQ ID NO 16
<211> LENGTH: 1118
<212> TYPE: PRT
<213> ORGANISM: Homo sapiens

<400> SEQUENCE: 16

```
Met Pro Ala Val Ala Ser Val Pro Lys Glu Leu Tyr Leu Ser Ser
1               5                   10                  15

Leu Lys Asp Leu Asn Lys Lys Thr Glu Val Lys Pro Glu Lys Ile Ser
                20                  25                  30

Thr Lys Ser Tyr Val His Ser Ala Leu Lys Ile Phe Lys Thr Ala Glu
            35                  40                  45

Glu Cys Arg Leu Asp Arg Asp Glu Glu Arg Ala Tyr Val Leu Tyr Met
        50                  55                  60

Lys Tyr Val Thr Val Tyr Asn Leu Ile Lys Lys Arg Pro Asp Phe Lys
65                  70                  75                  80

Gln Gln Gln Asp Tyr Phe His Ser Ile Leu Gly Pro Gly Asn Ile Lys
                85                  90                  95

Lys Ala Val Glu Glu Ala Glu Arg Leu Ser Glu Ser Leu Lys Leu Arg
            100                 105                 110

Tyr Glu Glu Ala Glu Val Arg Lys Lys Leu Glu Glu Lys Asp Arg Gln
```

```
                115                 120                 125
Glu Glu Ala Gln Arg Leu Gln Gln Lys Arg Gln Glu Thr Gly Arg Glu
            130                 135                 140

Asp Gly Gly Thr Leu Ala Lys Gly Ser Leu Glu Asn Val Leu Asp Ser
145                 150                 155                 160

Lys Asp Lys Thr Gln Lys Ser Asn Gly Glu Lys Asn Glu Lys Cys Glu
                165                 170                 175

Thr Lys Glu Lys Gly Ala Ile Thr Ala Lys Glu Leu Tyr Thr Met Met
            180                 185                 190

Thr Asp Lys Asn Ile Ser Leu Ile Ile Met Asp Ala Arg Arg Met Gln
            195                 200                 205

Asp Tyr Gln Asp Ser Cys Ile Leu His Ser Leu Ser Val Pro Glu Glu
210                 215                 220

Ala Ile Ser Pro Gly Val Thr Ala Ser Trp Ile Glu Ala His Leu Pro
225                 230                 235                 240

Asp Asp Ser Lys Asp Thr Trp Lys Lys Arg Gly Asn Val Glu Tyr Val
                245                 250                 255

Val Leu Leu Asp Trp Phe Ser Ser Ala Lys Asp Leu Gln Ile Gly Thr
            260                 265                 270

Thr Leu Arg Ser Leu Lys Asp Ala Leu Phe Lys Trp Glu Ser Lys Thr
            275                 280                 285

Val Leu Arg Asn Glu Pro Leu Val Leu Glu Gly Gly Tyr Glu Asn Trp
            290                 295                 300

Leu Leu Cys Tyr Pro Gln Tyr Thr Thr Asn Ala Lys Val Thr Pro Pro
305                 310                 315                 320

Pro Arg Arg Gln Asn Glu Glu Val Ser Ile Ser Leu Asp Phe Thr Tyr
                325                 330                 335

Pro Ser Leu Glu Glu Ser Ile Pro Ser Lys Pro Ala Ala Gln Thr Pro
            340                 345                 350

Pro Ala Ser Ile Glu Val Asp Glu Asn Ile Glu Leu Ile Ser Gly Gln
            355                 360                 365

Asn Glu Arg Met Gly Pro Leu Asn Ile Ser Thr Pro Val Glu Pro Val
370                 375                 380

Ala Ala Ser Lys Ser Asp Val Ser Pro Ile Ile Gln Pro Val Pro Ser
385                 390                 395                 400

Ile Lys Asn Val Pro Gln Ile Asp Arg Thr Lys Lys Pro Ala Val Lys
                405                 410                 415

Leu Pro Glu Glu His Arg Ile Lys Ser Glu Ser Thr Asn His Glu Gln
            420                 425                 430

Gln Ser Pro Gln Ser Gly Lys Val Ile Pro Asp Arg Ser Thr Lys Pro
            435                 440                 445

Val Val Phe Ser Pro Thr Leu Met Leu Thr Asp Glu Lys Ala Arg
            450                 455                 460

Ile His Ala Glu Thr Ala Leu Leu Met Glu Lys Asn Lys Gln Glu Lys
465                 470                 475                 480

Glu Leu Arg Glu Arg Gln Gln Glu Gln Lys Glu Lys Leu Arg Lys
                485                 490                 495

Glu Glu Gln Glu Gln Lys Ala Lys Lys Lys Gln Glu Ala Glu Glu Asn
            500                 505                 510

Glu Ile Thr Glu Lys Gln Gln Lys Ala Lys Glu Glu Met Glu Lys Lys
            515                 520                 525

Glu Ser Glu Gln Ala Lys Lys Glu Asp Lys Glu Thr Ser Ala Lys Arg
530                 535                 540
```

```
Gly Lys Glu Ile Thr Gly Val Lys Arg Gln Ser Lys Ser Glu His Glu
545                 550                 555                 560

Thr Ser Asp Ala Lys Lys Ser Val Glu Asp Arg Gly Lys Arg Cys Pro
                565                 570                 575

Thr Pro Glu Ile Gln Lys Lys Ser Thr Gly Asp Val Pro His Thr Ser
            580                 585                 590

Val Thr Gly Asp Ser Gly Ser Gly Lys Pro Phe Lys Ile Lys Gly Gln
        595                 600                 605

Pro Glu Ser Gly Ile Leu Arg Thr Gly Thr Phe Arg Glu Asp Thr Asp
    610                 615                 620

Asp Thr Glu Arg Asn Lys Ala Gln Arg Glu Pro Leu Thr Arg Ala Arg
625                 630                 635                 640

Ser Glu Glu Met Gly Arg Ile Val Pro Gly Leu Pro Ser Gly Trp Ala
                645                 650                 655

Lys Phe Leu Asp Pro Ile Thr Gly Thr Phe Arg Tyr Tyr His Ser Pro
            660                 665                 670

Thr Asn Thr Val His Met Tyr Pro Pro Glu Met Ala Pro Ser Ser Ala
        675                 680                 685

Pro Pro Ser Thr Pro Pro Thr His Lys Ala Lys Pro Gln Ile Pro Ala
    690                 695                 700

Glu Arg Asp Arg Glu Pro Ser Lys Leu Lys Arg Ser Tyr Ser Ser Pro
705                 710                 715                 720

Asp Ile Thr Gln Ala Ile Gln Glu Glu Lys Arg Lys Pro Thr Val
                725                 730                 735

Thr Pro Thr Val Asn Arg Glu Asn Lys Pro Thr Cys Tyr Pro Lys Ala
                740                 745                 750

Glu Ile Ser Arg Leu Ser Ala Ser Gln Ile Arg Asn Leu Asn Pro Val
                755                 760                 765

Phe Gly Gly Ser Gly Pro Ala Leu Thr Gly Leu Arg Asn Leu Gly Asn
            770                 775                 780

Thr Cys Tyr Met Asn Ser Ile Leu Gln Cys Leu Cys Asn Ala Pro His
785                 790                 795                 800

Leu Ala Asp Tyr Phe Asn Arg Asn Cys Tyr Gln Asp Asp Ile Asn Arg
                805                 810                 815

Ser Asn Leu Leu Gly His Lys Gly Glu Val Ala Glu Glu Phe Gly Ile
            820                 825                 830

Ile Met Lys Ala Leu Trp Thr Gly Gln Tyr Arg Tyr Ile Ser Pro Lys
        835                 840                 845

Asp Phe Lys Ile Thr Ile Gly Lys Ile Asn Asp Gln Phe Ala Gly Tyr
    850                 855                 860

Ser Gln Gln Asp Ser Gln Glu Leu Leu Leu Phe Leu Met Asp Gly Leu
865                 870                 875                 880

His Glu Asp Leu Asn Lys Ala Asp Asn Arg Lys Arg Tyr Lys Glu Glu
                885                 890                 895

Asn Asn Asp His Leu Asp Asp Phe Lys Ala Ala Glu His Ala Trp Gln
            900                 905                 910

Lys His Lys Gln Leu Asn Glu Ser Ile Ile Val Ala Leu Phe Gln Gly
        915                 920                 925

Gln Phe Lys Ser Thr Val Gln Cys Leu Thr Cys His Lys Lys Ser Arg
    930                 935                 940

Thr Phe Glu Ala Phe Met Tyr Leu Ser Leu Pro Leu Ala Ser Thr Ser
945                 950                 955                 960
```

Lys Cys Thr Leu Gln Asp Cys Leu Arg Leu Phe Ser Lys Glu Glu Lys
                    965                 970                 975

Leu Thr Asp Asn Asn Arg Phe Tyr Cys Ser His Cys Arg Ala Arg Arg
                980                 985                 990

Asp Ser Leu Lys Lys Ile Glu Ile Trp Lys Leu Pro Pro Val Leu Leu
            995                 1000                1005

Val His Leu Lys Arg Phe Ser Tyr Asp Gly Arg Trp Lys Gln Lys Leu
        1010                1015                1020

Gln Thr Ser Val Asp Phe Pro Leu Glu Asn Leu Asp Leu Ser Gln Tyr
1025                1030                1035                1040

Val Ile Gly Pro Lys Asn Asn Leu Lys Lys Tyr Asn Leu Phe Ser Val
                1045                1050                1055

Ser Asn His Tyr Gly Gly Leu Asp Gly Gly His Tyr Thr Ala Tyr Cys
                1060                1065                1070

Lys Asn Ala Ala Arg Gln Arg Trp Phe Lys Phe Asp Asp His Glu Val
            1075                1080                1085

Ser Asp Ile Ser Val Ser Val Lys Ser Ser Ala Ala Tyr Ile Leu
        1090                1095                1100

Phe Tyr Thr Ser Leu Gly Pro Arg Val Thr Asp Val Ala Thr
1105                1110                1115

<210> SEQ ID NO 17
<211> LENGTH: 2397
<212> TYPE: DNA
<213> ORGANISM: Homo sapiens

<400> SEQUENCE: 17

```
atggccctcc acagcccgca gtatattttt ggagatttta gccctgatga attcaatcaa        60
ttctttgtga ctcctcgatc ttcagttgag cttcctccat acagtggaac agttctgtgt       120
ggcacacagg ctgtggataa actacctgat ggacaagaat atcagagaat gagtttggt        180
gtcgatgaag tcattgaacc cagtgacact ttgccgagaa cccccagcta cagtatttca       240
agcacactga accctcaggc ccctgaattt attctcggtt gtacagcttc caaaataacc       300
cctgatggta tcactaaaga agcaagctat ggctccatcg actgccagta cccaggctct       360
gccctcgctt tggatggaag ttctaatgtg gaggcggaag ttttggaaaa tgatggtgtc       420
tcaggtggtc ttggacaaag ggagcgtaaa aagaagaaaa gcggccacc  tggatattac       480
agctatttga agatggtgg cgatgatagt atctccacag aagccctggt caatggccat       540
gccaattcag cagtcccgaa cagtgtcagt gcagaggatg cagaatttat gggtgacatg       600
cctccgccac ttacgcccag gacttgtaac agccccagg  actccacaga ctctgtcagt       660
gacattgtgc ctgacagtcc tttccccgga gcactcggca gtgacaccag gactgcaggg       720
cagccagagg ggggcccgg  ggctgatttt ggtcagtcct gcttccctgc agaggctggc       780
agagacaccc tgtcaaggac agctggggct cagccctgcg ttggtaccga tactactgaa       840
aaccttggag ttgctaatgg acaaatactt gaatcctcgg gtgagggcac agctaccaac       900
ggggtggagt tgcacaccac ggaaagcata gacttggacc caaccaaacc cgagagtgca       960
tcacctcctg ctgacggcac gggctctgca tcaggcaccc ttcctgtcag ccagcccaag      1020
tcctgggcca gctctttca  tgattctaag cccctcttcct cctcgccggt ggcctatgtg      1080
gaaactaagt attcccctcc cgccatatct cccctggttt ctgaaaagca ggttgaagtc      1140
aaagaagggc ttgttccggt ttcagaggat cctgtagcca taagattgc  agagttgctg      1200
gagaatgtaa ccctaatcca taaaccagtg tcgttgcaac cccgtgggct gatcaataaa      1260
```

-continued

```
gggaactggt gctacattaa tgctacactg caggcattgg ttgcttgccc gccgatgtac    1320
cacctgatga agttcattcc tctgtattcc aaagtgcaaa ggccttgtac gtcaacaccc    1380
atgatagaca gctttgttcg gctaatgaat gagttcacta atatgccagt acctccaaaa    1440
ccccgacaag ctcttggaga taaaatcgtg agggatattc gccctggagc tgcctttgag    1500
cccacatata tttacagact cctgacagtt aacaagtcaa gcctgtctga aagggtcga    1560
caagaagatg ctgaggaata cttaggcttc attctaaatg gacttcatga ggaaatgttg    1620
aacctaaaga agcttctctc accaagtaat gaaaaactta cgatttccaa cggccccaaa    1680
aaccactcgg tcaatgaaga agagcaggaa gaacaaggtg aaggaagcga ggatgaatgg    1740
gaacaagtgg gcccccggaa caagacttcc gtcacccgcc aggcggattt tgttcagact    1800
ccaatcaccg gcatttttgg tggacacatc aggtctgtgg tttaccagca gagttcaaaa    1860
gaatctgcca ctttgcagcc attttttcacg ttgcagttgg atatccagtc agacaagata    1920
cgcacagtcc aggatgcact ggagagcttg gtggcaagag aatctgtcca aggttatacc    1980
acaaaaacca acaagaggt tgagataagt cgaagagtga ctctggaaaa actccctcct    2040
gtcctcgtgc tgcacctgaa acgattcgtt tatgagaaga ctggtggggtg ccagaagctt    2100
atcaaaaata ttgaatatcc tgtggacttg gaaattagta agaactgct ttctccaggg    2160
gttaaaaata agaattttaa atgccaccga acctatcggc tctttgcagt ggtctaccat    2220
cacggcaaca gtgcgacggg cggccattac actacagacg tcttccagat cggtctgaat    2280
ggctggctgc gcatcgatga ccagacagtc aaggtgatca accagtacca ggtggtgaaa    2340
ccaactgctg aacgcacagc ctacctcctg tattaccgcc gagtggacct gctgtaa      2397
```

<210> SEQ ID NO 18
<211> LENGTH: 798
<212> TYPE: PRT
<213> ORGANISM: Homo sapiens

<400> SEQUENCE: 18

```
Met Ala Leu His Ser Pro Gln Tyr Ile Phe Gly Asp Phe Ser Pro Asp
1               5                   10                  15

Glu Phe Asn Gln Phe Phe Val Thr Pro Arg Ser Ser Val Glu Leu Pro
            20                  25                  30

Pro Tyr Ser Gly Thr Val Leu Cys Gly Thr Gln Ala Val Asp Lys Leu
        35                  40                  45

Pro Asp Gly Gln Glu Tyr Gln Arg Ile Glu Phe Gly Val Asp Glu Val
    50                  55                  60

Ile Glu Pro Ser Asp Thr Leu Pro Arg Thr Pro Ser Tyr Ser Ile Ser
65                  70                  75                  80

Ser Thr Leu Asn Pro Gln Ala Pro Glu Phe Ile Leu Gly Cys Thr Ala
                85                  90                  95

Ser Lys Ile Thr Pro Asp Gly Ile Thr Lys Glu Ala Ser Tyr Gly Ser
            100                 105                 110

Ile Asp Cys Gln Tyr Pro Gly Ser Ala Leu Ala Leu Asp Gly Ser Ser
        115                 120                 125

Asn Val Glu Ala Glu Val Leu Glu Asn Asp Gly Val Ser Gly Gly Leu
    130                 135                 140

Gly Gln Arg Glu Arg Lys Lys Lys Lys Arg Pro Pro Gly Tyr Tyr
145                 150                 155                 160

Ser Tyr Leu Lys Asp Gly Gly Asp Asp Ser Ile Ser Thr Glu Ala Leu
                165                 170                 175
```

```
Val Asn Gly His Ala Asn Ser Ala Val Pro Asn Ser Val Ser Ala Glu
            180                 185                 190

Asp Ala Glu Phe Met Gly Asp Met Pro Pro Leu Thr Pro Arg Thr
        195                 200                 205

Cys Asn Ser Pro Gln Asn Ser Thr Asp Ser Val Ser Asp Ile Val Pro
    210                 215                 220

Asp Ser Pro Phe Pro Gly Ala Leu Gly Ser Asp Thr Arg Thr Ala Gly
225                 230                 235                 240

Gln Pro Glu Gly Gly Pro Gly Ala Asp Phe Gly Gln Ser Cys Phe Pro
                245                 250                 255

Ala Glu Ala Gly Arg Asp Thr Leu Ser Arg Thr Ala Gly Ala Gln Pro
            260                 265                 270

Cys Val Gly Thr Asp Thr Thr Glu Asn Leu Gly Val Ala Asn Gly Gln
        275                 280                 285

Ile Leu Glu Ser Ser Gly Glu Gly Thr Ala Thr Asn Gly Val Glu Leu
    290                 295                 300

His Thr Thr Glu Ser Ile Asp Leu Asp Pro Thr Lys Pro Glu Ser Ala
305                 310                 315                 320

Ser Pro Pro Ala Asp Gly Thr Gly Ser Ala Ser Gly Thr Leu Pro Val
                325                 330                 335

Ser Gln Pro Lys Ser Trp Ala Ser Leu Phe His Asp Ser Lys Pro Ser
            340                 345                 350

Ser Ser Ser Pro Val Ala Tyr Val Glu Thr Lys Tyr Ser Pro Pro Ala
        355                 360                 365

Ile Ser Pro Leu Val Ser Glu Lys Gln Val Glu Val Lys Glu Gly Leu
    370                 375                 380

Val Pro Val Ser Glu Asp Pro Val Ala Ile Lys Ile Ala Glu Leu Leu
385                 390                 395                 400

Glu Asn Val Thr Leu Ile His Lys Pro Val Ser Leu Gln Pro Arg Gly
                405                 410                 415

Leu Ile Asn Lys Gly Asn Trp Cys Tyr Ile Asn Ala Thr Leu Gln Ala
            420                 425                 430

Leu Val Ala Cys Pro Pro Met Tyr His Leu Met Lys Phe Ile Pro Leu
        435                 440                 445

Tyr Ser Lys Val Gln Arg Pro Cys Thr Ser Thr Pro Met Ile Asp Ser
    450                 455                 460

Phe Val Arg Leu Met Asn Glu Phe Thr Asn Met Pro Val Pro Pro Lys
465                 470                 475                 480

Pro Arg Gln Ala Leu Gly Asp Lys Ile Val Arg Asp Ile Arg Pro Gly
                485                 490                 495

Ala Ala Phe Glu Pro Thr Tyr Ile Tyr Arg Leu Leu Thr Val Asn Lys
            500                 505                 510

Ser Ser Leu Ser Glu Lys Gly Arg Gln Glu Asp Ala Glu Glu Tyr Leu
        515                 520                 525

Gly Phe Ile Leu Asn Gly Leu His Glu Glu Met Leu Asn Leu Lys Lys
    530                 535                 540

Leu Leu Ser Pro Ser Asn Glu Lys Leu Thr Ile Ser Asn Gly Pro Lys
545                 550                 555                 560

Asn His Ser Val Asn Glu Glu Gln Glu Gln Gly Glu Gly Ser
                565                 570                 575

Glu Asp Glu Trp Glu Gln Val Gly Pro Arg Asn Lys Thr Ser Val Thr
            580                 585                 590
```

Arg Gln Ala Asp Phe Val Gln Thr Pro Ile Thr Gly Ile Phe Gly Gly
            595                 600                 605

His Ile Arg Ser Val Val Tyr Gln Gln Ser Ser Lys Glu Ser Ala Thr
        610                 615                 620

Leu Gln Pro Phe Phe Thr Leu Gln Leu Asp Ile Gln Ser Asp Lys Ile
625                 630                 635                 640

Arg Thr Val Gln Asp Ala Leu Glu Ser Leu Val Ala Arg Glu Ser Val
                645                 650                 655

Gln Gly Tyr Thr Thr Lys Thr Lys Gln Glu Val Glu Ile Ser Arg Arg
            660                 665                 670

Val Thr Leu Glu Lys Leu Pro Pro Val Leu Val Leu His Leu Lys Arg
        675                 680                 685

Phe Val Tyr Glu Lys Thr Gly Gly Cys Gln Lys Leu Ile Lys Asn Ile
    690                 695                 700

Glu Tyr Pro Val Asp Leu Glu Ile Ser Lys Glu Leu Leu Ser Pro Gly
705                 710                 715                 720

Val Lys Asn Lys Asn Phe Lys Cys His Arg Thr Tyr Arg Leu Phe Ala
                725                 730                 735

Val Val Tyr His His Gly Asn Ser Ala Thr Gly Gly His Tyr Thr Thr
            740                 745                 750

Asp Val Phe Gln Ile Gly Leu Asn Gly Trp Leu Arg Ile Asp Asp Gln
        755                 760                 765

Thr Val Lys Val Ile Asn Gln Tyr Gln Val Val Lys Pro Thr Ala Glu
    770                 775                 780

Arg Thr Ala Tyr Leu Leu Tyr Tyr Arg Arg Val Asp Leu Leu
785                 790                 795

<210> SEQ ID NO 19
<211> LENGTH: 2763
<212> TYPE: DNA
<213> ORGANISM: Homo sapiens

<400> SEQUENCE: 19
atggcgacgg tcgcagcaaa tccagctgct gctgcggcgg ctgtggcggc ggcagcggcg      60
gtgactgagg atagagagcc acagcacgag gagctgccag gcctggacag ccagtggcgc     120
cagatagaaa acggcgagag tgggcgagaa cgtccactgc gggccggcga agctggttc      180 cttgtggaga agcactggta taagcagtgg gaggcatacg tgcagggagg ggaccaggac     240
tccagcacct ccctggctg catcaacaat gccacactct ttcaagatga gataaactgg     300
cgcctcaagg agggactggt ggaaggcgag gattatgtgc tgctcccagc agctgcttgg     360
cattacctgg tcagctggta tggtctagag catggccagc cacccattga acgcaaggtc     420
atagagctgc ccaacatcca gaaggtcgaa gtgtacccag tagaactgct gcttgtccgg     480
cacaatgatt tgggcaaatc tcacactgtt cagttcagcc ataccgattc tattggccta     540
gtattgcgca cagctcggga gcggtttctg gtggagcccc aggaagacac tcggctttgg     600
gccaagaact cagaaggctc tttggatagg ttgtatgaca cacacatcac ggttctcgat     660
gcggcccttg agactgggca gttgatcatc atggagaccc gcaagaaaga tggcacttgg     720
cccagcgcac agctgcatgt catgaacaac aacatgtcgg aagaggatga ggacttcaag     780
ggtcagccag gcatctgtgg cctcaccaat ctgggcaaca cgtgcttcat gaactcggcc     840
ctgcagtgcc tcagcaatgt gccacagctc accgagtact ccctcaacaa ctgctacctg     900
gaggagctca acttccgcaa cccactgggc atgaagggtg agatcgcaga ggcctatgca     960

```
gacctggtga agcaggcgtg gtctggccac caccgctcca ttgtgccaca tgtgttcaag    1020
aacaaggttg ccatttttgc atcccaattt ctgggctacc agcagcatga ctctcaggag    1080
ctgctgtcat tcctcctgga cgggctgcat gaggacctta atcgggtgaa gaagaaggag    1140
tatgtggagc tgtgcgatgc tgctgggcga ccggatcagg aggtggcaca ggaggcatgg    1200
caaaaccaca acggcggaa cgattctgtg atcgtggaca ctttccacgg cctcttcaag    1260
tccacgctgg tgtgccccga ttgtggcaat gtatctgtga ccttcgaccc cttctgctac    1320
ctcagtgttc cactgcctat cagccacaag agggtcttgg aggtcttctt tatccccatg    1380
gatccgcgcc gcaagccaga gcagcaccgg ctcgtggtcc caagaaagg caagatctcg    1440 gatctatgtg tggctctgtc caaacacacg ggcatctcgc cagagaggat gatggtggct    1500
gatgtcttca gtcaccgctt ctataagctc tatcagctag aggagcctct gagcagcatc    1560
ttggaccgtg atgatatctt cgtctatgag gtgtcaggtc gcattgaggc cattgagggc    1620
tcaagagagg acatcgtggt tcctgtctac ctgcgggagc gcacccctgc ccgtgactac    1680
aacaactcct actacggcct gatgcttttt ggacaccccc tcctggtatc agtgccccgg    1740
gaccgcttca cctgggaggg cctgtataac gtcctgatgt accggctctc acgctacgtg    1800
accaaaccca actcagatga tgaggacgat ggggatgaga agaagatga cgaggaggat    1860 aaagatgacg tccctgggcc ctcaactggg ggcagcctcc gagaccctga gccagagcag    1920
gctgggccca gctctggagt cacgaacagg tgcccgttcc tcctggacaa ttgccttggc    1980
acatctcagt ggcccccaag gcgacgacgc aagcagctgt tcaccctgca gacggtgaac    2040
tccaatggga ccagcgaccg cacaacctcc cctgaagaag tccatgccca gccgtacatt    2100
gctatcgact gggagccaga gatgaagaag cgttactatg acgaggtaga ggctgagggc    2160
tacgtgaagc atgactgcgt cgggtacgtg atgaagaagg ctcccgtgcg gctgcaggag    2220
tgcattgagc tcttcaccac tgtggagacc ctggagaagg aaaaccctg gtactgccct    2280 tcctgcaagc agcaccagct ggcaaccaag aagctggacc tgtggatgct gccggagatt    2340
ctcatcatcc acctgaaacg ctttttccta ccaagttct cccgagagaa gctggacacc    2400
ctcgtggagt ttcctatccg ggacctggac ttctctgagt ttgtcatcca gccacagaat    2460
gagtcgaatc cggagctgta caaatatgac ctcatcgcgg tttccaacca ttatgggggc    2520
atgcgtgatg acactacac aacatttgcc tgcaacaagg acagcggcca gtggcactac    2580
tttgatgaca cagcgtctc ccctgtcaat gagaatcaga tcgagtccaa ggcagcctat    2640
gtcctcttct accaacgcca ggacgtgcg cgacgcctgc tgtccccggc cggctcatct    2700
ggcgccccag cctcccctgc ctgcagctcc ccacccagct ctgagttcat ggatgttaat    2760
tga                                                                2763
```

<210> SEQ ID NO 20
<211> LENGTH: 920
<212> TYPE: PRT
<213> ORGANISM: Homo sapiens

<400> SEQUENCE: 20

Met Ala Thr Val Ala Ala Asn Pro Ala Ala Ala Ala Val Ala
1               5                   10                  15

Ala Ala Ala Ala Val Thr Glu Asp Arg Glu Pro Gln His Glu Glu Leu
                20                  25                  30

Pro Gly Leu Asp Ser Gln Trp Arg Gln Ile Glu Asn Gly Glu Ser Gly
        35                  40                  45

```
Arg Glu Arg Pro Leu Arg Ala Gly Glu Ser Trp Phe Leu Val Glu Lys
 50                  55                  60

His Trp Tyr Lys Gln Trp Glu Ala Tyr Val Gln Gly Gly Asp Gln Asp
 65                      70                  75                  80

Ser Ser Thr Phe Pro Gly Cys Ile Asn Asn Ala Thr Leu Phe Gln Asp
                     85                  90                  95

Glu Ile Asn Trp Arg Leu Lys Glu Gly Leu Val Glu Gly Glu Asp Tyr
                100                 105                 110

Val Leu Leu Pro Ala Ala Ala Trp His Tyr Leu Val Ser Trp Tyr Gly
             115                 120                 125

Leu Glu His Gly Gln Pro Pro Ile Glu Arg Lys Val Ile Glu Leu Pro
 130                 135                 140

Asn Ile Gln Lys Val Glu Val Tyr Pro Val Glu Leu Leu Val Arg
 145                 150                 155                 160

His Asn Asp Leu Gly Lys Ser His Thr Val Gln Phe Ser His Thr Asp
                165                 170                 175

Ser Ile Gly Leu Val Leu Arg Thr Ala Arg Glu Arg Phe Leu Val Glu
                180                 185                 190

Pro Gln Glu Asp Thr Arg Leu Trp Ala Lys Asn Ser Glu Gly Ser Leu
         195                 200                 205

Asp Arg Leu Tyr Asp Thr His Ile Thr Val Leu Asp Ala Ala Leu Glu
 210                 215                 220

Thr Gly Gln Leu Ile Ile Met Glu Thr Arg Lys Lys Asp Gly Thr Trp
 225                 230                 235                 240

Pro Ser Ala Gln Leu His Val Met Asn Asn Met Ser Glu Glu Asp
             245                 250                 255

Glu Asp Phe Lys Gly Gln Pro Gly Ile Cys Gly Leu Thr Asn Leu Gly
             260                 265                 270

Asn Thr Cys Phe Met Asn Ser Ala Leu Gln Cys Leu Ser Asn Val Pro
             275                 280                 285

Gln Leu Thr Glu Tyr Phe Leu Asn Asn Cys Tyr Leu Glu Glu Leu Asn
 290                 295                 300

Phe Arg Asn Pro Leu Gly Met Lys Gly Glu Ile Ala Glu Ala Tyr Ala
 305                 310                 315                 320

Asp Leu Val Lys Gln Ala Trp Ser Gly His His Arg Ser Ile Val Pro
             325                 330                 335

His Val Phe Lys Asn Lys Val Gly His Phe Ala Ser Gln Phe Leu Gly
             340                 345                 350

Tyr Gln Gln His Asp Ser Gln Glu Leu Leu Ser Phe Leu Leu Asp Gly
             355                 360                 365

Leu His Glu Asp Leu Asn Arg Val Lys Lys Lys Glu Tyr Val Glu Leu
 370                 375                 380

Cys Asp Ala Ala Gly Arg Pro Asp Gln Glu Val Ala Gln Glu Ala Trp
 385                 390                 395                 400

Gln Asn His Lys Arg Arg Asn Asp Ser Val Ile Val Asp Thr Phe His
             405                 410                 415

Gly Leu Phe Lys Ser Thr Leu Val Cys Pro Asp Cys Gly Asn Val Ser
             420                 425                 430

Val Thr Phe Asp Pro Phe Cys Tyr Leu Ser Val Pro Leu Pro Ile Ser
             435                 440                 445

His Lys Arg Val Leu Glu Val Phe Phe Ile Pro Met Asp Pro Arg Arg
 450                 455                 460

Lys Pro Glu Gln His Arg Leu Val Val Pro Lys Lys Gly Lys Ile Ser
```

```
              465                 470                 475                 480
Asp Leu Cys Val Ala Leu Ser Lys His Thr Gly Ile Ser Pro Glu Arg
                485                 490                 495
Met Met Val Ala Asp Val Phe Ser His Arg Phe Tyr Lys Leu Tyr Gln
                500                 505                 510
Leu Glu Glu Pro Leu Ser Ser Ile Leu Asp Arg Asp Ile Phe Val
                515                 520                 525
Tyr Glu Val Ser Gly Arg Ile Glu Ala Ile Glu Gly Ser Arg Glu Asp
                530                 535                 540
Ile Val Val Pro Val Tyr Leu Arg Glu Arg Thr Pro Ala Arg Asp Tyr
545                 550                 555                 560
Asn Asn Ser Tyr Tyr Gly Leu Met Leu Phe Gly His Pro Leu Leu Val
                565                 570                 575
Ser Val Pro Arg Asp Arg Phe Thr Trp Glu Gly Leu Tyr Asn Val Leu
                580                 585                 590
Met Tyr Arg Leu Ser Arg Tyr Val Thr Lys Pro Asn Ser Asp Asp Glu
                595                 600                 605
Asp Asp Gly Asp Glu Lys Glu Asp Glu Glu Asp Lys Asp Val
                610                 615                 620
Pro Gly Pro Ser Thr Gly Gly Ser Leu Arg Asp Pro Glu Pro Glu Gln
625                 630                 635                 640
Ala Gly Pro Ser Ser Gly Val Thr Asn Arg Cys Pro Phe Leu Leu Asp
                645                 650                 655
Asn Cys Leu Gly Thr Ser Gln Trp Pro Pro Arg Arg Arg Lys Gln
                660                 665                 670
Leu Phe Thr Leu Gln Thr Val Asn Ser Asn Gly Thr Ser Asp Arg Thr
                675                 680                 685
Thr Ser Pro Glu Glu Val His Ala Gln Pro Tyr Ile Ala Ile Asp Trp
                690                 695                 700
Glu Pro Glu Met Lys Lys Arg Tyr Tyr Asp Glu Val Glu Ala Glu Gly
705                 710                 715                 720
Tyr Val Lys His Asp Cys Val Gly Tyr Val Met Lys Lys Ala Pro Val
                725                 730                 735
Arg Leu Gln Glu Cys Ile Glu Leu Phe Thr Thr Val Glu Thr Leu Glu
                740                 745                 750
Lys Glu Asn Pro Trp Tyr Cys Pro Ser Cys Lys Gln His Gln Leu Ala
                755                 760                 765
Thr Lys Lys Leu Asp Leu Trp Met Leu Pro Glu Ile Leu Ile Ile His
                770                 775                 780
Leu Lys Arg Phe Ser Tyr Thr Lys Phe Ser Arg Glu Lys Leu Asp Thr
785                 790                 795                 800
Leu Val Glu Phe Pro Ile Arg Asp Leu Asp Phe Ser Glu Phe Val Ile
                805                 810                 815
Gln Pro Gln Asn Glu Ser Asn Pro Glu Leu Tyr Lys Tyr Asp Leu Ile
                820                 825                 830
Ala Val Ser Asn His Tyr Gly Gly Met Arg Asp Gly His Tyr Thr Thr
                835                 840                 845
Phe Ala Cys Asn Lys Asp Ser Gly Gln Trp His Tyr Phe Asp Asp Asn
                850                 855                 860
Ser Val Ser Pro Val Asn Glu Asn Gln Ile Glu Ser Lys Ala Ala Tyr
865                 870                 875                 880
Val Leu Phe Tyr Gln Arg Gln Asp Val Ala Arg Arg Leu Leu Ser Pro
                885                 890                 895
```

Ala Gly Ser Ser Gly Ala Pro Ala Ser Pro Ala Cys Ser Ser Pro Pro
            900                 905                 910

Ser Ser Glu Phe Met Asp Val Asn
        915                 920

<210> SEQ ID NO 21
<211> LENGTH: 1113
<212> TYPE: DNA
<213> ORGANISM: Homo sapiens

<400> SEQUENCE: 21

| | | | | | |
|---|---|---|---|---|---|
| atggaaatcc | taatgacagt | ctccaaattc | gcctccatct | gtaccatggg cgccaatgct | 60 |
| tcggcattag | agaaagagat | tggtccagaa | cagtttccgg | tcaatgagca ctattttgga | 120 |
| ttagtcaatt | ttgggaatac | ctgctactgc | aattcagttc | ttcaagcact ttattttgt | 180 |
| cgtccatttc | gggaaaaagt | tcttgcgtat | aagagtcaac | ctaggaaaaa ggagagcctt | 240 |
| cttacatgct | tagcagatct | cttccatagc | atagccactc | agaagaaaaa ggttggagta | 300 |
| atacccccta | agaagttcat | cacaagatta | cggaagaaa | atgagctttt tgacaactac | 360 |
| atgcaacaag | atgcccatga | attcttaaat | tacctactaa | atacaattgc tgatatttta | 420 |
| caagaagaga | gaaagcagga | aaaacaaaat | ggtcgtttac | ctaatggtaa tattgataat | 480 |
| gaaaataata | acagcacacc | agcccaacg | tgggttcatg | agattttttca gggaacatta | 540 |
| actaatgaaa | ccagatgtct | tacttgtgaa | actataagca | gcaaagatga agatttttta | 600 |
| gacctttctg | ttgacgtgga | acaaaataca | tcaattactc | actgcttaag gggtttcagc | 660 |
| aacacagaaa | ctctgtgcag | tgaatacaag | tattactgtg | aagagtgtcg cagcaaacag | 720 |
| gaagcacaca | aacggatgaa | agttaaaaaa | ctgcccatga | ttctagctct acacctgaag | 780 |
| agatttaaat | atatggatca | acttcatcga | tatacaaaac | tctcttaccg ggtagttttt | 840 |
| cctttagaac | ttcgtctgtt | taacacttca | ggtgatgcca | ccaatccaga cagaatgtac | 900 |
| gaccttgttg | ctgttgtggt | tcactgtgga | agtggtccca | atcgaggcca ttatattgca | 960 |
| atagttaaga | gtcatgattt | tggttgttg | tttgatgacg | acattgtaga aaaaatagat | 1020 |
| gcacaagcta | ttgaagaatt | ctacggggttg | acatcagata | tctcaaagaa ctctgagtct | 1080 |
| ggttacatcc | ttttctatca | gtctcgggac | tga | | 1113 |

<210> SEQ ID NO 22
<211> LENGTH: 370
<212> TYPE: PRT
<213> ORGANISM: Homo sapiens

<400> SEQUENCE: 22

Met Glu Ile Leu Met Thr Val Ser Lys Phe Ala Ser Ile Cys Thr Met
1               5                   10                  15

Gly Ala Asn Ala Ser Ala Leu Glu Lys Glu Ile Gly Pro Glu Gln Phe
            20                  25                  30

Pro Val Asn Glu His Tyr Phe Gly Leu Val Asn Phe Gly Asn Thr Cys
        35                  40                  45

Tyr Cys Asn Ser Val Leu Gln Ala Leu Tyr Phe Cys Arg Pro Phe Arg
    50                  55                  60

Glu Lys Val Leu Ala Tyr Lys Ser Gln Pro Arg Lys Lys Glu Ser Leu
65                  70                  75                  80

Leu Thr Cys Leu Ala Asp Leu Phe His Ser Ile Ala Thr Gln Lys Lys
                85                  90                  95

```
Lys Val Gly Val Ile Pro Pro Lys Lys Phe Ile Thr Arg Leu Arg Lys
            100                 105                 110

Glu Asn Glu Leu Phe Asp Asn Tyr Met Gln Gln Asp Ala His Glu Phe
        115                 120                 125

Leu Asn Tyr Leu Leu Asn Thr Ile Ala Asp Ile Leu Gln Glu Glu Arg
    130                 135                 140

Lys Gln Glu Lys Gln Asn Gly Arg Leu Pro Asn Gly Asn Ile Asp Asn
145                 150                 155                 160

Glu Asn Asn Asn Ser Thr Pro Asp Pro Thr Trp Val His Glu Ile Phe
                165                 170                 175

Gln Gly Thr Leu Thr Asn Glu Thr Arg Cys Leu Thr Cys Glu Thr Ile
            180                 185                 190

Ser Ser Lys Asp Glu Asp Phe Leu Asp Leu Ser Val Asp Val Glu Gln
        195                 200                 205

Asn Thr Ser Ile Thr His Cys Leu Arg Gly Phe Ser Asn Thr Glu Thr
    210                 215                 220

Leu Cys Ser Glu Tyr Lys Tyr Tyr Cys Glu Glu Cys Arg Ser Lys Gln
225                 230                 235                 240

Glu Ala His Lys Arg Met Lys Val Lys Lys Leu Pro Met Ile Leu Ala
                245                 250                 255

Leu His Leu Lys Arg Phe Lys Tyr Met Asp Gln Leu His Arg Tyr Thr
            260                 265                 270

Lys Leu Ser Tyr Arg Val Val Phe Pro Leu Glu Leu Arg Leu Phe Asn
        275                 280                 285

Thr Ser Gly Asp Ala Thr Asn Pro Asp Arg Met Tyr Asp Leu Val Ala
    290                 295                 300

Val Val His Cys Gly Ser Gly Pro Asn Arg Gly His Tyr Ile Ala
305                 310                 315                 320

Ile Val Lys Ser His Asp Phe Trp Leu Leu Phe Asp Asp Ile Val
                325                 330                 335

Glu Lys Ile Asp Ala Gln Ala Ile Glu Glu Phe Tyr Gly Leu Thr Ser
            340                 345                 350

Asp Ile Ser Lys Asn Ser Glu Ser Gly Tyr Ile Leu Phe Tyr Gln Ser
        355                 360                 365

Arg Asp
    370

<210> SEQ ID NO 23
<211> LENGTH: 1485
<212> TYPE: DNA
<213> ORGANISM: Homo sapiens

<400> SEQUENCE: 23
atgccgctct actccgttac tgtaaaatgg ggaaaggaga atttgaagg tgtagaattg      60 aatacagatg aacctccaat ggtattcaag gctcagctgt ttgcgttgac tggagtccag     120
cctgccagac agaaagttat ggtgaaagga ggaacgctaa aggatgatga ttggggaaac     180
atcaaaataa aaatggaat gactctacta atgatgggt cagcagatgc tcttccagaa      240
gaaccctcag ccaaaactgt cttcgtagaa gacatgacag aagaacagtt agcatctgct     300
atggagttac catgtggatt gacaaaacct tggtaacactt gttacatgaa tgccacagtt     360
cagtgtattc gttctgtgcc tgaactcaaa gatgccctta aaggtatgc aggtgccttg      420 agagcttcag gggaaatggc ttcagcgcag tatattactg cagcccttag agatttgttt     480
gattccatgg ataaaacttc ttccagtatt ccacctatta ttctactgca gttttttgcac    540
```

```
atggctttcc cacagtttgc cgagaaaggt gaacaaggac agtatcttca acaggatgct    600
aatgaatgtt ggatacaaat gatgcgagta ttgcaacaga aattggaagc aatagaggat    660
gattctgtta aagagacaga ctcctcatct gcatcggcag cgacaccttc taaaaagaaa    720
agtttaatcg atcagttctt cggtgttgag tttgaaacta ccatgaaatg tacagaatct    780
gaagaagaag aagtcaccaa aggaaaggaa aatcaacttc agcttagctg ttttatcaat    840
caggaagtca agtatctttt tacaggactt aaattgcgac ttcaggaaga aatcaccaaa    900
cagtctccaa cgttgcaaag aaatgccttg tatatcaaat cttccaagat cagccggctg    960
cctgcttact tgaccattca gatggttcga tttttttata aagagaagga atctgtgaat   1020
gccaaagttc ttaaggatgt taaatttcct cttatgttgg atatgtatga actgtgtaca   1080
ccagaacttc aagagaaaat ggtgtctttt cgatccaaat tcaaggatct agaagataaa   1140
aaagtgaatc agcagccaaa tacaagtgac aaaaagagta gtccccagaa agaagttaag   1200
tatgaaccct tttcttttgc tgatgatatt ggctccaata attgtggata ctatgactta   1260
caagcagtac taacacacca gggaaggtct agttcttcag gtcattatgt atcatgggtg   1320
aaaaggaaac aagatgaatg gattaagttt gatgatgaca agtcagcat cgtaacacca   1380 gaagatatct tacggctttc tggtggtgga gactggcata tcgcttacgt tctactctat   1440
gggcctcgca gagttgaaat aatggaagag gaaagtgaac agtaa                    1485

<210> SEQ ID NO 24
<211> LENGTH: 494
<212> TYPE: PRT
<213> ORGANISM: Homo sapiens

<400> SEQUENCE: 24

Met Pro Leu Tyr Ser Val Thr Val Lys Trp Gly Lys Glu Lys Phe Glu
1               5                   10                  15

Gly Val Glu Leu Asn Thr Asp Glu Pro Pro Met Val Phe Lys Ala Gln
            20                  25                  30

Leu Phe Ala Leu Thr Gly Val Gln Pro Ala Arg Gln Lys Val Met Val
        35                  40                  45

Lys Gly Gly Thr Leu Lys Asp Asp Trp Gly Asn Ile Lys Ile Lys
    50                  55                  60

Asn Gly Met Thr Leu Leu Met Met Gly Ser Ala Asp Ala Leu Pro Glu
65                  70                  75                  80

Glu Pro Ser Ala Lys Thr Val Phe Val Glu Asp Met Thr Glu Glu Gln
                85                  90                  95

Leu Ala Ser Ala Met Glu Leu Pro Cys Gly Leu Thr Asn Leu Gly Asn
            100                 105                 110

Thr Cys Tyr Met Asn Ala Thr Val Gln Cys Ile Arg Ser Val Pro Glu
        115                 120                 125

Leu Lys Asp Ala Leu Lys Arg Tyr Ala Gly Ala Leu Arg Ala Ser Gly
    130                 135                 140

Glu Met Ala Ser Ala Gln Tyr Ile Thr Ala Ala Leu Arg Asp Leu Phe
145                 150                 155                 160

Asp Ser Met Asp Lys Thr Ser Ser Ile Pro Pro Ile Ile Leu Leu
                165                 170                 175

Gln Phe Leu His Met Ala Phe Pro Gln Phe Ala Glu Lys Gly Glu Gln
            180                 185                 190

Gly Gln Tyr Leu Gln Gln Asp Ala Asn Glu Cys Trp Ile Gln Met Met
        195                 200                 205
```

Arg Val Leu Gln Gln Lys Leu Glu Ala Ile Glu Asp Asp Ser Val Lys
        210                 215                 220

Glu Thr Asp Ser Ser Ala Ser Ala Ala Thr Pro Ser Lys Lys Lys
225                 230                 235                 240

Ser Leu Ile Asp Gln Phe Phe Gly Val Glu Phe Glu Thr Thr Met Lys
            245                 250                 255

Cys Thr Glu Ser Glu Glu Glu Val Thr Lys Gly Lys Glu Asn Gln
        260                 265                 270

Leu Gln Leu Ser Cys Phe Ile Asn Gln Glu Val Lys Tyr Leu Phe Thr
        275                 280                 285

Gly Leu Lys Leu Arg Leu Gln Glu Glu Ile Thr Lys Gln Ser Pro Thr
290                 295                 300

Leu Gln Arg Asn Ala Leu Tyr Ile Lys Ser Ser Lys Ile Ser Arg Leu
305                 310                 315                 320

Pro Ala Tyr Leu Thr Ile Gln Met Val Arg Phe Phe Tyr Lys Glu Lys
            325                 330                 335

Glu Ser Val Asn Ala Lys Val Leu Lys Asp Val Lys Phe Pro Leu Met
        340                 345                 350

Leu Asp Met Tyr Glu Leu Cys Thr Pro Glu Leu Gln Glu Lys Met Val
        355                 360                 365

Ser Phe Arg Ser Lys Phe Lys Asp Leu Glu Asp Lys Lys Val Asn Gln
370                 375                 380

Gln Pro Asn Thr Ser Asp Lys Lys Ser Ser Pro Gln Lys Glu Val Lys
385                 390                 395                 400

Tyr Glu Pro Phe Ser Phe Ala Asp Asp Ile Gly Ser Asn Asn Cys Gly
            405                 410                 415

Tyr Tyr Asp Leu Gln Ala Val Leu Thr His Gln Gly Arg Ser Ser Ser
        420                 425                 430

Ser Gly His Tyr Val Ser Trp Val Lys Arg Lys Gln Asp Glu Trp Ile
        435                 440                 445

Lys Phe Asp Asp Asp Lys Val Ser Ile Val Thr Pro Glu Asp Ile Leu
        450                 455                 460

Arg Leu Ser Gly Gly Gly Asp Trp His Ile Ala Tyr Val Leu Leu Tyr
465                 470                 475                 480

Gly Pro Arg Arg Val Glu Ile Met Glu Glu Glu Ser Glu Gln
            485                 490

<210> SEQ ID NO 25
<211> LENGTH: 2859
<212> TYPE: DNA
<213> ORGANISM: Homo sapiens

<400> SEQUENCE: 25
atggcggaag gcggagcggc ggatctggac acccagcggt ctgacatcgc gacgctgctc      60
aaaacctcgc tccggaaagg ggacacctgg tacctagtcg atagtcgctg gttcaaacag     120
tggaaaaaat atgttggctt tgacagttgg acaaatacc agatgggaga tcaaaatgtg     180
tatcctggac ccattgataa ctctggactt ctcaaagatg gtgatgccca gtcacttaag     240 gaacaccttta ttgatgaatt ggattacata ctgttgccaa ctgaaggttg aataaactt     300 gtcagctggt acacattgat ggaaggtcaa gagccaatag cacgaaaggt ggttgaacag     360
ggtatgtttg taaagcactg caaagtagaa gtatatctca cagaattgaa gctatgtgaa     420
aatggaaaca tgaataatgt tgtaactcga agatttagca aagctgacac aatagataca     480

-continued

```
attgaaaagg aaataagaaa aatcttcagt attccagatg aaaaggagac cagattgtgg    540
aacaaataca tgagtaacac atttgaacca ctgaataaac cagacagcac cattcaggat    600
gctggtttat accaaggaca ggtattagtg atagaacaga aaaatgaaga tggaacatgg    660
ccaaggggtc cttctactcc taatgtgaaa aactcaaatt actgtcttcc atcatatacc    720
gcttataaga actatgatta ttcggaacct ggaagaaaca atgaacagcc aggcctctgt    780
ggcctaagta acttgggaaa tacgtgtttc atgaactcag ctattcagtg tttgagcaac    840
acacctccac ttactgagta tttcctcaat gataagtatc aagaagaact gaattttgac    900
aatcccttag gaatgagagg tgaaatagct aaatcttatg ccgaactgat caagcaaatg    960
tggtctggaa agtttagcta cgtcacccca agagccttta agacacaggt aggacgtttt   1020
gcacctcagt tctctggata tcagcagcaa gactgtcaag aactgttagc tttcctatta   1080
gatggattac atgaggattt gaatagaatt aggaaaaaac catatataca attaaaagat   1140
gcagatggaa ggccagataa ggtggttgcc gaagaagcct gggaaaacca tttaaaacga   1200
aatgattcta tcatagtaga tatatttcat ggccttttca aatcaacttt agtttgtcct   1260
gagtgtgcta agatttcagt aacatttgat ccttttttgtt acttgacact tccattgccc   1320
atgaaaaaag aacgcacctt ggaagtttac ttagttagaa tggatccact taccaaacct   1380
atgcagtaca aagtggttgt ccccaaaatt ggaaacatat tagatctttg tacagcattg   1440
tctgctttgt caggaatacc tgcagataag atgatagtta ctgatatata caatcataga   1500
tttcacagaa tattcgctat ggatgaaaac cttagtagta ttatggaacg ggatgatatt   1560
tatgtgtttg aaattaacat caataggaca gaagatacag agcacgtgat tattcctgtt   1620
tgcctaagag aaaaattcag acactcgagt tatacccacc atactggttc ttcactttt   1680 ggtcagccct ttcttatggc tgtaccacga acaatactg aagacaaact ttataatctc   1740
ctgctcttga gaatgtgccg atatgtcaaa atatctactg aaactgaaga aactgaagga   1800
tccctacact gctgtaagga ccaaaatatt aatgggaatg cccaaatgg catacatgaa   1860 gaaggctcac caagtgaaat ggaaacagat gagccagatg atgaatccag ccaggatcaa   1920
gaacttccct cagagaatga aaacagtcag tctgaagatt cagttggagg agataatgat   1980
tctgaaaatg gattatgtac tgaggatact tgcaaaggtc aactcacggg acacaaaaaa   2040
cgattgttta cattccagtt caacaactta ggcaatactg atatcaacta catcaaagat   2100
gataccaggc atataagatt tgatgatagg cagcttaggc tagatgaaag attttttctt   2160
gctttggatt gggatcctga tttgaaaaaa agatattttg atgaaaatgc tgccgaggac   2220
tttgaaaaac atgaaagtgt ggagtataaa cctcctaaaa aacccttgt gaaattaaaa   2280 gattgcattg aacttttac aacaaaagaa aagctaggtg ctgaagatcc ctggtattgt   2340
ccgaattgta agaacatca gcaagccaca aagaaattgg atttatggtc cctgcctcca   2400
gtacttgtag tacatctcaa gcgatttcct tacagtcgat acatgagaga caagttggat   2460
accttagttg atttttcctat caatgacttg gatatgtcgg aattcttaat taatccaaat   2520
gcaggtcctt gccgctataa tctgattgct gtttccaacc actatggagg gatgggagga   2580
ggacactata ctgcttttgc aaaaaataaa gatgatggaa aatggtacta ttttgatgac   2640
agtagtgtct ccactgcatc tgaagaccaa attgtgtcca aagcagcata tgtactcttc   2700
taccagagac aagacacttt cagtggaact ggctttttc ctcttgaccg agaaactaaa   2760
ggtgcttcag ctgccactgg catcccatta gaaagtgatg aagatagcaa tgataatgac   2820
aatgatatag aaaatgaaaa ctgtatgcac actaactaa                          2859
```

```
<210> SEQ ID NO 26
<211> LENGTH: 952
<212> TYPE: PRT
<213> ORGANISM: Homo sapiens

<400> SEQUENCE: 26

Met Ala Glu Gly Gly Ala Ala Asp Leu Asp Thr Gln Arg Ser Asp Ile
1               5                   10                  15

Ala Thr Leu Leu Lys Thr Ser Leu Arg Lys Gly Asp Thr Trp Tyr Leu
            20                  25                  30

Val Asp Ser Arg Trp Phe Lys Gln Trp Lys Lys Tyr Val Gly Phe Asp
        35                  40                  45

Ser Trp Asp Lys Tyr Gln Met Gly Asp Gln Asn Val Tyr Pro Gly Pro
    50                  55                  60

Ile Asp Asn Ser Gly Leu Leu Lys Asp Gly Asp Ala Gln Ser Leu Lys
65                  70                  75                  80

Glu His Leu Ile Asp Glu Leu Asp Tyr Ile Leu Leu Pro Thr Glu Gly
                85                  90                  95

Trp Asn Lys Leu Val Ser Trp Tyr Thr Leu Met Glu Gly Gln Glu Pro
            100                 105                 110

Ile Ala Arg Lys Val Val Glu Gln Gly Met Phe Val Lys His Cys Lys
        115                 120                 125

Val Glu Val Tyr Leu Thr Glu Leu Lys Leu Cys Glu Asn Gly Asn Met
    130                 135                 140

Asn Asn Val Val Thr Arg Arg Phe Ser Lys Ala Asp Thr Ile Asp Thr
145                 150                 155                 160

Ile Glu Lys Glu Ile Arg Lys Ile Phe Ser Ile Pro Asp Glu Lys Glu
                165                 170                 175

Thr Arg Leu Trp Asn Lys Tyr Met Ser Asn Thr Phe Glu Pro Leu Asn
            180                 185                 190

Lys Pro Asp Ser Thr Ile Gln Asp Ala Gly Leu Tyr Gln Gly Gln Val
        195                 200                 205

Leu Val Ile Glu Gln Lys Asn Glu Asp Gly Thr Trp Pro Arg Gly Pro
    210                 215                 220

Ser Thr Pro Asn Val Lys Asn Ser Asn Tyr Cys Leu Pro Ser Tyr Thr
225                 230                 235                 240

Ala Tyr Lys Asn Tyr Asp Tyr Ser Glu Pro Gly Arg Asn Asn Glu Gln
                245                 250                 255

Pro Gly Leu Cys Gly Leu Ser Asn Leu Gly Asn Thr Cys Phe Met Asn
            260                 265                 270

Ser Ala Ile Gln Cys Leu Ser Asn Thr Pro Pro Leu Thr Glu Tyr Phe
        275                 280                 285

Leu Asn Asp Lys Tyr Gln Glu Glu Leu Asn Phe Asp Asn Pro Leu Gly
    290                 295                 300

Met Arg Gly Glu Ile Ala Lys Ser Tyr Ala Glu Leu Ile Lys Gln Met
305                 310                 315                 320

Trp Ser Gly Lys Phe Ser Tyr Val Thr Pro Arg Ala Phe Lys Thr Gln
                325                 330                 335

Val Gly Arg Phe Ala Pro Gln Phe Ser Gly Tyr Gln Gln Gln Asp Cys
            340                 345                 350

Gln Glu Leu Leu Ala Phe Leu Leu Asp Gly Leu His Glu Asp Leu Asn
        355                 360                 365

Arg Ile Arg Lys Lys Pro Tyr Ile Gln Leu Lys Asp Ala Asp Gly Arg
```

```
            370                 375                 380
Pro Asp Lys Val Val Ala Glu Glu Ala Trp Glu Asn His Leu Lys Arg
385                 390                 395                 400

Asn Asp Ser Ile Ile Val Asp Ile Phe His Gly Leu Phe Lys Ser Thr
                405                 410                 415

Leu Val Cys Pro Glu Cys Ala Lys Ile Ser Val Thr Phe Asp Pro Phe
            420                 425                 430

Cys Tyr Leu Thr Leu Pro Leu Pro Met Lys Lys Glu Arg Thr Leu Glu
        435                 440                 445

Val Tyr Leu Val Arg Met Asp Pro Leu Thr Lys Pro Met Gln Tyr Lys
    450                 455                 460

Val Val Val Pro Lys Ile Gly Asn Ile Leu Asp Leu Cys Thr Ala Leu
465                 470                 475                 480

Ser Ala Leu Ser Gly Ile Pro Ala Asp Lys Met Ile Val Thr Asp Ile
                485                 490                 495

Tyr Asn His Arg Phe His Arg Ile Phe Ala Met Asp Glu Asn Leu Ser
            500                 505                 510

Ser Ile Met Glu Arg Asp Ile Tyr Val Phe Glu Ile Asn Ile Asn
        515                 520                 525

Arg Thr Glu Asp Thr Glu His Val Ile Ile Pro Val Cys Leu Arg Glu
    530                 535                 540

Lys Phe Arg His Ser Ser Tyr Thr His Thr Gly Ser Ser Leu Phe
545                 550                 555                 560

Gly Gln Pro Phe Leu Met Ala Val Pro Arg Asn Asn Thr Glu Asp Lys
                565                 570                 575

Leu Tyr Asn Leu Leu Leu Arg Met Cys Arg Tyr Val Lys Ile Ser
            580                 585                 590

Thr Glu Thr Glu Glu Thr Glu Gly Ser Leu His Cys Cys Lys Asp Gln
        595                 600                 605

Asn Ile Asn Gly Asn Gly Pro Asn Gly Ile His Glu Glu Gly Ser Pro
    610                 615                 620

Ser Glu Met Glu Thr Asp Glu Pro Asp Asp Glu Ser Ser Gln Asp Gln
625                 630                 635                 640

Glu Leu Pro Ser Glu Asn Glu Asn Ser Gln Ser Glu Asp Ser Val Gly
                645                 650                 655

Gly Asp Asn Asp Ser Glu Asn Gly Leu Cys Thr Glu Asp Thr Cys Lys
            660                 665                 670

Gly Gln Leu Thr Gly His Lys Lys Arg Leu Phe Thr Phe Gln Phe Asn
        675                 680                 685

Asn Leu Gly Asn Thr Asp Ile Asn Tyr Ile Lys Asp Asp Thr Arg His
    690                 695                 700

Ile Arg Phe Asp Asp Arg Gln Leu Arg Leu Asp Arg Phe Phe Leu
705                 710                 715                 720

Ala Leu Asp Trp Asp Pro Asp Leu Lys Lys Arg Tyr Phe Asp Glu Asn
                725                 730                 735

Ala Ala Glu Asp Phe Glu Lys His Glu Ser Val Glu Tyr Lys Pro Pro
            740                 745                 750

Lys Lys Pro Phe Val Lys Leu Lys Asp Cys Ile Glu Leu Phe Thr Thr
        755                 760                 765

Lys Glu Lys Leu Gly Ala Glu Asp Pro Trp Tyr Cys Pro Asn Cys Lys
    770                 775                 780

Glu His Gln Gln Ala Thr Lys Lys Leu Asp Leu Trp Ser Leu Pro Pro
785                 790                 795                 800
```

```
Val Leu Val Val His Leu Lys Arg Phe Ser Tyr Ser Arg Tyr Met Arg
                805                 810                 815

Asp Lys Leu Asp Thr Leu Val Asp Phe Pro Ile Asn Asp Leu Asp Met
            820                 825                 830

Ser Glu Phe Leu Ile Asn Pro Asn Ala Gly Pro Cys Arg Tyr Asn Leu
        835                 840                 845

Ile Ala Val Ser Asn His Tyr Gly Gly Met Gly Gly Gly His Tyr Thr
850                 855                 860

Ala Phe Ala Lys Asn Lys Asp Asp Gly Lys Trp Tyr Tyr Phe Asp Asp
865                 870                 875                 880

Ser Ser Val Ser Thr Ala Ser Glu Asp Gln Ile Val Ser Lys Ala Ala
                885                 890                 895

Tyr Val Leu Phe Tyr Gln Arg Gln Asp Thr Phe Ser Gly Thr Gly Phe
            900                 905                 910

Phe Pro Leu Asp Arg Glu Thr Lys Gly Ala Ser Ala Ala Thr Gly Ile
        915                 920                 925

Pro Leu Glu Ser Asp Glu Asp Ser Asn Asp Asn Asp Asn Asp Ile Glu
930                 935                 940

Asn Glu Asn Cys Met His Thr Asn
945                 950

<210> SEQ ID NO 27
<211> LENGTH: 1227
<212> TYPE: DNA
<213> ORGANISM: Homo sapiens

<400> SEQUENCE: 27
atgggaaaga acggacaaa gggaaaaact gttccaatcg atgattcctc tgaaacttta      60
gaacctgtgt gcagacacat tagaaaagga ttggaacaag gtaatttgaa aaaggcttta     120
gtgaatgtgg aatggaatat ctgccaagac tgtaagactg acaataaagt gaaagataaa     180
gctgaagaag aaacagaaga aaagccttca gtttggctgt gtcttaaatg tggccatcag     240
ggctgtggca gaaattctca ggagcagcat gccttgaagc actatctgac gccaagatct     300
gaacctcact gtctggttct tagtttggac aactggagtg tatggtgtta cgtatgtgat     360
aatgaggtcc agtattgtag ttcaaaccag ttgggtcaag tggttgatta tgtcagaaaa     420
caagccagca ttacaactcc aaagccagca gagaaagata tggaaatat tgaacttgaa      480 aataaaaaat tagaaaaaga gagtaagaat aacaagagag agaaaagaa ggaaaacatg      540 gctaaagaga atcctcccat gaattctcct tgccaaataa ccgtgaaagg actcagtaat     600
ttgggaaaca catgtttctt caatgcagtt atgcagaact tgtcacaaac accagtgctt     660
agagaactac taaagaagt gaaaatgtct ggaacaattg taaaaattga accacctgat      720
ttggcattaa cagaaccatt agaaataaac cttgagcctc aggccctct tactttagcc      780 atgagccagt tcttaatga gatgcaagag accaaaaagg gggttgtgac accgaaagaa      840 ctctttctc aggtctgtaa aaaagcagtg cggtttaaag gctatcagca gcaagacagc      900
caggagctgc ttcgctactt attggatggg atgagagcag aagaacacca agagtgagt      960 aaaggaatac ttaaagcatt tggtaattct actgaaaagt tggatgaaga actaaaaat      1020 aaagttaaag attatgagaa gaaaaaatca atgccaagtt ttgttgaccg catctttggt     1080
ggtgaactaa ctagtatgat catgtgtgat caatgcagaa ctgtctcctt ggttcatgaa     1140
tctttccttg atttgtccct cccagtttta gatgatcagg taagactatt gaatttattt     1200
```
tattcaagta gatttttttt cctgtaa                                          1227

<210> SEQ ID NO 28
<211> LENGTH: 408
<212> TYPE: PRT
<213> ORGANISM: Homo sapiens

<400> SEQUENCE: 28

Met Gly Lys Lys Arg Thr Lys Gly Lys Thr Val Pro Ile Asp Asp Ser
1               5                   10                  15

Ser Glu Thr Leu Glu Pro Val Cys Arg His Ile Arg Lys Gly Leu Glu
                20                  25                  30

Gln Gly Asn Leu Lys Lys Ala Leu Val Asn Val Glu Trp Asn Ile Cys
            35                  40                  45

Gln Asp Cys Lys Thr Asp Asn Lys Val Lys Asp Lys Ala Glu Glu Glu
        50                  55                  60

Thr Glu Glu Lys Pro Ser Val Trp Leu Cys Leu Lys Cys Gly His Gln
65                  70                  75                  80

Gly Cys Gly Arg Asn Ser Gln Glu Gln His Ala Leu Lys His Tyr Leu
                85                  90                  95

Thr Pro Arg Ser Glu Pro His Cys Leu Val Leu Ser Leu Asp Asn Trp
            100                 105                 110

Ser Val Trp Cys Tyr Val Cys Asp Asn Glu Val Gln Tyr Cys Ser Ser
        115                 120                 125

Asn Gln Leu Gly Gln Val Val Asp Tyr Val Arg Lys Gln Ala Ser Ile
130                 135                 140

Thr Thr Pro Lys Pro Ala Glu Lys Asp Asn Gly Asn Ile Glu Leu Glu
145                 150                 155                 160

Asn Lys Lys Leu Glu Lys Glu Ser Lys Asn Glu Gln Glu Arg Glu Lys
                165                 170                 175

Lys Glu Asn Met Ala Lys Glu Asn Pro Pro Met Asn Ser Pro Cys Gln
            180                 185                 190

Ile Thr Val Lys Gly Leu Ser Asn Leu Gly Asn Thr Cys Phe Phe Asn
        195                 200                 205

Ala Val Met Gln Asn Leu Ser Gln Thr Pro Val Leu Arg Glu Leu Leu
210                 215                 220

Lys Glu Val Lys Met Ser Gly Thr Ile Val Lys Ile Glu Pro Pro Asp
225                 230                 235                 240

Leu Ala Leu Thr Glu Pro Leu Glu Ile Asn Leu Glu Pro Pro Gly Pro
                245                 250                 255

Leu Thr Leu Ala Met Ser Gln Phe Leu Asn Glu Met Gln Glu Thr Lys
            260                 265                 270

Lys Gly Val Val Thr Pro Lys Glu Leu Phe Ser Gln Val Cys Lys Lys
        275                 280                 285

Ala Val Arg Phe Lys Gly Tyr Gln Gln Gln Asp Ser Gln Glu Leu Leu
290                 295                 300

Arg Tyr Leu Leu Asp Gly Met Arg Ala Glu Glu His Gln Arg Val Ser
305                 310                 315                 320

Lys Gly Ile Leu Lys Ala Phe Gly Asn Ser Thr Glu Lys Leu Asp Glu
                325                 330                 335

Glu Leu Lys Asn Lys Val Lys Asp Tyr Glu Lys Lys Ser Met Pro
            340                 345                 350

Ser Phe Val Asp Arg Ile Phe Gly Gly Glu Leu Thr Ser Met Ile Met
        355                 360                 365

Cys Asp Gln Cys Arg Thr Val Ser Leu Val His Glu Ser Phe Leu Asp
    370                 375                 380

Leu Ser Leu Pro Val Leu Asp Asp Gln Val Arg Leu Leu Asn Leu Phe
385                 390                 395                 400

Tyr Ser Ser Arg Phe Phe Phe Leu
                405

<210> SEQ ID NO 29
<211> LENGTH: 1593
<212> TYPE: DNA
<213> ORGANISM: Homo sapiens

<400> SEQUENCE: 29

```
atggaggacg actcactcta cttgggaggt gagtggcagt tcaaccactt ttcaaaactc      60
acatcttctc ggccagatgc agcttttgct gaaatccagc ggacttctct ccctgagaag     120
tcaccactct catctgaggc ccgtgtcgac ctctgtgatg atttggctcc tgtggcaaga     180
cagcttgctc ccagggagaa gcttcctctg agtagcagga gacctgctgc ggtgggggct     240
gggctccaga atatgggaaa tacctgctac agaaacgctt ccctgcagtg cctgacatac     300
acaccgcccc ttgccaacta catgctgtcc cgggagcact ctcaaacatg tcagcgtccc     360
aagtgctgca tgctctgtac tatgcaagct cacatcacat gggccctcca cagtcctggt     420
catgtcatcc agccctcaca ggcattggct gctggcttcc atagaggcaa gcaggaagat     480
gcccatgaat ttctcatgtt cactgtggat gccatgaaaa aggcatgcct tcccggccac     540
aagcaggtag atcatcactc taaggacacc accctcatcc accaaatatt tggaggctgc     600
tggagatctc aaatcaagtg tctccactgc acgggattcc agacactttt tgacccttac     660
ctggacatcg ccctggatat ccaggcagct cagagtgtca agcaagcttt ggaacagttg     720
gtgaagcccg aagaactcaa tggagagaat gcctatcatt gtggtctttg tctccagagg     780
gcgccggcct ccaagacgtt aactttacac acttctgcca aggtcctcat ccttgtmttg     840
aagagattct ccgatgtcac aggcaacaaa cttgccaaga atgtgcaata tcctgagtgc     900
cttgacatgc agccatacat gtctcagcag aacacaggac ctcttgtcta tgtcctctat     960
gctgtgctgg tccacgctgg gtggagttgt cacaacggac attacttctc ttatgtcaaa    1020
gctcaagaag ccagtggta taaaatggat gatgccgagg tcaccgcctc tagcatcact    1080
tctgtcctga gtcaacaggc ctacgtcctc ttttacatcc agaagagtga atgggaaaga    1140
cacagtgaga gtgtgtcaag aggcagggaa ccaagagccc ttggcgcaga agacacagac    1200
aggcgagcaa cgcaaggaga gctcaagaga gaccaccct gcctccaggc cccgagttg    1260 gacgagcact tggtggaaag agccactcag gaaagcacct tagaccactg gaaattcctt    1320
caagagcaaa acaaaacgaa gcctgagttc aacgtcagaa aagtcgaagg taccctgcct    1380
cccgacgtac ttgtgattca tcaatcaaaa tacaagtgtg ggatgaagaa ccatcatcct    1440
gaacagcaaa gctccctgct aaacctctct tcgacgaccc cgacacatca ggagtccatg    1500
aacactggca cactcgcttc cctgcgaggg agggccagga gatccaaagg gaagaacaaa    1560
cacagcaaga gggctctgct tgtgtgccag tga                                 1593
```

<210> SEQ ID NO 30
<211> LENGTH: 530
<212> TYPE: PRT
<213> ORGANISM: Homo sapiens

<400> SEQUENCE: 30

```
Met Glu Asp Asp Ser Leu Tyr Leu Gly Gly Glu Trp Gln Phe Asn His
 1               5                  10                  15

Phe Ser Lys Leu Thr Ser Ser Arg Pro Asp Ala Ala Phe Ala Glu Ile
             20                  25                  30

Gln Arg Thr Ser Leu Pro Glu Lys Ser Pro Leu Ser Ser Glu Ala Arg
         35                  40                  45

Val Asp Leu Cys Asp Asp Leu Ala Pro Val Ala Arg Gln Leu Ala Pro
 50                  55                  60

Arg Glu Lys Leu Pro Leu Ser Ser Arg Arg Pro Ala Ala Val Gly Ala
 65                  70                  75                  80

Gly Leu Gln Asn Met Gly Asn Thr Cys Tyr Glu Asn Ala Ser Leu Gln
                 85                  90                  95

Cys Leu Thr Tyr Thr Pro Pro Leu Ala Asn Tyr Met Leu Ser Arg Glu
                100                 105                 110

His Ser Gln Thr Cys Gln Arg Pro Lys Cys Cys Met Leu Cys Thr Met
            115                 120                 125

Gln Ala His Ile Thr Trp Ala Leu His Ser Pro Gly His Val Ile Gln
        130                 135                 140

Pro Ser Gln Ala Leu Ala Ala Gly Phe His Arg Gly Lys Gln Glu Asp
145                 150                 155                 160

Ala His Glu Phe Leu Met Phe Thr Val Asp Ala Met Lys Lys Ala Cys
                165                 170                 175

Leu Pro Gly His Lys Gln Val Asp His His Ser Lys Asp Thr Thr Leu
                180                 185                 190

Ile His Gln Ile Phe Gly Gly Cys Trp Arg Ser Gln Ile Lys Cys Leu
            195                 200                 205

His Cys His Gly Ile Pro Asp Thr Phe Asp Pro Tyr Leu Asp Ile Ala
        210                 215                 220

Leu Asp Ile Gln Ala Ala Gln Ser Val Lys Gln Ala Leu Glu Gln Leu
225                 230                 235                 240

Val Lys Pro Glu Glu Leu Asn Gly Glu Asn Ala Tyr His Cys Gly Leu
                245                 250                 255

Cys Leu Gln Arg Ala Pro Ala Ser Lys Thr Leu Thr Leu His Thr Ser
                260                 265                 270

Ala Lys Val Leu Ile Leu Val Leu Lys Arg Phe Ser Asp Val Thr Gly
            275                 280                 285

Asn Lys Leu Ala Lys Asn Val Gln Tyr Pro Glu Cys Leu Asp Met Gln
        290                 295                 300

Pro Tyr Met Ser Gln Gln Asn Thr Gly Pro Leu Val Tyr Val Leu Tyr
305                 310                 315                 320

Ala Val Leu Val His Ala Gly Trp Ser Cys His Asn Gly His Tyr Phe
                325                 330                 335

Ser Tyr Val Lys Ala Gln Glu Gly Gln Trp Tyr Lys Met Asp Asp Ala
            340                 345                 350

Glu Val Thr Ala Ser Ser Ile Thr Ser Val Leu Ser Gln Gln Ala Tyr
        355                 360                 365

Val Leu Phe Tyr Ile Gln Lys Ser Glu Trp Glu Arg His Ser Glu Ser
    370                 375                 380

Val Ser Arg Gly Arg Glu Pro Arg Ala Leu Gly Ala Glu Asp Thr Asp
385                 390                 395                 400

Arg Arg Ala Thr Gln Gly Glu Leu Lys Arg Asp His Pro Cys Leu Gln
                405                 410                 415

Ala Pro Glu Leu Asp Glu His Leu Val Glu Arg Ala Thr Gln Glu Ser
```

```
            420                 425                 430
Thr Leu Asp His Trp Lys Phe Leu Gln Glu Gln Asn Lys Thr Lys Pro
        435                 440                 445

Glu Phe Asn Val Arg Lys Val Glu Gly Thr Leu Pro Pro Asp Val Leu
    450                 455                 460

Val Ile His Gln Ser Lys Tyr Lys Cys Gly Met Lys Asn His His Pro
465                 470                 475                 480

Glu Gln Gln Ser Ser Leu Leu Asn Leu Ser Ser Thr Thr Pro Thr His
                485                 490                 495

Gln Glu Ser Met Asn Thr Gly Thr Leu Ala Ser Leu Arg Gly Arg Ala
            500                 505                 510

Arg Arg Ser Lys Gly Lys Asn Lys His Ser Lys Arg Ala Leu Leu Val
        515                 520                 525

Cys Gln
    530

<210> SEQ ID NO 31
<211> LENGTH: 1119
<212> TYPE: DNA
<213> ORGANISM: Homo sapiens

<400> SEQUENCE: 31
atgagcaagg cgtttgggct cctgaggcaa atctgtcagt ccatcctggc tgagtcctcg      60
cagtccccgg cagatcttga agaaaagaag gaagaagaca gcaacatgaa gagagagcag     120
cccagagagc gtcccagggc ctgggactac cctcatggcc tggttggttt acacaacatt     180
ggacagacct gctgccttaa ctccttgatt caggtgttcg taatgaatgt ggacttcacc     240
aggatattga gaggatcac ggtgcccagg ggagctgacg agcagaggag aagcgtccct      300
ttccagatgc ttctgctgct ggagaagatg caggacagcc ggcagaaagc agtgcggccc     360
ctggagctgg cctactgcct gcagaagtgc aacgtgccct tgtttgtcca acatgatgct     420
gcccaactgt acctcaaact ctggaacctg attaaggacc agatcactga tgtgcacttg     480
gtggagagac tgcaggccct gtatacgatc cgggtgaagg actccttgat ttgcgttgac     540
tgtgccatgg agagtagcag aaacagcagc atgctcaccc tcccactttc tcttttttgat     600 gtggactcaa agcccctgaa gacactggag gacgccctgc actgcttctt ccagcccagg     660
gagttatcaa gcaaaagcaa gtgcttctgt gagaactgtg gaagaagac ccgtgggaaa     720 caggtcttga agctgaccca tttgccccag accctgacaa tccacctcat gcgattctcc     780
atcaggaatt cacagacgag aaagatctgc cactccctgt acttccccca gagcttggat     840
ttcagccaga tccttccaat gaagcgagag tcttgtgatg ctgaggagca gtctggaggg     900
cagtatgagc ttttgctgt gattgcgcac gtgggaatgg cagactccgg tcattactgt     960
gtctacatcc ggaatgctgt ggatggaaaa tggttctgct tcaatgactc caatatttgc    1020
ttggtgtcct gggaagacat ccagtgtacc tacggaaatc ctaactacca ctggcaggaa    1080
actgcatatc ttctggtttta catgaagatg gagtgctaa                          1119

<210> SEQ ID NO 32
<211> LENGTH: 372
<212> TYPE: PRT
<213> ORGANISM: Homo sapiens

<400> SEQUENCE: 32

Met Ser Lys Ala Phe Gly Leu Leu Arg Gln Ile Cys Gln Ser Ile Leu
1               5                   10                  15
```

Ala Glu Ser Ser Gln Ser Pro Ala Asp Leu Glu Glu Lys Lys Glu Glu
            20                  25                  30

Asp Ser Asn Met Lys Arg Glu Gln Pro Arg Glu Arg Pro Arg Ala Trp
        35                  40                  45

Asp Tyr Pro His Gly Leu Val Gly Leu His Asn Ile Gly Gln Thr Cys
    50                  55                  60

Cys Leu Asn Ser Leu Ile Gln Val Phe Val Met Asn Val Asp Phe Thr
65                  70                  75                  80

Arg Ile Leu Lys Arg Ile Thr Val Pro Arg Gly Ala Asp Glu Gln Arg
                85                  90                  95

Arg Ser Val Pro Phe Gln Met Leu Leu Leu Glu Lys Met Gln Asp
            100                 105                 110

Ser Arg Gln Lys Ala Val Arg Pro Leu Glu Leu Ala Tyr Cys Leu Gln
        115                 120                 125

Lys Cys Asn Val Pro Leu Phe Val Gln His Asp Ala Ala Gln Leu Tyr
130                 135                 140

Leu Lys Leu Trp Asn Leu Ile Lys Asp Gln Ile Thr Asp Val His Leu
145                 150                 155                 160

Val Glu Arg Leu Gln Ala Leu Tyr Thr Ile Arg Val Lys Asp Ser Leu
                165                 170                 175

Ile Cys Val Asp Cys Ala Met Glu Ser Ser Arg Asn Ser Ser Met Leu
            180                 185                 190

Thr Leu Pro Leu Ser Leu Phe Asp Val Asp Ser Lys Pro Leu Lys Thr
        195                 200                 205

Leu Glu Asp Ala Leu His Cys Phe Phe Gln Pro Arg Glu Leu Ser Ser
    210                 215                 220

Lys Ser Lys Cys Phe Cys Glu Asn Cys Gly Lys Lys Thr Arg Gly Lys
225                 230                 235                 240

Gln Val Leu Lys Leu Thr His Leu Pro Gln Thr Leu Thr Ile His Leu
                245                 250                 255

Met Arg Phe Ser Ile Arg Asn Ser Gln Thr Arg Lys Ile Cys His Ser
            260                 265                 270

Leu Tyr Phe Pro Gln Ser Leu Asp Phe Ser Gln Ile Leu Pro Met Lys
        275                 280                 285

Arg Glu Ser Cys Asp Ala Glu Glu Gln Ser Gly Gly Gln Tyr Glu Leu
    290                 295                 300

Phe Ala Val Ile Ala His Val Gly Met Ala Asp Ser Gly His Tyr Cys
305                 310                 315                 320

Val Tyr Ile Arg Asn Ala Val Asp Gly Lys Trp Phe Cys Phe Asn Asp
                325                 330                 335

Ser Asn Ile Cys Leu Val Ser Trp Glu Asp Ile Gln Cys Thr Tyr Gly
            340                 345                 350

Asn Pro Asn Tyr His Trp Gln Glu Thr Ala Tyr Leu Leu Val Tyr Met
        355                 360                 365

Lys Met Glu Cys
    370

<210> SEQ ID NO 33
<211> LENGTH: 3957
<212> TYPE: DNA
<213> ORGANISM: Homo sapiens

<400> SEQUENCE: 33
atgtctggcg gggccagtgc cacaggccca aggagagggc ccccaggact ggaggacacc      60

```
actagtaaga agaagcagaa ggatcgagca aaccaggaga gcaaggatgg agatcctagg    120
aaagagacag ggtctcgata tgttgcccag gctggtcttg aacctctggc ctcaggtgat    180
ccttctgcct cagcctccca tgcagctggg atcacaggct cacgccaccg tacccggctg    240
ttctttcctt catcgtcagg gtcagcatcc actcctcaag aggagcagac caaagaggga    300
gcttgtgaag accctcatga tctcttggct actcccactc cagagttgtt gctcgattgg    360
aggcagagtg cagaagaggt gattgtcaag cttcgtgtgg gagtaggtcc cctgcagctg    420
gaggatgtag atgctgcttt cacagataca gactgtgtgg tgcggtttgc aggtggtcag    480
cagtggggtg gtgtcttcta tgctgagata aaaagctctt gtgctaaagt gcaaacccgc    540
aagggcagtc tcctgcacct gacactgccc aaaaaggtgc ctatgctcac gtggccctcc    600
ctcctggttg aggctgatga acagctttgc ataccaccgc tgaactccca aacctgcctc    660
ctgggctcag aggagaattt agccccttt̃g gcaggagaga aagcagtgcc tcccgggaat    720
gacccagtct ctccagccat ggtccggagc agaaaccctg ggaaagatga ctgtgccaag    780
gaggagatgg cagtggcagc agatgctgca accttggtgg atgagcccga gtcgatggtg    840
aacctggcgt ttgtcaagaa tgactcgtat gagaagggcc cggattcagt ggtggtgcac    900
gtgtacgtga aggagatctg cagggacacc tcaagagtac ttttccgtga gcaggacttc    960
acgctcatct tccagaccag ggatggaaac ttcctgaggc tgcacccggg ctgtgggccc   1020
cacaccacct tccgttggca ggtgaagctc aggaatctga ttgagccaga gcagtgcacc   1080
ttctgtttca cggcttctcg catcgacatc tgccttcgta agaggcagag tcagcgctgg   1140
gggggcctgg aggccccggc tgcacgagtg ggtggtgcaa aggttgccgt gccgacaggt   1200
ccaacccctc tggattcaac cccaccagga ggtgctcccc accccctgac aggccaggag   1260
gaggcccggg ctgtggagaa ggataaatcc aaggcacgat ctgaggacac agggctagac   1320
agtgtggcaa cccgcacacc catggagcat gtaaccccaa agccagagac acacctggcc   1380
tcgcccaagc ctacatgcat ggtgcctccc atgccccaca gcccagttag tggagacagc   1440
gtggaggagg aggaagagga agagaagaag gtgtgtctgc caggcttcac tggccttgtc   1500
aatttaggca acacctgctt catgaacagc gtcattcagt ctctgtccaa cactcgggaa   1560
ctccgggact tcttccatga ccgctccttt gaggctgaga tcaactacaa caacccacta   1620
gggactggtg ggcgtctggc cattggcttt gccgtgctgc ttcgggcgct gtggaagggc   1680
acccaccatg ccttccagcc ttccaagttg aaggccattg tggcgagtaa ggccagccag   1740
ttcacaggct atgcacagca tgatgcccag gagttcatgg ctttcctgct ggatgggctg   1800
cacgaggacc tgaatcgcat tcagaacaag ccctacacag agaccgtgga ttcagatggg   1860
cggcccgatg aggtggtagc tgaggaagca tggcagcggc acaagatgag gaatgactct   1920
ttcatcgtgg acctatttca ggggcagtac aagtcgaagc tggtgtgccc tgtgtgtgcc   1980
aaggtctcca tcacttttga cccgtttctt tatctgccgg tgcccttgcc acaaaagcaa   2040
aaggttctcc ctgtcttttta ttttgcccga gagccccaca gcaagcccat caagttcctg   2100
gtgagcgtca gcaaggagaa ctccactgcg agcgaagtat tggactccct ctctcagagt   2160
gttcatgtga agcctgagaa cctgcgtttg gcggaggtaa ttaagaatcg ttttcatcgt   2220
gtgttcctac cctcccactc actggacact gtgtccccat ctgatacgct cctctgcttt   2280
gagctgctat cctcagagtt ggctaaggag cgggtagtgg tgctagaggt gcaacagcgc   2340
ccccaggtgc ccagcgtccc catctccaag tgtgcagcct gccagcggaa gcaacagtcg   2400
```

-continued

```
gaggatgaaa agctgaagcg ctgtacccgg tgctaccgtg tgggctactg caaccagctc    2460
tgccagaaaa cccactggcc tgaccacaag ggcctctgcc gacctgagaa cattggctac    2520
cccttcctgg tcagtgtacc tgcctcacgc ctcacttatg cccgcctcgc tcagttgcta    2580
gagggctatg cccggtactc tgtgagtgta ttccagccac cctttcagcc aggccgcatg    2640
gccttggagt ctcagagccc tggctgcacc acactgctct ccacaggttc cctggaggct    2700
ggggacagcg agagaccc cattcagcca cctgagctcc agctggtgac ccctatggct    2760
gaggggggaca cagggcttcc ccgggtgtgg gcagccctg accggggtcc tgtgcccagc    2820
accagtggaa tttcttctga gatgctggcc agtgggccca ttgaggttgg ctccttgcca    2880
gctggcgaga gggtgtcccg acccgaagct gctgtgcctg gtaccagca tccaagtgaa    2940
gctatgaatg cccacacacc ccagttcttc atctataaaa ttgattcatc caaccgagag    3000
cagcggctag aggacaaagg agacacccca ctggagctgg gtgacgactg tagcctggct    3060
ctcgtctggc ggaacaatga cgccttgcag gagtttgtgt tggtagcctc caaggagctg    3120
gaatgtgctg aggatccagg ctctgccggt gaggctgccc gggccggcca cttcaccctg    3180
gaccagtgcc tcaacctctt cacacggcct gaggtgctgg cacccgagga ggcctggtac    3240
tgcccacagt gcaaacagca ccgtgaggcc tccaagcagc tgttgctatg cgcctgcca    3300
aatgttctca tcgtgcagct caagcgcttc tcctttcgta gttttatctg gcgtgacaag    3360
atcaatgact tggtggagtt ccctgttagg aacctggacc tgagcaagtt ctgcattggt    3420
cagaaagagg agcagctgcc cagctacgat ctatatgctg tcatcaacca ctatggaggc    3480
atgattggtg gccactacac tgcctgtgca cgcctgccca tgatcgtag cagtcagcgc    3540
agtgacgtgg gctggcgctt gtttgatgac agcacagtga caacggtaga cgagagccag    3600
gttgtgacgc gttatgccta tgtactcttc taccgccggc ggaactctcc tgtggagagg    3660
cccccagggg caggtcactc tgagcaccac ccagacctag gccctgcagc tgaggctgct    3720
gccagccagg cttcccggat ttggcaggag ctggaggctg aggaggagcc ggtgcctgag    3780
gggtctgggc ccctgggtcc ctgggggccc caagactggg tgggccccct accacgtggc    3840
cctaccacac cagatgaggg ctgcctccgg tactttgtcc tgggcaccgt ggcggctttg    3900
gtggccctcg tgctcaacgt gttctatcct ctggtatccc agagtcgctg gagatga     3957
```

<210> SEQ ID NO 34
<211> LENGTH: 1318
<212> TYPE: PRT
<213> ORGANISM: Homo sapiens

<400> SEQUENCE: 34

```
Met Ser Gly Gly Ala Ser Ala Thr Gly Pro Arg Arg Gly Pro Pro Gly
1               5                   10                  15

Leu Glu Asp Thr Thr Ser Lys Lys Gln Lys Asp Arg Ala Asn Gln
            20                  25                  30

Glu Ser Lys Asp Gly Asp Pro Arg Lys Glu Thr Gly Ser Arg Tyr Val
        35                  40                  45

Ala Gln Ala Gly Leu Glu Pro Leu Ala Ser Gly Asp Pro Ser Ala Ser
    50                  55                  60

Ala Ser His Ala Ala Gly Ile Thr Gly Ser His Arg Thr Arg Leu
65                  70                  75                  80

Phe Phe Pro Ser Ser Ser Gly Ser Ala Ser Thr Pro Gln Glu Glu Gln
                85                  90                  95

Thr Lys Glu Gly Ala Cys Glu Asp Pro His Asp Leu Leu Ala Thr Pro
```

```
                100             105             110
Thr Pro Glu Leu Leu Asp Trp Arg Gln Ser Ala Glu Val Ile
            115             120             125
Val Lys Leu Arg Val Gly Val Gly Pro Leu Gln Leu Glu Asp Val Asp
            130             135             140
Ala Ala Phe Thr Asp Thr Asp Cys Val Val Arg Phe Ala Gly Gly Gln
145             150             155             160
Gln Trp Gly Gly Val Phe Tyr Ala Glu Ile Lys Ser Ser Cys Ala Lys
            165             170             175
Val Gln Thr Arg Lys Gly Ser Leu Leu His Leu Thr Leu Pro Lys Lys
            180             185             190
Val Pro Met Leu Thr Trp Pro Ser Leu Leu Val Glu Ala Asp Glu Gln
            195             200             205
Leu Cys Ile Pro Pro Leu Asn Ser Gln Thr Cys Leu Leu Gly Ser Glu
            210             215             220
Glu Asn Leu Ala Pro Leu Ala Gly Glu Lys Ala Val Pro Pro Gly Asn
225             230             235             240
Asp Pro Val Ser Pro Ala Met Val Arg Ser Arg Asn Pro Gly Lys Asp
            245             250             255
Asp Cys Ala Lys Glu Met Ala Val Ala Ala Asp Ala Ala Thr Leu
            260             265             270
Val Asp Glu Pro Glu Ser Met Val Asn Leu Ala Phe Val Lys Asn Asp
            275             280             285
Ser Tyr Glu Lys Gly Pro Asp Ser Val Val His Val Tyr Val Lys
            290             295             300
Glu Ile Cys Arg Asp Thr Ser Arg Val Leu Phe Arg Glu Gln Asp Phe
305             310             315             320
Thr Leu Ile Phe Gln Thr Arg Asp Gly Asn Phe Leu Arg Leu His Pro
            325             330             335
Gly Cys Gly Pro His Thr Thr Phe Arg Trp Gln Val Lys Leu Arg Asn
            340             345             350
Leu Ile Glu Pro Glu Gln Cys Thr Phe Cys Phe Thr Ala Ser Arg Ile
            355             360             365
Asp Ile Cys Leu Arg Lys Arg Gln Ser Gln Arg Trp Gly Gly Leu Glu
            370             375             380
Ala Pro Ala Ala Arg Val Gly Gly Ala Lys Val Ala Val Pro Thr Gly
385             390             395             400
Pro Thr Pro Leu Asp Ser Thr Pro Pro Gly Gly Ala Pro His Pro Leu
            405             410             415
Thr Gly Gln Glu Glu Ala Arg Ala Val Glu Lys Asp Lys Ser Lys Ala
            420             425             430
Arg Ser Glu Asp Thr Gly Leu Asp Ser Val Ala Thr Arg Thr Pro Met
            435             440             445
Glu His Val Thr Pro Lys Pro Glu Thr His Leu Ala Ser Pro Lys Pro
            450             455             460
Thr Cys Met Val Pro Pro Met Pro His Ser Pro Val Ser Gly Asp Ser
465             470             475             480
Val Glu Glu Glu Glu Glu Glu Lys Lys Val Cys Leu Pro Gly Phe
            485             490             495
Thr Gly Leu Val Asn Leu Gly Asn Thr Cys Phe Met Asn Ser Val Ile
            500             505             510
Gln Ser Leu Ser Asn Thr Arg Glu Leu Arg Asp Phe Phe His Asp Arg
            515             520             525
```

```
Ser Phe Glu Ala Glu Ile Asn Tyr Asn Asn Pro Leu Gly Thr Gly Gly
    530                 535                 540

Arg Leu Ala Ile Gly Phe Ala Val Leu Leu Arg Ala Leu Trp Lys Gly
545                 550                 555                 560

Thr His His Ala Phe Gln Pro Ser Lys Leu Lys Ala Ile Val Ala Ser
                565                 570                 575

Lys Ala Ser Gln Phe Thr Gly Tyr Ala Gln His Asp Ala Gln Glu Phe
                580                 585                 590

Met Ala Phe Leu Leu Asp Gly Leu His Glu Asp Leu Asn Arg Ile Gln
                595                 600                 605

Asn Lys Pro Tyr Thr Glu Thr Val Asp Ser Asp Gly Arg Pro Asp Glu
                610                 615                 620

Val Val Ala Glu Glu Ala Trp Gln Arg His Lys Met Arg Asn Asp Ser
625                 630                 635                 640

Phe Ile Val Asp Leu Phe Gln Gly Gln Tyr Lys Ser Lys Leu Val Cys
                645                 650                 655

Pro Val Cys Ala Lys Val Ser Ile Thr Phe Asp Pro Phe Leu Tyr Leu
                660                 665                 670

Pro Val Pro Leu Pro Gln Lys Gln Lys Val Leu Pro Val Phe Tyr Phe
                675                 680                 685

Ala Arg Glu Pro His Ser Lys Pro Ile Lys Phe Leu Val Ser Val Ser
                690                 695                 700

Lys Glu Asn Ser Thr Ala Ser Glu Val Leu Asp Ser Leu Ser Gln Ser
705                 710                 715                 720

Val His Val Lys Pro Glu Asn Leu Arg Leu Ala Glu Val Ile Lys Asn
                725                 730                 735

Arg Phe His Arg Val Phe Leu Pro Ser His Ser Leu Asp Thr Val Ser
                740                 745                 750

Pro Ser Asp Thr Leu Leu Cys Phe Glu Leu Leu Ser Ser Glu Leu Ala
                755                 760                 765

Lys Glu Arg Val Val Leu Glu Val Gln Gln Arg Pro Gln Val Pro
770                 775                 780

Ser Val Pro Ile Ser Lys Cys Ala Ala Cys Gln Arg Lys Gln Gln Ser
785                 790                 795                 800

Glu Asp Glu Lys Leu Lys Arg Cys Thr Arg Cys Tyr Arg Val Gly Tyr
                805                 810                 815

Cys Asn Gln Leu Cys Gln Lys Thr His Trp Pro Asp His Lys Gly Leu
                820                 825                 830

Cys Arg Pro Glu Asn Ile Gly Tyr Pro Phe Leu Val Ser Val Pro Ala
                835                 840                 845

Ser Arg Leu Thr Tyr Ala Arg Leu Ala Gln Leu Leu Glu Gly Tyr Ala
850                 855                 860

Arg Tyr Ser Val Ser Val Phe Gln Pro Pro Phe Gln Pro Gly Arg Met
865                 870                 875                 880

Ala Leu Glu Ser Gln Ser Pro Gly Cys Thr Thr Leu Leu Ser Thr Gly
                885                 890                 895

Ser Leu Glu Ala Gly Asp Ser Glu Arg Asp Pro Ile Gln Pro Pro Glu
                900                 905                 910

Leu Gln Leu Val Thr Pro Met Ala Glu Gly Asp Thr Gly Leu Pro Arg
                915                 920                 925

Val Trp Ala Ala Pro Asp Arg Gly Pro Val Pro Ser Thr Ser Gly Ile
930                 935                 940
```

Ser Ser Glu Met Leu Ala Ser Gly Pro Ile Glu Val Gly Ser Leu Pro
945                 950                 955                 960

Ala Gly Glu Arg Val Ser Arg Pro Glu Ala Val Pro Gly Tyr Gln
            965                 970                 975

His Pro Ser Glu Ala Met Asn Ala His Thr Pro Gln Phe Phe Ile Tyr
            980                 985                 990

Lys Ile Asp Ser Ser Asn Arg Glu Gln Arg Leu Glu Asp Lys Gly Asp
            995                 1000                1005

Thr Pro Leu Glu Leu Gly Asp Asp Cys Ser Leu Ala Leu Val Trp Arg
    1010                1015                1020

Asn Asn Glu Arg Leu Gln Glu Phe Val Leu Val Ala Ser Lys Glu Leu
1025                1030                1035                1040

Glu Cys Ala Glu Asp Pro Gly Ser Ala Gly Glu Ala Ala Arg Ala Gly
                1045                1050                1055

His Phe Thr Leu Asp Gln Cys Leu Asn Leu Phe Thr Arg Pro Glu Val
                1060                1065                1070

Leu Ala Pro Glu Glu Ala Trp Tyr Cys Pro Gln Cys Lys Gln His Arg
            1075                1080                1085

Glu Ala Ser Lys Gln Leu Leu Leu Trp Arg Leu Pro Asn Val Leu Ile
            1090                1095                1100

Val Gln Leu Lys Arg Phe Ser Phe Arg Ser Phe Ile Trp Arg Asp Lys
1105                1110                1115                1120

Ile Asn Asp Leu Val Glu Phe Pro Val Arg Asn Leu Asp Leu Ser Lys
                1125                1130                1135

Phe Cys Ile Gly Gln Lys Glu Glu Gln Leu Pro Ser Tyr Asp Leu Tyr
            1140                1145                1150

Ala Val Ile Asn His Tyr Gly Gly Met Ile Gly Gly His Tyr Thr Ala
            1155                1160                1165

Cys Ala Arg Leu Pro Asn Asp Arg Ser Ser Gln Arg Ser Asp Val Gly
    1170                1175                1180

Trp Arg Leu Phe Asp Asp Ser Thr Val Thr Thr Val Asp Glu Ser Gln
1185                1190                1195                1200

Val Val Thr Arg Tyr Ala Tyr Val Leu Phe Tyr Arg Arg Arg Asn Ser
                1205                1210                1215

Pro Val Glu Arg Pro Pro Arg Ala Gly His Ser Glu His His Pro Asp
            1220                1225                1230

Leu Gly Pro Ala Ala Glu Ala Ala Ser Gln Ala Ser Arg Ile Trp
            1235                1240                1245

Gln Glu Leu Glu Ala Glu Glu Pro Val Pro Glu Gly Ser Gly Pro
1250                1255                1260

Leu Gly Pro Trp Gly Pro Gln Asp Trp Val Gly Pro Leu Arg Gly
1265                1270                1275                1280

Pro Thr Thr Pro Asp Glu Gly Cys Leu Arg Tyr Phe Val Leu Gly Thr
    1285                1290                1295

Val Ala Ala Leu Val Ala Leu Val Leu Asn Val Phe Tyr Pro Leu Val
                1300                1305                1310

Ser Gln Ser Arg Trp Arg
        1315

<210> SEQ ID NO 35
<211> LENGTH: 2742
<212> TYPE: DNA
<213> ORGANISM: Homo sapiens

<400> SEQUENCE: 35

-continued

```
atgggggact ccagggacct ttgccctcac cttgactcca taggagaggt gaccaaagag    60
gacttgctgc tcaaatctaa gggaacctgt cagtcgtgtg gggtcaccgg accaaaccta   120
tgggcctgtc tgcaggttgc ctgccccrat gttggctgcg gagaatcctt cgctgaccac   180
agcaccattc atgcacaggc aaaaaagcac aacttgaccg tgaacctgac cacgttccga   240
ctgtggtgtt acgcctgtga aaggaggta ttcctggagc agcggctggc agcccctctg   300
ctgggctcct cttccaagtt ctctgaacag gactccccgc caccctccca ccctctgaaa   360
gctgttccta ttgctgtggc tgatgaagga gagtctgagt cagaggatga tgacctgaaa   420
cctcgaggcc tcacgggcat gaagaacctc gggaactcct gctacatgaa cgccgccctg   480
caggccctgt ccaattgccc gccgctgact cagttcttct ggagtgtgg cggcctggtg   540
cgcacagata agaagccagc cctgtgcaag agctaccaga agctggtctc tgaggtctgg   600
cataagaaac ggccaagcta cgtggtcccc accagtctgt ctcatgggat caagttggtc   660
aacccaatgt tccgaggcta tgcccagcag gacacccaag agttccttcg ctgcctgatg   720
gaccagctgc acgaggagct caaggagccg gtggtggcca cggtggcgct gacggaggct   780
cgggactcag attcgagtga cacggatgag aaacggagg gtgaccggag cccatcagaa   840
gatgagttct tgtcctgtga ctcgagcagt gaccggggtg agggtgacgg gcaggggcgt   900
ggcggggca gctcgcaggc cgagacggag ctgctgatcc cagatgaggc gggccgagcc   960
atctctgaga aggagcggat gaaggaccgc aagttctcct ggggccagca gcgtacaaac  1020
tcggagcaag tggacgagga cgctgatgtg gacactgcca tggctgccct tgaccagccc  1080
gcggaggccc agcccccgtc accacggtcc tccagcccct gccggacgcc agagccggac  1140
aatgatgctc acctacgcag ctcctctcgc ccctgcagcc ccgtccacca ccacgagggc  1200
catgccaagc tgtctagcag ccccccctcgt gcaagcccg tgaggatggc accgtcgtac  1260
gtgctcaaga aagcccaggt attgagtgct ggcagccgga ggcggaagga gcagcgctac  1320
cgcagcgtca tctcagacat cttttgacggc tccattctca gcctcgtgca gtgtctcacc  1380
tgtgaccggg tatccaccac agtggaaacg ttccaggact tatcactgcc cattcctgga  1440
aaggaggacc tggccaagct ccattcagcc atctaccaga atgtgccggc caagccaggc  1500
gcctgtgggg acagctatgc cgcccagggc tggctggcct tcattgtgga gtacatccga  1560
cggtttgtgg tatcctgtac ccccagctgg ttttgggggc ctgtcgtcac cctgaaagac  1620
tgccttgctg ccttctttgc cgctgatgag ttaaagggtg acaacatgta cagctgtgag  1680
cggtgtaaga agctgcggaa cggagtgaag tactgcaaag tcctgcggtt gcccgagatc  1740
ctgtgcattc acctaaagcg ctttcggcac gaggtgatgt actcattcaa gatcaacagc  1800
cacgtctcct tcccctcga ggggctcgac ctgcgcccct tccttgccaa ggagtgcaca  1860
tcccagatca ccacctacga cctcctctcg gtcatctgcc accacggcac ggcaggcagt  1920
gggcactaca tcgcctactg ccagaacgtg atcaatgggc agtggtacga gtttgatgac  1980
cagtacgtca cagaagtcca cgagacggtg gtgcagaacg ccgagggcta cgtactcttc  2040
tacaggaaga gcagcgagga ggccatgcgg gagcgacagc aggtggtgtc cctggccgcc  2100
atgcgggagc ccagcctgct gcggttctac gtgtcccgcg agtggctcaa caagttcaac  2160
accttcgcgg agccaggccc catcaccaac cagaccttcc tctgctccca cggaggcatc  2220
ccgcccaca ataccacta catcgacgac ctggtggtca tcctgcccca gaacgtctgg  2280
gagcacctgt acaacagatt cggggtggc cccgccgtga accacctgta cgtgtgctcc  2340
```

-continued

```
atctgccagg tggagatcga ggcactggcc aagcgcagga ggatcgagat cgacaccttc      2400
atcaagttga acaaggcctt ccaggccgag gagtcgccgg gcgtcatcta ctgcatcagc      2460
atgcagtggt tccgggagtg ggaggcgttc gtcaaggga aggacaacga gccccccggg       2520
cccattgaca cagcaggat tgcacaggtc aaaggaagcg ccatgtccca gctgaagcag       2580
ggagctgact acgggcagat ttcggaggag acctggacct acctgaacag cctgtatgga      2640
ggtggccccg agattgccat ccgccagagt gtggcgcagc cgctgggccc agagaacctg      2700 cacgggagc agaagatcga agccgagacg cgggccgtgt ga                          2742
```

<210> SEQ ID NO 36
<211> LENGTH: 913
<212> TYPE: PRT
<213> ORGANISM: Homo sapiens

<400> SEQUENCE: 36

```
Met Gly Asp Ser Arg Asp Leu Cys Pro His Leu Asp Ser Ile Gly Glu
1               5                   10                  15

Val Thr Lys Glu Asp Leu Leu Lys Ser Lys Gly Thr Cys Gln Ser
            20                  25                  30

Cys Gly Val Thr Gly Pro Asn Leu Trp Ala Cys Leu Gln Val Ala Cys
        35                  40                  45

Pro Tyr Val Gly Cys Gly Glu Ser Phe Ala Asp His Ser Thr Ile His
    50                  55                  60

Ala Gln Ala Lys Lys His Asn Leu Thr Val Asn Leu Thr Thr Phe Arg
65                  70                  75                  80

Leu Trp Cys Tyr Ala Cys Glu Lys Glu Val Phe Leu Glu Gln Arg Leu
                85                  90                  95

Ala Ala Pro Leu Leu Gly Ser Ser Lys Phe Ser Gly Gln Asp Ser
            100                 105                 110

Pro Pro Pro Ser His Pro Leu Lys Ala Val Pro Ile Ala Val Ala Asp
        115                 120                 125

Glu Gly Glu Ser Glu Ser Glu Asp Asp Leu Lys Pro Arg Gly Leu
    130                 135                 140

Thr Gly Met Lys Asn Leu Gly Asn Ser Cys Tyr Met Asn Ala Ala Leu
145                 150                 155                 160

Gln Ala Leu Ser Asn Cys Pro Pro Leu Thr Gln Phe Phe Leu Glu Cys
                165                 170                 175

Gly Gly Leu Val Arg Thr Asp Lys Lys Pro Ala Leu Cys Lys Ser Tyr
            180                 185                 190

Gln Lys Leu Val Ser Glu Val Trp His Lys Lys Arg Pro Ser Tyr Val
        195                 200                 205

Val Pro Thr Ser Leu Ser His Gly Ile Lys Leu Val Asn Pro Met Phe
    210                 215                 220

Arg Gly Tyr Ala Gln Gln Asp Thr Gln Glu Phe Leu Arg Cys Leu Met
225                 230                 235                 240

Asp Gln Leu His Glu Glu Leu Lys Glu Pro Val Val Ala Thr Val Ala
                245                 250                 255

Leu Thr Glu Ala Arg Asp Ser Asp Ser Ser Asp Thr Asp Glu Lys Arg
            260                 265                 270

Glu Gly Asp Arg Ser Pro Ser Glu Asp Glu Phe Leu Ser Cys Asp Ser
        275                 280                 285

Ser Ser Asp Arg Gly Glu Gly Asp Gly Gln Gly Arg Gly Gly Gly Ser
    290                 295                 300
```

-continued

```
Ser Gln Ala Glu Thr Glu Leu Leu Ile Pro Asp Ala Gly Arg Ala
305                 310                 315                 320

Ile Ser Glu Lys Glu Arg Met Lys Asp Arg Lys Phe Ser Trp Gly Gln
            325                 330                 335

Gln Arg Thr Asn Ser Glu Gln Val Asp Glu Asp Ala Asp Val Asp Thr
            340                 345                 350

Ala Met Ala Ala Leu Asp Gln Pro Ala Glu Ala Gln Pro Pro Ser Pro
            355                 360                 365

Arg Ser Ser Pro Cys Arg Thr Pro Glu Pro Asp Asn Asp Ala His
    370                 375                 380

Leu Arg Ser Ser Ser Arg Pro Cys Ser Pro Val His His Glu Gly
385                 390                 395                 400

His Ala Lys Leu Ser Ser Pro Pro Arg Ala Ser Pro Val Arg Met
            405                 410                 415

Ala Pro Ser Tyr Val Leu Lys Lys Ala Gln Val Leu Ser Ala Gly Ser
            420                 425                 430

Arg Arg Arg Lys Glu Gln Arg Tyr Arg Ser Val Ile Ser Asp Ile Phe
    435                 440                 445

Asp Gly Ser Ile Leu Ser Leu Val Gln Cys Leu Thr Cys Asp Arg Val
    450                 455                 460

Ser Thr Thr Val Glu Thr Phe Gln Asp Leu Ser Leu Pro Ile Pro Gly
465                 470                 475                 480

Lys Glu Asp Leu Ala Lys Leu His Ser Ala Ile Tyr Gln Asn Val Pro
            485                 490                 495

Ala Lys Pro Gly Ala Cys Gly Asp Ser Tyr Ala Ala Gln Gly Trp Leu
            500                 505                 510

Ala Phe Ile Val Glu Tyr Ile Arg Arg Phe Val Val Ser Cys Thr Pro
            515                 520                 525

Ser Trp Phe Trp Gly Pro Val Val Thr Leu Glu Asp Cys Leu Ala Ala
            530                 535                 540

Phe Phe Ala Ala Asp Glu Leu Lys Gly Asp Asn Met Tyr Ser Cys Glu
545                 550                 555                 560

Arg Cys Lys Lys Leu Arg Asn Gly Val Lys Tyr Cys Lys Val Leu Arg
            565                 570                 575

Leu Pro Glu Ile Leu Cys Ile His Leu Lys Arg Phe Arg His Glu Val
            580                 585                 590

Met Tyr Ser Phe Lys Ile Asn Ser His Val Ser Phe Pro Leu Glu Gly
            595                 600                 605

Leu Asp Leu Arg Pro Phe Leu Ala Lys Glu Cys Thr Ser Gln Ile Thr
610                 615                 620

Thr Tyr Asp Leu Leu Ser Val Ile Cys His His Gly Thr Ala Gly Ser
625                 630                 635                 640

Gly His Tyr Ile Ala Tyr Cys Gln Asn Val Ile Asn Gly Gln Trp Tyr
            645                 650                 655

Glu Phe Asp Asp Gln Tyr Val Thr Glu Val His Glu Thr Val Val Gln
            660                 665                 670

Asn Ala Glu Gly Tyr Val Leu Phe Tyr Arg Lys Ser Ser Glu Glu Ala
            675                 680                 685

Met Arg Glu Arg Gln Gln Val Ser Leu Ala Ala Met Arg Glu Pro
            690                 695                 700

Ser Leu Leu Arg Phe Tyr Val Ser Arg Glu Trp Leu Asn Lys Phe Asn
705                 710                 715                 720

Thr Phe Ala Glu Pro Gly Pro Ile Thr Asn Gln Thr Phe Leu Cys Ser
```

```
                725                 730                 735
His Gly Gly Ile Pro Pro His Lys Tyr His Tyr Ile Asp Asp Leu Val
            740                 745                 750

Val Ile Leu Pro Gln Asn Val Trp Glu His Leu Tyr Asn Arg Phe Gly
            755                 760                 765

Gly Gly Pro Ala Val Asn His Leu Tyr Val Cys Ser Ile Cys Gln Val
        770                 775                 780

Glu Ile Glu Ala Leu Ala Lys Arg Arg Arg Ile Glu Ile Asp Thr Phe
785                 790                 795                 800

Ile Lys Leu Asn Lys Ala Phe Gln Ala Glu Glu Ser Pro Gly Val Ile
                805                 810                 815

Tyr Cys Ile Ser Met Gln Trp Phe Arg Glu Trp Ala Phe Val Lys
            820                 825                 830

Gly Lys Asp Asn Glu Pro Pro Gly Pro Ile Asp Asn Ser Arg Ile Ala
        835                 840                 845

Gln Val Lys Gly Ser Gly His Val Gln Leu Lys Gln Gly Ala Asp Tyr
    850                 855                 860

Gly Gln Ile Ser Glu Glu Thr Trp Thr Tyr Leu Asn Ser Leu Tyr Gly
865                 870                 875                 880

Gly Gly Pro Glu Ile Ala Ile Arg Gln Ser Val Ala Gln Pro Leu Gly
                885                 890                 895

Pro Glu Asn Leu His Gly Glu Gln Lys Ile Ala Glu Thr Arg Ala
            900                 905                 910

Val

<210> SEQ ID NO 37
<211> LENGTH: 3168
<212> TYPE: DNA
<213> ORGANISM: Homo sapiens

<400> SEQUENCE: 37
atgaccgtgg agcagaacgt gctgcagcag agcgcggcgc agaagcacca gcagacgttt       60
ttgaatcaac tgagagaaat tacgggggatt aatgacaccc agatactaca gcaagccttg     120
```

-continued

| | |
|---|---|
| atgattgaag gagaaattga gtctttacat tcagagaatt caggaaaatc aggccaagag | 1080 |
| cattggttta ctgaattacc acctgtgtta acatttgaat tgtcaagatt tgaatttaat | 1140 |
| caggcattgg gaagaccaga aaaaattcac aacaaattag aatttcccca gttttatat | 1200 |
| ttggacagat acatgcacag aaacagagaa ataacaagaa ttaagaggga agagatcaag | 1260 |
| agactgaaag attacctcac ggtattacaa caaaggctag aaagatattt aagctatggt | 1320 |
| tccggtccca aacgattccc cttggtagat gttcttcagt atgcattgga atttgcctca | 1380 |
| agtaaacctg tttgcacttc tcctgttgac gatattgacg ctagttcccc acctagtggt | 1440 |
| tccataccat cacagacatt accaagcaca acagaacaac agggagccct atcttcagaa | 1500 |
| ctgccaagca catcaccttc atcagttgct gccatttcat cgagatcagt aatacacaaa | 1560 |
| ccatttactc agtcccggat acctccagat ttgcccatgc atccggcacc aaggcacata | 1620 |
| acggaggaag aactttctgt gctggaaagt tgtttacatc gctggaggac agaaatagaa | 1680 |
| aatgacacca gagatttgca ggaaagcata tccagaatcc atcgaacaat tgaattaatg | 1740 |
| tactctgaca aatctatgat acaagttcct tatcgattac atgccgtttt agttcacgaa | 1800 |
| ggccaagcta atgctgggca ctactgggca tatattttg atcatcgtga aagcagatgg | 1860 |
| atgaagtaca atgatattgc tgtgacaaaa tcatcatggg aagagctagt gagggactct | 1920 |
| tttggtggtt atagaaatgc cagtgcatac tgtttaatgt acataaatga taaggcacag | 1980 |
| ttcctaatac aagaggagtt taataaagaa actgggcagc cccttgttgg tatagaaaca | 2040 |
| ttaccaccgg atttgagaga ttttgttgag gaagacaacc aacgatttga aaaagaacta | 2100 |
| gaagaatggg atgcacaact tgcccagaaa gctttgcagg aaaagctttt agcgtctcag | 2160 |
| aaattgagag agtcagagac ttctgtgaca acagcacaag cagcaggaga cccagaatat | 2220 |
| ctagagcagc catcaagaag tgatttctca agcacttga aagaagaaac tattcaaata | 2280 |
| attaccaagg catcacatga gcatgaagat aaaagtcctg aaacagtttt gcagtcggca | 2340 |
| attaagttgg aatatgcaag gttggttaag ttggccaag aagacacccc accagaaacc | 2400 |
| gattatcgtt tacatcatgt agtggtctac tttatccaga accaggcacc aaagaaaatt | 2460 |
| attgagaaaa cattactaga acaatttgga gatagaaatt tgagttttga tgaaaggtgt | 2520 |
| cacaacataa tgaaagttgc tcaagccaaa ctggaaatga taaaacctga agaagtaaac | 2580 |
| ttggaggaat atgaggagtg gcatcaggat tataggaaat tcagggaaac aactatgtat | 2640 |
| ctcataattg ggctagaaaa ttttcaaaga gaaagttata tagattcctt gctgttcctc | 2700 |
| atctgtgctt atcagaataa caaagaactc ttgtctaaag gcttatacag aggacatgat | 2760 |
| gaagaattga tatcacatta tagaagagaa tgtttgctaa aattaaatga gcaagccgca | 2820 |
| gaactcttcg aatctggaga ggatcgagaa gtaaacaatg gttttgattat catgaatgag | 2880 |
| tttattgtcc catttttgcc attattactg gtggatgaaa tggaagaaaa ggatatacta | 2940 |
| gctgtagaag atatgagaaa tcgatggtgt tcctaccttg gtcaagaaat ggaaccacac | 3000 |
| ctccaagaaa agctgacaga ttttttgcca aaactgcttg attgttctat ggagattaaa | 3060 |
| agtttccatg agccaccgaa gttaccttca tattccacgc atgaactctg tgagcgattt | 3120 |
| gcccgaatca tgttgtccct cagtcgaact cctgctgatg aagataa | 3168 |

<210> SEQ ID NO 38
<211> LENGTH: 1055
<212> TYPE: PRT
<213> ORGANISM: Homo sapiens

<400> SEQUENCE: 38

```
Met Thr Val Glu Gln Asn Val Leu Gln Gln Ser Ala Ala Gln Lys His
1               5                   10                  15

Gln Gln Thr Phe Leu Asn Gln Leu Arg Glu Ile Thr Gly Ile Asn Asp
                20                  25                  30

Thr Gln Ile Leu Gln Gln Ala Leu Lys Asp Ser Asn Gly Asn Leu Glu
            35                  40                  45

Leu Ala Val Ala Phe Leu Thr Ala Lys Asn Ala Lys Thr Pro Gln Gln
50                      55                  60

Glu Glu Thr Thr Tyr Tyr Gln Thr Ala Leu Pro Gly Asn Asp Arg Tyr
65                  70                  75                  80

Ile Ser Val Gly Ser Gln Ala Asp Thr Asn Val Ile Asp Leu Thr Gly
                85                  90                  95

Asp Asp Lys Asp Leu Gln Arg Ala Ile Ala Leu Ser Leu Ala Glu
                100                 105                 110

Ser Asn Arg Ala Phe Arg Glu Thr Gly Ile Thr Asp Glu Glu Gln Ala
        115                 120                 125

Ile Ser Arg Val Leu Glu Ala Ser Ile Ala Glu Asn Lys Ala Cys Leu
        130                 135                 140

Lys Arg Thr Pro Thr Glu Val Trp Arg Asp Ser Arg Asn Pro Tyr Asp
145                 150                 155                 160

Arg Lys Arg Gln Asp Lys Ala Pro Val Gly Leu Lys Asn Val Gly Asn
                165                 170                 175

Thr Cys Trp Phe Ser Ala Val Ile Gln Ser Leu Phe Asn Leu Leu Glu
            180                 185                 190

Phe Arg Arg Leu Val Leu Asn Tyr Lys Pro Pro Ser Asn Ala Gln Asp
        195                 200                 205

Leu Pro Arg Asn Gln Lys Glu His Arg Asn Leu Pro Phe Met Arg Glu
210                 215                 220

Leu Arg Tyr Leu Phe Ala Leu Leu Val Gly Thr Lys Arg Lys Tyr Val
225                 230                 235                 240

Asp Pro Ser Arg Ala Val Glu Ile Leu Lys Asp Ala Phe Lys Ser Asn
                245                 250                 255

Asp Ser Gln Gln Gln Asp Val Ser Glu Phe Thr His Lys Leu Leu Asp
            260                 265                 270

Trp Leu Glu Asp Ala Phe Gln Met Lys Ala Glu Glu Thr Asp Glu
        275                 280                 285

Glu Lys Pro Lys Asn Pro Met Val Glu Leu Phe Tyr Gly Arg Phe Leu
290                 295                 300

Ala Val Gly Val Leu Glu Gly Lys Lys Phe Glu Asn Thr Glu Met Phe
305                 310                 315                 320

Gly Gln Tyr Pro Leu Gln Val Asn Gly Phe Lys Asp Leu His Glu Cys
                325                 330                 335

Leu Glu Ala Ala Met Ile Glu Gly Ile Glu Ser Leu His Ser Glu
            340                 345                 350

Asn Ser Gly Lys Ser Gly Gln Glu His Trp Phe Thr Glu Leu Pro Pro
        355                 360                 365

Val Leu Thr Phe Glu Leu Ser Arg Phe Glu Phe Asn Gln Ala Leu Gly
370                 375                 380

Arg Pro Glu Lys Ile His Asn Lys Leu Glu Phe Pro Gln Val Leu Tyr
385                 390                 395                 400

Leu Asp Arg Tyr Met His Arg Asn Arg Glu Ile Thr Arg Ile Lys Arg
                405                 410                 415
```

```
Glu Glu Ile Lys Arg Leu Lys Asp Tyr Leu Thr Val Leu Gln Gln Arg
                420                 425                 430

Leu Glu Arg Tyr Leu Ser Tyr Gly Ser Gly Pro Lys Arg Phe Pro Leu
            435                 440                 445

Val Asp Val Leu Gln Tyr Ala Leu Glu Phe Ala Ser Ser Lys Pro Val
        450                 455                 460

Cys Thr Ser Pro Val Asp Asp Ile Asp Ala Ser Ser Pro Pro Ser Gly
465                 470                 475                 480

Ser Ile Pro Ser Gln Thr Leu Pro Ser Thr Thr Glu Gln Gln Gly Ala
                485                 490                 495

Leu Ser Ser Glu Leu Pro Ser Thr Ser Pro Ser Ser Val Ala Ala Ile
            500                 505                 510

Ser Ser Arg Ser Val Ile His Lys Pro Phe Thr Gln Ser Arg Ile Pro
        515                 520                 525

Pro Asp Leu Pro Met His Pro Ala Pro Arg His Ile Thr Glu Glu Glu
        530                 535                 540

Leu Ser Val Leu Glu Ser Cys Leu His Arg Trp Arg Thr Glu Ile Glu
545                 550                 555                 560

Asn Asp Thr Arg Asp Leu Gln Glu Ser Ile Ser Arg Ile His Arg Thr
                565                 570                 575

Ile Glu Leu Met Tyr Ser Asp Lys Ser Met Ile Gln Val Pro Tyr Arg
            580                 585                 590

Leu His Ala Val Leu Val His Glu Gly Gln Ala Asn Ala Gly His Tyr
        595                 600                 605

Trp Ala Tyr Ile Phe Asp His Arg Glu Ser Arg Trp Met Lys Tyr Asn
610                 615                 620

Asp Ile Ala Val Thr Lys Ser Ser Trp Glu Glu Leu Val Arg Asp Ser
625                 630                 635                 640

Phe Gly Gly Tyr Arg Asn Ala Ser Ala Tyr Cys Leu Met Tyr Ile Asn
                645                 650                 655

Asp Lys Ala Gln Phe Leu Ile Gln Glu Glu Phe Asn Lys Glu Thr Gly
            660                 665                 670

Gln Pro Leu Val Gly Ile Glu Thr Leu Pro Pro Asp Leu Arg Asp Phe
        675                 680                 685

Val Glu Glu Asp Asn Gln Arg Phe Glu Lys Glu Leu Glu Glu Trp Asp
        690                 695                 700

Ala Gln Leu Ala Gln Lys Ala Leu Gln Glu Lys Leu Leu Ala Ser Gln
705                 710                 715                 720

Lys Leu Arg Glu Ser Glu Thr Ser Val Thr Thr Ala Gln Ala Ala Gly
                725                 730                 735

Asp Pro Glu Tyr Leu Glu Gln Pro Ser Arg Ser Asp Phe Ser Lys His
            740                 745                 750

Leu Lys Glu Glu Thr Ile Gln Ile Ile Thr Lys Ala Ser His Glu His
        755                 760                 765

Glu Asp Lys Ser Pro Glu Thr Val Leu Gln Ser Ala Ile Lys Leu Glu
        770                 775                 780

Tyr Ala Arg Leu Val Lys Leu Ala Gln Glu Asp Thr Pro Pro Glu Thr
785                 790                 795                 800

Asp Tyr Arg Leu His His Val Val Val Tyr Phe Ile Gln Asn Gln Ala
                805                 810                 815

Pro Lys Lys Ile Ile Glu Lys Thr Leu Leu Glu Gln Phe Gly Asp Arg
            820                 825                 830

Asn Leu Ser Phe Asp Glu Arg Cys His Asn Ile Met Lys Val Ala Gln
```

```
                835                 840                 845
Ala Lys Leu Glu Met Ile Lys Pro Glu Glu Val Asn Leu Glu Glu Tyr
            850                 855                 860
Glu Glu Trp His Gln Asp Tyr Arg Lys Phe Arg Glu Thr Thr Met Tyr
865                 870                 875                 880
Leu Ile Ile Gly Leu Glu Asn Phe Gln Arg Glu Ser Tyr Ile Asp Ser
                885                 890                 895
Leu Leu Phe Leu Ile Cys Ala Tyr Gln Asn Asn Lys Glu Leu Leu Ser
            900                 905                 910
Lys Gly Leu Tyr Arg Gly His Asp Glu Glu Leu Ile Ser His Tyr Arg
                915                 920                 925
Arg Glu Cys Leu Leu Lys Leu Asn Glu Gln Ala Ala Glu Leu Phe Glu
            930                 935                 940
Ser Gly Glu Asp Arg Glu Val Asn Asn Gly Leu Ile Ile Met Asn Glu
945                 950                 955                 960
Phe Ile Val Pro Phe Leu Pro Leu Leu Val Asp Glu Met Glu Glu
                965                 970                 975
Lys Asp Ile Leu Ala Val Glu Asp Met Arg Asn Arg Trp Cys Ser Tyr
            980                 985                 990
Leu Gly Gln Glu Met Glu Pro His Leu Gln Glu Lys Leu Thr Asp Phe
            995                 1000                1005
Leu Pro Lys Leu Leu Asp Cys Ser Met Glu Ile Lys Ser Phe His Glu
        1010                1015                1020
Pro Pro Lys Leu Pro Ser Tyr Ser Thr His Glu Leu Cys Glu Arg Phe
1025                1030                1035                1040
Ala Arg Ile Met Leu Ser Leu Ser Arg Thr Pro Ala Asp Gly Arg
            1045                1050                1055

<210> SEQ ID NO 39
<211> LENGTH: 3264
<212> TYPE: DNA
<213> ORGANISM: Homo sapiens

<400> SEQUENCE: 39
atgaccgtgg agcagaacgt gctgcagcag agcgcggcgc agaagcacca gcagacgttt       60
ttgaatcaac tgagagaaat tacggggatt aatgacaccc agatactaca gcaagccttg      120
aaggatagta tggaaacttt ggaattagca gtggctttcc ttactgcgaa gaatgctaag      180 accccctcagc aggaggagac aacttactac caaacagcac ttcctggcaa tgatagatac      240
atcagtgtgg aagccaagc agatacaaat gtgattgatc tcactggaga tgataaagat      300
gatcttcaga gagcaattgc cttgagtttg gccgaatcaa acagggcatt cagggagact      360
ggaataactg atgaggaaca agccattagc agagttcttg aagccagcat agcagagaat      420
aaagcatgtt tgaagaggac acctacagaa gtttggaggg attctcgaaa cccttatgat      480
agaaaaagac aggacaaagc tcccgttggg ctaaagaatg ttggcaatac ttgttggttt      540
agtgctgtta ttcagtcatt atttaatctt ttggaattta agattagt tctgaattac      600 aagcctccat caaatgctca agatttaccc cgaaaccaaa aggaacatcg gaatttgcct      660
tttatgcgtg agctgaggta tctatttgca cttcttgttg gtaccaaaag gaagtatgtt      720
gatccatcaa gagcagttga aattcttaag gatgctttca atcaaatga ctcacagcag      780 caagatgtga gtgagtttac acacaaatta ttagattggt tagaagatgc cttccaaatg      840
aaagctgaag aggagacgga tgaagagaag ccaaagaacc ccatggtaga gttgttctat      900
```

```
ggcagattcc tggctgtggg agtacttgaa ggtaaaaaat ttgaaaacac tgaaatgttt    960
ggtcagtacc cacttcaggt caatgggttc aaagatctgc atgagtgcct agaagctgca   1020
atgattgaag gagaaattga gtctttacat tcagagaatt caggaaaatc aggccaagag   1080
cattggttta ctgaattacc acctgtgtta acatttgaat tgtcaagatt tgaatttaat   1140
caggcattgg gaagaccaga aaaaattcac aacaaattag aatttcccca agttttatat   1200
ttggacagat acatgcacag aaacagagaa ataacaagaa ttaagaggga agagatcaag   1260
agactgaaag attacctcac ggtattacaa caaaggctag aaagatattt aagctatggt   1320
tccggtccca aacgattccc cttggtagat gttcttcagt atgcattgga atttgcctca   1380
agtaaacctg tttgcacttc tcctgttgac gatattgacg ctagttcccc acctagtggt   1440
tccataccat cacagacatt accaagcaca acagaacaac agggagccct atcttcagaa   1500
ctgccaagca catcaccttc atcagttgct gccatttcat cgagatcagt aatacacaaa   1560
ccatttactc agtcccggat acctccagat ttgcccatgc atccggcacc aaggcacata   1620
acggaggaaa aactttctgt gctggaaagt tgtttacatc gctggaggac agaaatagaa   1680
aatgacacca gagatttgca ggaaaagcata tccagaatcc atcgaacaat tgaattaatg   1740
tactctgaca aatctatgat acaagttcct tatcgattac atgccgtttt agttcacgaa   1800
ggccaagcta atgctgggca ctactgggca tatattttg atcatcgtga aagcagatgg   1860
atgaagtaca atgatattgc tgtgacaaaa tcatcatggg aagagctagt gagggactct   1920
tttggtggtt atagaaatgc cagtgcatac tgtttaatgt acataaatga taaggcacag   1980
ttcctaatac aagaggagtt taataaagaa actgggcagc cccttgttgg tatagaaaca   2040
ttaccaccgg atttgagaga ttttgttgag gaagacaacc aacgatttga aaaagaacta   2100
gaagaatggg atgcacaact tgcccagaaa gctttgcagg aaaagctttt agcgtctcag   2160
aaattgagag agtcagagac ttctgtgaca acagcacaag cagcaggaga cccagaatat   2220
ctagagcagc catcaagaag tgatttctca aagcacttga agaagaaac tattcaaata   2280
attaccaagg catcacatga gcatgaagat aaaagtcctg aaacagtttt gcagtcgatc   2340
atgatgacac cgaacatgca aggtattatc atggcgatag gtaaatccag gagtgtatat   2400
gacaggtgtg gccctgaagc agggttcttt aaggcaatta agttggaata tgcaaggttg   2460
gttaagttgg cccaagaaga caccccacca gaaaccgatt atcgtttaca tcatgtagtg   2520
gtctacttta tccagaacca ggcaccaaag aaaattattg agaaaacatt actagaacaa   2580
tttggagata gaaatttgag ttttgatgaa aggtgtcaca acataatgaa agttgctcaa   2640
gccaaactgg aaatgataaa acctgaagaa gtaaacttgg aggaatatga ggagtggcat   2700
caggattata ggaaattcag ggaaacaact atgtatctca taattgggct agaaaatttt   2760
caaagagaaa gttatataga ttccttgctg ttcctcatct gtgcttatca gaataacaaa   2820
gaactcttgt ctaaaggctt atacagagga catgatgaag aattgatatc acattataga   2880
agagaatgtt tgctaaaatt aaatgagcaa gccgcagaac tcttcgaatc tggagaggat   2940
cgagaagtaa acaatggttt gattatcatg aatgagttta ttgtcccatt tttgccatta   3000
ttactggtgg atgaaatgga agaaaaggat atactagctg tagaagatat gagaaatcga   3060
tggtgttcct accttggtca gaaatggaa ccacacctcc aagaaaagct gacagatttt   3120
ttgccaaaac tgcttgattg ttctatggag attaaaagtt tccatgagcc accgaagtta   3180
ccttcatatt ccacgcatga actctgtgag cgatttgccc gaatcatgtt gtccctcagt   3240
cgaactcctg ctgatggaag ataa                                          3264
```

<210> SEQ ID NO 40
<211> LENGTH: 1087
<212> TYPE: PRT
<213> ORGANISM: Homo sapiens

<400> SEQUENCE: 40

Met Thr Val Glu Gln Asn Val Leu Gln Gln Ser Ala Ala Gln Lys His
1               5                   10                  15

Gln Gln Thr Phe Leu Asn Gln Leu Arg Glu Ile Thr Gly Ile Asn Asp
                20                  25                  30

Thr Gln Ile Leu Gln Gln Ala Leu Lys Asp Ser Asn Gly Asn Leu Glu
            35                  40                  45

Leu Ala Val Ala Phe Leu Thr Ala Lys Asn Ala Lys Thr Pro Gln Gln
50                  55                  60

Glu Glu Thr Thr Tyr Tyr Gln Thr Ala Leu Pro Gly Asn Asp Arg Tyr
65                  70                  75                  80

Ile Ser Val Gly Ser Gln Ala Asp Thr Asn Val Ile Asp Leu Thr Gly
                85                  90                  95

Asp Asp Lys Asp Asp Leu Gln Arg Ala Ile Ala Leu Ser Leu Ala Glu
            100                 105                 110

Ser Asn Arg Ala Phe Arg Glu Thr Gly Ile Thr Asp Glu Glu Gln Ala
        115                 120                 125

Ile Ser Arg Val Leu Glu Ala Ser Ile Ala Glu Asn Lys Ala Cys Leu
    130                 135                 140

Lys Arg Thr Pro Thr Glu Val Trp Arg Asp Ser Arg Asn Pro Tyr Asp
145                 150                 155                 160

Arg Lys Arg Gln Asp Lys Ala Pro Val Gly Leu Lys Asn Val Gly Asn
                165                 170                 175

Thr Cys Trp Phe Ser Ala Val Ile Gln Ser Leu Phe Asn Leu Leu Glu
            180                 185                 190

Phe Arg Arg Leu Val Leu Asn Tyr Lys Pro Pro Ser Asn Ala Gln Asp
        195                 200                 205

Leu Pro Arg Asn Gln Lys Glu His Arg Asn Leu Pro Phe Met Arg Glu
    210                 215                 220

Leu Arg Tyr Leu Phe Ala Leu Leu Val Gly Thr Lys Arg Lys Tyr Val
225                 230                 235                 240

Asp Pro Ser Arg Ala Val Glu Ile Leu Lys Asp Ala Phe Lys Ser Asn
                245                 250                 255

Asp Ser Gln Gln Gln Asp Val Ser Glu Phe Thr His Lys Leu Leu Asp
            260                 265                 270

Trp Leu Glu Asp Ala Phe Gln Met Lys Ala Glu Glu Thr Asp Glu
        275                 280                 285

Glu Lys Pro Lys Asn Pro Met Val Glu Leu Phe Tyr Gly Arg Phe Leu
    290                 295                 300

Ala Val Gly Val Leu Glu Gly Lys Lys Phe Glu Asn Thr Glu Met Phe
305                 310                 315                 320

Gly Gln Tyr Pro Leu Gln Val Asn Gly Phe Lys Asp Leu His Glu Cys
                325                 330                 335

Leu Glu Ala Ala Met Ile Glu Gly Ile Glu Ser Leu His Ser Glu
            340                 345                 350

Asn Ser Gly Lys Ser Gly Gln Glu His Trp Phe Thr Glu Leu Pro Pro
        355                 360                 365

Val Leu Thr Phe Glu Leu Ser Arg Phe Glu Phe Asn Gln Ala Leu Gly

```
                370                 375                 380
Arg Pro Glu Lys Ile His Asn Lys Leu Glu Phe Pro Gln Val Leu Tyr
385                 390                 395                 400

Leu Asp Arg Tyr Met His Arg Asn Arg Glu Ile Thr Arg Ile Lys Arg
                405                 410                 415

Glu Glu Ile Lys Arg Leu Lys Asp Tyr Leu Thr Val Leu Gln Gln Arg
                420                 425                 430

Leu Glu Arg Tyr Leu Ser Tyr Gly Ser Gly Pro Lys Arg Phe Pro Leu
                435                 440                 445

Val Asp Val Leu Gln Tyr Ala Leu Glu Phe Ala Ser Ser Lys Pro Val
450                 455                 460

Cys Thr Ser Pro Val Asp Ile Asp Ala Ser Ser Pro Pro Ser Gly
465                 470                 475                 480

Ser Ile Pro Ser Gln Thr Leu Pro Ser Thr Glu Gln Gln Gly Ala
                485                 490                 495

Leu Ser Ser Glu Leu Pro Ser Thr Ser Pro Ser Ser Val Ala Ala Ile
                500                 505                 510

Ser Ser Arg Ser Val Ile His Lys Pro Phe Thr Gln Ser Arg Ile Pro
                515                 520                 525

Pro Asp Leu Pro Met His Pro Ala Pro Arg His Ile Thr Glu Glu Lys
                530                 535                 540

Leu Ser Val Leu Glu Ser Cys Leu His Arg Trp Arg Thr Glu Ile Glu
545                 550                 555                 560

Asn Asp Thr Arg Asp Leu Gln Glu Ser Ile Ser Arg Ile His Arg Thr
                565                 570                 575

Ile Glu Leu Met Tyr Ser Asp Lys Ser Met Ile Gln Val Pro Tyr Arg
                580                 585                 590

Leu His Ala Val Leu Val His Glu Gly Gln Ala Asn Ala Gly His Tyr
                595                 600                 605

Trp Ala Tyr Ile Phe Asp His Arg Glu Ser Arg Trp Met Lys Tyr Asn
                610                 615                 620

Asp Ile Ala Val Thr Lys Ser Ser Trp Glu Glu Leu Val Arg Asp Ser
625                 630                 635                 640

Phe Gly Gly Tyr Arg Asn Ala Ser Ala Tyr Cys Leu Met Tyr Ile Asn
                645                 650                 655

Asp Lys Ala Gln Phe Leu Ile Gln Glu Glu Phe Asn Lys Glu Thr Gly
                660                 665                 670

Gln Pro Leu Val Gly Ile Glu Thr Leu Pro Pro Asp Leu Arg Asp Phe
                675                 680                 685

Val Glu Glu Asp Asn Gln Arg Phe Glu Lys Glu Leu Glu Glu Trp Asp
690                 695                 700

Ala Gln Leu Ala Gln Lys Ala Leu Gln Glu Lys Leu Leu Ala Ser Gln
705                 710                 715                 720

Lys Leu Arg Glu Ser Glu Thr Ser Val Thr Thr Ala Gln Ala Ala Gly
                725                 730                 735

Asp Pro Glu Tyr Leu Glu Gln Pro Ser Arg Ser Asp Phe Ser Lys His
                740                 745                 750

Leu Lys Glu Glu Thr Ile Gln Ile Ile Thr Lys Ala Ser His Glu His
                755                 760                 765

Glu Asp Lys Ser Pro Glu Thr Val Leu Gln Ser Ile Met Met Thr Pro
                770                 775                 780

Asn Met Gln Gly Ile Ile Met Ala Ile Gly Lys Ser Arg Ser Val Tyr
785                 790                 795                 800
```

Asp Arg Cys Gly Pro Glu Ala Gly Phe Phe Lys Ala Ile Lys Leu Glu
                805                 810                 815

Tyr Ala Arg Leu Val Lys Leu Ala Gln Glu Asp Thr Pro Pro Glu Thr
            820                 825                 830

Asp Tyr Arg Leu His His Val Val Tyr Phe Ile Gln Asn Gln Ala
        835                 840                 845

Pro Lys Lys Ile Ile Glu Lys Thr Leu Leu Glu Gln Phe Gly Asp Arg
    850                 855                 860

Asn Leu Ser Phe Asp Glu Arg Cys His Asn Ile Met Lys Val Ala Gln
865                 870                 875                 880

Ala Lys Leu Glu Met Ile Lys Pro Glu Glu Val Asn Leu Glu Glu Tyr
                885                 890                 895

Glu Glu Trp His Gln Asp Tyr Arg Lys Phe Arg Glu Thr Thr Met Tyr
            900                 905                 910

Leu Ile Ile Gly Leu Glu Asn Phe Gln Arg Glu Ser Tyr Ile Asp Ser
        915                 920                 925

Leu Leu Phe Leu Ile Cys Ala Tyr Gln Asn Asn Lys Glu Leu Leu Ser
    930                 935                 940

Lys Gly Leu Tyr Arg Gly His Asp Glu Glu Leu Ile Ser His Tyr Arg
945                 950                 955                 960

Arg Glu Cys Leu Leu Lys Leu Asn Glu Gln Ala Ala Glu Leu Phe Glu
                965                 970                 975

Ser Gly Glu Asp Arg Glu Val Asn Asn Gly Leu Ile Ile Met Asn Glu
            980                 985                 990

Phe Ile Val Pro Phe Leu Pro Leu Leu Leu Val Asp Glu Met Glu Glu
        995                 1000                1005

Lys Asp Ile Leu Ala Val Glu Asp Met Arg Asn Arg Trp Cys Ser Tyr
    1010                1015                1020

Leu Gly Gln Glu Met Glu Pro His Leu Gln Glu Lys Leu Thr Asp Phe
1025                1030                1035                1040

Leu Pro Lys Leu Leu Asp Cys Ser Met Glu Ile Lys Ser Phe His Glu
                1045                1050                1055

Pro Pro Lys Leu Pro Ser Tyr Ser Thr His Glu Leu Cys Glu Arg Phe
            1060                1065                1070

Ala Arg Ile Met Leu Ser Leu Ser Arg Thr Pro Ala Asp Gly Arg
        1075                1080                1085

<210> SEQ ID NO 41
<211> LENGTH: 3234
<212> TYPE: DNA
<213> ORGANISM: Homo sapiens

<400> SEQUENCE: 41
atgactgcgg agctgcagca ggacgacgcg gccggcgcgg cagacggcca cggctcgagc      60
tgccaaatgc tgttaaatca actgagagaa atcacaggca ttcaggaccc ttcctttctc     120
catgaagctc tgaaggccag taatggtgac attactcagg cagtcagcct tctcactgat     180
gagagagtta aggagcccag tcaagacact gttgctacag aaccatctga agtagagggg     240
agtgctgcca acaaggaagt attagcaaaa gttatagacc ttactcatga taacaaagat     300
gatcttcagg ctgccattgc tttgagtcta ctggagtctc ccaaaattca agctgatgga     360
agagatctta caggatgca tgaagcaacc tctgcagaaa ctaaacgctc aaagagaaaa     420
cgctgtgaag tctggggaga aaaccccaat cccaatgact ggaggagagt tgatggttgg     480

```
ccagttgggc tgaaaaatgt tggcaataca tgttggttta gtgctgttat tcagtctctc    540
tttcaattgc ctgaatttcg aagacttgtt ctcagttata gtctgccaca aaatgtactt    600
gaaaattgtc gaagtcatac agaaaagaga aatatcatgt ttatgcaaga gcttcagtat    660
ttgtttgctc taatgatggg atcaaataga aaatttgtag acccgtctgc agccctggat    720
ctattaaagg gagcattccg atcatctgag gaacagcagc aagatgtgag tgaattcaca    780
cacaagctcc tggattggct agaggacgca ttccagctag ctgttaatgt taacagtccc    840
aggaacaaat ctgaaaatcc aatggtgcag ctgttctatg gtactttcct gactgaaggg    900
gttcgtgaag gaaaaccctt ttgtaacaat gagaccttcg gccagtatcc tcttcaggta    960
aacggttatc gcaacttaga cgagtgtttg gaaggggcca tggtggaggg tgatgttgag   1020
cttcttccct ccgatcactc ggtgaagtat ggacaagagc gttggtttac aaagctacct   1080
ccagtgttga cctttgaact ctcaagattt gagtttaatc agtcccttgg gcagccagag   1140
aaaattcaca ataagctgga atttcctcag attatttata tggacaggta catgtacagg   1200
agcaaggagc ttattcgaaa taagagagag tgtattcgaa agttgaagga ggaaataaaa   1260
attctgcagc aaaaattgga aaggtatgtg aaatatggct caggcccagc tcggttcccg   1320
ctcccggaca tgctgaaata tgttattgaa tttgctagta caaaacctgc tcagaaagc    1380 tgtccacctg aaagtgacac acatatgaca ttaccactt cttcagtgca ctgctcggtt    1440
tctgaccaga catccaagga aagtacaagt acagaaagc cttctcagga tgttgaaagt    1500 acctttctt ctcctgaaga ttctttaccc aagtctaaac cactgacatc ttctcggtct    1560
tccatggaaa tgccttcaca gccagctcca cgaacagtca cagatgagga gataaatttt   1620
gttaagacct gtcttcagag atggaggagt gagattgaac aagatataca agatttaaag   1680
acttgtattg caagtactac tcagactatt gaacagatgt actgcgatcc tctccttcgt   1740
caggtgcctt atcgcttgca tgcagttctt gttcatgaag acaagcaaa tgctggacac   1800 tattgggcct atatctataa tcaaccccga cagagctggc tcaagtacaa tgacatctct   1860
gttactgaat cttcctggga agaagttgaa agagattcct atggaggcct gagaaatgtt   1920 agtgctact gtctgatgta cattaatgac aaactaccct acttcaatgc agaggcagcc   1980
ccaactgaat cagatcaaat gtcagaagtg gaagccctat ctgtggaact caagcattac   2040
attcaggagg ataactggcg gtttgagcag gaagtagagg agtgggaaga agagcagtct   2100
tgcaaaatcc ctcaaatgga gtcctccacc aactcctcat cacaggacta ctctacatca   2160
caagagcctt cagtagcctc ttctcatggg gttcgctgct tgtcatctga gcatgctgtg   2220
attgtaaagg agcaaactgc ccaggctatt gcaaacacag cccgtgccta tgagaagagc   2280
ggtgtagaag cggcactgag tgaggtgatg ctgagccctg ccatgcaagg ggtcatcctg   2340
gccatagcta aagcccgtca gacctttgac cgagatgggc tgaagcagg gctgattaag   2400 gcattccatg aagaatactc caggctctat cagcttgcca agagaccccc cacctctcac   2460
agtgatcctc gacttcagca tgtccttgtc tactttttcc aaaatgaagc acccaaaagg   2520
gtagtagaac gaacccttct ggaacagttt gcagataaaa atcttagcta tgatgaaaga   2580
tcaatcagca ttatgaaggt ggctcaagcg aaactgaagg aaattggtcc agatgacatg   2640
aatatggaag agtacaagaa gtggcatgaa gattatagtt tgttccgaaa agtgtctgtg   2700
tatctcctaa caggcctaga actctatcaa aaaggaaagt accaagaggc actttcctac   2760
ctggtatatg cctaccagag caatgctgcc ctgctgatga gggggcccg ccgggggtc    2820 aaagaatccg tgattgcttt ataccgaaga aaatgccttc tggagctgaa tgccaaagca   2880
```

-continued

```
gcttctcttt ttgaaacaaa tgatgatcac tccgtaactg agggcattaa tgtgatgaat    2940
gaactgatca tccctgcat tcaccttatc attaataatg acatttccaa ggatgatctg     3000
gatgccattg aggtcatgag aaaccattgg tgctcttacc ttgggcaaga tattgcagaa    3060
aatctgcagc tgtgcctagg ggagtttcta cccagacttc tagatccttc tgcagaaatc    3120
atcgtcttga aagagcctcc aactattcga cccaattctc cctatgacct atgtagccga    3180
tttgcagctg tcatggagtc aattcaggga gtttcaactg tgacagtgaa ataa          3234
```

<210> SEQ ID NO 42
<211> LENGTH: 1077
<212> TYPE: PRT
<213> ORGANISM: Homo sapiens

<400> SEQUENCE: 42

| | | | | | | | | | | | | | | |
|---|---|---|---|---|---|---|---|---|---|---|---|---|---|---|
| Met | Thr | Ala | Glu | Leu | Gln | Gln | Asp | Asp | Ala | Gly | Ala | Ala | Asp | Gly |
| 1 | | | | 5 | | | | | 10 | | | | | 15 |
| His | Gly | Ser | Ser | Cys | Gln | Met | Leu | Leu | Asn | Gln | Leu | Arg | Glu | Ile | Thr |
| | | | 20 | | | | | 25 | | | | | 30 | | |
| Gly | Ile | Gln | Asp | Pro | Ser | Phe | Leu | His | Glu | Ala | Leu | Lys | Ala | Ser | Asn |
| | | | 35 | | | | 40 | | | | | 45 | | | |
| Gly | Asp | Ile | Thr | Gln | Ala | Val | Ser | Leu | Leu | Thr | Asp | Glu | Arg | Val | Lys |
| | 50 | | | | | 55 | | | | | 60 | | | | |
| Glu | Pro | Ser | Gln | Asp | Thr | Val | Ala | Thr | Glu | Pro | Ser | Glu | Val | Glu | Gly |
| 65 | | | | | 70 | | | | | 75 | | | | | 80 |
| Ser | Ala | Ala | Asn | Lys | Glu | Val | Leu | Ala | Lys | Val | Ile | Asp | Leu | Thr | His |
| | | | | 85 | | | | | 90 | | | | | 95 | |
| Asp | Asn | Lys | Asp | Asp | Leu | Gln | Ala | Ala | Ile | Ala | Leu | Ser | Leu | Leu | Glu |
| | | | 100 | | | | | 105 | | | | | 110 | | |
| Ser | Pro | Lys | Ile | Gln | Ala | Asp | Gly | Arg | Asp | Leu | Asn | Arg | Met | His | Glu |
| | | 115 | | | | | 120 | | | | | 125 | | | |
| Ala | Thr | Ser | Ala | Glu | Thr | Lys | Arg | Ser | Lys | Arg | Lys | Arg | Cys | Glu | Val |
| | 130 | | | | | 135 | | | | | 140 | | | | |
| Trp | Gly | Glu | Asn | Pro | Asn | Pro | Asn | Asp | Trp | Arg | Arg | Val | Asp | Gly | Trp |
| 145 | | | | | 150 | | | | | 155 | | | | | 160 |
| Pro | Val | Gly | Leu | Lys | Asn | Val | Gly | Asn | Thr | Cys | Trp | Phe | Ser | Ala | Val |
| | | | | 165 | | | | | 170 | | | | | 175 | |
| Ile | Gln | Ser | Leu | Phe | Gln | Leu | Pro | Glu | Phe | Arg | Arg | Leu | Val | Leu | Ser |
| | | | 180 | | | | | 185 | | | | | 190 | | |
| Tyr | Ser | Leu | Pro | Gln | Asn | Val | Leu | Glu | Asn | Cys | Arg | Ser | His | Thr | Glu |
| | | 195 | | | | | 200 | | | | | 205 | | | |
| Lys | Arg | Asn | Ile | Met | Phe | Met | Gln | Glu | Leu | Gln | Tyr | Leu | Phe | Ala | Leu |
| | 210 | | | | | 215 | | | | | 220 | | | | |
| Met | Met | Gly | Ser | Asn | Arg | Lys | Phe | Val | Asp | Pro | Ser | Ala | Ala | Leu | Asp |
| 225 | | | | | 230 | | | | | 235 | | | | | 240 |
| Leu | Leu | Lys | Gly | Ala | Phe | Arg | Ser | Ser | Glu | Gln | Gln | Gln | Asp | Val |
| | | | | 245 | | | | | 250 | | | | | 255 |
| Ser | Glu | Phe | Thr | His | Lys | Leu | Leu | Asp | Trp | Leu | Glu | Asp | Ala | Phe | Gln |
| | | | 260 | | | | | 265 | | | | | 270 | | |
| Leu | Ala | Val | Asn | Val | Asn | Ser | Pro | Arg | Asn | Lys | Ser | Glu | Asn | Pro | Met |
| | | 275 | | | | | 280 | | | | | 285 | | | |
| Val | Gln | Leu | Phe | Tyr | Gly | Thr | Phe | Leu | Thr | Glu | Gly | Val | Arg | Glu | Gly |
| | 290 | | | | | 295 | | | | | 300 | | | | |
| Lys | Pro | Phe | Cys | Asn | Asn | Glu | Thr | Phe | Gly | Gln | Tyr | Pro | Leu | Gln | Val |

```
            305                 310                 315                 320
        Asn Gly Tyr Arg Asn Leu Asp Glu Cys Leu Glu Gly Ala Met Val Glu
                        325                 330                 335
        Gly Asp Val Glu Leu Leu Pro Ser Asp His Ser Val Lys Tyr Gly Gln
                        340                 345                 350
        Glu Arg Trp Phe Thr Lys Leu Pro Val Leu Thr Phe Glu Leu Ser
                        355                 360                 365
        Arg Phe Glu Phe Asn Gln Ser Leu Gly Gln Pro Glu Lys Ile His Asn
                        370                 375                 380
        Lys Leu Glu Phe Pro Gln Ile Ile Tyr Met Asp Arg Tyr Met Tyr Arg
        385                 390                 395                 400
        Ser Lys Glu Leu Ile Arg Asn Lys Arg Glu Cys Ile Arg Lys Leu Lys
                        405                 410                 415
        Glu Glu Ile Lys Ile Leu Gln Gln Lys Leu Glu Arg Tyr Val Lys Tyr
                        420                 425                 430
        Gly Ser Gly Pro Ala Arg Phe Pro Leu Pro Asp Met Leu Lys Tyr Val
                        435                 440                 445
        Ile Glu Phe Ala Ser Thr Lys Pro Ala Ser Glu Ser Cys Pro Pro Glu
                        450                 455                 460
        Ser Asp Thr His Met Thr Leu Pro Leu Ser Ser Val His Cys Ser Val
        465                 470                 475                 480
        Ser Asp Gln Thr Ser Lys Glu Ser Thr Ser Thr Glu Ser Ser Ser Gln
                        485                 490                 495
        Asp Val Glu Ser Thr Phe Ser Ser Pro Glu Asp Ser Leu Pro Lys Ser
                        500                 505                 510
        Lys Pro Leu Thr Ser Ser Arg Ser Ser Met Glu Met Pro Ser Gln Pro
                        515                 520                 525
        Ala Pro Arg Thr Val Thr Asp Glu Glu Ile Asn Phe Val Lys Thr Cys
                        530                 535                 540
        Leu Gln Arg Trp Arg Ser Glu Ile Glu Gln Asp Ile Gln Asp Leu Lys
        545                 550                 555                 560
        Thr Cys Ile Ala Ser Thr Thr Gln Thr Ile Glu Gln Met Tyr Cys Asp
                        565                 570                 575
        Pro Leu Leu Arg Gln Val Pro Tyr Arg Leu His Ala Val Leu Val His
                        580                 585                 590
        Glu Gly Gln Ala Asn Ala Gly His Tyr Trp Ala Tyr Ile Tyr Asn Gln
                        595                 600                 605
        Pro Arg Gln Ser Trp Leu Lys Tyr Asn Asp Ile Ser Val Thr Glu Ser
                        610                 615                 620
        Ser Trp Glu Glu Val Glu Arg Asp Ser Tyr Gly Gly Leu Arg Asn Val
        625                 630                 635                 640
        Ser Ala Tyr Cys Leu Met Tyr Ile Asn Asp Lys Leu Pro Tyr Phe Asn
                        645                 650                 655
        Ala Glu Ala Ala Pro Thr Glu Ser Asp Gln Met Ser Glu Val Glu Ala
                        660                 665                 670
        Leu Ser Val Glu Leu Lys His Tyr Ile Gln Glu Asp Asn Trp Arg Phe
                        675                 680                 685
        Glu Gln Glu Val Glu Glu Trp Glu Glu Glu Gln Ser Cys Lys Ile Pro
                        690                 695                 700
        Gln Met Glu Ser Ser Thr Asn Ser Ser Ser Gln Asp Tyr Ser Thr Ser
        705                 710                 715                 720
        Gln Glu Pro Ser Val Ala Ser Ser His Gly Val Arg Cys Leu Ser Ser
                        725                 730                 735
```

Glu His Ala Val Ile Val Lys Glu Gln Thr Ala Gln Ala Ile Ala Asn
            740                 745                 750

Thr Ala Arg Ala Tyr Glu Lys Ser Gly Val Glu Ala Ala Leu Ser Glu
        755                 760                 765

Val Met Leu Ser Pro Ala Met Gln Gly Val Ile Leu Ala Ile Ala Lys
770                 775                 780

Ala Arg Gln Thr Phe Asp Arg Asp Gly Ser Glu Ala Gly Leu Ile Lys
785                 790                 795                 800

Ala Phe His Glu Glu Tyr Ser Arg Leu Tyr Gln Leu Ala Lys Glu Thr
                805                 810                 815

Pro Thr Ser His Ser Asp Pro Arg Leu Gln His Val Leu Val Tyr Phe
            820                 825                 830

Phe Gln Asn Glu Ala Pro Lys Arg Val Val Glu Arg Thr Leu Leu Glu
        835                 840                 845

Gln Phe Ala Asp Lys Asn Leu Ser Tyr Asp Glu Arg Ser Ile Ser Ile
850                 855                 860

Met Lys Val Ala Gln Ala Lys Leu Lys Glu Ile Gly Pro Asp Asp Met
865                 870                 875                 880

Asn Met Glu Glu Tyr Lys Lys Trp His Glu Asp Tyr Ser Leu Phe Arg
                885                 890                 895

Lys Val Ser Val Tyr Leu Leu Thr Gly Leu Glu Leu Tyr Gln Lys Gly
            900                 905                 910

Lys Tyr Gln Glu Ala Leu Ser Tyr Leu Val Tyr Ala Tyr Gln Ser Asn
        915                 920                 925

Ala Ala Leu Leu Met Lys Gly Pro Arg Arg Gly Val Lys Glu Ser Val
930                 935                 940

Ile Ala Leu Tyr Arg Arg Lys Cys Leu Leu Glu Leu Asn Ala Lys Ala
945                 950                 955                 960

Ala Ser Leu Phe Glu Thr Asn Asp Asp His Ser Val Thr Glu Gly Ile
                965                 970                 975

Asn Val Met Asn Glu Leu Ile Ile Pro Cys Ile His Leu Ile Ile Asn
            980                 985                 990

Asn Asp Ile Ser Lys Asp Leu Asp Ala Ile Glu Val Met Arg Asn
        995                 1000                1005

His Trp Cys Ser Tyr Leu Gly Gln Asp Ile Ala Glu Asn Leu Gln Leu
    1010                1015                1020

Cys Leu Gly Glu Phe Leu Pro Arg Leu Leu Asp Pro Ser Ala Glu Ile
1025                1030                1035                1040

Ile Val Leu Lys Glu Pro Pro Thr Ile Arg Pro Asn Ser Pro Tyr Asp
                1045                1050                1055

Leu Cys Ser Arg Phe Ala Ala Val Met Glu Ser Ile Gln Gly Val Ser
            1060                1065                1070

Thr Val Thr Val Lys
        1075

<210> SEQ ID NO 43
<211> LENGTH: 1554
<212> TYPE: DNA
<213> ORGANISM: Homo sapiens

<400> SEQUENCE: 43
atgctgagct cccgggccga ggcggcgatg accgcggccg acagggccat ccagcgcttc      60
ctgcggaccg gggcggccgt cagatataaa gtcatgaaga actggggagt tataggtgga     120

```
attgctgctg ctcttgcagc aggaatatat gttatttggg gtcccattac agaaagaaag    180
aagcgtagaa aagggcttgt gcctggcctt gttaatttag ggaacacctg cttcatgaac    240
tccctgctac aaggcctgtc tgcctgtcct gctttcatca ggtggctgga agagttcacc    300
tcccagtact ccagggatca gaaggagccc cctcacacc agtatttatc cttaacactc     360
ttgcaccttc tgaaagcctt gtcctgccaa gaagttactg atgatgaggt cttagatgca    420
agctgcttgt tggatgtctt aagaatgtac agatggcaga tctcatcatt tgaagaacag    480
gatgctcacg aattattcca tgtcattacc tcgtcattgg aagatgagcg agaccgccag    540
cctcgggtca cacatttgtt tgatgtgcat tccctggagc agcagtcaga ataactccc     600 aaacaaatta cctgccgcac aagagggtca cctcaccca catccaatca ctggaagtct     660
caacatcctt ttcatggaag actcactagt aatatggtct gcaaacactg tgaacaccag    720
agtcctgttc gatttgatac ctttgatagc ctttcactaa gtattccagc cgccacatgg    780
ggtcacccat tgaccctgga ccactgcctt caccacttca tctcatcaga atcagtgcgg    840
gatgttgtgt gtgacaactg tacaaagatt gaagccaagg gaacgttgaa cggggaaaag    900
gtggaacacc agaggaccac ttttgttaaa cagttaaaac tagggaagct ccctcagtgt    960
ctctgcatcc acctacagcg gctgagctgg tccagccacg gcacgcctct gaagcggcat   1020
gagcacgtgc agttcaatga gttcctgatg atggacattt acaagtacca cctccttgga   1080
cataaaccta gtcaacacaa ccctaaactg aacaagaacc cagggcctac actggagctg   1140
caggatgggc cgggagcccc cacaccagtt ctgaatcagc caggggcccc caaaacacag   1200 attttttatga atggcgcctg ctccccatct ttattgccaa cgctgtcagc gccgatgccc   1260
ttccctctcc cagttgttcc cgactacagc tcctccacat acctcttccg gctgatggca   1320
gttgtcgtcc accatggaga catgcactct ggacactttg tcacttaccg acggtccca   1380 ccttctgcca ggaaccctct ctcaactagc aatcagtggc tgtgggtctc cgatgacact   1440
gtccgcaagg ccagcctgca ggaggtcctg tcctccagcg cctacctgct gttctacgag   1500
cgcgtccttt ccaggatgca gcaccagagc caggagtgca agtctgaaga atga           1554
```

<210> SEQ ID NO 44
<211> LENGTH: 517
<212> TYPE: PRT
<213> ORGANISM: Homo sapiens

<400> SEQUENCE: 44

```
Met Leu Ser Ser Arg Ala Glu Ala Ala Met Thr Ala Ala Asp Arg Ala
1               5                   10                  15

Ile Gln Arg Phe Leu Arg Thr Gly Ala Ala Val Arg Tyr Lys Val Met
                20                  25                  30

Lys Asn Trp Gly Val Ile Gly Ile Ala Ala Ala Leu Ala Ala Gly
            35                  40                  45

Ile Tyr Val Ile Trp Gly Pro Ile Thr Glu Arg Lys Lys Arg Arg Lys
    50                  55                  60

Gly Leu Val Pro Gly Leu Val Asn Leu Gly Asn Thr Cys Phe Met Asn
65                  70                  75                  80

Ser Leu Leu Gln Gly Leu Ser Ala Cys Pro Ala Phe Ile Arg Trp Leu
                85                  90                  95

Glu Glu Phe Thr Ser Gln Tyr Ser Arg Asp Gln Lys Glu Pro Pro Ser
                100                 105                 110

His Gln Tyr Leu Ser Leu Thr Leu Leu His Leu Leu Lys Ala Leu Ser
            115                 120                 125
```

```
Cys Gln Glu Val Thr Asp Asp Glu Val Leu Asp Ala Ser Cys Leu Leu
            130                 135                 140

Asp Val Leu Arg Met Tyr Arg Trp Gln Ile Ser Ser Phe Glu Glu Gln
145                 150                 155                 160

Asp Ala His Glu Leu Phe His Val Ile Thr Ser Ser Leu Glu Asp Glu
                165                 170                 175

Arg Asp Arg Gln Pro Arg Val Thr His Leu Phe Asp Val His Ser Leu
            180                 185                 190

Glu Gln Gln Ser Glu Ile Thr Pro Lys Gln Ile Thr Cys Arg Thr Arg
        195                 200                 205

Gly Ser Pro His Pro Thr Ser Asn His Trp Lys Ser Gln His Pro Phe
210                 215                 220

His Gly Arg Leu Thr Ser Asn Met Val Cys Lys His Cys Glu His Gln
225                 230                 235                 240

Ser Pro Val Arg Phe Asp Thr Phe Asp Ser Leu Ser Leu Ser Ile Pro
                245                 250                 255

Ala Ala Thr Trp Gly His Pro Leu Thr Leu Asp His Cys Leu His His
            260                 265                 270

Phe Ile Ser Ser Glu Ser Val Arg Asp Val Val Cys Asp Asn Cys Thr
        275                 280                 285

Lys Ile Glu Ala Lys Gly Thr Leu Asn Gly Glu Lys Val Glu His Gln
290                 295                 300

Arg Thr Thr Phe Val Lys Gln Leu Lys Leu Gly Lys Leu Pro Gln Cys
305                 310                 315                 320

Leu Cys Ile His Leu Gln Arg Leu Ser Trp Ser Ser His Gly Thr Pro
                325                 330                 335

Leu Lys Arg His Glu His Val Gln Phe Asn Glu Phe Leu Met Met Asp
            340                 345                 350

Ile Tyr Lys Tyr His Leu Leu Gly His Lys Pro Ser Gln His Asn Pro
        355                 360                 365

Lys Leu Asn Lys Asn Pro Gly Pro Thr Leu Glu Leu Gln Asp Gly Pro
370                 375                 380

Gly Ala Pro Thr Pro Val Leu Asn Gln Pro Gly Ala Pro Lys Thr Gln
385                 390                 395                 400

Ile Phe Met Asn Gly Ala Cys Ser Pro Ser Leu Leu Pro Thr Leu Ser
                405                 410                 415

Ala Pro Met Pro Phe Pro Leu Pro Val Val Pro Asp Tyr Ser Ser Ser
            420                 425                 430

Thr Tyr Leu Phe Arg Leu Met Ala Val Val His His Gly Asp Met
        435                 440                 445

His Ser Gly His Phe Val Thr Tyr Arg Arg Ser Pro Pro Ser Ala Arg
450                 455                 460

Asn Pro Leu Ser Thr Ser Asn Gln Trp Leu Trp Val Ser Asp Asp Thr
465                 470                 475                 480

Val Arg Lys Ala Ser Leu Gln Glu Val Leu Ser Ser Ala Tyr Leu
                485                 490                 495

Leu Phe Tyr Glu Arg Val Leu Ser Arg Met Gln His Gln Ser Gln Glu
            500                 505                 510

Cys Lys Ser Glu Glu
        515

<210> SEQ ID NO 45
<211> LENGTH: 2487
```

<212> TYPE: DNA
<213> ORGANISM: Homo sapiens

<400> SEQUENCE: 45

```
atgacaggat caaattcaca cataacgata ttaaccttaa aggtgttacc tcattttgaa      60
agtcttggga acaggaaaaa aattcctaac aaaatgtcag cttttcgaaa tcattgtcca     120
catttggatt cagttggtga aataacaaaa gaagatttga tacaaaaatc ccttggtact     180
tgtcaggatt gtaaagtcca aggaccaaat ctttgggcat gtctggagaa tagatgttca     240
tatgttggct gtggtgaatc acaagtagat cacagcacca tacattctca ggagacaaag     300
cattatctaa ctgtgaacct taccactctt cgagtatggt gttatgcttg cagcaaagaa     360
gtattttggg ataggaaatt aggaactcag ccttcattgc ctcatgtaag acaacctcac     420
caaatacaag aaaacagtgt ccaggatttt aaaatacccca gtaatacaac attaaaaact     480
cctctggttg ccgtatttga tgatctggat atagaagcgg atgaagaaga tgaacttagg     540
gccagaggtc ttacaggttt gaaaaatatt ggaaatactt gttacatgaa tgcagctttg     600
caggctcttt ctaattgccc acctttgaca cagttttttc ttgattgtgg aggactagct     660
cgaacagata gaaacctgc catttgtaaa agttatctca aactaatgac agagctgtgg     720
cataaaagca ggccaggatc tgttgtgcct actactctgt ttcaaggaat taaaactgta     780
aatccaacat ttcgggggta ttctcagcag gatgctcaag aattccttcg atgtttaatg     840
gatttgcttc atgaagaatt gaaagagcaa gtcatggaag tagaagaaga tccgcaaacc     900
ataaccactg aggagacaat ggaagaagac aagagccagt cggatgtaga ttttcagtct     960
tgtgaatctt gtagcaacag tgatagagca gaaaatgaaa atggctctag atgcttttct    1020
gaagataata tgaaacaac aatgttaatt caggatgatg aaaacaattc agaaatgtca    1080
aaggattggc aaaagagaa gatgtgcaat aagattaata agtaaattc tgaaggcgaa    1140
tttgataaag atagagactc tatatctgaa acagtcgact taaacaacca ggaaactgtc    1200
aaagtgcaaa tacacagcag agcttcagaa tatatcactg atgtccattc gaatgacctg    1260
tctacaccac agatccttcc atcaaatgaa ggtgttaatc cacgtttatc ggcaagccct    1320
cctaaatcag gcaatttgtg gccaggattg gcaccaccac acaaaaaagc tcagtctgca    1380
tctccaaaga gaaaaaaaca gcacaagaaa tacagaagtg ttatttcaga catatttgat    1440
ggaacaatca ttagttcagt gcagtgtctg acttgtgaca gggtgtctgt aaccctcgag    1500
acctttcaag atctgtcctt gccaattcct ggcaaggaag accttgctaa gctgcattca    1560
tcaagtcatc caacttctat agtcaaagca ggatcatgtg gcgaagcata tgctccacaa    1620
gggtggatag ctttttttcat ggaatatgtg aagagctggt tttggggtcc agtagtaacc    1680
ttgcaagatt gtcttgctgc cttctttgcc agagatgaac taaaaggtga caatatgtac    1740
agttgtgaaa aatgcaaaaa gttgagaaat ggagtgaagt tttgtaaagt acaaaacttt    1800
cctgagattt tgtgcatcca ccttaaaaga ttcagacatg aactaatgtt ttccaccaaa    1860
atcagtaccc atgtttcatt tccgctagaa ggcttggatc ttcagccatt tcttgctaag    1920
gatagtccag ctcaaattgt gacatatgat cttctgtcag tcatttgcca tcatggaact    1980
gcaagtagtg gacactatat agcctactgc cgaaacaatc taataatct ctggtatgaa    2040
tttgatgatc agagtgtcac tgaagtttca gaatctactg tacaaaatgc agaagcttac    2100
gttctttttct ataggaagag cagcgaagag gcacaaaaag agaggagaag gatatcaaat    2160
ttattgaaca taatgaacc aagcctcctt cagtttata tttctcgaca gtggcttaat    2220
```

-continued

```
aaatttaaga cctttgccga acctggccct atttcaaata atgactttct ttgtattcat    2280
ggaggtgttc ctccaagaaa agctggttat attgaagacc tggttttgat gctgcctcag    2340
aacatttggg ataacctata tagcaggtat ggtggaggac cagctgtcaa ccatctgtac    2400
atttgtcata cttgccaaat tgaggcggag aaaattgaaa aagaagaaa aactgaattg    2460 gaaattttta ttcgggtaaa aaagtga                                         2487

<210> SEQ ID NO 46
<211> LENGTH: 828
<212> TYPE: PRT
<213> ORGANISM: Homo sapiens

<400> SEQUENCE: 46

Met Thr Gly Ser Asn Ser His Ile Thr Ile Leu Thr Leu Lys Val Leu
1               5                   10                  15

Pro His Phe Glu Ser Leu Gly Lys Gln Glu Lys Ile Pro Asn Lys Met
            20                  25                  30

Ser Ala Phe Arg Asn His Cys Pro His Leu Asp Ser Val Gly Glu Ile
        35                  40                  45

Thr Lys Glu Asp Leu Ile Gln Lys Ser Leu Gly Thr Cys Gln Asp Cys
    50                  55                  60

Lys Val Gln Gly Pro Asn Leu Trp Ala Cys Leu Glu Asn Arg Cys Ser
65                  70                  75                  80

Tyr Val Gly Cys Gly Glu Ser Gln Val Asp His Ser Thr Ile His Ser
                85                  90                  95

Gln Glu Thr Lys His Tyr Leu Thr Val Asn Leu Thr Thr Leu Arg Val
            100                 105                 110

Trp Cys Tyr Ala Cys Ser Lys Glu Val Phe Leu Asp Arg Lys Leu Gly
        115                 120                 125

Thr Gln Pro Ser Leu Pro His Val Arg Gln Pro His Gln Ile Gln Glu
    130                 135                 140

Asn Ser Val Gln Asp Phe Lys Ile Pro Ser Asn Thr Thr Leu Lys Thr
145                 150                 155                 160

Pro Leu Val Ala Val Phe Asp Asp Leu Asp Ile Glu Ala Asp Glu Glu
                165                 170                 175

Asp Glu Leu Arg Ala Arg Gly Leu Thr Gly Leu Lys Asn Ile Gly Asn
            180                 185                 190

Thr Cys Tyr Met Asn Ala Ala Leu Gln Ala Leu Ser Asn Cys Pro Pro
        195                 200                 205

Leu Thr Gln Phe Phe Leu Asp Cys Gly Gly Leu Ala Arg Thr Asp Lys
    210                 215                 220

Lys Pro Ala Ile Cys Lys Ser Tyr Leu Lys Leu Met Thr Glu Leu Trp
225                 230                 235                 240

His Lys Ser Arg Pro Gly Ser Val Val Pro Thr Thr Leu Phe Gln Gly
                245                 250                 255

Ile Lys Thr Val Asn Pro Thr Phe Arg Gly Tyr Ser Gln Gln Asp Ala
            260                 265                 270

Gln Glu Phe Leu Arg Cys Leu Met Asp Leu Leu His Glu Glu Leu Lys
        275                 280                 285

Glu Gln Val Met Glu Val Glu Asp Pro Gln Thr Ile Thr Thr Glu
    290                 295                 300

Glu Thr Met Glu Glu Asp Lys Ser Gln Ser Asp Val Asp Phe Gln Ser
305                 310                 315                 320

Cys Glu Ser Cys Ser Asn Ser Asp Arg Ala Glu Asn Glu Asn Gly Ser
```

```
            325                 330                 335
Arg Cys Phe Ser Glu Asp Asn Asn Glu Thr Thr Met Leu Ile Gln Asp
            340                 345                 350

Asp Glu Asn Asn Ser Glu Met Ser Lys Asp Trp Gln Lys Glu Lys Met
            355                 360                 365

Cys Asn Lys Ile Asn Lys Val Asn Ser Glu Gly Glu Phe Asp Lys Asp
            370                 375                 380

Arg Asp Ser Ile Ser Glu Thr Val Asp Leu Asn Asn Gln Glu Thr Val
385                 390                 395                 400

Lys Val Gln Ile His Ser Arg Ala Ser Glu Tyr Ile Thr Asp Val His
                405                 410                 415

Ser Asn Asp Leu Ser Thr Pro Gln Ile Leu Pro Ser Asn Glu Gly Val
            420                 425                 430

Asn Pro Arg Leu Ser Ala Ser Pro Pro Lys Ser Gly Asn Leu Trp Pro
            435                 440                 445

Gly Leu Ala Pro Pro His Lys Lys Ala Gln Ser Ala Ser Pro Lys Arg
450                 455                 460

Lys Lys Gln His Lys Lys Tyr Arg Ser Val Ile Ser Asp Ile Phe Asp
465                 470                 475                 480

Gly Thr Ile Ile Ser Ser Val Gln Cys Leu Thr Cys Asp Arg Val Ser
                485                 490                 495

Val Thr Leu Glu Thr Phe Gln Asp Leu Ser Leu Pro Ile Pro Gly Lys
            500                 505                 510

Glu Asp Leu Ala Lys Leu His Ser Ser Ser His Pro Thr Ser Ile Val
            515                 520                 525

Lys Ala Gly Ser Cys Gly Glu Ala Tyr Ala Pro Gln Gly Trp Ile Ala
530                 535                 540

Phe Phe Met Glu Tyr Val Lys Ser Trp Phe Trp Gly Pro Val Val Thr
545                 550                 555                 560

Leu Gln Asp Cys Leu Ala Ala Phe Phe Ala Arg Asp Glu Leu Lys Gly
                565                 570                 575

Asp Asn Met Tyr Ser Cys Glu Lys Cys Lys Lys Leu Arg Asn Gly Val
            580                 585                 590

Lys Phe Cys Lys Val Gln Asn Phe Pro Glu Ile Leu Cys Ile His Leu
            595                 600                 605

Lys Arg Phe Arg His Glu Leu Met Phe Ser Thr Lys Ile Ser Thr His
            610                 615                 620

Val Ser Phe Pro Leu Glu Gly Leu Asp Leu Gln Pro Phe Leu Ala Lys
625                 630                 635                 640

Asp Ser Pro Ala Gln Ile Val Thr Tyr Asp Leu Leu Ser Val Ile Cys
                645                 650                 655

His His Gly Thr Ala Ser Ser Gly His Tyr Ile Ala Tyr Cys Arg Asn
            660                 665                 670

Asn Leu Asn Asn Leu Trp Tyr Glu Phe Asp Asp Gln Ser Val Thr Glu
            675                 680                 685

Val Ser Glu Ser Thr Val Gln Asn Ala Glu Ala Tyr Val Leu Phe Tyr
            690                 695                 700

Arg Lys Ser Ser Glu Glu Ala Gln Lys Glu Arg Arg Arg Ile Ser Asn
705                 710                 715                 720

Leu Leu Asn Ile Met Glu Pro Ser Leu Leu Gln Phe Tyr Ile Ser Arg
                725                 730                 735

Gln Trp Leu Asn Lys Phe Lys Thr Phe Ala Glu Pro Gly Pro Ile Ser
            740                 745                 750
```

```
Asn Asn Asp Phe Leu Cys Ile His Gly Gly Val Pro Pro Arg Lys Ala
            755                 760                 765
Gly Tyr Ile Glu Asp Leu Val Leu Met Leu Pro Gln Asn Ile Trp Asp
    770                 775                 780
Asn Leu Tyr Ser Arg Tyr Gly Gly Pro Ala Val Asn His Leu Tyr
785                 790                 795                 800
Ile Cys His Thr Cys Gln Ile Glu Ala Glu Lys Ile Glu Lys Arg Arg
            805                 810                 815
Lys Thr Glu Leu Glu Ile Phe Ile Arg Val Lys Lys
            820                 825
```

<210> SEQ ID NO 47
<211> LENGTH: 10188
<212> TYPE: DNA
<213> ORGANISM: Homo sapiens

<400> SEQUENCE: 47

| | | | | | |
|---|---|---|---|---|---|
| atgagaagga | aaaactctta | ctatgtgtgg | caaaaaattt | ttcaaattca | gtttcccttta | 60 |
| tatactgctt | acaagcataa | tactcaccct | actattgagg | atatatcaac | tcaagaaagt | 120 |
| aacatattag | gggcattctg | tgatatgaat | gatgtagaag | taccattgca | tttgcttcgt | 180 |
| tatgtatgtt | tgttttgtgg | gaaaaatggc | ctttctctca | tgaaggattg | ctttgaatat | 240 |
| ggaactcctg | aaactttgcc | atttcttata | gcacatgcgt | ttattacagt | tgtgtctaat | 300 |
| attagaatat | ggctacatat | tcccgctgtc | atgcagcaca | ttataccttt | taggacctat | 360 |
| gttattaggt | atttatgcaa | gctctcggat | caggagttac | gacagagtgc | agctcgtaac | 420 |
| atggctgact | taatgtggag | cacagtcaaa | gaaccattgg | atacaacatt | atgctttgat | 480 |
| aaagaaagcc | tagatcttgc | atttaagtac | tttatgtcac | ctactttgac | tatgaggttg | 540 |
| gctggattga | gtcagataac | aaatcaactc | ataccttca | atgatgtgtg | caataatgaa | 600 |
| tcattagtat | cggacacaga | aacgtccatt | gcaaaagaac | ttgcagactg | gcttattagc | 660 |
| aacaatgtgg | tggagcatat | atttggacca | aatttacata | ttgagattat | caaacagtgc | 720 |
| caagtgattt | tgaattttt | ggcagcagaa | gggcgactga | gtactcaaca | tattgactgt | 780 |
| atttgggctg | cagcacagtt | gaaacattgt | agtcggtata | tacatgactt | atttccttca | 840 |
| ctcatcaaga | atttggatcc | cgtaccactt | agacatctac | ttaatctggt | ctcagctctt | 900 |
| gagccaagtg | ttcatactga | acagacactg | tacttggcat | ccatgttaat | taaagcactg | 960 |
| tggaataacg | cactagcagc | taaggctcag | ttatctaaac | agagttcttt | tgcatcttta | 1020 |
| ttaaatacta | atattcccat | tggaaataag | aaagaggaag | aagagcttag | aagaacagct | 1080 |
| ccatcacctt | ggtcacctgc | agctagtcct | caaagcagtg | ataatagcga | tacacatcaa | 1140 |
| agtggaggta | gtgacattga | atggatgag | caacttatta | tagaaccaa | acatgtgcaa | 1200 |
| caacgacttt | cagacacaga | ggaatccatg | cagggaagtt | ctgacgaaac | tgccaacagt | 1260 |
| ggtgaagatg | gaagcagtgg | tcctggtagc | agtagtgggc | atagtgatgg | atctagcaat | 1320 |
| gaggttaatt | ctagccacgc | aagccagtca | gctgggagcc | ctggcagtga | ggtacagtca | 1380 |
| gaagacattg | cagatattga | agccctcaaa | gaggaagatg | aagacgatga | tcatggtcat | 1440 |
| aatcctccca | aaagcagttg | tggtacagat | cttcggaata | gaaagttaga | gagtcaagca | 1500 |
| ggcatttgcc | tgggggactc | ccaaggcacg | tcagaaagaa | atgggacaag | cagcggaaca | 1560 |
| ggaaaggacc | tggtttttaa | cactgaatca | ttgccatcag | tagataatcg | aatgcgaatg | 1620 |
| ctggatgctt | gttcacactc | tgaagaccca | gaacatgata | tttcagggga | aatgaatgct | 1680 |

```
actcatatag cacaagggtc tcaggagtct tgtatcacac gaactgggga cttccttggg    1740
gagactattg ggaatgaatt atttaattgt cgacaattta ttggtccaca gcatcaccac    1800
caccaccacc accatcacca ccaccacgat gggcatatgg ttgatgatat gctaagtgca    1860
gatgatgtca gttgtagtag ctcccaggtt agtgcaaaat cagaaaaaaa tatggctgat    1920
tttgatggtg aagaatctgg atgtgaagag gagctagttc agattaattc acatgcggaa    1980
ctgacatctc acctccaaca acatcttccc aatttagctt ccatttacca tgaacatctt    2040
agtcaaggac ctgtagttca taaacatcaa ttcaacagta atgctgttac agacattaat    2100
ttggataatg tttgcaagaa aggaaatact ttgttgtggg atatagtcca agatgaagat    2160
gcagttaatc tttctgaagg attaataaat gaagcagaga aacttctttg ttcgttagta    2220
tgttggttta cagatagaca aattcgaatg agattcattg aaggttgcct tgaaaacttg    2280
ggaaacaaca gatcagtagt aatttcactt cgtcttcttc caaaactatt tggtactttt    2340
cagcagtttg ggagcagtta cgatacacac tggataacaa tgtgggcaga aaagaactg    2400 aacatgatga agcttttctt tgataatttg gtatactaca ttcaaactgt gagagaagga    2460
agacaaaaac atgcactgta cagccatagt gctgaagttc aagttcgtct tcaattcttg    2520
acttgtgtat tttcaactct gggatcacct gatcatttca ggttaagttt agagcaagtt    2580
gacatcttat ggcattgttt agtagaagat tctgaatgtt atgatgatgc actccattgg    2640
tttttaaatc aagttcgaag taaagatcaa catgctatgg gtatggaaac ctacaaacat    2700 ctttttcctgg agaagatgcc ccagctaaaa cctgaaacaa ttagcatgac tggcttaaac    2760
ctgtttcagc atctctgtaa cttggctcga ttggctacca gtgcctatga tggttgttca    2820
aattctgagc tgtgtggtat ggaccaattt tggggcattg cttttaagagc acaatctggt    2880 gatgtcagtc gagcagctat ccagtatatt aactcctatt atattaatgg taaaacaggt    2940
ttggagaagg agcaagaatt tattagtaag tgcatggaga gtcttatgat agcttctagc    3000
agtcttgaac aggaatcaca ctcaagtctc atggttatag aaagaggact ccttatgctg    3060
aagacacatc tggaagcgtt taggagaagg tttgcatatc atctgagaca gtggcaaatt    3120
gaaggcactg gtattagtag tcatttgaaa gcactgagtg acaaacagtc tctgccgcta    3180
agggttgtat gccagccagc tggacttcct gacaagatga ctattgaaat gtatcctagt    3240
gaccaggtag cagatcttag ggctgaagta actcattggt atgaaaattt acagaaagaa    3300
caaataaatc aacaagctca gcttcaggag tttggtcaaa gcaaccgaaa aggagagttt    3360
cctggaggcc tcatgggacc tgtcaggatg atttcatctg gacacgagtt aacaacagat    3420
tatgatgaaa aagcacttca tgagcttggt tttaaggata tgcagatggt atttgtatct    3480
ttgggtgcac caaggagaga gcggaaaggg gaaggtgttc agctgccagc atcttgcctc    3540
ccaccccctc agaaggacaa cattccaatg ctttttgcttt tacaagagcc tcatttaact    3600 actcttttttg atttattaga gatgcttgca tcatttaaac cacccctcagg aaaagtggca    3660 gtggatgata gtgagagctt acgatgtgaa gaacttcatc ttcatgcaga aaatctgtct    3720
aggcgggtct gggagctact gatgcttctt cctacatgtc ctaatatgtt gatggcattc    3780
cagaatatct cagatgagca gagtaatgat ggatttaatt ggaaagaact tctcaaaatt    3840
aagagcgccc acaagctatt gtatgctctg gaaattattg aagcactggg aaaacctaat    3900
agaagaataa ggagggagtc tacgggaagt tacagtgatc tttatccaga ttcagatgat    3960
tcaagtgagg atcaagtgga aaatagtaaa aattcctgga gttgcaagtt tgttgctgct    4020
```

```
ggagggcttc aacagttatt agaaatttt aattctggaa ttctagagcc taaagagcag    4080
gaatcatgga ctgtgtggca gctagactgt cttgcttgct tgctgaagtt aatatgccag    4140
tttgcagtag atccatccga tttggattta gcttatcatg atgtctttgc ctggtctggt    4200
atagcggaaa gccataggaa aagaacctgg cctggcaaat caaggaaggc tgctggtgat    4260
catgctaagg gtcttcatat accacgatta acagaggtat ttcttgttct tgtccaagga    4320
accagtttga ttcagcgact tatgtctgtt gcttatacgt atgataatct ggctcctaga    4380
gttttaaaag ctcagtctga tcacaggtct agacatgaag tttcacatta ttcaatgtgg    4440
ctcttggtga gttgggctca ttgctgttct ttagtgaaat ctagccttgc tgatagcgat    4500
catttacaag attggctaaa gaaattgact ctccttattc ctgagactgc agttcgtcat    4560
gaatcatgca gtggtctcta taagttatcc ctgtcagggc tggatggagg agactcaatc    4620
aatcgttctt ttctgctatt ggctgcctca acattattga aatttcttcc tgatgctcaa    4680
gcactcaaac ctattaggat agatgattat gaggaagaac caatattaaa accaggatgt    4740
aaagagtatt tttggttgtt atgcaaatta gttgacaaca tacatataaa ggacgctagt    4800
cagacaacgc tcctcgactt agatgccttg gcaagacatt tggctgactg tattcgaagt    4860
agggagatcc ttgatcatca ggatggtaat gtagaagatg atgggcttac aggactccta    4920
aggcttgcaa caagtgttgt taaacacaaa ccaccctta aattttcaag gaaggacag     4980 gaattttga gagatatctt caatctcctg ttttgttgc caagtctaaa ggaccgacaa    5040
cagccaaagt gcaaatcaca ttcttcaaga gctgccgctt acgatttgtt agtagagatg    5100 gtaaagggt ctgttgagaa ctacaggcta atacacaact gggttatggc acaacacatg    5160
cagtcccatg caccttataa atgggattac tggcctcatg aagatgtccg tgctgaatgt    5220
agatttgttg gccttactaa ccttggagct acttgttact tagcttctac tattcagcaa    5280
ctttatatga tacctgaggc aagacaggct gtcttcactg ccaagtattc agaggatatg    5340
aagcacaaga ccactcttct ggagcttcag aaaatgttta catattaat ggagagtgaa    5400 tgcaaagcat ataatcctag accttcctgt aaaacataca ccatggataa gcagcctctg    5460
aatactgggg aacagaaaga tatgacagag ttttttactg atctaattac caaaatcgaa    5520
gaaatgtctc ccgaactgaa aaataccgtc aaaagtttat ttggaggtgt aattacaaac    5580
aatgttgtat ccttggattg tgaacatgtt agtcaaactg ctgaagagtt ttatactgtg    5640
aggtgccaag tggctgatat gaagaacatt tatgaatctc ttgatgaagt tactataaaa    5700
gacactttgg aaggtgataa catgtatact tgttctcatt gtgggaagaa agtacgagct    5760
gaaaaaaggg catgttttaa gaaattgcct cgcattttga gtttcaatac tatgagatac    5820
acatttaata tggtcacgat gatgaaagag aaagtgaata cacactttc cttcccatta    5880 cgtttggaca tgacgcccta tacagaagat tttcttatgg gaaagagtga gaggaaagaa    5940
ggttttaaag aagtcagtga tcattccaaa gactcagaga gctatgaata tgacttgata    6000
ggagtgactg ttcacacagg aacggcagat ggtggacact attatagctt tatcagagat    6060
atagtaaatc cccatgctta taaaacaat aaatggtatc ttttaatga tgctgaggta    6120 aaaccttttg attctgctca acttgcatct gaatgttttg gtggagagat gacgaccaag    6180
acctatgatt ctgttacaga taaatttatg gacttctctt ttgaaaagac acacagtgca    6240
tatatgctgt tttacaaacg catggaacca gaggaagaaa atggcagaga atacaaattt    6300
gatgtttcgt cagagttact agagtggatt tggcatgata acatgcagtt tcttcaagac    6360
aaaaacattt ttgaacatac atattttgga tttatgtggc aattgtgtag ttgtattccc    6420
```

| | | | | | |
|---|---|---|---|---|---|
| agtacattac | cagatcctaa | agctgtgtcc | ttaatgacag | caaagttaag | cacttccttt | 6480 |
| gtcctagaga | catttattca | ttctaaagaa | aagcccacga | tgcttcagtg | gattgaactg | 6540 |
| ttgacgaaac | agtttaataa | tagtcaggca | gcttgtgagt | ggttttttaga | tcgtatggct | 6600 |
| gatgacgact | ggtggccaat | gcagatacta | attaagtgcc | ctaatcaaat | tgtgagacag | 6660 |
| atgtttcagc | gtttgtgtat | ccatgtgatt | cagaggctga | gacctgtgca | tgctcatctc | 6720 |
| tatttgcagc | caggaatgga | agatgggtca | gatgatatgg | atacctcagt | agaagatatt | 6780 |
| ggtggtcgtt | catgtgtcac | tcgctttgtg | agaaccctgt | tattaattat | ggaacatggt | 6840 |
| gtaaaacctc | acagtaaaca | tcttacagag | tattttgcct | tcctttacga | atttgcaaaa | 6900 |
| atgggtgaag | aagagagcca | attttttgctt | tcattgcaag | ctatatctac | aatggtacat | 6960 |
| ttttacatgg | gaacaaaagg | acctgaaaat | cctcaagttg | aagtgttatc | agaggaagaa | 7020 |
| ggggaagaag | aagaggagga | agaagatatc | ctctctctgg | cagaagaaaa | atacaggcca | 7080 |
| gctgcccttg | aaaagatgat | agctttagtt | gctcttttgg | ttgaacagtc | tcgatcagaa | 7140 |
| aggcatttga | cattatcaca | gactgacatg | gcagcattaa | caggaggaaa | gggatttccc | 7200 |
| ttcttgtttc | aacatattcg | tgatggcatc | aatataagac | aaacttgtaa | tctgatttttc | 7260 |
| agcctgtgtc | gatacaataa | tcgacttgca | gaacatattg | tatctatgct | tttcacatca | 7320 |
| atagcaaagt | tgactcctga | ggcagccaat | ccttttcttta | agttgttgac | tatgctaatg | 7380 |
| gagtttgctg | gtggacctcc | aggaatgcct | ccctttgcat | cttatattct | gcagaggata | 7440 |
| tgggaggtga | ttgaatacaa | tccttctcag | tgtctagatt | ggttggcagt | gcagacaccc | 7500 |
| cgaaataaac | tggcacacag | ctgggtctta | cagaatatgg | aaaactgggt | cgagcggttt | 7560 |
| cttttggctc | acaattatcc | tagagtgagg | acttctgcag | cttatcttct | ggtgtcccttt | 7620 |
| ataccaagca | attcattccg | tcagatgttc | cggtcaacaa | ggtctttgca | catcccaacc | 7680 |
| cgtgaccttc | cactcagtcc | agacacaaca | gtagtcctac | atcaggtcta | caacgtgctc | 7740 |
| cttggtttgc | tctcaagagc | caaactttat | gttgatgctg | ctgttcatgg | cactacaaag | 7800 |
| ctagtgccct | attttagctt | tatgacttac | tgtttaatttt | ccaaaactga | gaagctgatg | 7860 |
| ttttccacat | atttcatgga | tttgtggaac | cttttccagc | ctaaactttc | tgagccagca | 7920 |
| atagctacaa | atcacaataa | acaggctttg | ctttcattttt | ggtacaatgt | ctgtgctgac | 7980 |
| tgtccagaga | atatccgcct | tattgttcag | aacccagtgg | taaccaagaa | cattgccttc | 8040 |
| aattacatcc | ttgctgacca | tgatgatcag | gatgtggtgc | ttttttaaccg | tgggatgctg | 8100 |
| ccagcgtact | atggcattct | gaggctctgc | tgtgagcagt | ctcctgcatt | cacacgacaa | 8160 |
| ctggcttctc | accagaacat | ccagtgggcc | tttaagaatc | ttacaccaca | tgccagccaa | 8220 |
| taccctggag | cagtagaaga | actgtttaac | ctgatgcagc | tgtttatagc | tcagaggcca | 8280 |
| gatatgagag | aagaagaatt | agaagatatt | aaacagttca | agaaaacaac | cataagttgt | 8340 |
| tacttacgtt | gctagatgg | ccgctcctgc | tggactactt | taataagtgc | cttcagaata | 8400 |
| ctattagaat | ctgatgaaga | cagacttctt | gttgtattta | atcgaggatt | gattctaatg | 8460 |
| acagagtctt | tcaacacttt | gcacatgatg | tatcacgaag | ctacagcttg | ccatgtgact | 8520 |
| ggagatttag | tagaacttct | gtcaatattt | cttttcggttt | tgaagtctac | acgcccttat | 8580 |
| cttcagagaa | aagatgtgaa | acaagcatta | atccagtggc | aggagcgaat | tgaatttgcc | 8640 |
| cataaactgt | taactcttct | taattcctat | agtcctccag | aacttagaaa | tgcctgtata | 8700 |
| gatgtcctca | aggaacttgt | actttgtgagt | ccccatgatt | ttcttcatac | tctggttccc | 8760 |

```
tttctacaac acaaccattg tacttaccat cacagtaata taccaatgtc tcttggacct    8820
tatttccctt gtcgagaaaa tatcaagcta ataggaggga aaagcaatat tcggcctccg    8880
cgccctgaac tcaatatgtg cctcttgccc acaatggtgg aaaccagtaa gggcaaagat    8940
gacgtttatg atcgtatgct gctagactac ttcttttctt atcatcagtt catccatcta    9000
ttatgccgag ttgcaatcaa ctgtgaaaaa tttactgaaa cattagttaa gctgagtgtc    9060
ctagttgcct atgaaggttt gccacttcat cttgcactgt tccccaaact ttggactgag    9120
ctatgccaga ctcagtctgc tatgtcaaaa aactgcatca agcttttgtg tgaagatcct    9180
gttttcgcag aatatattaa atgtatccta atggatgaaa aacttttttt aaacaacaac    9240
attgtctaca cgttcatgac acatttcctt ctaaaggttc aaagtcaagt gttttctgaa    9300
gcaaactgtg ccaatttgat cagcactctt attacaaact tgataagcca gtatcagaac    9360
ctacagtctg atttctccaa ccgagttgaa atttccaaag caagtgcttc tttaaatggg    9420
gacctgaggg cactcgcttt gctcctgtca gtacacactc ccaaacagtt aaacccagct    9480
ctaattccaa ctctgcaaga gctttttaagc aaatgcagga cttgtctgca acagagaaac    9540
tcactccaag agcaagaagc caaagaaaga aaaactaaag atgatgaagg agcaactccc    9600
attaaaaggc ggcgtgttag cagtgatgag gagcacactg tagacagctg catcagtgac    9660
atgaaaacag aaaccaggga ggtcctgacc ccaacgagca cttctgacaa tgagaccaga    9720
gactcctcaa ttattgatcc aggaactgag caagatcttc cttccctga aaatagttct    9780
gttaaagaat accgaatgga agttccatct tcgttttcag aagacatgtc aaatatcagg    9840
tcacagcatg cagaagaaca gtccaacaat ggtagatatg acgattgtaa agaatttaaa    9900
gacctccact gttccaagga ttctacccta gctgaggaag aatctgagtt cccttctact    9960
tctatctctg cagttctgtc tgacttagct gacttgagaa gctgtgatgg ccaagctttg   10020
ccctcccagg accctgaggt tgctttatct ctcagttgtg gccattccag aggactcttt   10080
agtcatatgc agcaacatga cattttagat accctgtgta ggaccattga atctacaatc   10140
catgtcgtca caaggatatc tggcaaagga aaccaagctg cttcttga                10188
```

<210> SEQ ID NO 48
<211> LENGTH: 3395
<212> TYPE: PRT
<213> ORGANISM: Homo sapiens

<400> SEQUENCE: 48

```
Met Arg Arg Lys Asn Ser Tyr Tyr Val Trp Gln Lys Ile Phe Gln Ile
1               5                   10                  15

Gln Phe Pro Leu Tyr Thr Ala Tyr Lys His Asn Thr His Pro Thr Ile
            20                  25                  30

Glu Asp Ile Ser Thr Gln Glu Ser Asn Ile Leu Gly Ala Phe Cys Asp
        35                  40                  45

Met Asn Asp Val Glu Val Pro Leu His Leu Leu Arg Tyr Val Cys Leu
    50                  55                  60

Phe Cys Gly Lys Asn Gly Leu Ser Leu Met Lys Asp Cys Phe Glu Tyr
65                  70                  75                  80

Gly Thr Pro Glu Thr Leu Pro Phe Leu Ile Ala His Ala Phe Ile Thr
                85                  90                  95

Val Val Ser Asn Ile Arg Ile Trp Leu His Ile Pro Ala Val Met Gln
            100                 105                 110

His Ile Ile Pro Phe Arg Thr Tyr Val Ile Arg Tyr Leu Cys Lys Leu
        115                 120                 125
```

```
Ser Asp Gln Glu Leu Arg Gln Ser Ala Ala Arg Asn Met Ala Asp Leu
130                 135                 140

Met Trp Ser Thr Val Lys Glu Pro Leu Asp Thr Thr Leu Cys Phe Asp
145                 150                 155                 160

Lys Glu Ser Leu Asp Leu Ala Phe Lys Tyr Phe Met Ser Pro Thr Leu
                165                 170                 175

Thr Met Arg Leu Ala Gly Leu Ser Gln Ile Thr Asn Gln Leu His Thr
            180                 185                 190

Phe Asn Asp Val Cys Asn Asn Glu Ser Leu Val Ser Asp Thr Glu Thr
        195                 200                 205

Ser Ile Ala Lys Glu Leu Ala Asp Trp Leu Ile Ser Asn Asn Val Val
210                 215                 220

Glu His Ile Phe Gly Pro Asn Leu His Ile Glu Ile Lys Gln Cys
225                 230                 235                 240

Gln Val Ile Leu Asn Phe Leu Ala Ala Glu Gly Arg Leu Ser Thr Gln
                245                 250                 255

His Ile Asp Cys Ile Trp Ala Ala Gln Leu Lys His Cys Ser Arg
            260                 265                 270

Tyr Ile His Asp Leu Phe Pro Ser Leu Ile Lys Asn Leu Asp Pro Val
        275                 280                 285

Pro Leu Arg His Leu Leu Asn Leu Val Ser Ala Leu Glu Pro Ser Val
290                 295                 300

His Thr Glu Gln Thr Leu Tyr Leu Ala Ser Met Leu Ile Lys Ala Leu
305                 310                 315                 320

Trp Asn Asn Ala Leu Ala Ala Lys Ala Gln Leu Ser Lys Gln Ser Ser
                325                 330                 335

Phe Ala Ser Leu Leu Asn Thr Asn Ile Pro Ile Gly Asn Lys Lys Glu
            340                 345                 350

Glu Glu Glu Leu Arg Arg Thr Ala Pro Ser Pro Trp Ser Pro Ala Ala
        355                 360                 365

Ser Pro Gln Ser Ser Asp Asn Ser Asp Thr His Gln Ser Gly Gly Ser
370                 375                 380

Asp Ile Glu Met Asp Glu Gln Leu Ile Asn Arg Thr Lys His Val Gln
385                 390                 395                 400

Gln Arg Leu Ser Asp Thr Glu Glu Ser Met Gln Gly Ser Ser Asp Glu
                405                 410                 415

Thr Ala Asn Ser Gly Glu Asp Gly Ser Ser Gly Pro Gly Ser Ser Ser
            420                 425                 430

Gly His Ser Asp Gly Ser Ser Asn Glu Val Asn Ser Ser His Ala Ser
        435                 440                 445

Gln Ser Ala Gly Ser Pro Gly Ser Glu Val Gln Ser Glu Asp Ile Ala
450                 455                 460

Asp Ile Glu Ala Leu Lys Glu Glu Asp Glu Asp Asp His Gly His
465                 470                 475                 480

Asn Pro Pro Lys Ser Ser Cys Gly Thr Asp Leu Arg Asn Arg Lys Leu
                485                 490                 495

Glu Ser Gln Ala Gly Ile Cys Leu Gly Asp Ser Gln Gly Thr Ser Glu
            500                 505                 510

Arg Asn Gly Thr Ser Ser Gly Thr Gly Lys Asp Leu Val Phe Asn Thr
        515                 520                 525

Glu Ser Leu Pro Ser Val Asp Asn Arg Met Arg Met Leu Asp Ala Cys
530                 535                 540
```

```
Ser His Ser Glu Asp Pro Glu His Asp Ile Ser Gly Glu Met Asn Ala
545                 550                 555                 560

Thr His Ile Ala Gln Gly Ser Gln Glu Ser Cys Ile Thr Arg Thr Gly
            565                 570                 575

Asp Phe Leu Gly Glu Thr Ile Gly Asn Glu Leu Phe Asn Cys Arg Gln
        580                 585                 590

Phe Ile Gly Pro Gln His His His His His His His His His His His
    595                 600                 605

His Asp Gly His Met Val Asp Met Leu Ser Ala Asp Asp Val Ser
610                 615                 620

Cys Ser Ser Ser Gln Val Ser Ala Lys Ser Glu Lys Asn Met Ala Asp
625                 630                 635                 640

Phe Asp Gly Glu Glu Ser Gly Cys Glu Glu Glu Leu Val Gln Ile Asn
            645                 650                 655

Ser His Ala Glu Leu Thr Ser His Leu Gln Gln His Leu Pro Asn Leu
        660                 665                 670

Ala Ser Ile Tyr His Glu His Leu Ser Gln Gly Pro Val Val His Lys
    675                 680                 685

His Gln Phe Asn Ser Asn Ala Val Thr Asp Ile Asn Leu Asp Asn Val
690                 695                 700

Cys Lys Lys Gly Asn Thr Leu Leu Trp Asp Ile Val Gln Asp Glu Asp
705                 710                 715                 720

Ala Val Asn Leu Ser Glu Gly Leu Ile Asn Glu Ala Glu Lys Leu Leu
            725                 730                 735

Cys Ser Leu Val Cys Trp Phe Thr Asp Arg Gln Ile Arg Met Arg Phe
        740                 745                 750

Ile Glu Gly Cys Leu Glu Asn Leu Gly Asn Asn Arg Ser Val Val Ile
    755                 760                 765

Ser Leu Arg Leu Leu Pro Lys Leu Phe Gly Thr Phe Gln Gln Phe Gly
770                 775                 780

Ser Ser Tyr Asp Thr His Trp Ile Thr Met Trp Ala Glu Lys Glu Leu
785                 790                 795                 800

Asn Met Met Lys Leu Phe Phe Asp Asn Leu Val Tyr Tyr Ile Gln Thr
            805                 810                 815

Val Arg Glu Gly Arg Gln Lys His Ala Leu Tyr Ser His Ser Ala Glu
        820                 825                 830

Val Gln Val Arg Leu Gln Phe Leu Thr Cys Val Phe Ser Thr Leu Gly
    835                 840                 845

Ser Pro Asp His Phe Arg Leu Ser Leu Glu Gln Val Asp Ile Leu Trp
850                 855                 860

His Cys Leu Val Glu Asp Ser Glu Cys Tyr Asp Asp Ala Leu His Trp
865                 870                 875                 880

Phe Leu Asn Gln Val Arg Ser Lys Asp Gln His Ala Met Gly Met Glu
            885                 890                 895

Thr Tyr Lys His Leu Phe Leu Glu Lys Met Pro Gln Leu Lys Pro Glu
        900                 905                 910

Thr Ile Ser Met Thr Gly Leu Asn Leu Phe Gln His Leu Cys Asn Leu
    915                 920                 925

Ala Arg Leu Ala Thr Ser Ala Tyr Asp Gly Cys Ser Asn Ser Glu Leu
930                 935                 940

Cys Gly Met Asp Gln Phe Trp Gly Ile Ala Leu Arg Ala Gln Ser Gly
945                 950                 955                 960

Asp Val Ser Arg Ala Ala Ile Gln Tyr Ile Asn Ser Tyr Tyr Ile Asn
```

```
                        965                 970                 975
Gly Lys Thr Gly Leu Glu Lys Glu Gln Glu Phe Ile Ser Lys Cys Met
                    980                 985                 990
Glu Ser Leu Met Ile Ala Ser Ser Leu Glu Gln Glu Ser His Ser
                995                1000               1005
Ser Leu Met Val Ile Glu Arg Gly Leu Leu Met Leu Lys Thr His Leu
           1010                1015               1020
Glu Ala Phe Arg Arg Phe Ala Tyr His Leu Arg Gln Trp Gln Ile
1025               1030               1035               1040
Glu Gly Thr Gly Ile Ser Ser His Leu Lys Ala Leu Ser Asp Lys Gln
                1045               1050               1055
Ser Leu Pro Leu Arg Val Val Cys Gln Pro Ala Gly Leu Pro Asp Lys
           1060               1065               1070
Met Thr Ile Glu Met Tyr Pro Ser Asp Gln Val Ala Asp Leu Arg Ala
           1075               1080               1085
Glu Val Thr His Trp Tyr Glu Asn Leu Gln Lys Glu Gln Ile Asn Gln
           1090               1095               1100
Gln Ala Gln Leu Gln Glu Phe Gly Gln Ser Asn Arg Lys Gly Glu Phe
1105               1110               1115               1120
Pro Gly Gly Leu Met Gly Pro Val Arg Met Ile Ser Ser Gly His Glu
                1125               1130               1135
Leu Thr Asp Tyr Asp Glu Lys Ala Leu His Glu Leu Gly Phe Lys
           1140               1145               1150
Asp Met Gln Met Val Phe Val Ser Leu Gly Ala Pro Arg Arg Glu Arg
           1155               1160               1165
Lys Gly Glu Gly Val Gln Leu Pro Ala Ser Cys Leu Pro Pro Pro Gln
1170               1175               1180
Lys Asp Asn Ile Pro Met Leu Leu Leu Gln Glu Pro His Leu Thr
1185               1190               1195               1200
Thr Leu Phe Asp Leu Leu Glu Met Leu Ala Ser Phe Lys Pro Pro Ser
           1205               1210               1215
Gly Lys Val Ala Val Asp Asp Ser Glu Ser Leu Arg Cys Glu Glu Leu
           1220               1225               1230
His Leu His Ala Glu Asn Leu Ser Arg Arg Val Trp Glu Leu Leu Met
1235               1240               1245
Leu Leu Pro Thr Cys Pro Asn Met Leu Met Ala Phe Gln Asn Ile Ser
           1250               1255               1260
Asp Glu Gln Ser Asn Asp Gly Phe Asn Trp Lys Glu Leu Leu Lys Ile
1265               1270               1275               1280
Lys Ser Ala His Lys Leu Leu Tyr Ala Leu Glu Ile Ile Glu Ala Leu
           1285               1290               1295
Gly Lys Pro Asn Arg Arg Ile Arg Arg Glu Ser Thr Gly Ser Tyr Ser
           1300               1305               1310
Asp Leu Tyr Pro Asp Ser Asp Ser Ser Glu Asp Gln Val Glu Asn
           1315               1320               1325
Ser Lys Asn Ser Trp Ser Cys Lys Phe Val Ala Ala Gly Gly Leu Gln
           1330               1335               1340
Gln Leu Leu Glu Ile Phe Asn Ser Gly Ile Leu Glu Pro Lys Glu Gln
1345               1350               1355               1360
Glu Ser Trp Thr Val Trp Gln Leu Asp Cys Leu Ala Cys Leu Leu Lys
                1365               1370               1375
Leu Ile Cys Gln Phe Ala Val Asp Pro Ser Asp Leu Asp Leu Ala Tyr
           1380               1385               1390
```

```
His Asp Val Phe Ala Trp Ser Gly Ile Ala Glu Ser His Arg Lys Arg
        1395                1400                1405

Thr Trp Pro Gly Lys Ser Arg Lys Ala Ala Gly Asp His Ala Lys Gly
        1410                1415                1420

Leu His Ile Pro Arg Leu Thr Glu Val Phe Leu Val Leu Val Gln Gly
1425                1430                1435                1440

Thr Ser Leu Ile Gln Arg Leu Met Ser Val Ala Tyr Thr Tyr Asp Asn
        1445                1450                1455

Leu Ala Pro Arg Val Leu Lys Ala Gln Ser Asp His Arg Ser Arg His
        1460                1465                1470

Glu Val Ser His Tyr Ser Met Trp Leu Leu Val Ser Trp Ala His Cys
        1475                1480                1485

Cys Ser Leu Val Lys Ser Ser Leu Ala Asp Ser Asp His Leu Gln Asp
        1490                1495                1500

Trp Leu Lys Lys Leu Thr Leu Leu Ile Pro Glu Thr Ala Val Arg His
1505                1510                1515                1520

Glu Ser Cys Ser Gly Leu Tyr Lys Leu Ser Leu Ser Gly Leu Asp Gly
        1525                1530                1535

Gly Asp Ser Ile Asn Arg Ser Phe Leu Leu Ala Ala Ser Thr Leu
        1540                1545                1550

Leu Lys Phe Leu Pro Asp Ala Gln Ala Leu Lys Pro Ile Arg Ile Asp
        1555                1560                1565

Asp Tyr Glu Glu Glu Pro Ile Leu Lys Pro Gly Cys Lys Glu Tyr Phe
        1570                1575                1580

Trp Leu Leu Cys Lys Leu Val Asp Asn Ile His Ile Lys Asp Ala Ser
1585                1590                1595                1600

Gln Thr Thr Leu Leu Asp Leu Asp Ala Leu Ala Arg His Leu Ala Asp
        1605                1610                1615

Cys Ile Arg Ser Arg Glu Ile Leu Asp His Gln Asp Gly Asn Val Glu
        1620                1625                1630

Asp Asp Gly Leu Thr Gly Leu Leu Arg Leu Ala Thr Ser Val Val Lys
        1635                1640                1645

His Lys Pro Pro Phe Lys Phe Ser Arg Glu Gly Gln Glu Phe Leu Arg
        1650                1655                1660

Asp Ile Phe Asn Leu Leu Phe Leu Leu Pro Ser Leu Lys Asp Arg Gln
1665                1670                1675                1680

Gln Pro Lys Cys Lys Ser His Ser Ser Arg Ala Ala Tyr Asp Leu
        1685                1690                1695

Leu Val Glu Met Val Lys Gly Ser Val Glu Asn Tyr Arg Leu Ile His
        1700                1705                1710

Asn Trp Val Met Ala Gln His Met Gln Ser His Ala Pro Tyr Lys Trp
        1715                1720                1725

Asp Tyr Trp Pro His Glu Asp Val Arg Ala Glu Cys Arg Phe Val Gly
        1730                1735                1740

Leu Thr Asn Leu Gly Ala Thr Cys Tyr Leu Ala Ser Thr Ile Gln Gln
1745                1750                1755                1760

Leu Tyr Met Ile Pro Glu Ala Arg Gln Ala Val Phe Thr Ala Lys Tyr
        1765                1770                1775

Ser Glu Asp Met Lys His Lys Thr Thr Leu Leu Glu Leu Gln Lys Met
        1780                1785                1790

Phe Thr Tyr Leu Met Glu Ser Glu Cys Lys Ala Tyr Asn Pro Arg Pro
        1795                1800                1805
```

Phe Cys Lys Thr Tyr Thr Met Asp Lys Gln Pro Leu Asn Thr Gly Glu
    1810                1815                1820

Gln Lys Asp Met Thr Glu Phe Phe Thr Asp Leu Ile Thr Lys Ile Glu
1825                1830                1835                1840

Glu Met Ser Pro Glu Leu Lys Asn Thr Val Lys Ser Leu Phe Gly Gly
                1845                1850                1855

Val Ile Thr Asn Asn Val Val Ser Leu Asp Cys Glu His Val Ser Gln
                1860                1865                1870

Thr Ala Glu Glu Phe Tyr Thr Val Arg Cys Gln Val Ala Asp Met Lys
            1875                1880                1885

Asn Ile Tyr Glu Ser Leu Asp Glu Val Thr Ile Lys Asp Thr Leu Glu
    1890                1895                1900

Gly Asp Asn Met Tyr Thr Cys Ser His Cys Gly Lys Lys Val Arg Ala
1905                1910                1915                1920

Glu Lys Arg Ala Cys Phe Lys Lys Leu Pro Arg Ile Leu Ser Phe Asn
                1925                1930                1935

Thr Met Arg Tyr Thr Phe Asn Met Val Thr Met Lys Glu Lys Val
                1940                1945                1950

Asn Thr His Phe Ser Phe Pro Leu Arg Leu Asp Met Thr Pro Tyr Thr
    1955                1960                1965

Glu Asp Phe Leu Met Gly Lys Ser Glu Arg Lys Glu Gly Phe Lys Glu
    1970                1975                1980

Val Ser Asp His Ser Lys Asp Ser Glu Ser Tyr Glu Tyr Asp Leu Ile
1985                1990                1995                2000

Gly Val Thr Val His Thr Gly Thr Ala Asp Gly Gly His Tyr Tyr Ser
                2005                2010                2015

Phe Ile Arg Asp Ile Val Asn Pro His Ala Tyr Lys Asn Asn Lys Trp
    2020                2025                2030

Tyr Leu Phe Asn Asp Ala Glu Val Lys Pro Phe Asp Ser Ala Gln Leu
    2035                2040                2045

Ala Ser Glu Cys Phe Gly Gly Glu Met Thr Thr Lys Thr Tyr Asp Ser
    2050                2055                2060

Val Thr Asp Lys Phe Met Asp Phe Ser Phe Glu Lys Thr His Ser Ala
2065                2070                2075                2080

Tyr Met Leu Phe Tyr Lys Arg Met Glu Pro Glu Glu Asn Gly Arg
                2085                2090                2095

Glu Tyr Lys Phe Asp Val Ser Ser Glu Leu Leu Glu Trp Ile Trp His
                2100                2105                2110

Asp Asn Met Gln Phe Leu Gln Asp Lys Asn Ile Phe Glu His Thr Tyr
    2115                2120                2125

Phe Gly Phe Met Trp Gln Leu Cys Ser Cys Ile Pro Ser Thr Leu Pro
    2130                2135                2140

Asp Pro Lys Ala Val Ser Leu Met Thr Ala Lys Leu Ser Thr Ser Phe
2145                2150                2155                2160

Val Leu Glu Thr Phe Ile His Ser Lys Glu Lys Pro Thr Met Leu Gln
                2165                2170                2175

Trp Ile Glu Leu Leu Thr Lys Gln Phe Asn Asn Ser Gln Ala Ala Cys
                2180                2185                2190

Glu Trp Phe Leu Asp Arg Met Ala Asp Asp Trp Trp Pro Met Gln
            2195                2200                2205

Ile Leu Ile Lys Cys Pro Asn Gln Ile Val Arg Gln Met Phe Gln Arg
    2210                2215                2220

Leu Cys Ile His Val Ile Gln Arg Leu Arg Pro Val His Ala His Leu

```
                2225                2230                2235                2240
Tyr Leu Gln Pro Gly Met Glu Asp Gly Ser Asp Asp Met Asp Thr Ser
                2245                2250                2255
Val Glu Asp Ile Gly Gly Arg Ser Cys Val Thr Arg Phe Val Arg Thr
                2260                2265                2270
Leu Leu Leu Ile Met Glu His Gly Val Lys Pro His Ser Lys His Leu
                2275                2280                2285
Thr Glu Tyr Phe Ala Phe Leu Tyr Glu Phe Ala Lys Met Gly Glu Glu
                2290                2295                2300
Glu Ser Gln Phe Leu Leu Ser Leu Gln Ala Ile Ser Thr Met Val His
2305                2310                2315                2320
Phe Tyr Met Gly Thr Lys Gly Pro Glu Asn Pro Gln Val Glu Val Leu
                2325                2330                2335
Ser Glu Glu Glu Gly Glu Glu Glu Glu Glu Asp Ile Leu Ser
                2340                2345                2350
Leu Ala Glu Glu Lys Tyr Arg Pro Ala Ala Leu Glu Lys Met Ile Ala
                2355                2360                2365
Leu Val Ala Leu Leu Val Glu Gln Ser Arg Ser Glu Arg His Leu Thr
                2370                2375                2380
Leu Ser Gln Thr Asp Met Ala Ala Leu Thr Gly Gly Lys Gly Phe Pro
2385                2390                2395                2400
Phe Leu Phe Gln His Ile Arg Asp Gly Ile Asn Ile Arg Gln Thr Cys
                2405                2410                2415
Asn Leu Ile Phe Ser Leu Cys Arg Tyr Asn Asn Arg Leu Ala Glu His
                2420                2425                2430
Ile Val Ser Met Leu Phe Thr Ser Ile Ala Lys Leu Thr Pro Glu Ala
                2435                2440                2445
Ala Asn Pro Phe Phe Lys Leu Leu Thr Met Leu Met Glu Phe Ala Gly
                2450                2455                2460
Gly Pro Pro Gly Met Pro Pro Phe Ala Ser Tyr Ile Leu Gln Arg Ile
2465                2470                2475                2480
Trp Glu Val Ile Glu Tyr Asn Pro Ser Gln Cys Leu Asp Trp Leu Ala
                2485                2490                2495
Val Gln Thr Pro Arg Asn Lys Leu Ala His Ser Trp Val Leu Gln Asn
                2500                2505                2510
Met Glu Asn Trp Val Glu Arg Phe Leu Leu Ala His Asn Tyr Pro Arg
                2515                2520                2525
Val Arg Thr Ser Ala Ala Tyr Leu Leu Val Ser Leu Ile Pro Ser Asn
                2530                2535                2540
Ser Phe Arg Gln Met Phe Arg Ser Thr Arg Ser Leu His Ile Pro Thr
2545                2550                2555                2560
Arg Asp Leu Pro Leu Ser Pro Asp Thr Thr Val Leu His Gln Val
                2565                2570                2575
Tyr Asn Val Leu Leu Gly Leu Leu Ser Arg Ala Lys Leu Tyr Val Asp
                2580                2585                2590
Ala Ala Val His Gly Thr Thr Lys Leu Val Pro Tyr Phe Ser Phe Met
                2595                2600                2605
Thr Tyr Cys Leu Ile Ser Lys Thr Glu Lys Leu Met Phe Ser Thr Tyr
                2610                2615                2620
Phe Met Asp Leu Trp Asn Leu Phe Gln Pro Lys Leu Ser Glu Pro Ala
2625                2630                2635                2640
Ile Ala Thr Asn His Asn Lys Gln Ala Leu Leu Ser Phe Trp Tyr Asn
                2645                2650                2655
```

```
Val Cys Ala Asp Cys Pro Glu Asn Ile Arg Leu Ile Val Gln Asn Pro
            2660                2665                2670

Val Val Thr Lys Asn Ile Ala Phe Asn Tyr Ile Leu Ala Asp His Asp
2675                2680                2685

Asp Gln Asp Val Val Leu Phe Asn Arg Gly Met Leu Pro Ala Tyr Tyr
        2690                2695                2700

Gly Ile Leu Arg Leu Cys Cys Glu Gln Ser Pro Ala Phe Thr Arg Gln
2705                2710                2715                2720

Leu Ala Ser His Gln Asn Ile Gln Trp Ala Phe Lys Asn Leu Thr Pro
                2725                2730                2735

His Ala Ser Gln Tyr Pro Gly Ala Val Glu Glu Leu Phe Asn Leu Met
        2740                2745                2750

Gln Leu Phe Ile Ala Gln Arg Pro Asp Met Arg Glu Glu Glu Leu Glu
            2755                2760                2765

Asp Ile Lys Gln Phe Lys Lys Thr Thr Ile Ser Cys Tyr Leu Arg Cys
2770                2775                2780

Leu Asp Gly Arg Ser Cys Trp Thr Thr Leu Ile Ser Ala Phe Arg Ile
2785                2790                2795                2800

Leu Leu Glu Ser Asp Glu Asp Arg Leu Leu Val Val Phe Asn Arg Gly
            2805                2810                2815

Leu Ile Leu Met Thr Glu Ser Phe Asn Thr Leu His Met Met Tyr His
            2820                2825                2830

Glu Ala Thr Ala Cys His Val Thr Gly Asp Leu Val Glu Leu Leu Ser
        2835                2840                2845

Ile Phe Leu Ser Val Leu Lys Ser Thr Arg Pro Tyr Leu Gln Arg Lys
    2850                2855                2860

Asp Val Lys Gln Ala Leu Ile Gln Trp Gln Glu Arg Ile Glu Phe Ala
2865                2870                2875                2880

His Lys Leu Leu Thr Leu Leu Asn Ser Tyr Ser Pro Pro Glu Leu Arg
            2885                2890                2895

Asn Ala Cys Ile Asp Val Leu Lys Glu Leu Val Leu Ser Pro His
            2900                2905                2910

Asp Phe Leu His Thr Leu Val Pro Phe Leu Gln His Asn His Cys Thr
        2915                2920                2925

Tyr His His Ser Asn Ile Pro Met Ser Leu Gly Pro Tyr Phe Pro Cys
        2930                2935                2940

Arg Glu Asn Ile Lys Leu Ile Gly Gly Lys Ser Asn Ile Arg Pro Pro
2945                2950                2955                2960

Arg Pro Glu Leu Asn Met Cys Leu Leu Pro Thr Met Val Glu Thr Ser
            2965                2970                2975

Lys Gly Lys Asp Asp Val Tyr Asp Arg Met Leu Leu Asp Tyr Phe Phe
        2980                2985                2990

Ser Tyr His Gln Phe Ile His Leu Leu Cys Arg Val Ala Ile Asn Cys
        2995                3000                3005

Glu Lys Phe Thr Glu Thr Leu Val Lys Leu Ser Val Leu Val Ala Tyr
        3010                3015                3020

Glu Gly Leu Pro Leu His Leu Ala Leu Phe Pro Lys Leu Trp Thr Glu
3025                3030                3035                3040

Leu Cys Gln Thr Gln Ser Ala Met Ser Lys Asn Cys Ile Lys Leu Leu
            3045                3050                3055

Cys Glu Asp Pro Val Phe Ala Glu Tyr Ile Lys Cys Ile Leu Met Asp
            3060                3065                3070
```

```
Glu Arg Thr Phe Leu Asn Asn Asn Ile Val Tyr Thr Phe Met Thr His
        3075                3080                3085

Phe Leu Leu Lys Val Gln Ser Gln Val Phe Ser Glu Ala Asn Cys Ala
        3090                3095                3100

Asn Leu Ile Ser Thr Leu Ile Thr Asn Leu Ile Ser Gln Tyr Gln Asn
3105                3110                3115                3120

Leu Gln Ser Asp Phe Ser Asn Arg Val Glu Ile Ser Lys Ala Ser Ala
            3125                3130                3135

Ser Leu Asn Gly Asp Leu Arg Ala Leu Ala Leu Leu Ser Val His
        3140                3145                3150

Thr Pro Lys Gln Leu Asn Pro Ala Leu Ile Pro Thr Leu Gln Glu Leu
        3155                3160                3165

Leu Ser Lys Cys Arg Thr Cys Leu Gln Gln Arg Asn Ser Leu Gln Glu
        3170                3175                3180

Gln Glu Ala Lys Glu Arg Lys Thr Lys Asp Asp Glu Gly Ala Thr Pro
3185                3190                3195                3200

Ile Lys Arg Arg Arg Val Ser Ser Asp Glu Glu His Thr Val Asp Ser
            3205                3210                3215

Cys Ile Ser Asp Met Lys Thr Glu Thr Arg Glu Val Leu Thr Pro Thr
        3220                3225                3230

Ser Thr Ser Asp Asn Glu Thr Arg Asp Ser Ser Ile Ile Asp Pro Gly
        3235                3240                3245

Thr Glu Gln Asp Leu Pro Ser Pro Glu Asn Ser Ser Val Lys Glu Tyr
        3250                3255                3260

Arg Met Glu Val Pro Ser Ser Phe Ser Glu Asp Met Ser Asn Ile Arg
3265                3270                3275                3280

Ser Gln His Ala Glu Glu Gln Ser Asn Asn Gly Arg Tyr Asp Asp Cys
            3285                3290                3295

Lys Glu Phe Lys Asp Leu His Cys Ser Lys Asp Ser Thr Leu Ala Glu
        3300                3305                3310

Glu Glu Ser Glu Phe Pro Ser Thr Ser Ile Ser Ala Val Leu Ser Asp
        3315                3320                3325

Leu Ala Asp Leu Arg Ser Cys Asp Gly Gln Ala Leu Pro Ser Gln Asp
        3330                3335                3340

Pro Glu Val Ala Leu Ser Leu Ser Cys Gly His Ser Arg Gly Leu Phe
3345                3350                3355                3360

Ser His Met Gln Gln His Asp Ile Leu Asp Thr Leu Cys Arg Thr Ile
            3365                3370                3375

Glu Ser Thr Ile His Val Val Thr Arg Ile Ser Gly Lys Gly Asn Gln
        3380                3385                3390

Ala Ala Ser
    3395

<210> SEQ ID NO 49
<211> LENGTH: 3057
<212> TYPE: DNA
<213> ORGANISM: Homo sapiens

<400> SEQUENCE: 49
atggacaaga tcttggaggc ggtggtgacg tcgtcatacc cggtcagcgt gaagcagggg     60
ctggttcggc gcgtgctgga ggcggcgcgg cagccgctgg agcgtgagca gtgcctggcg    120
ctgctggcgc tgggcgcgcg cctctacgtg ggcggcgcgg aggagctgcc gcgccgcgtg    180
ggctgccagc tgctgcacgt ggccggccgc caccaccccg acgtcttcgc cgagttcttc    240
```

```
agcgcgcgtc gcgtgctgcg cctgctgcag ggtggcgccg gcccccgggg ccccgcgcg    300
ctcgcctgcg tgcagctggg tctgcagctg ctgcccgagg ggcctgcggc cgacgaggtg    360
ttcgcgctgc tgcggcgcga ggtgctgcgc accgtgtgcg agcgcccggg ccccgcggcc    420
tgcgcgcagg tggcacggct gctggctcgc caccgcgct gtgtgcccga cggaccccac     480
cgcctgctct tctgccagca gctggtgcgt tgcctcggcc gcttccgctg cccagccgaa    540
ggcgaggagg cgccgtgga gttcctagag caggcccagc aggtgagcgg gctcctggcg     600
cagctgtggc gcgcacagcc cgccgccatc ctgccctgcc tcaaagagct gttcgcagtc    660
atctcctgcg cagaggagga gccaccatct agcgccctgg ccagcgtggt ccagcacctc    720
ccattggagc tcatggatgg tgttgtccgg aacctcagca atgatgacag tgtgacagac    780
tcgcagatgc tgactgccat tagcaggatg attgactggg tgtcctggcc cctggggaag    840
aatattgaca agtggatcat tgcactgctg aagggcctgg ctgctgttaa gaagttcagc    900
atcttgatcg aggtttcgct caccaaaatt gagaaggttt tctctaagct gctgtacccc    960
atcgtccggg gagctgcctt gtctgtgctc aagtacatgc tcctgacctt ccagcactcc   1020
cacgaagcct tccacctgct cctccctcac atccccccca tggtggcctc tctggtcaag   1080
gaggactcga actcggggac cagctgcctg gagcagctgg cggagctggt ccactgcatg   1140
gtgttccggt tcccgggctt cccggatctg tatgagcctg tcatggaggc catcaaggac   1200
ctccatgttc ccaatgagga ccgcatcaag cagctgctgg ggcaggatgc ctggacttcg   1260
cagaagagcg agctggcggg tttctatccc cggctcatgg ccaagtcaga cacgggcaag   1320
attggtctca tcaacctggg caacacatgc tatgtcaaca gcatccttca ggccttattc   1380
atggcgtctg acttcagaca ttgtgtgctc cgcttgactg agaacaactc acagccctg    1440
atgaccaagc tgcagtggct cttttggctt ctagaacaca gccagcggcc tgccatttcc   1500
ccagagaact tcctctccgc atcctggacg ccctggttca gccctggcac ccagcaggac   1560
tgctcggagt atctgaagta cctgctggat cggctgcacg aagaggagaa acgggcaca    1620
aggatctgcc agaaactcaa gcagtccagc tcgccctctc cgcccgagga gcccccggcc   1680
ccaagttcaa cctctgtgga aaaaatgttt ggaggcaaga tagtgactcg gatctgctgt   1740
ctctgctgcc tcaacgtctc ctcccgggag gaggccttca cggacctctc tctcgccttc   1800
cctcctcctg agcgctgtcg ccgccgcgc ctgggtctg tgatgcgccc cacagaagac     1860
atcacagccc gggagttgcc cccaccaacc agtgcacagg ggccaggcag ggtgggtcct   1920
cggaggcaaa ggaaacactg catcacagag gacacccccc ccaccagcct gtacatcgaa   1980
ggcctggact ccaaggaagc tggtgggcag agcagtcagg aggaaaggat agagagggag   2040
gaagaaggga aggaggagag aacggagaag gaagaagtgg gggaggagga ggaaagcacc   2100
agaggggaag gagagaggga gaaagaggag gaggtggaag aggaagaaga gaaggtggag   2160
aaggagacag aaaaggaggc tgagcaggaa aaggaagaag acagcctggg agcgggggacc  2220
caccccggatg ctgccatccc ctccggggag cggacatgtg gctctgaggg ctcccgctcc  2280
gtcctggacc tggttaacta cttcctgtcc cccgagaagc tgacagcaga aaaccgctac   2340
tactgcgagt cgtgtgcctc cctgcaggat gccgagaagg tggtggagct gagccaaggg   2400
ccgtgctacc tcatcctcac actgctgcgc ttctctttcg acctgcgcac catgcggcgc   2460
cgcaagatcc tggatgacgt ctccatcccc ctgctgctcc gcctgccact ggctggtggc   2520
cgtggccagg cctatgacct ctgcagtgtg gtggtgcact ctggagtgtc ttcggagagt   2580
ggtcactact actgctatgc ccgtgagggc gctgcccgcc ctgccgcttc tctgggaact   2640
```

-continued

```
gccgataggc cagagcccga gaaccagtgg tacctgttca atgacactcg ggtgtccttc    2700
tcttccttcg aatctgtcag caacgtcacc tccttcttcc ctaaggacac agcctatgtg    2760
ctgttttacc ggcagcggcc cagggagggg cccgaggctg agttgggctc ttctagagtc    2820
cggacagagc ccaccctgca caaggacttg atggaagcca tttccaaaga caacatcctt    2880
tacctacagg agcaggagaa ggaggcccgg agcagggcgg cctacatctc tgcactcccc    2940
acatctccgc actgggggag gggctttgat gaagacaagg atgaggatga aggctctcca    3000
gggggctgca atcctgcagg tggcaatggt ggtgacttcc acagactggt cttctaa      3057
```

<210> SEQ ID NO 50
<211> LENGTH: 1018
<212> TYPE: PRT
<213> ORGANISM: Homo sapiens

<400> SEQUENCE: 50

Met Asp Lys Ile Leu Glu Ala Val Val Thr Ser Ser Tyr Pro Val Ser
1               5                   10                  15

Val Lys Gln Gly Leu Val Arg Arg Val Leu Glu Ala Ala Arg Gln Pro
            20                  25                  30

Leu Glu Arg Glu Gln Cys Leu Ala Leu Leu Ala Leu Gly Ala Arg Leu
        35                  40                  45

Tyr Val Gly Gly Ala Glu Leu Pro Arg Arg Val Gly Cys Gln Leu
    50                  55                  60

Leu His Val Ala Gly Arg His Pro Asp Val Phe Ala Glu Phe Phe
65                  70                  75                  80

Ser Ala Arg Arg Val Leu Arg Leu Leu Gln Gly Gly Ala Gly Pro Pro
                85                  90                  95

Gly Pro Arg Ala Leu Ala Cys Val Gln Leu Gly Leu Gln Leu Leu Pro
            100                 105                 110

Glu Gly Pro Ala Ala Asp Glu Val Phe Ala Leu Leu Arg Arg Glu Val
        115                 120                 125

Leu Arg Thr Val Cys Glu Arg Pro Gly Pro Ala Ala Cys Ala Gln Val
    130                 135                 140

Ala Arg Leu Leu Ala Arg His Pro Arg Cys Val Pro Asp Gly Pro His
145                 150                 155                 160

Arg Leu Leu Phe Cys Gln Gln Leu Val Arg Cys Leu Gly Arg Phe Arg
                165                 170                 175

Cys Pro Ala Glu Gly Glu Glu Gly Ala Val Glu Phe Leu Glu Gln Ala
            180                 185                 190

Gln Gln Val Ser Gly Leu Leu Ala Gln Leu Trp Arg Ala Gln Pro Ala
        195                 200                 205

Ala Ile Leu Pro Cys Leu Lys Glu Leu Phe Ala Val Ile Ser Cys Ala
    210                 215                 220

Glu Glu Glu Pro Pro Ser Ser Ala Leu Ala Ser Val Val Gln His Leu
225                 230                 235                 240

Pro Leu Glu Leu Met Asp Gly Val Val Arg Asn Leu Ser Asn Asp Asp
                245                 250                 255

Ser Val Thr Asp Ser Gln Met Leu Thr Ala Ile Ser Arg Met Ile Asp
            260                 265                 270

Trp Val Ser Trp Pro Leu Gly Lys Asn Ile Asp Lys Trp Ile Ile Ala
        275                 280                 285

Leu Leu Lys Gly Leu Ala Ala Val Lys Lys Phe Ser Ile Leu Ile Glu
    290                 295                 300

```
Val Ser Leu Thr Lys Ile Glu Lys Val Phe Ser Lys Leu Leu Tyr Pro
305                 310                 315                 320

Ile Val Arg Gly Ala Ala Leu Ser Val Leu Lys Tyr Met Leu Leu Thr
                325                 330                 335

Phe Gln His Ser His Glu Ala Phe His Leu Leu Leu Pro His Ile Pro
            340                 345                 350

Pro Met Val Ala Ser Leu Val Lys Glu Asp Ser Asn Ser Gly Thr Ser
        355                 360                 365

Cys Leu Glu Gln Leu Ala Glu Leu Val His Cys Met Val Phe Arg Phe
370                 375                 380

Pro Gly Phe Pro Asp Leu Tyr Glu Pro Val Met Glu Ala Ile Lys Asp
385                 390                 395                 400

Leu His Val Pro Asn Glu Asp Arg Ile Lys Gln Leu Leu Gly Gln Asp
                405                 410                 415

Ala Trp Thr Ser Gln Lys Ser Glu Leu Ala Gly Phe Tyr Pro Arg Leu
            420                 425                 430

Met Ala Lys Ser Asp Thr Gly Lys Ile Gly Leu Ile Asn Leu Gly Asn
        435                 440                 445

Thr Cys Tyr Val Asn Ser Ile Leu Gln Ala Leu Phe Met Ala Ser Asp
450                 455                 460

Phe Arg His Cys Val Leu Arg Leu Thr Glu Asn Asn Ser Gln Pro Leu
465                 470                 475                 480

Met Thr Lys Leu Gln Trp Leu Phe Gly Phe Leu Glu His Ser Gln Arg
                485                 490                 495

Pro Ala Ile Ser Pro Glu Asn Phe Leu Ser Ala Ser Trp Thr Pro Trp
            500                 505                 510

Phe Ser Pro Gly Thr Gln Gln Asp Cys Ser Glu Tyr Leu Lys Tyr Leu
        515                 520                 525

Leu Asp Arg Leu His Glu Glu Lys Thr Gly Thr Arg Ile Cys Gln
530                 535                 540

Lys Leu Lys Gln Ser Ser Ser Pro Ser Pro Pro Glu Glu Pro Pro Ala
545                 550                 555                 560

Pro Ser Ser Thr Ser Val Glu Lys Met Phe Gly Gly Lys Ile Val Thr
                565                 570                 575

Arg Ile Cys Cys Leu Cys Cys Leu Asn Val Ser Ser Arg Glu Glu Ala
            580                 585                 590

Phe Thr Asp Leu Ser Leu Ala Phe Pro Pro Glu Arg Cys Arg Arg
        595                 600                 605

Arg Arg Leu Gly Ser Val Met Arg Pro Thr Glu Asp Ile Thr Ala Arg
610                 615                 620

Glu Leu Pro Pro Pro Thr Ser Ala Gln Gly Pro Gly Arg Val Gly Pro
625                 630                 635                 640

Arg Arg Gln Arg Lys His Cys Ile Thr Glu Asp Thr Pro Pro Thr Ser
                645                 650                 655

Leu Tyr Ile Glu Gly Leu Asp Ser Lys Glu Ala Gly Gly Gln Ser Ser
            660                 665                 670

Gln Glu Glu Arg Ile Glu Arg Glu Glu Gly Lys Glu Glu Arg Thr
        675                 680                 685

Glu Lys Glu Glu Val Gly Glu Glu Glu Ser Thr Arg Gly Glu Gly
        690                 695                 700

Glu Arg Glu Lys Glu Glu Glu Val Glu Glu Glu Glu Lys Val Glu
705                 710                 715                 720
```

-continued

```
Lys Glu Thr Glu Lys Glu Ala Glu Gln Glu Lys Glu Glu Asp Ser Leu
                725                 730                 735
Gly Ala Gly Thr His Pro Asp Ala Ala Ile Pro Ser Gly Glu Arg Thr
            740                 745                 750
Cys Gly Ser Glu Gly Ser Arg Ser Val Leu Asp Leu Val Asn Tyr Phe
        755                 760                 765
Leu Ser Pro Glu Lys Leu Thr Ala Glu Asn Arg Tyr Tyr Cys Glu Ser
    770                 775                 780
Cys Ala Ser Leu Gln Asp Ala Glu Lys Val Val Glu Leu Ser Gln Gly
785                 790                 795                 800
Pro Cys Tyr Leu Ile Leu Thr Leu Leu Arg Phe Ser Phe Asp Leu Arg
                805                 810                 815
Thr Met Arg Arg Arg Lys Ile Leu Asp Asp Val Ser Ile Pro Leu Leu
            820                 825                 830
Leu Arg Leu Pro Leu Ala Gly Gly Arg Gly Gln Ala Tyr Asp Leu Cys
        835                 840                 845
Ser Val Val Val His Ser Gly Val Ser Ser Glu Ser Gly His Tyr Tyr
    850                 855                 860
Cys Tyr Ala Arg Glu Gly Ala Ala Arg Pro Ala Ala Ser Leu Gly Thr
865                 870                 875                 880
Ala Asp Arg Pro Glu Pro Glu Asn Gln Trp Tyr Leu Phe Asn Asp Thr
                885                 890                 895
Arg Val Ser Phe Ser Ser Phe Glu Ser Val Ser Asn Val Thr Ser Phe
            900                 905                 910
Phe Pro Lys Asp Thr Ala Tyr Val Leu Phe Tyr Arg Gln Arg Pro Arg
        915                 920                 925
Glu Gly Pro Glu Ala Glu Leu Gly Ser Ser Arg Val Arg Thr Glu Pro
    930                 935                 940
Thr Leu His Lys Asp Leu Met Glu Ala Ile Ser Lys Asp Asn Ile Leu
945                 950                 955                 960
Tyr Leu Gln Glu Gln Glu Lys Glu Ala Arg Ser Arg Ala Ala Tyr Ile
                965                 970                 975
Ser Ala Leu Pro Thr Ser Pro His Trp Gly Arg Gly Phe Asp Glu Asp
            980                 985                 990
Lys Asp Glu Asp Glu Gly Ser Pro Gly Gly Cys Asn Pro Ala Gly Gly
        995                 1000                1005
Asn Gly Gly Asp Phe His Arg Leu Val Phe
    1010                1015
```

<210> SEQ ID NO 51
<211> LENGTH: 3372
<212> TYPE: DNA
<213> ORGANISM: Homo sapiens

<400> SEQUENCE: 51

```
atgccaatag tggataagtt gaaggaggcc ctgaaacccg gccgcaagga ctcggctgat    60
gatggagaac tggggaagct tcttgcctcc tctgccaaga aggtcctttt acagaaaatc   120
gagttcgagc cagccagcaa gagcttctcc taccagctgg aggccttaaa gagcaaatat   180
gtgttgctca accccaaaac agagggagct agtcgccaca agagtggaga tgacccaccg   240
gccaggagac agggcagtga gcacacgtat gagagctgtg tgacggagt cccagccccg   300
cagaaagtgc ttttcccccac ggagcgactg tctctgaggt gggagcgggt cttccgcgtg   360
ggcgcaggac tccacaacct tggcaacacc tgctttctca atgccaccat ccagtgcttg   420
```

-continued

```
acctacacac cacctctagc caactacctg ctctccaagg agcatgctcg cagctgccac      480
cagggaagct tctgcatgct gtgtgtcatg cagaaccaca ttgtccaggc cttcgccaac      540
agcggcaacg ccatcaagcc cgtctccttc atccgagacc tgaaaaagat cgcccgacac      600
ttccgctttg ggaaccagga ggacgcgcat gagttcctgc ggtacaccat cgacgccatg      660
cagaaagcct gcctgaatgg ctgtgccaag ttggatcgtc aaacgcaggc tactaccttg      720
gtccatcaaa tttttggagg gtatctcaga tcacgcgtga agtgctccgt gtgcaagagc      780
gtctcggaca cctacgaccc ctacttggac gtcgcgctgg agatccggca agctgcgaat      840
attgtgcgtg ctctggaact ttttgtgaaa gcagatgtcc tgagtggaga gaatgcctac      900
atgtgtgcta aatgcaagaa gaaggttcca gccagcaagc gcttcaccat ccacagaaca      960
tccaacgtct taacccttc cctcaagcgc tttgccaact tcagcggggg gaagatcacc     1020
aaggatgtag gctatccgga attcctcaac atacgtccgt atatgtccca gaataatggt     1080
gatcctgtca tgtatggact ctatgctgtc ctggtgcact cgggctacag ctgccatgcc     1140
gggcactatt actgctacgt gaaggcaagc aatggacagt ggtaccagat gaatgattcc     1200
ttggtccatt ccagcaacgt caaggtggtt ctgaaccagc aggcctacgt gctgttctat     1260
ctgcgaattc caggctctaa gaaaagtccc gagggcctca tctccaggac aggctcctcc     1320
tcccttcccg ccgcccgag tgtgattcca gatcactcca agaagaacat cggcaatggg     1380
attatttcct ccccactgac tggaaagcga caagactctg gacgatgaa gaagccgcac      1440 accactgaag agattggtgt gcccatatcc aggaatggct ccaccctggg cctgaagtcc     1500
cagaacggct gcattcctcc aaagctgccc tcggggtccc cttcccccaa actctcccag     1560
acacccacac acatgccaac catcctagac gaccctggaa agaaggtgaa gaagccagct     1620
cctccacagc acttttcccc cagaactgct caggggctgc ctgggaccag caactcgaat     1680
agcagcagat ctgggagcca aaggcagggc tcctgggaca gcaggatgt tgtcctctct     1740 acctcaccta gctcctggc tacagccact gccaacgggc atgggctgaa ggggaacgac     1800
gagagcgctg gcctcgacag gaggggctcc agcagctcca gcccagagca ctcggccagc     1860
agcgactcca ccaaggcccc ccagaccccc aggagtggag cggcccatct ctgcgattct     1920
caggaaacga actgttccac cgctggccac tccaaaacgc cgccaagtgg agcagattct     1980
aagacggtga agctgaagtc ccctgtcctg agcaacacca ccactgagcc tgcaagcacc     2040
atgtctcctc caccagccaa aaaactggcc cttttctgcca agaaggccag caccctgtgg     2100
agggcgaccg gcaatgacct ccgtccacct ccccccctcac catcctccga cctcacccac     2160
cccatgaaaa cctctcaccc cgtcgttgcc tccacttggc ccgtccatag agccagggct     2220
gtgtcacctg ctccccaatc atccagccgc ctgcaacccc ccttcagccc ccaccccaca     2280
ttgctgtcca gtaccccaa gccccaggg acgtcagaac cacggagctg ctcctccatc     2340 tcgacgcgc tgcctcaggt caacgaggac cttgtgtctc ttccacacca gttgccagag     2400
gccagtgagc cccccagag ccctctgag aagaggaaaa agacctttgt gggagagccg     2460
cagaggctgg gctcagagac gcgcctccca cagcacatca gggaggccac tgcggctccc     2520
cacgggaaga ggaagaggaa gaagaagaag cgcccggagg acacagctgc cagcgccctg     2580
caggaggggc agacacagag acagcctggg agccccatgt acaggaggga gggccaggca     2640
cagctgcccg ctgtcagacg gcaggaagat ggcacacagc cacaggtgaa tggccagcag     2700
gtgggatgtg ttacgacgg ccaccacgcg agcagcagga agcggaggag gaaaggagca     2760
gaaggtcttg gtgaagaagg cggcctgcac caggacccac ttcggcacag ctgctctccc     2820
```

```
atgggtgatg gtgatccaga ggccatggaa gagtctccaa ggaaaaagaa aaagaaaaaa    2880
agaaagcagg agacacagcg ggcagtagaa gaggatgggc atctcaaatg cccaaggagt    2940
gccaagcccc aagatgctgt tgtccccgag tccagcagct gcgcaccatc cgcgaatggc    3000
tggtgtcctg ggaccgcat ggggctgagc caggcccctc ctgtgtcttg aatggagag     3060 cgggagtctg atgtggtcca ggaactgctc aaatactcat ctgataaagc ttacgggaga    3120
aaagttctga cctgggatgg caagatgtcg gcggtcagtc aggatgctat tgaagacagc    3180
agacaggccc ggactgagac cgtggttgat gactgggacg aagagtttga ccgagggaag    3240
gaaaagaaaa ttaaaaaatt taagagagag aagaggagaa acttcaacgc cttccagaaa    3300
cttcagactc gacggaactt ctggtctgtg actcacccag caaaggctgc cagcctcagc    3360
tatcgccgct ga                                                         3372
```

<210> SEQ ID NO 52
<211> LENGTH: 1123
<212> TYPE: PRT
<213> ORGANISM: Homo sapiens

<400> SEQUENCE: 52

```
Met Pro Ile Val Asp Lys Leu Lys Glu Ala Leu Lys Pro Gly Arg Lys
1               5                   10                  15

Asp Ser Ala Asp Asp Gly Glu Leu Gly Lys Leu Leu Ala Ser Ser Ala
            20                  25                  30

Lys Lys Val Leu Leu Gln Lys Ile Glu Phe Glu Pro Ala Ser Lys Ser
        35                  40                  45

Phe Ser Tyr Gln Leu Glu Ala Leu Lys Ser Lys Tyr Val Leu Leu Asn
    50                  55                  60

Pro Lys Thr Glu Gly Ala Ser Arg His Lys Ser Gly Asp Asp Pro Pro
65                  70                  75                  80

Ala Arg Arg Gln Gly Ser Glu His Thr Tyr Glu Ser Cys Gly Asp Gly
                85                  90                  95

Val Pro Ala Pro Gln Lys Val Leu Phe Pro Thr Glu Arg Leu Ser Leu
            100                 105                 110

Arg Trp Glu Arg Val Phe Arg Val Gly Ala Gly Leu His Asn Leu Gly
        115                 120                 125

Asn Thr Cys Phe Leu Asn Ala Thr Ile Gln Cys Leu Thr Tyr Thr Pro
    130                 135                 140

Pro Leu Ala Asn Tyr Leu Leu Ser Lys Glu His Ala Arg Ser Cys His
145                 150                 155                 160

Gln Gly Ser Phe Cys Met Leu Cys Val Met Gln Asn His Ile Val Gln
                165                 170                 175

Ala Phe Ala Asn Ser Gly Asn Ala Ile Lys Pro Val Ser Phe Ile Arg
            180                 185                 190

Asp Leu Lys Lys Ile Ala Arg His Phe Arg Phe Gly Asn Gln Glu Asp
        195                 200                 205

Ala His Glu Phe Leu Arg Tyr Thr Ile Asp Ala Met Gln Lys Ala Cys
    210                 215                 220

Leu Asn Gly Cys Ala Lys Leu Asp Arg Gln Thr Gln Ala Thr Thr Leu
225                 230                 235                 240

Val His Gln Ile Phe Gly Gly Tyr Leu Arg Ser Arg Val Lys Cys Ser
                245                 250                 255

Val Cys Lys Ser Val Ser Asp Thr Tyr Asp Pro Tyr Leu Asp Val Ala
            260                 265                 270
```

```
Leu Glu Ile Arg Gln Ala Ala Asn Ile Val Arg Ala Leu Glu Leu Phe
        275                 280                 285

Val Lys Ala Asp Val Leu Ser Gly Glu Asn Ala Tyr Met Cys Ala Lys
    290                 295                 300

Cys Lys Lys Lys Val Pro Ala Ser Lys Arg Phe Thr Ile His Arg Thr
305                 310                 315                 320

Ser Asn Val Leu Thr Leu Ser Leu Lys Arg Phe Ala Asn Phe Ser Gly
                325                 330                 335

Gly Lys Ile Thr Lys Asp Val Gly Tyr Pro Glu Phe Leu Asn Ile Arg
                340                 345                 350

Pro Tyr Met Ser Gln Asn Gly Asp Pro Val Met Tyr Gly Leu Tyr
                355                 360                 365

Ala Val Leu Val His Ser Gly Tyr Ser Cys His Ala Gly His Tyr Tyr
        370                 375                 380

Cys Tyr Val Lys Ala Ser Asn Gly Gln Trp Tyr Gln Met Asn Asp Ser
385                 390                 395                 400

Leu Val His Ser Ser Asn Val Lys Val Val Leu Asn Gln Gln Ala Tyr
                405                 410                 415

Val Leu Phe Tyr Leu Arg Ile Pro Gly Ser Lys Ser Pro Glu Gly
                420                 425                 430

Leu Ile Ser Arg Thr Gly Ser Ser Leu Pro Gly Arg Pro Ser Val
        435                 440                 445

Ile Pro Asp His Ser Lys Lys Asn Ile Gly Asn Gly Ile Ile Ser Ser
        450                 455                 460

Pro Leu Thr Gly Lys Arg Gln Asp Ser Gly Thr Met Lys Lys Pro His
465                 470                 475                 480

Thr Thr Glu Glu Ile Gly Val Pro Ile Ser Arg Asn Gly Ser Thr Leu
                485                 490                 495

Gly Leu Lys Ser Gln Asn Gly Cys Ile Pro Pro Lys Leu Pro Ser Gly
                500                 505                 510

Ser Pro Ser Pro Lys Leu Ser Gln Thr Pro Thr His Met Pro Thr Ile
        515                 520                 525

Leu Asp Asp Pro Gly Lys Lys Val Lys Lys Pro Ala Pro Pro Gln His
        530                 535                 540

Phe Ser Pro Arg Thr Ala Gln Gly Leu Pro Gly Thr Ser Asn Ser Asn
545                 550                 555                 560

Ser Ser Arg Ser Gly Ser Gln Arg Gln Gly Ser Trp Asp Ser Arg Asp
                565                 570                 575

Val Val Leu Ser Thr Ser Pro Lys Leu Leu Ala Thr Ala Thr Ala Asn
                580                 585                 590

Gly His Gly Leu Lys Gly Asn Asp Glu Ser Ala Gly Leu Asp Arg Arg
                595                 600                 605

Gly Ser Ser Ser Ser Pro Glu His Ser Ala Ser Ser Asp Ser Thr
        610                 615                 620

Lys Ala Pro Gln Thr Pro Arg Ser Gly Ala Ala His Leu Cys Asp Ser
625                 630                 635                 640

Gln Glu Thr Asn Cys Ser Thr Ala Gly His Ser Lys Thr Pro Pro Ser
                645                 650                 655

Gly Ala Asp Ser Lys Thr Val Lys Leu Lys Ser Pro Val Leu Ser Asn
                660                 665                 670

Thr Thr Thr Glu Pro Ala Ser Thr Met Ser Pro Pro Ala Lys Lys
        675                 680                 685
```

```
Leu Ala Leu Ser Ala Lys Lys Ala Ser Thr Leu Trp Arg Ala Thr Gly
    690             695                 700

Asn Asp Leu Arg Pro Pro Pro Ser Pro Ser Ser Asp Leu Thr His
705             710             715                 720

Pro Met Lys Thr Ser His Pro Val Val Ala Ser Thr Trp Pro Val His
                725             730             735

Arg Ala Arg Ala Val Ser Pro Ala Pro Gln Ser Ser Arg Leu Gln
            740             745             750

Pro Pro Phe Ser Pro His Pro Thr Leu Leu Ser Ser Thr Pro Lys Pro
        755             760             765

Pro Gly Thr Ser Glu Pro Arg Ser Cys Ser Ser Ile Ser Thr Ala Leu
770             775                 780

Pro Gln Val Asn Glu Asp Leu Val Ser Leu Pro His Gln Leu Pro Glu
785             790             795                 800

Ala Ser Glu Pro Pro Gln Ser Pro Ser Glu Lys Arg Lys Lys Thr Phe
                805             810             815

Val Gly Glu Pro Gln Arg Leu Gly Ser Glu Thr Arg Leu Pro Gln His
            820             825             830

Ile Arg Glu Ala Thr Ala Ala Pro His Gly Lys Arg Lys Arg Lys Lys
            835             840             845

Lys Lys Arg Pro Glu Asp Thr Ala Ala Ser Ala Leu Gln Glu Gly Gln
850             855             860

Thr Gln Arg Gln Pro Gly Ser Pro Met Tyr Arg Arg Glu Gly Gln Ala
865             870             875             880

Gln Leu Pro Ala Val Arg Arg Gln Glu Asp Gly Thr Gln Pro Gln Val
            885             890             895

Asn Gly Gln Gln Val Gly Cys Val Thr Asp Gly His His Ala Ser Ser
            900             905             910

Arg Lys Arg Arg Arg Lys Gly Ala Glu Gly Leu Gly Glu Glu Gly Gly
            915             920             925

Leu His Gln Asp Pro Leu Arg His Ser Cys Ser Pro Met Gly Asp Gly
    930             935             940

Asp Pro Glu Ala Met Glu Glu Ser Pro Arg Lys Lys Lys Lys Lys
945             950             955             960

Arg Lys Gln Glu Thr Gln Arg Ala Val Glu Glu Asp Gly His Leu Lys
            965             970             975

Cys Pro Arg Ser Ala Lys Pro Gln Asp Ala Val Val Pro Glu Ser Ser
            980             985             990

Ser Cys Ala Pro Ser Ala Asn Gly Trp Cys Pro Gly Asp Arg Met Gly
        995             1000            1005

Leu Ser Gln Ala Pro Pro Val Ser Trp Asn Gly Glu Arg Glu Ser Asp
    1010            1015            1020

Val Val Gln Glu Leu Leu Lys Tyr Ser Ser Asp Lys Ala Tyr Gly Arg
1025            1030            1035            1040

Lys Val Leu Thr Trp Asp Gly Lys Met Ser Ala Val Ser Gln Asp Ala
            1045            1050            1055

Ile Glu Asp Ser Arg Gln Ala Arg Thr Glu Thr Val Val Asp Asp Trp
            1060            1065            1070

Asp Glu Glu Phe Asp Arg Gly Lys Glu Lys Lys Ile Lys Lys Phe Lys
                1075            1080            1085

Arg Glu Lys Arg Arg Asn Phe Asn Ala Phe Gln Lys Leu Gln Thr Arg
            1090            1095            1100

Arg Asn Phe Trp Ser Val Thr His Pro Ala Lys Ala Ala Ser Leu Ser
```

Tyr Arg Arg

<210> SEQ ID NO 53
<211> LENGTH: 2940
<212> TYPE: DNA
<213> ORGANISM: Homo sapiens

<400> SEQUENCE: 53

| | | | | | |
|---|---|---|---|---|---|
| atgtctcctc | tgaagataca | tggtcctatc | agaattcgaa | gtatgcagac | tgggattaca | 60 |
| aagtggaaag | aaggatcctt | tgaaattgta | gaaaaagaga | ataaagtcag | cctagtagtt | 120 |
| cactacaata | ctggaggaat | tccaaggata | tttcagctaa | gtcataacat | taaaaatgtg | 180 |
| gtgcttcgac | ccagtggagc | gaaacaaagc | cgcctaatgt | taactctgca | agataacagc | 240 |
| ttcttgtcta | ttgacaaagt | accaagtaag | gatgcagagg | aaatgaggtt | gtttctagat | 300 |
| gcagtccatc | aaaacagact | tcctgcagcc | atgaaaccgt | ctcaggggtc | tggtagtttt | 360 |
| ggagccattc | tgggcagcag | gacctcacag | aaggaaacca | gcaggcagct | ttcttactca | 420 |
| gacaatcagg | cttctgcaaa | aagaggaagt | ttggaaacta | agatgatat | tccatttcga | 480 |
| aaagttcttg | gtaatccggg | tagaggatcg | attaagactg | tagcaggaag | tggaatagct | 540 |
| cggacgattc | cttctttgac | atctacttca | acacctctta | gatcagggtt | gctagaaaat | 600 |
| cgtactgaaa | gaggaaaag | aatgatatca | actggctcag | aattgaatga | agattaccct | 660 |
| aaggaaaatg | attcatcatc | gaacaacaag | gccatgacag | atccctccag | aaagtattta | 720 |
| accagcagta | gagaaaagca | gctgagtttg | aaacagtcag | aagagaatag | gacatcaggg | 780 |
| cttttacctt | tacagtcatc | atccttttat | ggtagcagag | ctggatccaa | ggaacactct | 840 |
| tctggtggca | ctaacttaga | caggactaat | gtttcaagcc | agactccctc | tgccaaaaga | 900 |
| agtttgggat | tcttcctca | gccagttcct | cttttctgtta | aaaaactgag | gtgtaaccag | 960 |
| gattacactg | gctggaataa | accaagagtg | cccctttcct | ctcaccaaca | gcagcaactg | 1020 |
| cagggcttct | ccaatttggg | aaatacctgc | tatatgaatg | ctattctaca | atctctattt | 1080 |
| tcactccagt | catttgcaaa | tgacttgctt | aaacaaggta | tcccatggaa | gaaaattcca | 1140 |
| ctcaatgcac | ttatcagacg | ctttgcacac | ttgcttgtta | aaaagatat | ctgtaattca | 1200 |
| gagaccaaaa | aggatttact | caagaaggtt | aaaaatgcca | tttcagctac | agcagagaga | 1260 |
| ttctctggtt | atatgcagaa | tgatgctcat | gaattttaa | gtcagtgttt | ggaccagctg | 1320 |
| aaagaagata | tggaaaaatt | aaataaaact | tggaagactg | aacctgtttc | tggagaagaa | 1380 |
| aattcaccag | atatttcagc | taccagagca | tacacttgcc | ctgttattac | taatttggag | 1440 |
| tttgaggttc | agcactccat | catttgtaaa | gcatgtggag | agattatccc | caaaagagaa | 1500 |
| cagtttaatg | acctctctat | tgaccttcct | cgtaggaaaa | aaccactccc | tcctcgttca | 1560 |
| attcaagatt | ctcttgatct | tttctttagg | gccgaagaac | tggagtattc | ttgtgagaag | 1620 |
| tgtggtggga | agtgtgctct | tgtcaggcac | aaatttaaca | ggcttcctag | ggtcctcatt | 1680 |
| ctccatttga | acgatatag | cttcaatgtg | gctctctcgc | ttaacaataa | gattgggcag | 1740 |
| caagtcatca | ttccaagata | cctgaccctg | tcatctcatt | gcactgaaaa | tacaaaacca | 1800 |
| ccttttaccc | ttggttggag | tgcacatatg | gcaatttcta | gaccattgaa | agcctctcaa | 1860 |
| atggtgaatt | cctgcatcac | cagcccttct | acaccttcaa | agaaattcac | cttcaaatcc | 1920 |
| aagagctcct | ggcttttatg | ccttgattca | gacagtgagg | atgagctaaa | acgttctgtg | 1980 |
| gccctcagcc | agagactttg | tgaaatgtta | ggcaacgaac | agcagcagga | agacctggaa | 2040 |

```
aaagattcaa aattatgccc aatagagcct gacaagtctg aattggaaaa ctcaggattt    2100
gacagaatga gcgaagaaga gcttctagca gctgtcttgg agataagtaa gagagatgct    2160
tcaccatctc tgagtcatga agatgatgat aagccaacta gcagcccaga taccggattt    2220
gcagaagatg atattcaaga aatgccagaa atcccagaca ctatgaaaac tgagaagccc    2280
aaaacaatca cagagctgga tcctgccagt tttactgaga taactaaaga ctgtgatgag    2340
aataaagaaa acaaaactcc agaaggatct cagggagaag ttgattggct ccagcagtat    2400
gatatggagc gtgaaaggga agagcaagag cttcagcagg cactggctca gagccttcaa    2460
gagcaagagg cttgggaaca gaaagaagat gatgacctca aaagagctac cgagttaagt    2520
cttcaagagt ttaacaactc ctttgtggat gcattgggtt ctgatgagga ctctggaaat    2580
gaggatgttt ttgatatgga gtacacagaa gctgaagctg aggaactgaa agaaatgct    2640
gagacaggaa atctgcctca ttcgtaccgg ctcatcagtg ttgtcagtca cattggtagc    2700
acttcttctt caggtcatta cattagtgat gtatatgaca ttaagaagca agcgtggttt    2760
acttacaatg acctggaggt atcaaaaatc caagaggctg ccgtgcagag tgatcgagat    2820
cggagtggct acatcttctt ttatatgcac aaggagatct ttgatgagct gctggaaaca    2880
gaaaagaact ctcagtcact tagcacgaa gtggggaaga ctacccgtca ggccttgtga    2940
```

<210> SEQ ID NO 54  
<211> LENGTH: 978  
<212> TYPE: PRT  
<213> ORGANISM: Homo sapiens

<400> SEQUENCE: 54

```
Met Ser Pro Leu Lys Ile His Gly Pro Ile Arg Ile Arg Ser Met Gln
1               5                   10                  15

Thr Gly Ile Thr Lys Trp Lys Glu Gly Ser Phe Glu Ile Val Glu Lys
            20                  25                  30

Glu Asn Lys Val Ser Leu Val Val His Tyr Asn Thr Gly Gly Ile Pro
        35                  40                  45

Arg Ile Phe Gln Leu Ser His Asn Ile Lys Asn Val Val Leu Arg Pro
    50                  55                  60

Ser Gly Ala Lys Gln Ser Arg Leu Met Leu Thr Leu Gln Asp Asn Ser
65                  70                  75                  80

Phe Leu Ser Ile Asp Lys Val Pro Ser Lys Asp Ala Glu Glu Met Arg
                85                  90                  95

Leu Phe Leu Asp Ala Val His Gln Asn Arg Leu Pro Ala Ala Met Lys
            100                 105                 110

Pro Ser Gln Gly Ser Gly Ser Phe Gly Ala Ile Leu Gly Ser Arg Thr
        115                 120                 125

Ser Gln Lys Glu Thr Ser Arg Gln Leu Ser Tyr Ser Asp Asn Gln Ala
    130                 135                 140

Ser Ala Lys Arg Gly Ser Leu Glu Thr Lys Asp Asp Ile Pro Phe Arg
145                 150                 155                 160

Lys Val Leu Gly Asn Pro Gly Arg Gly Ser Ile Lys Thr Val Ala Gly
                165                 170                 175

Ser Gly Ile Ala Arg Thr Ile Pro Ser Leu Thr Ser Thr Ser Thr Pro
            180                 185                 190

Leu Arg Ser Gly Leu Leu Glu Asn Arg Thr Glu Lys Arg Lys Arg Met
        195                 200                 205

Ile Ser Thr Gly Ser Glu Leu Asn Glu Asp Tyr Pro Lys Glu Asn Asp
```

```
            210                 215                 220
Ser Ser Ser Asn Asn Lys Ala Met Thr Asp Pro Ser Arg Lys Tyr Leu
225                 230                 235                 240

Thr Ser Ser Arg Glu Lys Gln Leu Ser Leu Lys Gln Ser Glu Glu Asn
                245                 250                 255

Arg Thr Ser Gly Leu Leu Pro Leu Gln Ser Ser Phe Tyr Gly Ser
            260                 265                 270

Arg Ala Gly Ser Lys Glu His Ser Ser Gly Gly Thr Asn Leu Asp Arg
                275                 280                 285

Thr Asn Val Ser Ser Gln Thr Pro Ser Ala Lys Arg Ser Leu Gly Phe
            290                 295                 300

Leu Pro Gln Pro Val Pro Leu Ser Val Lys Lys Leu Arg Cys Asn Gln
305                 310                 315                 320

Asp Tyr Thr Gly Trp Asn Lys Pro Arg Val Pro Leu Ser Ser His Gln
                325                 330                 335

Gln Gln Gln Leu Gln Gly Phe Ser Asn Leu Gly Asn Thr Cys Tyr Met
            340                 345                 350

Asn Ala Ile Leu Gln Ser Leu Phe Ser Leu Gln Ser Phe Ala Asn Asp
                355                 360                 365

Leu Leu Lys Gln Gly Ile Pro Trp Lys Lys Ile Pro Leu Asn Ala Leu
370                 375                 380

Ile Arg Arg Phe Ala His Leu Leu Val Lys Lys Asp Ile Cys Asn Ser
385                 390                 395                 400

Glu Thr Lys Lys Asp Leu Leu Lys Lys Val Lys Asn Ala Ile Ser Ala
                405                 410                 415

Thr Ala Glu Arg Phe Ser Gly Tyr Met Gln Asn Asp Ala His Glu Phe
                420                 425                 430

Leu Ser Gln Cys Leu Asp Gln Leu Lys Glu Asp Met Glu Lys Leu Asn
            435                 440                 445

Lys Thr Trp Lys Thr Glu Pro Val Ser Gly Glu Glu Asn Ser Pro Asp
450                 455                 460

Ile Ser Ala Thr Arg Ala Tyr Thr Cys Pro Val Ile Thr Asn Leu Glu
465                 470                 475                 480

Phe Glu Val Gln His Ser Ile Ile Cys Lys Ala Cys Gly Glu Ile Ile
                485                 490                 495

Pro Lys Arg Glu Gln Phe Asn Asp Leu Ser Ile Asp Leu Pro Arg Arg
                500                 505                 510

Lys Lys Pro Leu Pro Pro Arg Ser Ile Gln Asp Ser Leu Asp Leu Phe
            515                 520                 525

Phe Arg Ala Glu Glu Leu Glu Tyr Ser Cys Glu Lys Cys Gly Gly Lys
530                 535                 540

Cys Ala Leu Val Arg His Lys Phe Asn Arg Leu Pro Arg Val Leu Ile
545                 550                 555                 560

Leu His Leu Lys Arg Tyr Ser Phe Asn Val Ala Leu Ser Leu Asn Asn
                565                 570                 575

Lys Ile Gly Gln Gln Val Ile Ile Pro Arg Tyr Leu Thr Leu Ser Ser
                580                 585                 590

His Cys Thr Glu Asn Thr Lys Pro Pro Phe Thr Leu Gly Trp Ser Ala
                595                 600                 605

His Met Ala Ile Ser Arg Pro Leu Lys Ala Ser Gln Met Val Asn Ser
            610                 615                 620

Cys Ile Thr Ser Pro Ser Thr Pro Ser Lys Lys Phe Thr Phe Lys Ser
625                 630                 635                 640
```

```
Lys Ser Ser Leu Ala Leu Cys Leu Asp Ser Asp Ser Glu Asp Glu Leu
                645                 650                 655

Lys Arg Ser Val Ala Leu Ser Gln Arg Leu Cys Glu Met Leu Gly Asn
            660                 665                 670

Glu Gln Gln Gln Glu Asp Leu Glu Lys Asp Ser Lys Leu Cys Pro Ile
        675                 680                 685

Glu Pro Asp Lys Ser Glu Leu Glu Asn Ser Gly Phe Asp Arg Met Ser
    690                 695                 700

Glu Glu Glu Leu Leu Ala Ala Val Leu Glu Ile Ser Lys Arg Asp Ala
705                 710                 715                 720

Ser Pro Ser Leu Ser His Glu Asp Asp Lys Pro Thr Ser Ser Pro
                725                 730                 735

Asp Thr Gly Phe Ala Glu Asp Ile Gln Glu Met Pro Glu Asn Pro
                740                 745                 750

Asp Thr Met Glu Thr Glu Lys Pro Lys Thr Ile Thr Glu Leu Asp Pro
            755                 760                 765

Ala Ser Phe Thr Glu Ile Thr Lys Asp Cys Asp Glu Asn Lys Glu Asn
770                 775                 780

Lys Thr Pro Glu Gly Ser Gln Gly Glu Val Asp Trp Leu Gln Gln Tyr
785                 790                 795                 800

Asp Met Glu Arg Glu Arg Glu Glu Gln Glu Leu Gln Gln Ala Leu Ala
                805                 810                 815

Gln Ser Leu Gln Glu Gln Glu Ala Trp Glu Gln Lys Glu Asp Asp Asp
            820                 825                 830

Leu Lys Arg Ala Thr Glu Leu Ser Leu Gln Glu Phe Asn Asn Ser Phe
        835                 840                 845

Val Asp Ala Leu Gly Ser Asp Glu Asp Ser Gly Asn Glu Asp Val Phe
    850                 855                 860

Asp Met Glu Tyr Thr Glu Ala Glu Ala Glu Glu Leu Lys Arg Asn Ala
865                 870                 875                 880

Glu Thr Gly Asn Leu Pro His Ser Tyr Arg Leu Ile Ser Val Val Ser
                885                 890                 895

His Ile Gly Ser Thr Ser Ser Ser Gly His Tyr Ile Ser Asp Val Tyr
            900                 905                 910

Asp Ile Lys Lys Gln Ala Trp Phe Thr Tyr Asn Asp Leu Glu Val Ser
        915                 920                 925

Lys Ile Gln Glu Ala Ala Val Gln Ser Asp Arg Asp Arg Ser Gly Tyr
    930                 935                 940

Ile Phe Phe Tyr Met His Lys Glu Ile Phe Asp Glu Leu Leu Glu Thr
945                 950                 955                 960

Glu Lys Asn Ser Gln Ser Leu Ser Thr Glu Val Gly Lys Thr Thr Arg
                965                 970                 975

Gln Ala

<210> SEQ ID NO 55
<211> LENGTH: 3015
<212> TYPE: DNA
<213> ORGANISM: Homo sapiens

<400> SEQUENCE: 55
atggacaaga tcctggaggg ccttgtgagt tcctcgcatc ccctgcccct caagcgggtg      60
attgtgcgga aggtggtgga atcggcggag cactggctag acgaggcgca gtgcgaggcc     120
atgtttgacc tgacgacccg gctcatcctg gagggccagg acccttttcca gcggcaggtg    180
```

```
gggcaccagg tgctggaggc ctacgcacga taccaccggc cagagttcga gtccttcttc      240
aacaagacct tcgtgttggg cctccttcat cagggctacc actctctgga caggaaggat      300
gtagccatcc tggactacat tcacaacggc ctgaagctga ttatgagctg tccgtcggtg      360
ctggatctct ttagcctcct gcaggtagag gtgttacgga tggtgtgtga gaggccggag      420
ccgcagctct gtgcccgact gagcgacctt ctgaccgact tgtgcaatg catccccaag       480 gggaaattgt ccatcacgtt ctgtcaacag ctggttcgaa cgataggcca tttccagtgc      540
gtgtccaccc aggaaagaga gctgcgggaa tatgtctccc aggtgacaaa agtgagtaac      600
ttgctgcaga acatctggaa ggccgagcct gccacactac tgccttccct gcaagaagtt      660
tttgcaagca tctcttccac agatgcatca tttgaacctt ctgtagcatt ggcaagcctt      720
gtgcagcata ttcctcttca gatgattaca gttctcatca ggagccttac tacggatcca      780
aatgtaaaag atgcaagtat gacccaagcc ctttgcagaa tgattgactg ctatcctgg      840 ccattggctc agcatgtgga tacatgggta attgcactcc tgaaaggact ggcagctgtc      900
cagaagttta ctattttgat agatgttact ttgctgaaaa tagaactggt ttttaatcga      960
cttttggttc ctcttgtgag acctggtgct cttgcagttc tttctcacat gctgcttagc      1020
tttcagcatt ctccagaggc gttccatttg attgttcctc atgtggttaa tttggttcat      1080
tctttcaaaa atgatggtct gccttcaagt acagccttct tagtacaatt aacagaattg      1140
atacactgta tgatgtatca ttattctgga tttccagatc tctatgaacc tattctggag      1200
gcaataaagg attttcctaa gcccagtgaa gagaagatta agttaattct caatcaaagt      1260
gcctggactt ctcaatccaa ttctttggcg tcttgcttgt ctagactttc tggaaaatct      1320
gaaactggga aaactggtct tattaaccta ggaaatacat gttatatgaa cagtgttata      1380
caagccttgt ttatggccac agatttcagg agacaagtat tatctttaaa tctaaatggg      1440
tgcaattcat taatgaaaaa attacagcat ctttttgcct ttctggccca tacacagagg      1500
gaagcatacg cacctcggat attctttgag gcttccagac ctccatggtt tactcccaga      1560
tcacagcaag actgttctga atacctcaga tttctccttg acaggctcca tgaagaagaa      1620
aagatcttga agttcaggc ctcacacaag ccttctgaaa ttctggaatg cagtgaaact       1680 tcttttacagg aagtagctag taaagcagca gtactaacag agacccctcg tacaagtgac      1740
ggtgagaaga ctttaataga aaaaatgttt ggaggaaaac tacgaactca catacgttgt      1800
ttgaactgca ggagtacctc acaaaaagtg gaagccttta cagatctttc gcttgccttt      1860
tgtccttcct cttctttgga aaacatgtct gtccaagatc cagcatcatc acccagtata      1920
caagatggtg gtctaatgca agcctctgta cccggtcctt cagaagaacc agtagtttat      1980
aatccaacaa cagctgcctt catctgtgac tcacttgtga atgaaaaaac cataggcagt      2040
cctcctaatg agttttactg ttctgaaaac acttctgtcc ctaacgaatc taacaagatt      2100
cttgttaata aagatgtacc tcagaaacca ggaggtgaaa ccacaccttc agtaactgac      2160
ttactaaatt attttttggc tccagagatt cttactggtg ataaccaata ttattgtgaa      2220
aactgtgcct ctctgcaaaa tgctgagaaa actatgcaaa tcacggagga acctgaatac      2280
cttattctta ctctcctgag attttcatat gatcagaagt atcatgtgag aaggaaaatt      2340
ttagacaatg tatcactgcc actggttttg gagttgccag ttaaaagaat tacttctttc      2400
tcttcattgt cagaaagttg gtctgtagat gttgacttca ctgatcttag tgagaacctt      2460
gctaaaaaat taaagccttc agggactgat gaagcttcct gcacaaaatt ggtgccctat      2520
```

-continued

```
ctattaagtt ccgttgtggt tcactctggt atatcctctg aaagtgggca ttactattct     2580
tatgccagaa atatcacaag tacagactct tcatatcaga tgtaccacca gtctgaggct     2640
ctggcattag catcctccca gagtcattta ctagggagag atagtcccag tgcagttttt     2700
gaacaggatt tggaaaataa ggaaatgtca aaagaatggt ttttatttaa tgacagtaga     2760
gtgacattta cttcatttca gtcagtccag aaaattacga gcaggtttcc aaaggacaca     2820
gcttatgtgc ttttgtataa aaacagcat agtactaatg gtttaagtgg taataaccca     2880
accagtggac tctggataaa tggagaccca cctctacaga aagaacttat ggatgctata     2940
acaaaagaca ataaactata tttacaggta agttggaaat acaagcttta tttgttgaaa     3000
atattaaaca attga                                                       3015
```

<210> SEQ ID NO 56
<211> LENGTH: 1004
<212> TYPE: PRT
<213> ORGANISM: Homo sapiens

<400> SEQUENCE: 56

```
Met Asp Lys Ile Leu Glu Gly Leu Val Ser Ser His Pro Leu Pro
1               5                   10                  15

Leu Lys Arg Val Ile Arg Lys Val Val Glu Ser Ala Glu His Trp
                20                  25                  30

Leu Asp Glu Ala Gln Cys Glu Ala Met Phe Asp Leu Thr Thr Arg Leu
                35                  40                  45

Ile Leu Glu Gly Gln Asp Pro Phe Gln Arg Gln Val Gly His Gln Val
        50                  55                  60

Leu Glu Ala Tyr Ala Arg Tyr His Arg Pro Glu Phe Glu Ser Phe Phe
65              70                  75                  80

Asn Lys Thr Phe Val Leu Gly Leu Leu His Gln Gly Tyr His Ser Leu
                85                  90                  95

Asp Arg Lys Asp Val Ala Ile Leu Asp Tyr Ile His Asn Gly Leu Lys
                100                 105                 110

Leu Ile Met Ser Cys Pro Ser Val Leu Asp Leu Phe Ser Leu Leu Gln
                115                 120                 125

Val Glu Val Leu Arg Met Val Cys Glu Arg Pro Glu Pro Gln Leu Cys
        130                 135                 140

Ala Arg Leu Ser Asp Leu Leu Thr Asp Phe Val Gln Cys Ile Pro Lys
145                 150                 155                 160

Gly Lys Leu Ser Ile Thr Phe Cys Gln Gln Leu Val Arg Thr Ile Gly
                165                 170                 175

His Phe Gln Cys Val Ser Thr Gln Glu Arg Glu Leu Arg Glu Tyr Val
                180                 185                 190

Ser Gln Val Thr Lys Val Ser Asn Leu Leu Gln Asn Ile Trp Lys Ala
        195                 200                 205

Glu Pro Ala Thr Leu Leu Pro Ser Leu Gln Glu Val Phe Ala Ser Ile
        210                 215                 220

Ser Ser Thr Asp Ala Ser Phe Glu Pro Ser Val Ala Leu Ala Ser Leu
225                 230                 235                 240

Val Gln His Ile Pro Leu Gln Met Ile Thr Val Leu Ile Arg Ser Leu
                245                 250                 255

Thr Thr Asp Pro Asn Val Lys Asp Ala Ser Met Thr Gln Ala Leu Cys
                260                 265                 270

Arg Met Ile Asp Trp Leu Ser Trp Pro Leu Ala Gln His Val Asp Thr
                275                 280                 285
```

-continued

```
Trp Val Ile Ala Leu Leu Lys Gly Leu Ala Val Gln Lys Phe Thr
    290             295             300
Ile Leu Ile Asp Val Thr Leu Leu Lys Ile Glu Leu Val Phe Asn Arg
305             310             315             320
Leu Trp Phe Pro Leu Val Arg Pro Gly Ala Leu Ala Val Leu Ser His
                325             330             335
Met Leu Leu Ser Phe Gln His Ser Pro Glu Ala Phe His Leu Ile Val
            340             345             350
Pro His Val Val Asn Leu Val His Ser Phe Lys Asn Asp Gly Leu Pro
        355             360             365
Ser Ser Thr Ala Phe Leu Val Gln Leu Thr Glu Leu Ile His Cys Met
    370             375             380
Met Tyr His Tyr Ser Gly Phe Pro Asp Leu Tyr Glu Pro Ile Leu Glu
385             390             395             400
Ala Ile Lys Asp Phe Pro Lys Pro Ser Glu Glu Lys Ile Lys Leu Ile
                405             410             415
Leu Asn Gln Ser Ala Trp Thr Ser Gln Ser Asn Ser Leu Ala Ser Cys
            420             425             430
Leu Ser Arg Leu Ser Gly Lys Ser Glu Thr Gly Lys Thr Gly Leu Ile
        435             440             445
Asn Leu Gly Asn Thr Cys Tyr Met Asn Ser Val Ile Gln Ala Leu Phe
    450             455             460
Met Ala Thr Asp Phe Arg Arg Gln Val Leu Ser Leu Asn Leu Asn Gly
465             470             475             480
Cys Asn Ser Leu Met Lys Lys Leu Gln His Leu Phe Ala Phe Leu Ala
                485             490             495
His Thr Gln Arg Glu Ala Tyr Ala Pro Arg Ile Phe Phe Glu Ala Ser
            500             505             510
Arg Pro Pro Trp Phe Thr Pro Arg Ser Gln Gln Asp Cys Ser Glu Tyr
        515             520             525
Leu Arg Phe Leu Leu Asp Arg Leu His Glu Glu Lys Ile Leu Lys
    530             535             540
Val Gln Ala Ser His Lys Pro Ser Glu Ile Leu Glu Cys Ser Glu Thr
545             550             555             560
Ser Leu Gln Glu Val Ala Ser Lys Ala Ala Val Leu Thr Glu Thr Pro
                565             570             575
Arg Thr Ser Asp Gly Glu Lys Thr Leu Ile Glu Lys Met Phe Gly Gly
            580             585             590
Lys Leu Arg Thr His Ile Arg Cys Leu Asn Cys Arg Ser Thr Ser Gln
        595             600             605
Lys Val Glu Ala Phe Thr Asp Leu Ser Leu Ala Phe Cys Pro Ser Ser
    610             615             620
Ser Leu Glu Asn Met Ser Val Gln Asp Pro Ala Ser Ser Pro Ser Ile
625             630             635             640
Gln Asp Gly Gly Leu Met Gln Ala Ser Val Pro Gly Pro Ser Glu Glu
                645             650             655
Pro Val Val Tyr Asn Pro Thr Thr Ala Ala Phe Ile Cys Asp Ser Leu
            660             665             670
Val Asn Glu Lys Thr Ile Gly Ser Pro Pro Asn Glu Phe Tyr Cys Ser
        675             680             685
Glu Asn Thr Ser Val Pro Asn Glu Ser Asn Lys Ile Leu Val Asn Lys
    690             695             700
```

Asp Val Pro Gln Lys Pro Gly Gly Glu Thr Thr Pro Ser Val Thr Asp
705                 710                 715                 720

Leu Leu Asn Tyr Phe Leu Ala Pro Glu Ile Leu Thr Gly Asp Asn Gln
            725                 730                 735

Tyr Tyr Cys Glu Asn Cys Ala Ser Leu Gln Asn Ala Glu Lys Thr Met
        740                 745                 750

Gln Ile Thr Glu Glu Pro Glu Tyr Leu Ile Leu Thr Leu Leu Arg Phe
    755                 760                 765

Ser Tyr Asp Gln Lys Tyr His Val Arg Arg Lys Ile Leu Asp Asn Val
770                 775                 780

Ser Leu Pro Leu Val Leu Glu Leu Pro Val Lys Arg Ile Thr Ser Phe
785                 790                 795                 800

Ser Ser Leu Ser Glu Ser Trp Ser Val Asp Val Asp Phe Thr Asp Leu
                805                 810                 815

Ser Glu Asn Leu Ala Lys Lys Leu Lys Pro Ser Gly Thr Asp Glu Ala
            820                 825                 830

Ser Cys Thr Lys Leu Val Pro Tyr Leu Leu Ser Val Val His
        835                 840                 845

Ser Gly Ile Ser Ser Glu Ser Gly His Tyr Tyr Ser Tyr Ala Arg Asn
850                 855                 860

Ile Thr Ser Thr Asp Ser Ser Tyr Gln Met Tyr His Gln Ser Glu Ala
865                 870                 875                 880

Leu Ala Leu Ala Ser Ser Gln Ser His Leu Leu Gly Arg Asp Ser Pro
                885                 890                 895

Ser Ala Val Phe Glu Gln Asp Leu Glu Asn Lys Glu Met Ser Lys Glu
            900                 905                 910

Trp Phe Leu Phe Asn Asp Ser Arg Val Thr Phe Thr Ser Phe Gln Ser
        915                 920                 925

Val Gln Lys Ile Thr Ser Arg Phe Pro Lys Asp Thr Ala Tyr Val Leu
    930                 935                 940

Leu Tyr Lys Lys Gln His Ser Thr Asn Gly Leu Ser Gly Asn Asn Pro
945                 950                 955                 960

Thr Ser Gly Leu Trp Ile Asn Gly Asp Pro Pro Leu Gln Lys Glu Leu
                965                 970                 975

Met Asp Ala Ile Thr Lys Asp Asn Lys Leu Tyr Leu Gln Val Ser Trp
            980                 985                 990

Lys Tyr Lys Leu Tyr Leu Leu Lys Ile Leu Asn Asn
        995                 1000

<210> SEQ ID NO 57
<211> LENGTH: 1698
<212> TYPE: DNA
<213> ORGANISM: Homo sapiens

<400> SEQUENCE: 57
atgtccggcc ggtctaagcg ggagtctcgc ggttccactc gcgggaagcg agagtctgag    60
tcgcggggca gctccggtcg cgtcaagcgg gagcgagatc gggagcggga gcctgaggcg   120
gcgagctccc gggcagccc tgtgcgcgtg aagcgggagt tcgagccggc gagcgcgcgc   180
gaggccccgg cttctgttgt cccgtttgtg cgggtgaagc gggagcgcga ggtcgatgag   240
gactcggagc tgagcgggga ggtgcgagca agaatggcc gagtggattc tgaggaccgg   300
aggagccgcc actgcccgta cctggacacc attaacagga gtgtgctgga ctttgacttt   360
gagaaactgt gttctatctc cctctcacac atcaatgctt atgcctgtct ggtgtgtggc   420

```
aagtactttc aaggccgggg tttgaagtct cacgcctaca ttcacagtgt ccagtttagc    480
caccatgttt tcctcaacct ccacaccctc aagttttact gccttccaga caactatgag    540
atcatcgatt cctcattgga ggatatcacg tatgtgttga agcccacttt cacaaagcag    600
caaattgcaa acttggacaa gcaagccaaa ttgtcccggg catatgatgg taccacttac    660
ctgccgggta ttgtgggact gaataacata aaggccaatg attatgccaa cgctgtcctt    720
caggctctat ctaatgttcc tcctctccgg aactactttc tggaagaaga caattataag    780
aacatcaaac gtcctccagg ggatatcatg ttcttgttgg tccagcgttt tggagagctg    840
atgagaaagc tctggaaccc tcgaaatttc aaggcacatg tgtctcccca tgagatgctt    900
caggcagttg tactttgcag taagaagact tttcagatca ccaaacaagg agatggcgtt    960
gactttctgt cttggtttct gaatgctctg cactcagctc tggggggcac aaagaagaaa   1020
aagaagacta ttgtgactga tgttttccag gggtccatga ggatcttcac taaaaagctt   1080
ccccatcctg atctgccagc agaagaaaaa gagcagttgc tccataatga cgagtaccag   1140
gagacaatgg tggagtccac ttttatgtac ctgacgctgg accttcctac tgcccccctc   1200
tacaaggacg agaaggagca gctcatcatt ccccaagtgc cactcttcaa catcctggct   1260
aagttcaatg gcatcactga aggaatatat aagacttaca aggagaactt tctgaagcgc   1320
ttccagctta ccaagttgcc tccatatcta atcttttgta tcaagagatt cactaagaac   1380
aacttctttg ttgagaagaa tccaactatt gtcaatttcc ctattacaaa tgtggatctg   1440
agagaatact tgtctgaaga agtacaagca gtacacaaga ataccaccta tgacctcatt   1500
gccaacatcg tgcatgacgg caagccctcc gagggctcct accggatcca cgtgcttcat   1560
catgggacag gcaaatggta tgaattacaa gacctccagg tgactgacat ccttccccag   1620
atgatcacac tgtcagaggc ttacattcag atttggaaga ggcgagataa tgatgaaacc   1680
aaccagcagg gggcttga                                                 1698
```

<210> SEQ ID NO 58
<211> LENGTH: 565
<212> TYPE: PRT
<213> ORGANISM: Homo sapiens

<400> SEQUENCE: 58

```
Met Ser Gly Arg Ser Lys Arg Glu Ser Arg Gly Ser Thr Arg Gly Lys
1               5                   10                  15

Arg Glu Ser Glu Ser Arg Gly Ser Ser Gly Arg Val Lys Arg Glu Arg
            20                  25                  30

Asp Arg Glu Arg Glu Pro Glu Ala Ala Ser Ser Arg Gly Ser Pro Val
        35                  40                  45

Arg Val Lys Arg Glu Phe Glu Pro Ala Ser Ala Arg Glu Ala Pro Ala
    50                  55                  60

Ser Val Val Pro Phe Val Arg Val Lys Arg Glu Arg Glu Val Asp Glu
65                  70                  75                  80

Asp Ser Glu Pro Glu Arg Glu Val Arg Ala Lys Asn Gly Arg Val Asp
                85                  90                  95

Ser Glu Asp Arg Arg Ser Arg His Cys Pro Tyr Leu Asp Thr Ile Asn
            100                 105                 110

Arg Ser Val Leu Asp Phe Asp Phe Glu Lys Leu Cys Ser Ile Ser Leu
        115                 120                 125

Ser His Ile Asn Ala Tyr Ala Cys Leu Val Cys Gly Lys Tyr Phe Gln
    130                 135                 140
```

-continued

```
Gly Arg Gly Leu Lys Ser His Ala Tyr Ile His Ser Val Gln Phe Ser
145                 150                 155                 160

His His Val Phe Leu Asn Leu His Thr Leu Lys Phe Tyr Cys Leu Pro
                165                 170                 175

Asp Asn Tyr Glu Ile Ile Asp Ser Ser Leu Glu Asp Ile Thr Tyr Val
            180                 185                 190

Leu Lys Pro Thr Phe Thr Lys Gln Gln Ile Ala Asn Leu Asp Lys Gln
        195                 200                 205

Ala Lys Leu Ser Arg Ala Tyr Asp Gly Thr Thr Tyr Leu Pro Gly Ile
210                 215                 220

Val Gly Leu Asn Asn Ile Lys Ala Asn Asp Tyr Ala Asn Ala Val Leu
225                 230                 235                 240

Gln Ala Leu Ser Asn Val Pro Pro Leu Arg Asn Tyr Phe Leu Glu Glu
                245                 250                 255

Asp Asn Tyr Lys Asn Ile Lys Arg Pro Pro Gly Asp Ile Met Phe Leu
            260                 265                 270

Leu Val Gln Arg Phe Gly Glu Leu Met Arg Lys Leu Trp Asn Pro Arg
        275                 280                 285

Asn Phe Lys Ala His Val Ser Pro His Glu Met Leu Gln Ala Val Val
290                 295                 300

Leu Cys Ser Lys Lys Thr Phe Gln Ile Thr Lys Gln Gly Asp Gly Val
305                 310                 315                 320

Asp Phe Leu Ser Trp Phe Leu Asn Ala Leu His Ser Ala Leu Gly Gly
                325                 330                 335

Thr Lys Lys Lys Lys Thr Ile Val Thr Asp Val Phe Gln Gly Ser
            340                 345                 350

Met Arg Ile Phe Thr Lys Lys Leu Pro His Pro Asp Leu Pro Ala Glu
        355                 360                 365

Glu Lys Glu Gln Leu Leu His Asn Asp Glu Tyr Gln Glu Thr Met Val
370                 375                 380

Glu Ser Thr Phe Met Tyr Leu Thr Leu Asp Leu Pro Thr Ala Pro Leu
385                 390                 395                 400

Tyr Lys Asp Glu Lys Glu Gln Leu Ile Ile Pro Gln Val Pro Leu Phe
                405                 410                 415

Asn Ile Leu Ala Lys Phe Asn Gly Ile Thr Glu Lys Glu Tyr Lys Thr
            420                 425                 430

Tyr Lys Glu Asn Phe Leu Lys Arg Phe Gln Leu Thr Lys Leu Pro Pro
        435                 440                 445

Tyr Leu Ile Phe Cys Ile Lys Arg Phe Thr Lys Asn Asn Phe Phe Val
450                 455                 460

Glu Lys Asn Pro Thr Ile Val Asn Phe Pro Ile Thr Asn Val Asp Leu
465                 470                 475                 480

Arg Glu Tyr Leu Ser Glu Glu Val Gln Ala Val His Lys Asn Thr Thr
                485                 490                 495

Tyr Asp Leu Ile Ala Asn Ile Val His Asp Gly Lys Pro Ser Glu Gly
            500                 505                 510

Ser Tyr Arg Ile His Val Leu His His Gly Thr Gly Lys Trp Tyr Glu
        515                 520                 525

Leu Gln Asp Leu Gln Val Thr Asp Ile Leu Pro Gln Met Ile Thr Leu
530                 535                 540

Ser Glu Ala Tyr Ile Gln Ile Trp Lys Arg Arg Asp Asn Asp Glu Thr
545                 550                 555                 560

Asn Gln Gln Gly Ala
```

<210> SEQ ID NO 59
<211> LENGTH: 2139
<212> TYPE: DNA
<213> ORGANISM: Homo sapiens

<400> SEQUENCE: 59

```
atgctagcaa tggatacgtg caaacatgtt gggcagctgc agcttgctca agaccattcc      60
agcctcaacc ctcagaaatg gcactgtgtg gactgcaaca cgaccgagtc catttgggct     120
tgccttagct gctcccatgt tgcctgtgga agatatattg aagagcatgc actcaagcac     180
tttcaagaaa gcagtcatcc tgttgcattg gaggtgaatg agatgtacgt tttttgttac     240
ctttgtgatg attatgttct gaatgataac gcaactggag acctgaagtt actacgacgt     300
acattaagtg ccatcaaaag tcaaaattat cactgcacaa ctcgtagtgg gaggttttta     360
cggtccatgg gtacaggtga tgattcttat ttcttacatg acggtgccca atctctgctt     420
caaagtgaag atcaactgta tactgctctt tggcacagga aaggatact aatgggtaaa      480
atctttcgaa catggtttga caatcaccc attggaagaa aaagcaaga gaaccattt       540
caggaaaaaa tagtagtaaa agagaagta agaaaagac ggcaggaatt ggagtatcaa      600
gttaaagcag aattggaaag tatgcctcca agaaagagtt tacgtttaca agggctcgct     660
cagtcgacca ataagaaat agtttctgtt caggtgccag cacaaacgcc agcatcacca     720
gcaaaagata agtactctc tacctcagaa atgaaatat ctcaaaaagt cagtgactcc      780
tcagttaaac gaaggccaat agtaactcct ggtgtaacag gattgagaaa tttgggaaat     840
acttgctata tgaattctgt tcttcaggtg ttgagtcatt tacttatttt tcgacaatgt     900
tttttaaagc ttgatctgaa ccaatggctg gctatgactg ctagcgagaa gacaagatct     960
tgtaagcatc caccagtcac agatacagta gtatatcaaa tgaatgaatg tcaggaaaaa    1020
gatacaggtt ttgtttgctc cagacaatca agtctgtcat caggactaag tggtggagca    1080
tcaaaaggta gaaagatgga acttattcag ccaaaggagc caacttcaca gtacatttct    1140
ctttgtcatg aattgcatac tttgttccaa gtcatgtggt ctggaaagtg ggcgttggtc    1200
tcaccatttg ctatgctaca ctcagtgtgg agactcattc ctgcctttcg tggttacgcc    1260
caacaagacg ctcaggaatt tctttgtgaa cttttagata aaatacaacg tgaattagag    1320
acaactggta ccagtttacc agctcttatc cccacttctc aaaggaaact catcaaacaa    1380
gttctgaatg ttgtaaataa cattttttcat ggacaacttc ttagtcaggt tacatgtctt    1440
gcatgtgaca acaaatcaaa taccatagaa cctttctggg acttgtcatt ggagtttcca    1500
gaaaggtatc aatgcagtgg aaaagatatt gcttcccagc catgtctggt tactgaaatg    1560
ttggccaaat ttacagaaac tgaagcttta gaaggaaaaa tctacgtatg tgaccagtgt    1620
aactcaaagc gtagaaggtt ttcctccaaa ccagttgtac tcacagaagc ccagaaacaa    1680
cttatgatat gccacctacc tcaggttctc agactgcacc tcaaacgatt caggtggtca    1740
ggacgtaata accgagagaa gattggtgtt catgttggct ttgaggaaat cttaaacatg    1800
gagccctatt gctgcaggga gaccctgaaa tccctcagac cagaatgctt tatctatgac    1860
ttgtccgcgg tggtgatgca ccatgggaaa ggatttggct cagggcacta cactgcctac    1920
tgctataatt ctgaaggagg gttctgggta cactgcaatg attccaaact aagcatgtgc    1980
actatggatg aagtatgcaa ggctcaagct tatatcttgt tttataccca acgagttact    2040
gagaatggac attctaaact tttgcctcca gagctcctgt tggggagcca acatcccaat    2100
```
gaagacgctg atacctcgtc taatgaaatc cttagctga　　　　　　　　　　　　　　2139

<210> SEQ ID NO 60
<211> LENGTH: 712
<212> TYPE: PRT
<213> ORGANISM: Homo sapiens

<400> SEQUENCE: 60

```
Met Leu Ala Met Asp Thr Cys Lys His Val Gly Gln Leu Gln Leu Ala
1               5                   10                  15

Gln Asp His Ser Ser Leu Asn Pro Gln Lys Trp His Cys Val Asp Cys
            20                  25                  30

Asn Thr Thr Glu Ser Ile Trp Ala Cys Leu Ser Cys Ser His Val Ala
        35                  40                  45

Cys Gly Arg Tyr Ile Glu Glu His Ala Leu Lys His Phe Gln Glu Ser
    50                  55                  60

Ser His Pro Val Ala Leu Glu Val Asn Glu Met Tyr Val Phe Cys Tyr
65                  70                  75                  80

Leu Cys Asp Asp Tyr Val Leu Asn Asp Asn Ala Thr Gly Asp Leu Lys
                85                  90                  95

Leu Leu Arg Arg Thr Leu Ser Ala Ile Lys Ser Gln Asn Tyr His Cys
            100                 105                 110

Thr Thr Arg Ser Gly Arg Phe Leu Arg Ser Met Gly Thr Gly Asp Asp
        115                 120                 125

Ser Tyr Phe Leu His Asp Gly Ala Gln Ser Leu Leu Gln Ser Glu Asp
    130                 135                 140

Gln Leu Tyr Thr Ala Leu Trp His Arg Arg Ile Leu Met Gly Lys
145                 150                 155                 160

Ile Phe Arg Thr Trp Phe Glu Gln Ser Pro Ile Gly Arg Lys Lys Gln
                165                 170                 175

Glu Glu Pro Phe Gln Glu Lys Ile Val Val Lys Arg Glu Val Lys Lys
            180                 185                 190

Arg Arg Gln Glu Leu Glu Tyr Gln Val Lys Ala Glu Leu Glu Ser Met
        195                 200                 205

Pro Pro Arg Lys Ser Leu Arg Leu Gln Gly Leu Ala Gln Ser Thr Ile
    210                 215                 220

Ile Glu Ile Val Ser Val Gln Val Pro Ala Gln Thr Pro Ala Ser Pro
225                 230                 235                 240

Ala Lys Asp Lys Val Leu Ser Thr Ser Glu Asn Glu Ile Ser Gln Lys
                245                 250                 255

Val Ser Asp Ser Ser Val Lys Arg Arg Pro Ile Val Thr Pro Gly Val
            260                 265                 270

Thr Gly Leu Arg Asn Leu Gly Asn Thr Cys Tyr Met Asn Ser Val Leu
        275                 280                 285

Gln Val Leu Ser His Leu Leu Ile Phe Arg Gln Cys Phe Leu Lys Leu
    290                 295                 300

Asp Leu Asn Gln Trp Leu Ala Met Thr Ala Ser Glu Lys Thr Arg Ser
305                 310                 315                 320

Cys Lys His Pro Pro Val Thr Asp Thr Val Tyr Gln Met Asn Glu
                325                 330                 335

Cys Gln Glu Lys Asp Thr Gly Phe Val Cys Ser Arg Gln Ser Ser Leu
            340                 345                 350

Ser Ser Gly Leu Ser Gly Gly Ala Ser Lys Gly Arg Lys Met Glu Leu
        355                 360                 365
```

```
Ile Gln Pro Lys Glu Pro Thr Ser Gln Tyr Ile Ser Leu Cys His Glu
    370                 375                 380

Leu His Thr Leu Phe Gln Val Met Trp Ser Gly Lys Trp Ala Leu Val
385                 390                 395                 400

Ser Pro Phe Ala Met Leu His Ser Val Trp Arg Leu Ile Pro Ala Phe
                405                 410                 415

Arg Gly Tyr Ala Gln Gln Asp Ala Gln Glu Phe Leu Cys Glu Leu Leu
            420                 425                 430

Asp Lys Ile Gln Arg Glu Leu Glu Thr Thr Gly Thr Ser Leu Pro Ala
        435                 440                 445

Leu Ile Pro Thr Ser Gln Arg Lys Leu Ile Lys Gln Val Leu Asn Val
    450                 455                 460

Val Asn Asn Ile Phe His Gly Gln Leu Leu Ser Gln Val Thr Cys Leu
465                 470                 475                 480

Ala Cys Asp Asn Lys Ser Asn Thr Ile Glu Pro Phe Trp Asp Leu Ser
                485                 490                 495

Leu Glu Phe Pro Glu Arg Tyr Gln Cys Ser Gly Lys Asp Ile Ala Ser
            500                 505                 510

Gln Pro Cys Leu Val Thr Glu Met Leu Ala Lys Phe Thr Glu Thr Glu
        515                 520                 525

Ala Leu Glu Gly Lys Ile Tyr Val Cys Asp Gln Cys Asn Ser Lys Arg
    530                 535                 540

Arg Arg Phe Ser Ser Lys Pro Val Val Leu Thr Glu Ala Gln Lys Gln
545                 550                 555                 560

Leu Met Ile Cys His Leu Pro Gln Val Leu Arg Leu His Leu Lys Arg
                565                 570                 575

Phe Arg Trp Ser Gly Arg Asn Asn Arg Glu Lys Ile Gly Val His Val
            580                 585                 590

Gly Phe Glu Glu Ile Leu Asn Met Glu Pro Tyr Cys Cys Arg Glu Thr
        595                 600                 605

Leu Lys Ser Leu Arg Pro Glu Cys Phe Ile Tyr Asp Leu Ser Ala Val
    610                 615                 620

Val Met His His Gly Lys Gly Phe Gly Ser Gly His Tyr Thr Ala Tyr
625                 630                 635                 640

Cys Tyr Asn Ser Glu Gly Gly Phe Trp Val His Cys Asn Asp Ser Lys
                645                 650                 655

Leu Ser Met Cys Thr Met Asp Glu Val Cys Lys Ala Gln Ala Tyr Ile
            660                 665                 670

Leu Phe Tyr Thr Gln Arg Val Thr Glu Asn Gly His Ser Lys Leu Leu
        675                 680                 685

Pro Pro Glu Leu Leu Leu Gly Ser Gln His Pro Asn Glu Asp Ala Asp
    690                 695                 700

Thr Ser Ser Asn Glu Ile Leu Ser
705                 710

<210> SEQ ID NO 61
<211> LENGTH: 1101
<212> TYPE: DNA
<213> ORGANISM: Homo sapiens

<400> SEQUENCE: 61
atgactgtcc gaaacatcgc ctccatctgt aatatgggca ccaatgcctc tgctctggaa      60
aaagacattg gtccagagca gtttccaatc aatgaacact atttcggatt ggtcaatttt     120
```

```
ggaaacacat gctactgtaa ctccgtgctt caggcattgt acttctgccg tccattccgg      180
gagaatgtgt tggcatacaa ggcccagcaa aagaagaagg aaaacttgct gacgtgcctg      240
gcggaccttt tccacagcat tgccacacag aagaagaagg ttggcgtcat cccaccaaag      300
aagttcattt caaggctgag aaaagagaat gatctctttg ataactacat gcagcaggat      360
gctcatgaat ttttaaatta tttgctaaac actattgcgg acatccttca ggaggagaag      420
aaacaggaaa aacaaaatgg aaaattaaaa aatggcaaca tgaacgaacc tgcggaaaat      480
aataaaccag aactcacctg ggtccatgag attttcagg gaacgcttac caatgaaact       540
cgatgcttga actgtgaaac tgttagtagc aaagatgaag attttcttga cctttctgtt      600
gatgtggagc agaatacatc cattacccac tgtctaagag acttcagcaa cacagaaaca      660
ctgtgtagtg aacaaaaata ttattgtgaa acatgctgca gcaaacaaga agcccagaaa      720
aggatgaggg taaaaaagct gcccatgatc ttggccctgc acctaaagcg gttcaagtac      780
atggagcagc tgcacagata caccaagctg tcttaccgtg tggtcttccc tctggaactc      840
cggctcttca acacctccag tgatgcagtg aacctggacc gcatgtatga cttggttgcg      900
gtggtcgttc actgtggcag tggtcctaat cgtgggcatt atatcactat tgtgaaaagt      960
cacggcttct ggcttttgtt tgatgatgac attgtagaga aaatagatgc tcaagctatt     1020
gaagaattct atggcctgac gtcagatata tcaaaaaatt cagaatctgg atatatttta     1080
ttctatcagt caagagagta a                                               1101
```

<210> SEQ ID NO 62
<211> LENGTH: 366
<212> TYPE: PRT
<213> ORGANISM: Homo sapiens

<400> SEQUENCE: 62

Met Thr Val Arg Asn Ile Ala Ser Ile Cys Asn Met Gly Thr Asn Ala
1               5                   10                  15

Ser Ala Leu Glu Lys Asp Ile Gly Pro Glu Gln Phe Pro Ile Asn Glu
            20                  25                  30

His Tyr Phe Gly Leu Val Asn Phe Gly Asn Thr Cys Tyr Cys Asn Ser
        35                  40                  45

Val Leu Gln Ala Leu Tyr Phe Cys Arg Pro Phe Arg Glu Asn Val Leu
    50                  55                  60

Ala Tyr Lys Ala Gln Gln Lys Lys Glu Asn Leu Leu Thr Cys Leu
65                  70                  75                  80

Ala Asp Leu Phe His Ser Ile Ala Thr Gln Lys Lys Val Gly Val
                85                  90                  95

Ile Pro Pro Lys Lys Phe Ile Ser Arg Leu Arg Lys Glu Asn Asp Leu
            100                 105                 110

Phe Asp Asn Tyr Met Gln Gln Asp Ala His Glu Phe Leu Asn Tyr Leu
        115                 120                 125

Leu Asn Thr Ile Ala Asp Ile Leu Gln Glu Glu Lys Lys Gln Glu Lys
    130                 135                 140

Gln Asn Gly Lys Leu Lys Asn Gly Asn Met Asn Glu Pro Ala Glu Asn
145                 150                 155                 160

Asn Lys Pro Glu Leu Thr Trp Val His Glu Ile Phe Gln Gly Thr Leu
                165                 170                 175

Thr Asn Glu Thr Arg Cys Leu Asn Cys Glu Thr Val Ser Ser Lys Asp
            180                 185                 190

Glu Asp Phe Leu Asp Leu Ser Val Asp Val Glu Gln Asn Thr Ser Ile

|  | 195 |  |  |  | 200 |  |  |  | 205 |  |  |
|---|---|---|---|---|---|---|---|---|---|---|---|

Thr His Cys Leu Arg Asp Phe Ser Asn Thr Glu Thr Leu Cys Ser Glu
210                 215                 220

Gln Lys Tyr Tyr Cys Glu Thr Cys Ser Lys Gln Glu Ala Gln Lys
225                 230                 235                 240

Arg Met Arg Val Lys Lys Leu Pro Met Ile Leu Ala Leu His Leu Lys
            245                 250                 255

Arg Phe Lys Tyr Met Glu Gln Leu His Arg Tyr Thr Lys Leu Ser Tyr
            260                 265                 270

Arg Val Val Phe Pro Leu Glu Leu Arg Leu Phe Asn Thr Ser Ser Asp
            275                 280                 285

Ala Val Asn Leu Asp Arg Met Tyr Asp Leu Val Ala Val Val His
290                 295                 300

Cys Gly Ser Gly Pro Asn Arg Gly His Tyr Ile Thr Ile Val Lys Ser
305                 310                 315                 320

His Gly Phe Trp Leu Leu Phe Asp Asp Asp Ile Val Glu Lys Ile Asp
            325                 330                 335

Ala Gln Ala Ile Glu Glu Phe Tyr Gly Leu Thr Ser Asp Ile Ser Lys
            340                 345                 350

Asn Ser Glu Ser Gly Tyr Ile Leu Phe Tyr Gln Ser Arg Glu
            355                 360                 365

<210> SEQ ID NO 63
<211> LENGTH: 1923
<212> TYPE: DNA
<213> ORGANISM: Homo sapiens

<400> SEQUENCE: 63

| atggatagat | gcaaacatgt | agggcggtta | cggctcgccc | aggaccactc | catcctgaac | 60 |
|---|---|---|---|---|---|---|
| cctcagaagt | ggtgctgctt | agagtgtgcc | accaccgagt | ccgtgtgggc | ctgcctcaag | 120 |
| tgctcccacg | tggcctgcgg | ccgctatatt | gaggaccacg | ccctgaaaca | ctttgaggag | 180 |
| acgggacacc | cgctagccat | ggaagtccgg | gatctctacg | tgttctgtta | cctgtgcaag | 240 |
| gactacgtgc | tcaatgataa | cccagagggg | gacctgaagc | tgctaagaag | ctccctcctg | 300 |
| gcggtccggg | gccagaaaca | ggacacgccg | gtgagacgtg | ggcggacgct | gcggtccatg | 360 |
| gcttcgggtg | aggacgtggt | cctgccgcag | cgcgctcctc | agggacagcc | gcagatgctc | 420 |
| acggctctgt | ggtaccggcg | tcagcgcctg | ctggccagga | cgctgcggct | gtggttcgag | 480 |
| aagagctccc | ggggccaggc | gaagctggag | cagcggcggc | aggaggaggc | cctggagcgc | 540 |
| aagaaggagg | aggcgcggag | gcggcggcgc | gaggtgaaac | ggcggctgct | ggaggagctg | 600 |
| gccagcaccc | ctccgcgcaa | gagtgcacgg | ctgctcctgc | acacgccccg | cgacgcgggc | 660 |
| ccggctgcct | cgcgccccgc | cgccctccct | acctcacgca | gagtgcccgc | cgccacactc | 720 |
| aagctgcgtc | gccagccggc | catggccccc | ggcgtcacgg | gcctgcgcaa | cctgggcaac | 780 |
| acctgctaca | tgaactccat | cctccaggtg | ctcagccacc | tccagaagtt | ccgagaatgt | 840 |
| ttcctcaacc | ttgacccttc | caaaacggaa | catctgtttc | caaagccac | caacgggaag | 900 |
| actcagcttt | ctggcaagcc | aaccaacagc | tcggccacgg | agctgtcctt | gagaaatgac | 960 |
| agggccgagg | catgcgagcg | ggagggcttc | tgctggaacg | gcagggcctc | cattagtcgg | 1020 |
| agtctggagc | tcatccagaa | caaggagccg | agttcaaagc | acatttccct | gccgtgaa | 1080 |
| ctgcacaccc | tcttccgagt | catgtggtcc | gggaagtggg | ccctagtgtc | gcccttcgcc | 1140 |
| atgctgcact | cagtgtggag | cctgatccct | gccttccgcg | gctacgacca | acaggacgcg | 1200 |

```
caggaatttc tctgcgagct gctgcacaag gtgcagcagg aactcgagtc tgagggcacc   1260
acacgccgga tcctcatccc cttctcccag aggaagctca ccaaacaggt cttaaaggtg   1320
gtgaatacca tatttcatgg gcagctgctc agtcaggtca catgtatatc atgcaattac   1380
aaatccaata ccattgagcc cttttgggac ctatccctgg aattccctga acgctatcac   1440
tgcatagaaa aggggtttgt ccctttgaat caaacagagt gcttgctcac tgagatgctg   1500
gccaaattca cagagacaga ggccctggaa gggagaatct acgcttgtga ccagtgtaac   1560
agcaaacgac gaaaatccaa tcccaaaccc cttgttctga gtgaagctag aaagcagtta   1620
atgatctaca gactacctca ggttctccgg ctgcacctta aaagattcag gtggtctggc   1680
cgtaatcatc gagagaagat tggggtccat gtcgtctttg accaggtatt aaccatggaa   1740
ccttactgct gcaggacat gctctcctct cttgacaaag agacctttgc ctatgatctc   1800
tccgcagtgg tcatgcatca cgggaaaggg tttggctcag acactacac agcctattgc   1860 tacaacacag agggaggtgc gtgcgcttta ctctgtgggg tgggggacac ggaaaggggt   1920
tga                                                                1923
```

<210> SEQ ID NO 64
<211> LENGTH: 640
<212> TYPE: PRT
<213> ORGANISM: Homo sapiens

<400> SEQUENCE: 64

```
Met Asp Arg Cys Lys His Val Gly Arg Leu Arg Leu Ala Gln Asp His
1               5                   10                  15

Ser Ile Leu Asn Pro Gln Lys Trp Cys Cys Leu Glu Cys Ala Thr Thr
            20                  25                  30

Glu Ser Val Trp Ala Cys Leu Lys Cys Ser His Val Ala Cys Gly Arg
        35                  40                  45

Tyr Ile Glu Asp His Ala Leu Lys His Phe Glu Thr Gly His Pro
    50                  55                  60

Leu Ala Met Glu Val Arg Asp Leu Tyr Val Phe Cys Tyr Leu Cys Lys
65                  70                  75                  80

Asp Tyr Val Leu Asn Asp Asn Pro Glu Gly Asp Leu Lys Leu Leu Arg
                85                  90                  95

Ser Ser Leu Leu Ala Val Arg Gly Gln Lys Gln Asp Thr Pro Val Arg
            100                 105                 110

Arg Gly Arg Thr Leu Arg Ser Met Ala Ser Gly Glu Asp Val Val Leu
        115                 120                 125

Pro Gln Arg Ala Pro Gln Gly Gln Pro Gln Met Leu Thr Ala Leu Trp
    130                 135                 140

Tyr Arg Arg Gln Arg Leu Leu Ala Arg Thr Leu Arg Leu Trp Phe Glu
145                 150                 155                 160

Lys Ser Ser Arg Gly Gln Ala Lys Leu Glu Gln Arg Gln Glu Glu
                165                 170                 175

Ala Leu Glu Arg Lys Lys Glu Glu Ala Arg Arg Arg Arg Glu Val
            180                 185                 190

Lys Arg Arg Leu Leu Glu Glu Leu Ala Ser Thr Pro Arg Lys Ser
        195                 200                 205

Ala Arg Leu Leu Leu His Thr Pro Arg Asp Ala Gly Pro Ala Ala Ser
    210                 215                 220

Arg Pro Ala Ala Leu Pro Thr Ser Arg Arg Val Pro Ala Ala Thr Leu
225                 230                 235                 240
```

```
Lys Leu Arg Arg Gln Pro Ala Met Ala Pro Gly Val Thr Gly Leu Arg
                245                 250                 255

Asn Leu Gly Asn Thr Cys Tyr Met Asn Ser Ile Leu Gln Val Leu Ser
            260                 265                 270

His Leu Gln Lys Phe Arg Glu Cys Phe Leu Asn Leu Asp Pro Ser Lys
        275                 280                 285

Thr Glu His Leu Phe Pro Lys Ala Thr Asn Gly Lys Thr Gln Leu Ser
    290                 295                 300

Gly Lys Pro Thr Asn Ser Ser Ala Thr Glu Leu Ser Leu Arg Asn Asp
305                 310                 315                 320

Arg Ala Glu Ala Cys Glu Arg Glu Gly Phe Cys Trp Asn Gly Arg Ala
                325                 330                 335

Ser Ile Ser Arg Ser Leu Glu Leu Ile Gln Asn Lys Glu Pro Ser Ser
            340                 345                 350

Lys His Ile Ser Leu Cys Arg Glu Leu His Thr Leu Phe Arg Val Met
        355                 360                 365

Trp Ser Gly Lys Trp Ala Leu Val Ser Pro Phe Ala Met Leu His Ser
    370                 375                 380

Val Trp Ser Leu Ile Pro Ala Phe Arg Gly Tyr Asp Gln Gln Asp Ala
385                 390                 395                 400

Gln Glu Phe Leu Cys Glu Leu Leu His Lys Val Gln Gln Glu Leu Glu
                405                 410                 415

Ser Glu Gly Thr Thr Arg Arg Ile Leu Ile Pro Phe Ser Gln Arg Lys
            420                 425                 430

Leu Thr Lys Gln Val Leu Lys Val Asn Thr Ile Phe His Gly Gln
        435                 440                 445

Leu Leu Ser Gln Val Thr Cys Ile Ser Cys Asn Tyr Lys Ser Asn Thr
    450                 455                 460

Ile Glu Pro Phe Trp Asp Leu Ser Leu Glu Phe Pro Glu Arg Tyr His
465                 470                 475                 480

Cys Ile Glu Lys Gly Phe Val Pro Leu Asn Gln Thr Glu Cys Leu Leu
                485                 490                 495

Thr Glu Met Leu Ala Lys Phe Thr Glu Thr Glu Ala Leu Glu Gly Arg
            500                 505                 510

Ile Tyr Ala Cys Asp Gln Cys Asn Ser Lys Arg Arg Lys Ser Asn Pro
        515                 520                 525

Lys Pro Leu Val Leu Ser Glu Ala Arg Lys Gln Leu Met Ile Tyr Arg
    530                 535                 540

Leu Pro Gln Val Leu Arg Leu His Leu Lys Arg Phe Arg Trp Ser Gly
545                 550                 555                 560

Arg Asn His Arg Glu Lys Ile Gly Val His Val Val Phe Asp Gln Val
                565                 570                 575

Leu Thr Met Glu Pro Tyr Cys Cys Arg Asp Met Leu Ser Ser Leu Asp
            580                 585                 590

Lys Glu Thr Phe Ala Tyr Asp Leu Ser Ala Val Val Met His His Gly
        595                 600                 605

Lys Gly Phe Gly Ser Gly His Tyr Thr Ala Tyr Cys Tyr Asn Thr Glu
    610                 615                 620

Gly Gly Ala Cys Ala Leu Leu Cys Gly Val Gly Asp Thr Glu Arg Gly
625                 630                 635                 640

<210> SEQ ID NO 65
<211> LENGTH: 657
```

<212> TYPE: DNA
<213> ORGANISM: Homo sapiens

<400> SEQUENCE: 65

```
atggacgggt ccggggagca gcccagaggc ggggggccca ccagctctga gcagatcatg      60
aagacagggg ccttttgct tcagggtttc atccaggatc gagcagggcg aatggggggg      120
gaggcacccg agctggccct ggaccgggtg cctcaggatg cgtccaccaa gaagctgagc     180
gagtgtctca agcgcatcgg ggacgaactg gacagtaaca tggagctgca gaggatgatt    240
gccgccgtgg acacagactc ccccgagag gtcttttttcc gagtggcagc tgacatgttt    300
tctgacggca acttcaactg gggccgggtt gtcgcccttt tctactttgc cagcaaactg    360
gtgctcaagg ccctgtgcac caaggtgccg gaactgatca gaaccatcat gggctggaca    420
ttggacttcc tccgggagcg gctgttgggc tggatccaag accagggtgg ttgggtgaga    480
ctcctcaagc tcctcacccc caccaccgc gccctcacca ccgcccctgc cccaccgtcc    540
ctgccccccg ccactcctct gggacccctgg gccttctgga gcaggtcaca gtggtgccct    600
ctccccatct tcagatcatc agatgtggtc tataatgcgt tttccttacg tgtctga       657
```

<210> SEQ ID NO 66
<211> LENGTH: 218
<212> TYPE: PRT
<213> ORGANISM: Homo sapiens

<400> SEQUENCE: 66

```
Met Asp Gly Ser Gly Glu Gln Pro Arg Gly Gly Pro Thr Ser Ser
1               5                   10                  15

Glu Gln Ile Met Lys Thr Gly Ala Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Val Arg
145                 150                 155                 160

Leu Leu Lys Pro Pro His Pro His His Arg Ala Leu Thr Thr Ala Pro
                165                 170                 175

Ala Pro Pro Ser Leu Pro Pro Ala Thr Pro Leu Gly Pro Trp Ala Phe
            180                 185                 190

Trp Ser Arg Ser Gln Trp Cys Pro Leu Pro Ile Phe Arg Ser Ser Asp
        195                 200                 205

Val Val Tyr Asn Ala Phe Ser Leu Arg Val
    210                 215
```

<210> SEQ ID NO 67

```
<211> LENGTH: 918
<212> TYPE: DNA
<213> ORGANISM: Homo sapiens

<400> SEQUENCE: 67
atgagtgtgg atccagcttg tccccaaagc ttgccttgct ttgaagcatc cgactgtaaa      60
gaatcttcac ctatgcctgt gatttgtggg cctgaagaaa actatccatc cttgcaaatg     120
tcttctgctg agatgcctca cacggagact gtctctcctc ttccctcctc catggatctg     180
cttattcagg acagccctga ttcttccacc agtcccaaag caaacaacc cacttctgca      240
gagaatagtg tcgcaaaaaa ggaagacaag gtcccagtca agaaacagaa gaccagaact     300
gtgttctctt ccacccagct gtgtgtactc aatgatagat tcagagaca gaaatacctc      360
agcctccagc agatgcaaga actctccaac atcctgaacc tcagctacaa acaggtgaag     420
acctggttcc agaaccagag aatgaaatct aagaggtggc agaaaaacaa ctggccgaag     480
aatagcaatg gtgtgacgca gaaggcctca gcacctacct accccagcct ctactcttcc     540
taccaccagg gatgcctggt gaacccgact gggaaccttc aatgtggag caaccagacc      600
tggaacaatt caacctggag caaccagacc cagaacatcc agtcctggag caaccactcc     660
tggaacactc agacctggtg cacccaatcc tggaacaatc aggcctggaa cagtcccttc     720
tataactgtg gagaggaatc tctgcagtcc tgcatgcagt ccagccaaa ttctcctgcc      780
agtgacttgg aggctgcttt ggaagctgct ggggaaggcc ttaatgtaat acagcagacc     840
actaggtatt ttagtactcc acaaaccatg gatttattcc taaactactc catgaacatg     900
caacctgaag acgtgtga                                                   918

<210> SEQ ID NO 68
<211> LENGTH: 305
<212> TYPE: PRT
<213> ORGANISM: Homo sapiens

<400> SEQUENCE: 68

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Trp Pro Lys
145                 150                 155                 160

Asn Ser Asn Gly Val Thr Gln Lys Ala Ser Ala Pro Thr Tyr Pro Ser
                165                 170                 175
```

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300
Val
305

<210> SEQ ID NO 69
<211> LENGTH: 18
<212> TYPE: DNA
<213> ORGANISM: Artificial Sequence
<220> FEATURE:
<223> OTHER INFORMATION: Forward primer for generating deletion mutants
      of Bax (1-219)

<400> SEQUENCE: 69
gaattcgcat ggacgggt                                                 18

<210> SEQ ID NO 70
<211> LENGTH: 19
<212> TYPE: DNA
<213> ORGANISM: Artificial Sequence
<220> FEATURE:
<223> OTHER INFORMATION: Forward primer for generating deletion mutants
      of Bax (220-334)

<400> SEQUENCE: 70
gaattccgat ggagctgca                                                19

<210> SEQ ID NO 71
<211> LENGTH: 20
<212> TYPE: DNA
<213> ORGANISM: Artificial Sequence
<220> FEATURE:
<223> OTHER INFORMATION: Forward primer for generating deletion mutants
      of Bax (335-579)

<400> SEQUENCE: 71
gaattcgcaa actggtgctc                                               20

<210> SEQ ID NO 72
<211> LENGTH: 20
<212> TYPE: DNA
<213> ORGANISM: Artificial Sequence
<220> FEATURE:
<223> OTHER INFORMATION: Reverse primer for generating deletion mutants
      of Bax (1-219)

<400> SEQUENCE: 72
ctcgagcggt tactgtccag                                               20

<210> SEQ ID NO 73
<211> LENGTH: 18
<212> TYPE: DNA
<213> ORGANISM: Artificial Sequence
<220> FEATURE:
<223> OTHER INFORMATION: Reverse primer for generating deletion mutants
      of Bax (220-334)

<400> SEQUENCE: 73
ctcgagccgc tggcaaag                                                 18

<210> SEQ ID NO 74
<211> LENGTH: 18
<212> TYPE: DNA
<213> ORGANISM: Artificial Sequence
<220> FEATURE:
<223> OTHER INFORMATION: Reverse primer for generating deletion mutants
      of Bax (335-579)

<400> SEQUENCE: 74
ctcgagcgtc agcccatc                                                 18

<210> SEQ ID NO 75
<211> LENGTH: 21
<212> TYPE: DNA
<213> ORGANISM: Artificial Sequence
<220> FEATURE:
<223> OTHER INFORMATION: Forward primer for point mutation of USP49
      (C262S)

<400> SEQUENCE: 75
ctgggcaaca ccagctacat g                                             21

<210> SEQ ID NO 76
<211> LENGTH: 21
<212> TYPE: DNA
<213> ORGANISM: Artificial Sequence
<220> FEATURE:
<223> OTHER INFORMATION: Reverse primer for point mutation of USP49
      (C262S)

<400> SEQUENCE: 76
tggagttcat gtagctggtg t                                             21

<210> SEQ ID NO 77
<211> LENGTH: 19
<212> TYPE: DNA
<213> ORGANISM: Artificial Sequence
<220> FEATURE:
<223> OTHER INFORMATION: Forward primer for generating deletion mutants
      of USP49 (1-762)

<400> SEQUENCE: 77
gaattcgatg gatagatgc                                                19

<210> SEQ ID NO 78
<211> LENGTH: 19
<212> TYPE: DNA
<213> ORGANISM: Artificial Sequence
<220> FEATURE:
<223> OTHER INFORMATION: Forward primer for generating deletion mutants
      of USP49 (763-1131)

<400> SEQUENCE: 78
gaattctctg cgcaacctg                                                19

-continued

<210> SEQ ID NO 79
<211> LENGTH: 20
<212> TYPE: DNA
<213> ORGANISM: Artificial Sequence
<220> FEATURE:
<223> OTHER INFORMATION: Forward primer for generating deletion mutants
      of USP49 (1132-2067)

<400> SEQUENCE: 79
tctagaaccc ttcgccatgc                                                 20

<210> SEQ ID NO 80
<211> LENGTH: 18
<212> TYPE: DNA
<213> ORGANISM: Artificial Sequence
<220> FEATURE:
<223> OTHER INFORMATION: Reverse primer for generating deletion mutants
      of USP49 (1-762)

<400> SEQUENCE: 80
ctcgaggccc gtgacgcc                                                   18

<210> SEQ ID NO 81
<211> LENGTH: 18
<212> TYPE: DNA
<213> ORGANISM: Artificial Sequence
<220> FEATURE:
<223> OTHER INFORMATION: Reverse primer for generating deletion mutants
      of USP49 (763-1131)

<400> SEQUENCE: 81
ctcgagcgac actagggc                                                   18

<210> SEQ ID NO 82
<211> LENGTH: 19
<212> TYPE: DNA
<213> ORGANISM: Artificial Sequence
<220> FEATURE:
<223> OTHER INFORMATION: Reverse primer for generating deletion mutants
      of USP49 (1132-2067)

<400> SEQUENCE: 82
tacgtatcaa cccctttcc                                                  19

<210> SEQ ID NO 83
<211> LENGTH: 19
<212> TYPE: DNA
<213> ORGANISM: Artificial Sequence
<220> FEATURE:
<223> OTHER INFORMATION: Target sequence #1 of shUSP49s

<400> SEQUENCE: 83
gtcttcactg tagctcaag                                                  19

<210> SEQ ID NO 84
<211> LENGTH: 19
<212> TYPE: DNA
<213> ORGANISM: Artificial Sequence
<220> FEATURE:
<223> OTHER INFORMATION: Target sequence #2 of shUSP49s

<400> SEQUENCE: 84
ggactacgtg ctcaatgat                                                  19

<210> SEQ ID NO 85
<211> LENGTH: 19
<212> TYPE: DNA

```
<213> ORGANISM: Artificial Sequence
<220> FEATURE:
<223> OTHER INFORMATION: Target sequence #3 of shUSP49s

<400> SEQUENCE: 85
ggactacgtg ctcaatgat                                                    19

<210> SEQ ID NO 86
<211> LENGTH: 24
<212> TYPE: DNA
<213> ORGANISM: Artificial Sequence
<220> FEATURE:
<223> OTHER INFORMATION: Forward primer for targeting USP49

<400> SEQUENCE: 86
aggactacgt gctcaatgat aacc                                              24

<210> SEQ ID NO 87
<211> LENGTH: 21
<212> TYPE: DNA
<213> ORGANISM: Artificial Sequence
<220> FEATURE:
<223> OTHER INFORMATION: Reverse primer for targeting USP49

<400> SEQUENCE: 87
gcaggagcag ccgtgcactc t                                                 21

<210> SEQ ID NO 88
<211> LENGTH: 18
<212> TYPE: DNA
<213> ORGANISM: Artificial Sequence
<220> FEATURE:
<223> OTHER INFORMATION: Forward primer for targeting GAPDH

<400> SEQUENCE: 88
atcccatcac catcttcc                                                     18

<210> SEQ ID NO 89
<211> LENGTH: 18
<212> TYPE: DNA
<213> ORGANISM: Artificial Sequence
<220> FEATURE:
<223> OTHER INFORMATION: Reverse primer for targeting GAPDH

<400> SEQUENCE: 89
ccatcacgcc acagtttc                                                     18
```